(12) United States Patent
Prakash et al.

(10) Patent No.: US 10,570,164 B2
(45) Date of Patent: Feb. 25, 2020

(54) STEVIOL GLYCOSIDES, THEIR COMPOSITIONS AND THEIR PURIFICATION

(71) Applicants: The Coca-Cola Company, Atlanta, GA (US); PureCircle Sdn Bhd, Negeri Sembilan (MY)

(72) Inventors: Indra Prakash, Alpharetta, GA (US); Venkata Sai Prakash Chaturvedula, Gilbert, AZ (US); Juvenal Higiro, Manhattan, KS (US); Avetik Markosyan, Kuala Lumpur (MY)

(73) Assignees: The Coca-Cola Company, Atlanta, GA (US); PureCircle SDN BHD, Negeri Sembilan (MY)

( * ) Notice: Subject to any disclaimer, the term of this patent is extended or adjusted under 35 U.S.C. 154(b) by 625 days.

(21) Appl. No.: 14/776,096

(22) PCT Filed: Mar. 18, 2014

(86) PCT No.: PCT/US2014/031129
§ 371 (c)(1),
(2) Date: Sep. 14, 2015

(87) PCT Pub. No.: WO2014/146135
PCT Pub. Date: Sep. 18, 2014

(65) Prior Publication Data
US 2016/0039856 A1 Feb. 11, 2016

Related U.S. Application Data

(60) Provisional application No. 61/788,633, filed on Mar. 15, 2013, provisional application No. 61/867,832, filed on Aug. 20, 2013.

(51) Int. Cl.
| | |
|---|---|
| *C07H 15/256* | (2006.01) |
| *A23L 27/30* | (2016.01) |
| *C07H 15/20* | (2006.01) |
| *C07H 13/08* | (2006.01) |
| *A23L 27/00* | (2016.01) |
| *A23G 4/10* | (2006.01) |
| *A23L 2/60* | (2006.01) |
| *C07H 1/00* | (2006.01) |
| *C07H 1/06* | (2006.01) |

(52) U.S. Cl.
CPC ............ *C07H 15/256* (2013.01); *A23G 4/10* (2013.01); *A23L 2/60* (2013.01); *A23L 27/00* (2016.08); *A23L 27/36* (2016.08); *C07H 1/00* (2013.01); *C07H 1/06* (2013.01); *C07H 13/08* (2013.01); *C07H 15/20* (2013.01)

(58) Field of Classification Search
CPC ............ A23L 2/60; A23L 27/36; A23L 27/00
See application file for complete search history.

(56) References Cited

U.S. PATENT DOCUMENTS

| | | |
|---|---|---|
| 4,612,942 A | 9/1986 | Dobberstein |
| 2009/0162484 A1 | 6/2009 | Bell |
| 2010/0092638 A1 | 4/2010 | Hansen et al. |
| 2010/0278993 A1 | 11/2010 | Prakash et al. |
| 2011/0092684 A1 | 4/2011 | Abelyan et al. |
| 2011/0160311 A1 | 6/2011 | Prakash et al. |
| 2011/0183056 A1 | 7/2011 | Morita et al. |
| 2012/0164083 A1 | 6/2012 | Palmer et al. |

FOREIGN PATENT DOCUMENTS

| | | | |
|---|---|---|---|
| CN | 102216313 A | 7/2011 | |
| WO | 2010/038911 A1 | 4/2010 | |
| WO | WO 2011/153378 | 12/2011 | |
| WO | WO-2012112180 A1 * | 8/2012 | ............ A61K 36/28 |
| WO | WO-2013102793 A1 * | 7/2013 | ............ C07H 15/24 |

OTHER PUBLICATIONS

Masaya Ohta et al., Characterization of Novel Steviol Glycosides from Leaves of *Stevia rebaudiana* Morita, J. Appl. Glycosci., vol. 57, 199-209 (2010), The Japanese Society of Applied Glycoscience.
International Search Report for PCT/US2014/031129, dated Nov. 10, 2014.
Chaturvedula et al. Enzymatic and acid hydrolysis of steviol and cucurbitane glycosides. Int J Pharm Biomed Res 2(2): 135-139, 2011.
Prakash et al. Structural Characterization of the Degradation Products of a Minor Natural Sweet Diterpene Glycoside Rebaudioside M under Acidic Conditions, Int J. Mol. Sci. 15(1); 1014-1025, Jan. 2014.
Sweetness and Mechanism of Picric in Stevioside, Wang Deji, China Food Additives, vol. 3, pp. 46-53, 2007.
Servant, et al., Trends in Pharmacological Sciences, Nov. 2011, vol. 32, No. 11, pp. 631-636.
Servant, et al. PNAS 2010, vol. 107, No. 10, pp. 4746-4751.

\* cited by examiner

*Primary Examiner* — Nikki H. Dees
(74) *Attorney, Agent, or Firm* — King & Spalding

(57) ABSTRACT

The present invention relates generally to steviol glycosides, as well as compositions comprising such steviol glycosides. The present invention further extends to methods of preparing and purifying such steviol glycosides and methods for enhancing the flavor or sweetness of consumables using these steviol glycosides and compositions. The present invention extends to consumables comprising steviol glycosides, where the such steviol glycosides are present in a concentration at or below their sweetness recognition threshold, and wherein such steviol glycosides enhance the sweetness of the consumable.

8 Claims, 14 Drawing Sheets

STEVIOL GLYCOSIDES, THEIR COMPOSITIONS AND THEIR PURIFICATION

CROSS REFERENCE TO RELATED APPLICATIONS

This application is a national phase application under 35 U.S.C. § 371 of International Application No. PCT/US2014/031129, filed on 18 Mar. 2014, which claims the benefit of U.S. Provisional Application No. 61/788,633, filed on Mar. 15, 2013 and U.S. Provisional Application No. 61/867,832, filed on Aug. 20, 2013, the disclosures of all of which are incorporated herein by reference.

FIELD OF THE INVENTION

The present invention relates generally to steviol glycosides, as well as compositions comprising such steviol glycosides. The present invention further extends to methods of preparing and purifying such steviol glycosides, methods for preparing compositions comprising such steviol glycosides (e.g., consumables) and methods for enhancing the flavor or sweetness of consumables using steviol glycosides and compositions comprising the same.

BACKGROUND OF THE INVENTION

Natural caloric sugars, such as sucrose, fructose and glucose, are utilized to provide a pleasant taste to beverages, foods, pharmaceuticals, and oral hygienic/cosmetic products. Sucrose, in particular, imparts a taste preferred by consumers. Although sucrose provides superior sweetness characteristics, it is caloric. Non-caloric or low caloric sweeteners have been introduced to satisfy consumer demand. However, sweeteners within this class differ from natural caloric sugars in ways that continue to frustrate consumers. On a taste basis, non-caloric or low caloric sweeteners exhibit a temporal profile, maximal response, flavor profile, mouth feel, and/or adaptation behavior that differ from sugar. Specifically, non-caloric or low caloric sweeteners exhibit delayed sweetness onset, lingering sweet aftertaste, bitter taste, metallic taste, astringent taste, cooling taste and/or licorice-like taste. On a source basis, many non-caloric or low caloric sweeteners are synthetic chemicals. The desire for a natural non-caloric or low caloric sweetener that tastes like sucrose remains high.

Stevia rebaudiana Bertoni is a perennial shrub of the Asteraceae (Compositae) family native to certain regions of South America. Its leaves have been traditionally used for hundreds of years in Paraguay and Brazil to sweeten local teas and medicines. The plant is commercially cultivated in Japan, Singapore, Taiwan, Malaysia, South Korea, China, Israel, India, Brazil, Australia and Paraguay.

The leaves of the plant contain a mixture containing diterpene glycosides in an amount ranging from about 10% to 20% of the total dry weight. These diterpene glycosides are about 150 to 450 times sweeter than sugar. Structurally, the diterpene glycosides are characterized by a single base, steviol, and differ by the presence of carbohydrate residues at positions C13 and C19. Typically, on a dry weight basis, the four major steviol glycosides found in the leaves of Stevia are dulcoside A (0.3%), rebaudioside C (0.6-1.0%), rebaudioside A (3.8%) and stevioside (9.1%). Other glycosides identified in Stevia extract include rebaudioside B, D, E, and F, steviolbioside and rubusoside. Among these, only stevioside and rebaudioside A are available on a commercial scale.

The use of steviol glycosides has been limited to date by certain undesirable taste properties, including licorice taste, bitterness, astringency, sweet aftertaste, bitter aftertaste, licorice aftertaste, and become more prominent with increase of concentration. These undesirable taste attributes are particularly prominent in carbonated beverages, where full replacement of sugar requires concentrations of steviol glycosides that exceed 500 mg/L. Use at that level results in significant deterioration in the final product taste.

Accordingly, there remains a need to develop natural reduced or non-caloric sweeteners that provide a temporal and flavor profile similar to that of sucrose.

There remains a further need for methods for purifying steviol glycosides from stevia.

SUMMARY OF THE INVENTION

The present invention relates generally to steviol glycosides and compositions comprising such steviol glycosides, as well as methods of preparing and purifying such steviol glycosides, methods of preparing compositions comprising such steviol glycosides (e.g., consumables) and methods for enhancing the flavor or sweetness of consumables using these steviol glycosides and compositions.

In one aspect, the present invention is a steviol glycoside of formula (1):

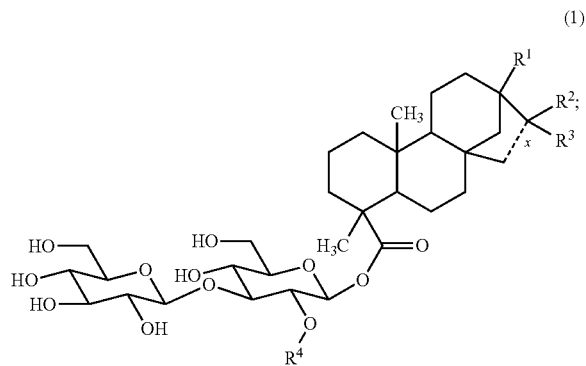

wherein $R^1$ is independently selected from the group consisting of a C-linked monosaccharide; an O-linked monosaccharide; a C-linked oligosaccharide; an O-linked oligosaccharide; hydrogen; hydroxyl; halo; acyl; substituted or unsubstituted ester; substituted or unsubstituted aryl; a substituted or unsubstituted heteroaryl; substituted or unsubstituted alkyl; substituted or unsubstituted ring of 5 to 7 members; substituted or unsubstituted heterocycle; substituted or unsubstituted alkoxy; substituted or unsubstituted alkoxyalkyl; substituted or unsubstituted alkylthio; substituted or unsubstituted alkylthioalkyl; substituted or unsubstituted alkylsulfonyl; substituted or unsubstituted alkylsulfonylalkyl; C1-C6 straight alkyl; C1-C6 branched alkyl; C2-C6 alkenyl; —$NH_2$; —$NHR_2$; —$NR_2$; —$OSO_3H$; —$OSO_2R$; —OC(O)R; —$OCO_2H$; —$CO_2R$; —C(O)$NH_2$; —C(O)NHR; —C(O)$NR_2$; —$SO_3H$; —$SO_2R$; —$SO_2NH_2$; —$SO_2NHR$; —$SO_2NR_2$; or —$OPO_3H$; and R is alkyl, substituted alkyl, alkenyl, substituted alkenyl, alkynyl, substituted alkynyl, substituted aryl, heteroaryl, substituted heteroaryl, or when attached to a nitrogen atom, two adjacent R groups may combine to form a ring of 5 to 7 members;

wherein x is a single bond or a double bond;

wherein when x is a single bond, $R^2$ and $R^3$, taken together, form a carbonyl or alkene; and wherein when x is a double bond, either $R^2$ or $R^3$ is absent; and wherein, $R^2$ and $R^3$ are independently selected from the group consisting of hydrogen; hydroxyl; hydoxyalkyl; halo; amino, thio, cyano, C1-C6 straight alkyl, C1-C6 branched alkyl, C2-C6 alkenyl, C3-C8 cyclic alkyl, heterocyclic, heteroaryl and aryl; C1-C6 alkyoxy; aryl; heteroaryl; heterocyclic, wherein all may be optionally substituted by one or more independently selected from the group consisting of halo, alkyl, lower alkyl, acyl, oxo, hydroxy, hydroxyalkyl, alkoxy, heterocyclic, heteroaryl, cyano, amino, aminoalkyl, and carboxy;

wherein $R^4$ is independently selected from the group consisting of a monosaccharide; an oligosaccharide; hydrogen; hydroxyl; halo; acyl; substituted or unsubstituted ester; substituted or unsubstituted aryl; a substituted or unsubstituted heteroaryl; substituted or unsubstituted alkyl; substituted or unsubstituted alkenyl; substituted or unsubstituted ring of 5 to 7 members; substituted or unsubstituted heterocycle; substituted or unsubstituted alkoxyalkyl; substituted or unsubstituted alkylamine; substituted or unsubstituted alkylthio; substituted or unsubstituted alkylthioalkyl; substituted or unsubstituted alkylsulfonyl; substituted or unsubstituted alkylsulfonylalkyl; —$SO_3H$; —$SO_2R$; —C(O)R; —$CO_2H$; —$CO_2R$; —C(O)$NH_2$; —C(O)NHR; —C(O)$NR_2$; —$SO_3H$; —$SO_2R$; —$SO_2NH_2$; —$SO_2NHR$; —$SO_2NR_2$; or —$PO_3H$.

In a more particular embodiment, x is a single bond and $R^2$ and $R^3$ taken together form an alkene or a carbonyl.

In another particular embodiment, x is a single bond and $R^2$ and $R^3$ are selected from C1-C6 straight alkyl and hydroxyl.

In further particular embodiments, $R^1$ and $R^4$ are each independently selected from hydrogen, methyl and an O-linked oligosaccharide, wherein the oligosaccharide comprises from two to five sugars.

In other embodiments, $R^1$ and $R^4$ are each independently an oligosaccharide comprising a monosaccharide selected from, but not limited to, the group consisting of glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, fucose, rhamnose, arabinose, turanose and sialose.

In a more particular embodiment, the present invention is a steviol glycoside selected from the group consisting of (1a), (1b), (1c), (1d), (1e), (1f), and (1g):

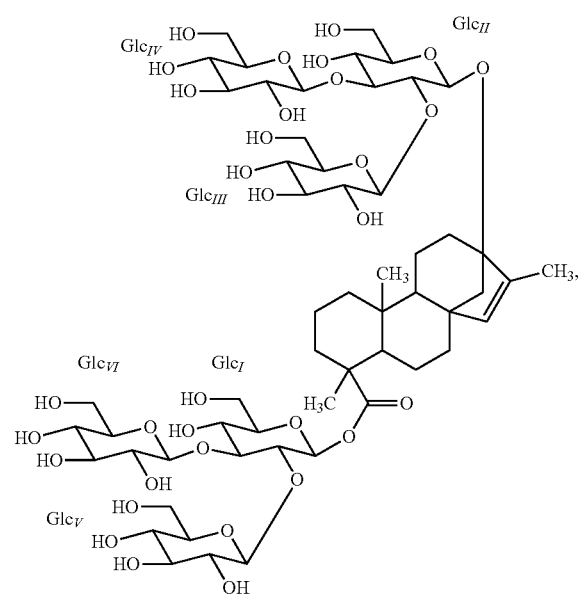

(1a)

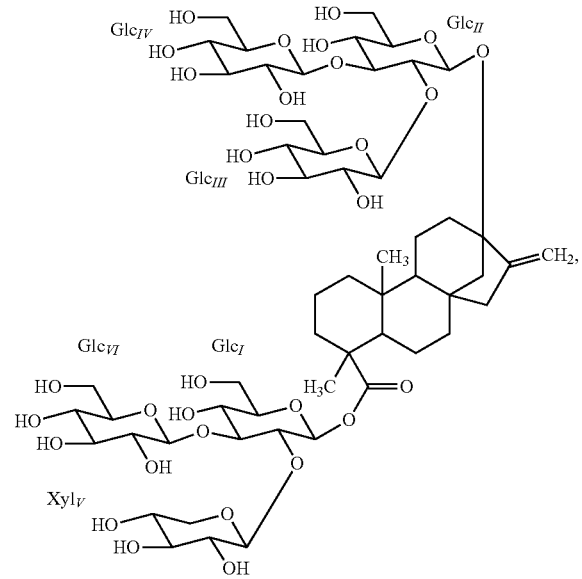

(1b)

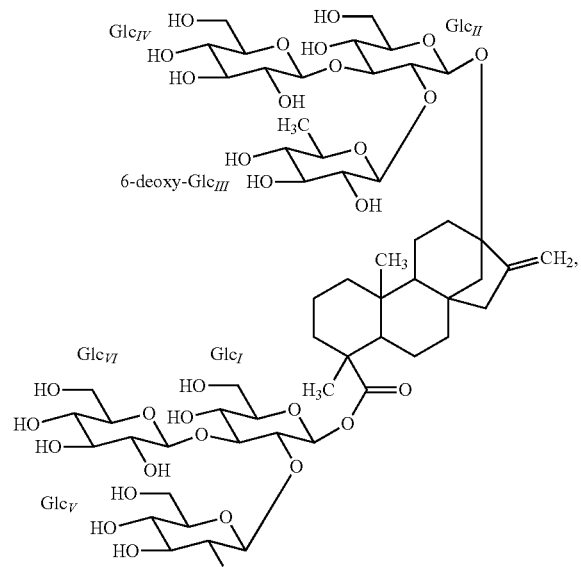
(1c)
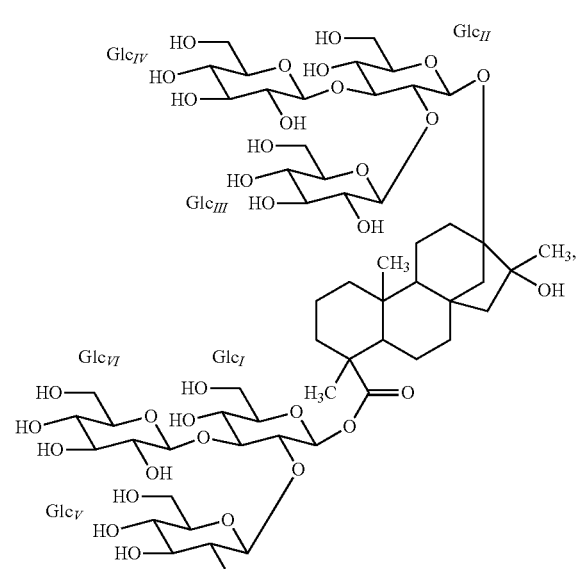
(1d)
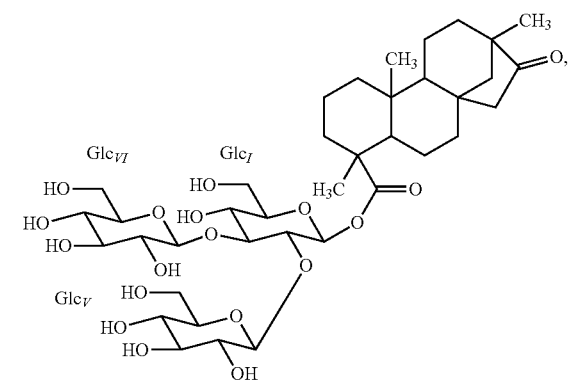
(1e)
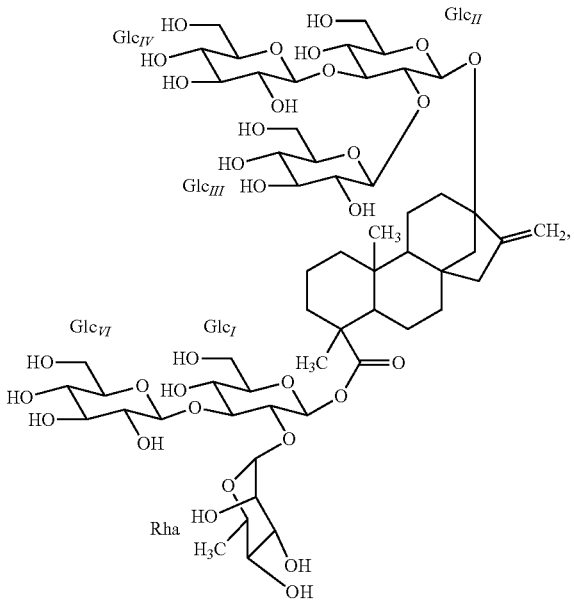
(1f)
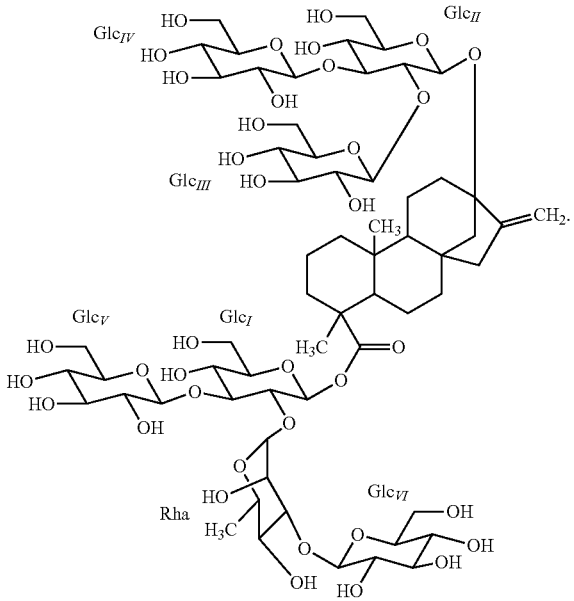
(1g)
In another embodiment, the present invention is a steviol glycoside of formula (2):
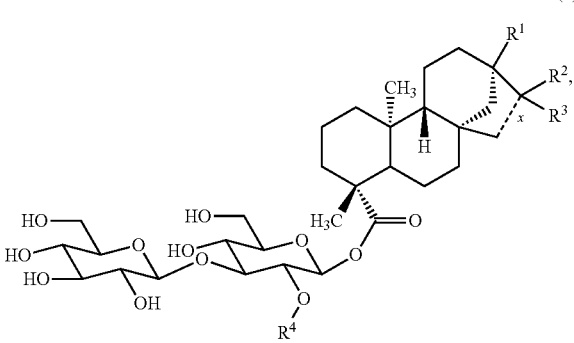
(2)
wherein $R^1$, $R^2$, $R^3$, and $R^4$ remain as defined above.

In a more particular embodiment, x is a single bond and $R^2$ and $R^3$ taken together form an alkene or a carbonyl.

In another particular embodiment, x is a single bond and $R^2$ and $R^3$ are selected from C1-C6 straight alkyl and hydroxyl.

In further particular embodiments, $R^1$ and $R^4$ are each independently selected from hydrogen, methyl and an O-linked oligosaccharide, wherein the oligosaccharide comprises from two to five sugars.

In further particular embodiments, $R^1$ and $R^4$ are each independently selected from hydrogen, methyl and an O-linked oligosaccharide, wherein the oligosaccharide comprises from two to five sugars.

In other embodiments, $R^1$ and $R^4$ are each independently an oligosaccharide comprising a monosaccharide selected from, but not limited to, the group consisting of glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, fucose, rhamnose, arabinose, turanose, and sialose.

In a particular embodiment, the oligosaccharide comprises one or more glucoses.

In more particular embodiment, the present invention is a steviol glycoside selected from (2a), (2b), (2c), (2d), (2e), (2f), and (2g):

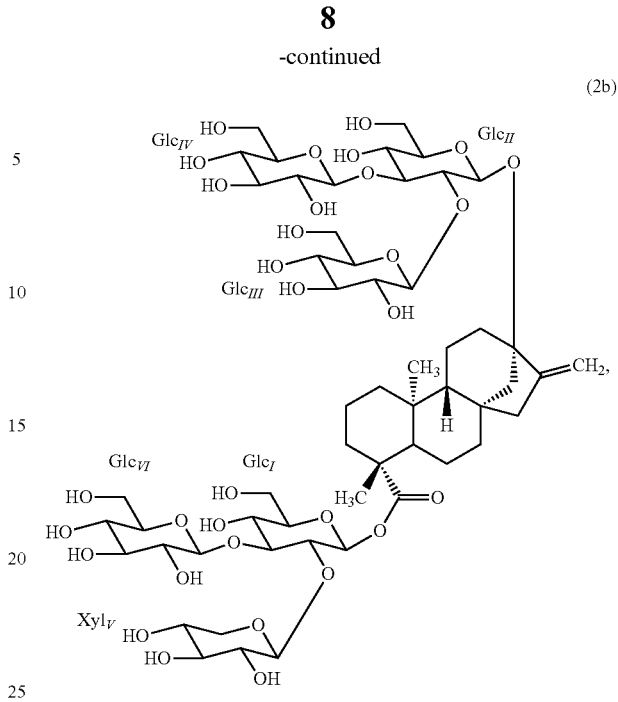

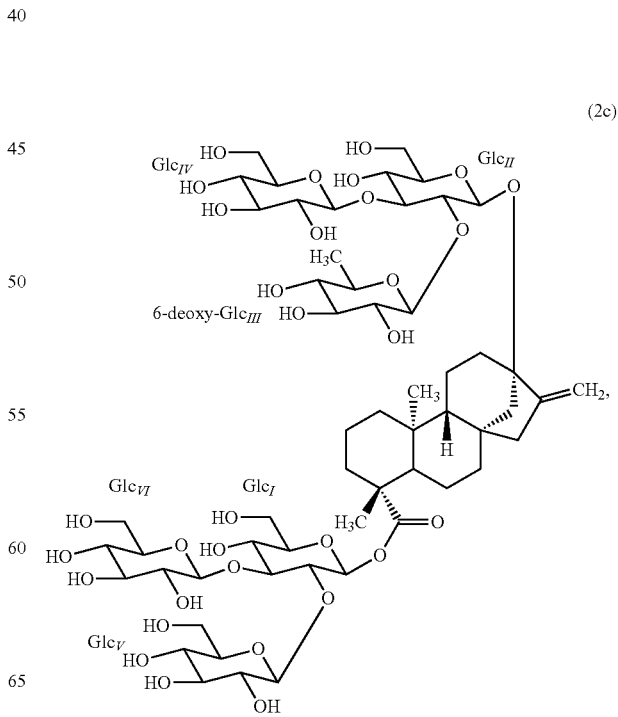

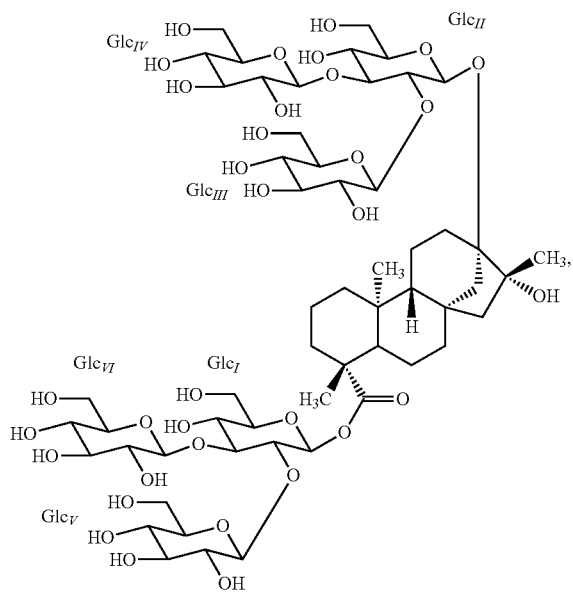

(2d)

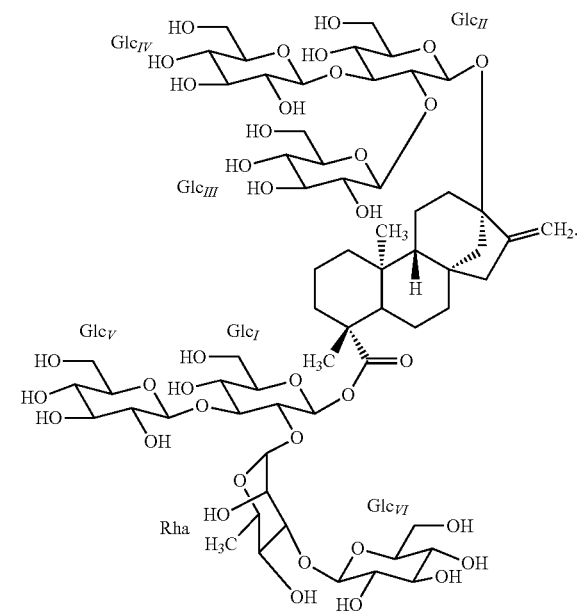

(2g)

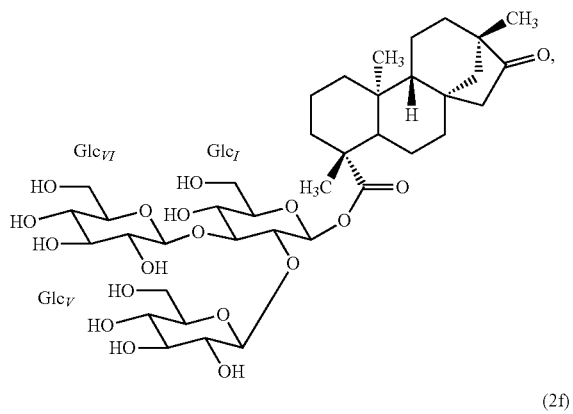

(2e)

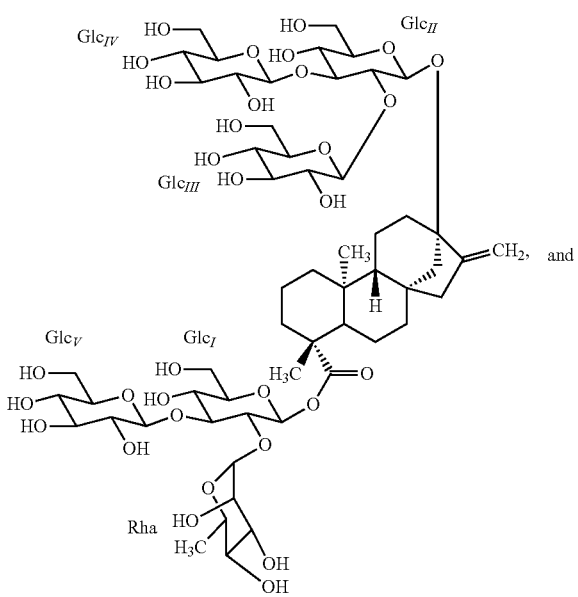

(2f)

Steviol glycoside (2f) is also referred to as rebaudioside N and steviol glycoside (2g) is also referred to as rebaudioside O.

In a further aspect, the present invention is a composition comprising a compound of formula (1).

In one embodiment, the present invention is a sweetener composition comprising a compound of formula (1).

In another embodiment, the present invention is a flavor-enhancing composition comprising a compound of formula (1), wherein the compound of formula (1) is present in an amount effective to provide a concentration at or below the threshold flavor recognition level of the compound of formula (1) when the flavor-enhancing composition is added to a consumable In a particular embodiment, the compound of formula (1) is present in an amount effective to provide a concentration below the threshold flavor recognition level of the compound of formula (1) when the flavor-enhancing composition is added to a consumable. In one embodiment, the compound of formula (1) is present in an amount effective to provide a concentration at least about 1%, at least about 5%, at least about 10%, at least about 15,% at least about 20% or at least about 25% or more below the threshold flavor recognition level of the compound of formula (1) when the flavor-enhancing composition is added to a consumable.

In yet another embodiment, the present invention is a sweetness-enhancing composition comprising a compound of formula (1), wherein the compound of formula (1) is present in an amount effective to provide a concentration at or below the threshold sweetness recognition level of the compound of formula (1) when the sweetness-enhancing composition is added to a consumable In a particular embodiment, the compound of formula (1) is present in an amount effective to provide a concentration below the threshold sweetness recognition level of the compound of formula (1) when the sweetness-enhancing composition is added to a consumable. In one embodiment, the compound of formula (1) is present in an amount effective to provide a concentration at least about 1%, at least about 5%, at least about 10%, at least about 15,% at least about 20% or at least about 25% or more below the threshold sweetness recognition level of the compound of formula (1) when the sweetness-enhancing composition is added to a consumable.

In yet another embodiment, the present invention is a consumable comprising a compound of formula (1). Suitable consumables include, but are not limited to, liquid-based or dry consumables, such as, for example, pharmaceutical compositions, edible gel mixes and compositions, dental compositions, foodstuffs, beverages and beverage products.

In a particular embodiment, the present invention is a beverage comprising a compound of formula (1). In a particular embodiment, the compound of formula (1) is present in the beverage at a concentration that is above, at or below the threshold sweetness recognition concentration of the compound of formula (1).

In another particular embodiment, the present invention is a beverage product comprising a compound of formula 1. In a particular embodiment, the compound of formula (1) is present in the beverage product at a concentration that is above, at or below the threshold flavor recognition concentration of the compound of formula (1).

In one embodiment, the present invention is a consumable comprising at least one sweetener and a compound of formula (1), wherein the at least one sweetener is present in the consumable in a concentration above its sweetness recognition threshold, wherein the compound of formula (1) is present in the consumable in a concentration at or below its sweetness recognition threshold, and wherein the compound of formula (1) enhances the sweetness of the consumable by an amount more than the detectable sweetness of a solution containing the same concentration of the compound of formula (1) in the absence of the at least one sweetener and/or the compound of formula (1) enhances the sweetness of the consumable by about 2.0% (w/v) sucrose equivalence or greater, such as, for example, about 2.0% (w/v) or greater. In another embodiment, the compound of formula (1) enhances the sweetness of the consumable by at least about 2.5% sucrose equivalence. In another embodiment, the compound of formula (1) enhances the sweetness of the consumable from about 2.0% (w/v) to about 3.0% (w/v) sucrose equivalence.

In another embodiment, the present invention is a consumable comprising at least one sweetener and a compound of formula (2), wherein the at least one sweetener is present in the consumable in a concentration above its sweetness recognition threshold, wherein the compound of formula (2) is present in the consumable in a concentration at or below its sweetness recognition threshold, and wherein the compound of formula (2) enhances the sweetness of the consumable by an amount more than the detectable sweetness of a solution containing the same concentration of the compound of formula (2) in the absence of the at least one sweetener and/or the compound of formula (2) and/or enhances the sweetness of the consumable by about 2.0% (w/v) sucrose equivalence or greater, such as, for example, about 2.0% (w/v) or greater. In another embodiment, the compound of formula (2) enhances the sweetness of the consumable by at least about 2.5% sucrose equivalence. In another embodiment, the compound of formula (2) enhances the sweetness of the consumable from about 2.0% (w/v) to about 3.0% (w/v) sucrose equivalence.

In yet another embodiment, the present invention provides a consumable comprising at least one sweetener and a sweetness enhancer selected from compounds (2f) and (2g), wherein the at least one sweetener is present in the consumable in a concentration above its sweetness recognition threshold, wherein compound (2f) or (2g) is present in the consumable in a concentration at or below its sweetness recognition threshold, and wherein compound (2f) or (2g) enhances the sweetness of the consumable by an amount more than the detectable sweetness of a solution containing the same concentration of compound (2f) or (2g) in the absence of the at least one sweetener and/or compound (2f) or (2g) enhances the sweetness of the consumable by about 2.0% (w/v) sucrose equivalence or greater, such as, for example, from about 2.0% (w/v) to about 3.0% (w/v). In one embodiment, compound (2f) enhances the sweetness of the consumable from about 2.5% (w/v) to about 3.0% (w/v) sucrose equivalence. In another embodiment, compound (2g) enhances the sweetness of the consumable about 2.0% (w/v).

The at least one sweetener can be any caloric sweetener, such as a carbohydrate sweetener. Rare sugars can also be used. In one embodiment, the sweetener is selected from the group consisting of sucrose, fructose, glucose, high fructose corn syrup, high fructose starch syrup, D-psicose, D-allose, D-turanose, D-tagatose, D-trehalose, D-leucrose, rare sugar syrup and/or a combination thereof.

In some embodiments, the compositions of the present invention contain one or more additional steviol glycosides, where the additional steviol glycosides are selected from the group consisting of a commercially available *stevia* extract, steviol glycosides prepared from plant material (e.g. leaves) of the *Stevia rebaudiana* Bertoni plant, the by-product of another isolation and purification processes of steviol glycosides, stevioside, rebaudioside A, rebaudioside C, dulcoside A, rubusoside, steviolbioside, rebaudioside B, rebaudioside D, rebaudioside F, and combinations thereof.

In other embodiments, the compositions of the present invention contain one or more sweeteners or additional sweeteners. In one embodiment, the additional sweetener is a natural sweetener or a synthetic sweetener. In a particular embodiment, the additional sweetener is a high intensity sweetener. In a particular embodiment, the additional sweetener is a steviol glycoside.

In some embodiments, the compositions of the present invention contain one or more additives. In a particular embodiment, the consumables, beverages and/or concentrate compositions contains additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, emulsifiers, weighing agents, gums, colorants, flavonoids, alcohols, polymers, essential oils, anti-fungal agents and combinations thereof.

In some embodiments, the compositions of the present invention contain one or more functional ingredients. In a particular embodiment, the functional ingredient is selected from the group consisting of saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

In some aspects, the present invention is a method of preparing compounds of formula (1), comprising (i) contacting a solution comprising rebaudioside X with an inorganic acid, (ii) heating the solution for sufficient time to provide a compound of formula (1) and (iii) recovering the compound of formula (1) from the solution.

In another aspect, the present invention is a method for purifying a compound of formula (1) comprising (1) passing a solution comprising steviol glycosides through an HPLC column and (ii) eluting fractions comprising a compound of formula (1). The HPLC column can be any suitable HPLC preparative scale column. The fractions may be eluted by adding an appropriate eluent. The eluent can be any suitable solvent or combination of solvents. In one embodiment, the eluent is water and/or acetonitrile. The method may optionally comprise additional steps, such as removal of solvents from the eluted solution to provide a concentrate comprising a compound of formula (1).

In another aspect, the present invention is a method for preparing a consumable comprising (i) providing a consumable matrix and (ii) adding a compound of formula (1) to the consumable matrix to provide a consumable. In a particular embodiment, the compound of formula (1) is present in the consumable in a concentration above, at or below the threshold sweetness recognition of the compound of formula (1). In another particular embodiment, the compound of formula (1) is present in the consumable in a concentration above, at or below the threshold flavor recognition of the compound of formula (1).

In a particular embodiment, the present invention is a method of preparing a beverage comprising (i) providing a beverage matrix and (ii) adding a compound of formula (1) to the consumable matrix to provide a beverage. In a particular embodiment, the compound of formula (1) is present in the consumable in a concentration above, at or below the threshold sweetness recognition of the compound of formula (1). In another particular embodiment, the compound of formula (1) is present in the consumable in a concentration above, at or below the threshold flavor recognition concentration of the compound of formula (1).

In a further aspect, the present invention is a method for enhancing the sweetness of a consumable comprising (i) providing a consumable comprising at least one sweetener in a concentration above its sweetness recognition threshold and (ii) adding a compound of formula (1) to the consumable in a concentration at or below the sweetness recognition threshold of the compound, wherein the compound of formula (1) enhances the sweetness of the consumable by an amount more than the detectable sweetness of a solution containing the same concentration of compound of formula (1) and/or the compound of formula (1) enhances the sweetness of the consumable by about 2.0% (w/v) sucrose equivalence or greater.

The another aspect, the present invention is a method for enhancing the sweetness of a consumable comprising (i) providing a consumable comprising at least one sweetener in a concentration above its sweetness recognition threshold and (ii) adding a compound of formula (2) to the consumable in a concentration at or below the sweetness recognition threshold of the compound, wherein the compound of formula (2) enhances the sweetness of the consumable by an amount more than the detectable sweetness of a solution containing the same concentration of compound of formula (2) and/or the compound of formula (2) enhances the sweetness of the consumable by about 2.0% (w/v) sucrose equivalence or greater.

In yet another aspect, the present invention is a method for enhancing the sweetness of a consumable comprising (i) providing a consumable comprising at least one sweetener in a concentration above its sweetness recognition threshold and (ii) adding compound (2f) or (2g) to the consumable in a concentration at or below the sweetness recognition threshold of (2f) or (2g), wherein compound (2f) or (2g) enhances the sweetness of the consumable by an amount more than the detectable sweetness of a solution containing the same concentration of compound (2f) or (2g) and/or compound (2f) or (2g) enhances the sweetness of the consumable by about 2.0% (w/v) sucrose equivalence or greater.

DETAILED DESCRIPTION OF THE INVENTION

I. Compounds

Figure 1:
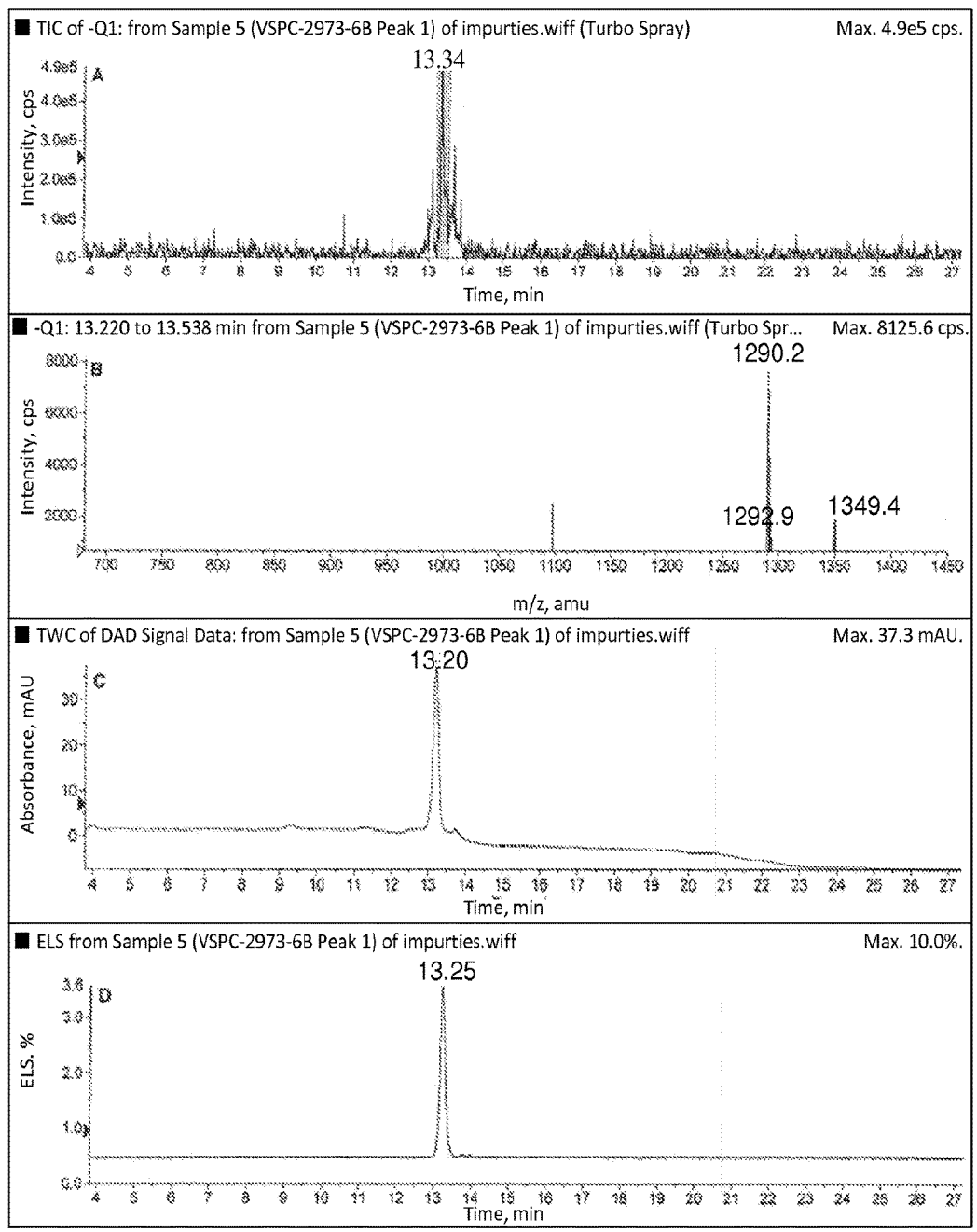
FIG. 1: LC-MS analysis of isolated sample of (2a) showing, from top to bottom, TIC, mass spectrum of the (2a) peak at 13.2 min, UV (210 nm) chromatogram and ELS chromatogram.

In one aspect, the present invention provides steviol glycosides compounds of formula (1):

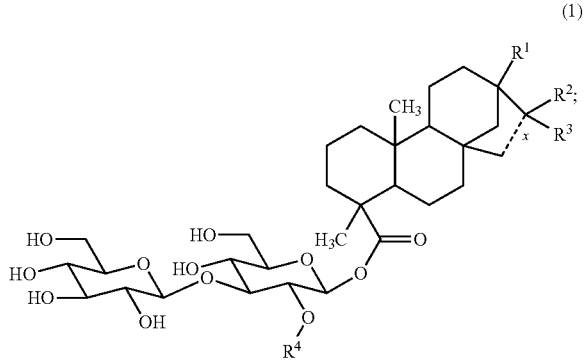

(1)

wherein $R^1$ is independently selected from the group consisting of a C-linked monosaccharide; an O-linked monosaccharide; a C-linked oligosaccharide; an O-linked oligosaccharide; hydrogen; hydroxyl; halo; acyl; substituted or unsubstituted ester; substituted or unsubstituted aryl; a substituted or unsubstituted heteroaryl; substituted or unsubstituted alkyl; substituted or unsubstituted ring of 5 to 7 members; substituted or unsubstituted heterocycle; substituted or unsubstituted alkoxy; substituted or unsubstituted alkoxyalkyl; substituted or unsubstituted alkylthio; substituted or unsubstituted alkylthioalkyl; substituted or unsubstituted alkylsulfonyl; substituted or unsubstituted alkylsulfonylalkyl; C1-C6 straight alkyl; C1-C6 branched alkyl; C2-C6 alkenyl; —$NH_2$; —$NHR_2$; —$NR_2$; —$OSO_3H$; —$OSO_2R$; —OC(O)R; —$OCO_2H$; —$CO_2R$; —C(O)$NH_2$; —C(O)NHR; —C(O)$NR_2$; —$SO_3H$; —$SO_2R$; —$SO_2NH_2$; —$SO_2NHR$; —$SO_2NR_2$; or —$OPO_3H$; and R is alkyl, substituted alkyl, alkenyl, substituted alkenyl, alkynyl, substituted alkynyl, substituted aryl, heteroaryl, substituted heteroaryl, or when attached to a nitrogen atom, two adjacent R groups may combine to form a ring of 5 to 7 members;

wherein x is a single bond or a double bond;

wherein when x is a single bond, $R^2$ and $R^3$, taken together, form a carbonyl or alkene; and wherein when x is a double bond, either $R^2$ or $R^3$ is absent; and wherein $R^2$ and $R^3$ are independently selected from the group consisting of hydrogen; hydroxyl; hydoxyalkyl; halo; amino, thio, cyano, C1-C6 straight alkyl, C1-C6 branched alkyl, C2-C6 alkenyl, C3-C8 cyclic alkyl, heterocyclic, heteroaryl and aryl; C1-C6 alkyoxy; aryl; heteroaryl; heterocyclic, wherein all may be optionally substituted by one or more independently selected from the group consisting of halo, alkyl, lower alkyl, acyl, oxo, hydroxy, hydroxyalkyl, alkoxy, heterocyclic, heteroaryl, cyano, amino, aminoalkyl, and carboxy;

wherein $R^4$ is independently selected from the group consisting of a monosaccharide; an oligosaccharide; hydrogen; hydroxyl; halo; acyl; substituted or unsubstituted ester; substituted or unsubstituted aryl; a substituted or unsubstituted heteroaryl; substituted or unsubstituted alkyl; substituted or unsubstituted alkenyl; substituted or unsubstituted ring of 5 to 7 members; substituted or unsubstituted heterocycle; substituted or unsubstituted alkoxyalkyl; substituted or unsubstituted alkylamine; substituted or unsubstituted alkylthio; substituted or unsubstituted alkylthioalkyl; substituted or unsubstituted alkylsulfonyl; substituted or unsubstituted alkylsulfonylalkyl; —$SO_3H$; —$SO_2R$; —C(O)R; —$CO_2H$; —$CO_2R$; —C(O)$NH_2$; —C(O)NHR; —C(O)$NR_2$; —$SO_3H$; —$SO_2R$; —$SO_2NH_2$; —$SO_2NHR$; —$SO_2NR_2$; or —$PO_3H$.

In a more particular embodiment, x is a single bond and $R^2$ and $R^3$ taken together form an alkene or a carbonyl.

In another particular embodiment, x is a single bond and $R^2$ and $R^3$ are selected from C1-C6 straight alkyl and hydroxyl.

In one embodiment, x is a single bond and $R^2$ and $R^3$ taken together are an alkene. In a particular embodiment, x is a single bond and $R^2$ and $R^3$ taken together are a carbonyl. In another embodiment, x is a single bond, $R^2$ is a methyl and $R^3$ is a hydroxyl.

In further particular embodiments, $R^1$ and $R^4$ are each independently selected from hydrogen, methyl and an O-linked oligosaccharide, wherein the oligosaccharide comprises from two to five sugars.

In some embodiments, $R^1$ is an O-linked oligosaccharide. In particular embodiments, $R^1$ is an O-linked oligosaccharide comprising monosaccharides including, but not limited to, glucose, 6-deoxy-glucose, and combinations thereof. In other embodiments, $R^1$ is a branched, O-linked oligosaccharide. In still other embodiment, $R^1$ is a linear, O-linked oligosaccharide.

In some embodiments, $R^4$ is an O-linked oligosaccharide. In particular embodiments, $R^4$ is an O-linked oligosaccharide comprising monosaccharides including, but not limited to, glucose, rhamnose, xylose and combinations thereof. In other embodiments, $R^4$ is a branched, O-linked oligosaccharide. In still other embodiment, $R^4$ is a linear, O-linked oligosaccharide.

In some embodiments, $R^1$ and $R^4$ are independently selected from a monosaccharide, an oligosaccharide comprising two sugars, an oligosaccharide comprising three sugars, an oligosaccharide comprising four sugars and an oligosaccharide comprising five sugars. In some embodiments, $R^1$ is an oligosaccharide selected from, but not limited to, the group consisting of glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, fucose, rhamnose, arabinose, turanose and sialose.

In some embodiments, $R^4$ is an oligosaccharide selected from, but not limited to, the group consisting of glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, fucose, rhamnose, arabinose, turanose and sialose.

One of ordinary skill in the art will appreciate that compounds of formula (1) comprise one or more stereocenters. Each stereocenter may be in either the R or S configuration, depending on the arrangement and orientation of the atoms in space. Unless otherwise indicated, it should be understood that the compound of formula (1) may be of any suitable stereochemical configuration.

In one embodiment, the present invention is a compound of formula (1a):

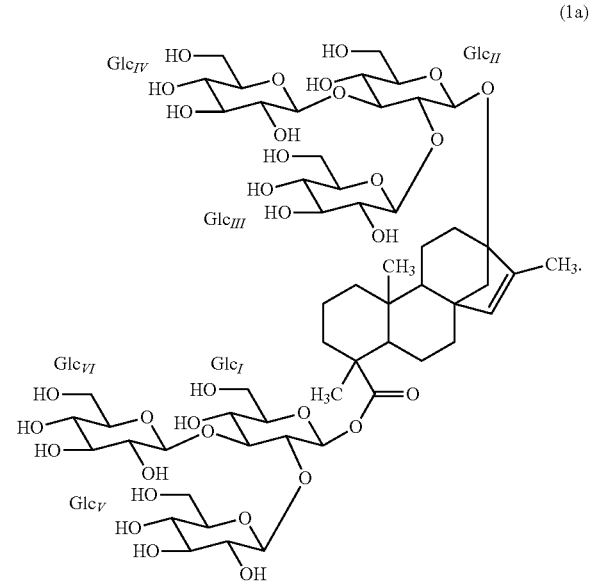 [SMILES: CC1=CC23CCC4C(C)(C(=O)OC5OC(CO)C(O)C(OC6OC(CO)C(O)C(O)C6O)C5OC5OC(CO)C(O)C(O)C5O)CCCC4(C)C2CCC1(OC1OC(CO)C(O)C(OC2OC(CO)C(O)C(O)C2O)C1OC1OC(CO)C(O)C(O)C1O)C3]

(1a)

In another embodiment, the present invention is the compound of formula (1b):

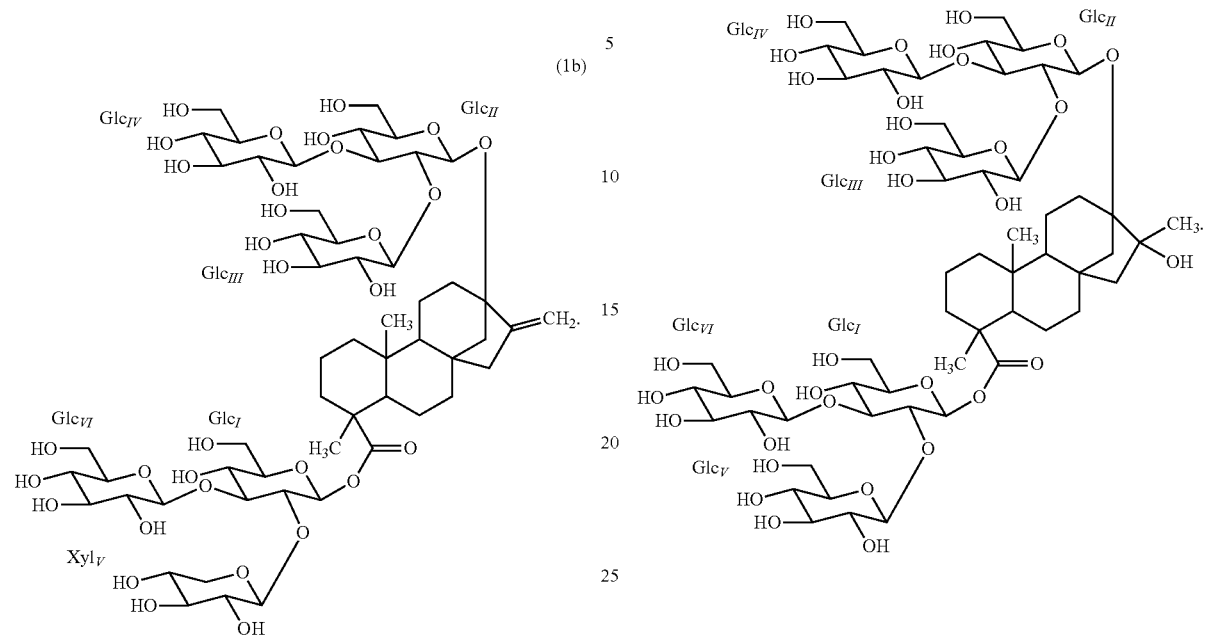

In still another embodiment, the present invention is the compound of formula (1c):

In another embodiment, the present invention is the compound of formula (1d):

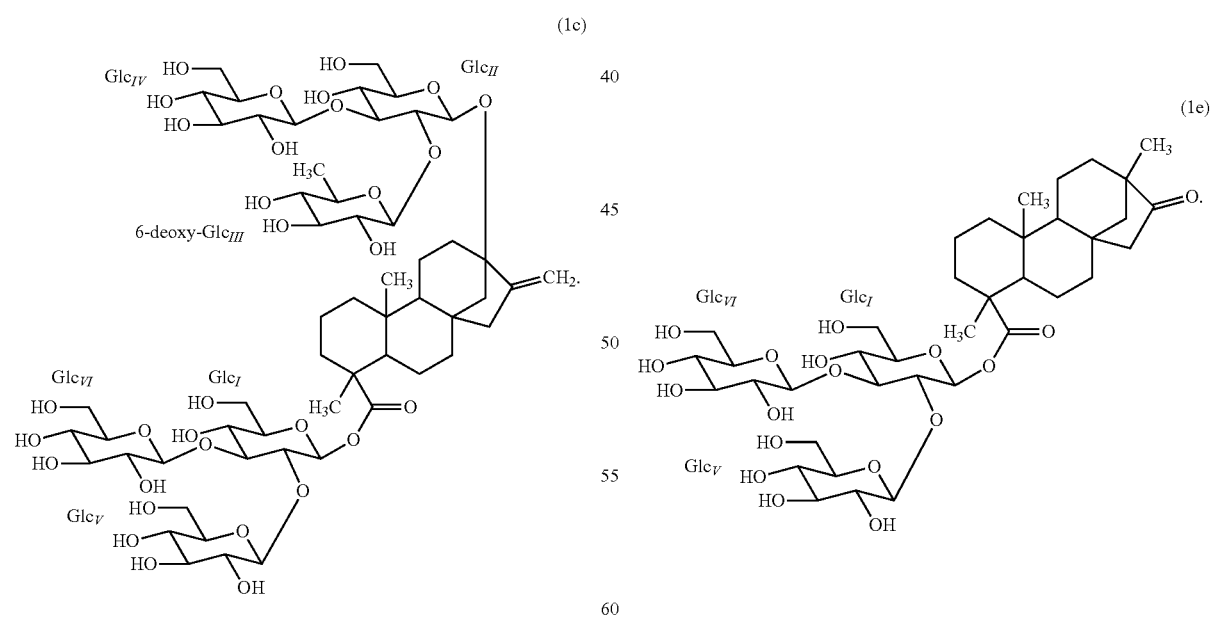

In another embodiment, the present invention is the compound of formula (1e):

In still another embodiment, the present invention is the compound of formula (1f):

(1f)

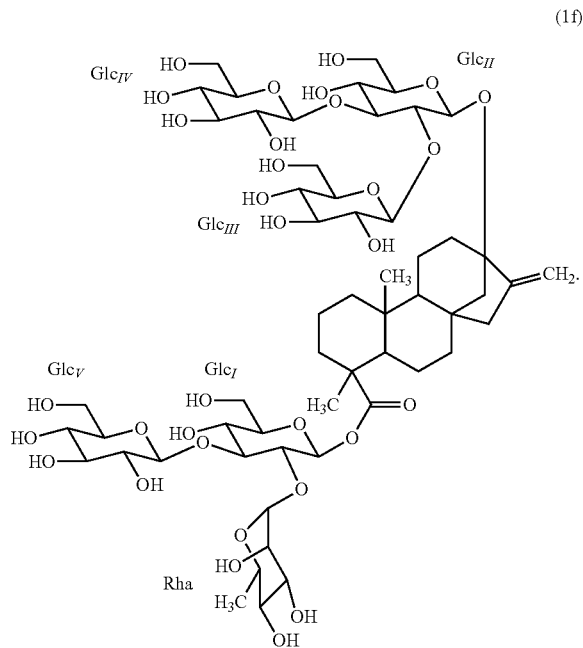 [SMILES: C=C1CC23CCC4C(C)(C(=O)OC5OC(CO)C(O)C(OC6OC(CO)C(O)C(O)C6O)C5OC5OC(C)C(O)C(O)C5O)CCCC4(C)C2CCC1(OC1OC(CO)C(O)C(OC2OC(CO)C(O)C(O)C2O)C1OC1OC(CO)C(O)C(O)C1O)C3]

In yet another embodiment, the present invention is the compound of formula (1g):

(1g)

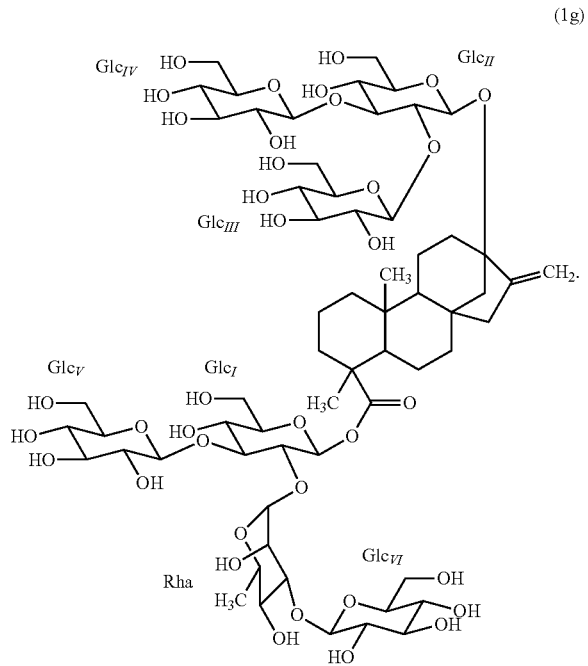 [SMILES: C=C1CC23CCC4C(C)(C(=O)OC5OC(CO)C(O)C(OC6OC(CO)C(O)C(O)C6O)C5OC5OC(C)C(O)C(OC6OC(CO)C(O)C(O)C6O)C5O)CCCC4(C)C2CCC1(OC1OC(CO)C(O)C(OC2OC(CO)C(O)C(O)C2O)C1OC1OC(CO)C(O)C(O)C1O)C3]

In other embodiments, the present invention is a compound of formula (2), wherein formula (2) is a subset of formula (1):

(2)

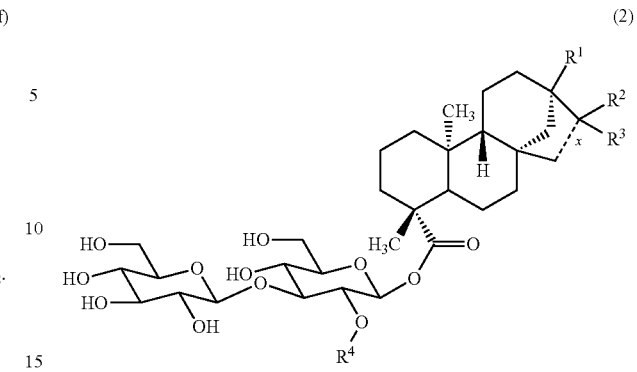

wherein $R^1$, $R^2$, $R^3$, and $R^4$ remain as set forth above.

In a more particular embodiment, x is a single bond and $R^2$ and $R^3$ taken together form an alkene or a carbonyl.

In another particular embodiment, x is a single bond and $R^2$ and $R^3$ are selected from C1-C6 straight alkyl and hydroxyl.

In one embodiment, x is a single bond and $R^2$ and $R^3$ taken together are an alkene. In a particular embodiment, x is a single bond and $R^2$ and $R^3$ taken together are a carbonyl. In another embodiment, x is a single bond, $R^2$ is a methyl and $R^3$ is a hydroxyl.

In further particular embodiments, $R^1$ and $R^4$ are each independently selected from hydrogen, methyl and an O-linked oligosaccharide, wherein the oligosaccharide comprises from two to five sugars.

In some embodiments, $R^1$ is an O-linked oligosaccharide. In particular embodiments, $R^1$ is an O-linked oligosaccharide comprising monosaccharides including, but not limited to, glucose, 6-deoxy-glucose, and combinations thereof. In other embodiments, $R^1$ is a branched, O-linked oligosaccharide. In still other embodiment, $R^1$ is a linear, O-linked oligosaccharide.

In some embodiments, $R^4$ is an O-linked oligosaccharide. In particular embodiments, $R^4$ is an O-linked oligosaccharide comprising monosaccharides including, but not limited to, glucose, rhamnose, xylose and combinations thereof. In other embodiments, $R^4$ is a branched, O-linked oligosaccharide. In still other embodiment, $R^4$ is a linear, O-linked oligosaccharide.

In some embodiments, $R^1$ and $R^4$ are independently selected from a monosaccharide, an oligosaccharide comprising two sugars, an oligosaccharide comprising three sugars, an oligosaccharide comprising four sugars and an oligosaccharide comprising five sugars.

In some embodiments, $R^1$ is an oligosaccharide selected from, but not limited to, the group consisting of glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, fucose, rhamnose, arabinose, turanose and sialose.

In some embodiments, $R^4$ is an oligosaccharide selected from, but not limited to, the group consisting of glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, fucose, rhamnose, arabinose, turanose and sialose.

In particular embodiments, $R^1$ and/or $R^4$ are oligosaccharides comprising one or more glucose.

The monosaccharides within a given oligosaccharide can be the same or different, i.e. an oligosaccharide can contain two or more of the same monosaccharides or may contain two or more different monosaccharides.

The bonds between the monosaccharides of an oligosaccharide, and between the oligosaccharide and the R position of formulae (1) or (2), can be β-linkages or α-linkages. In yet another embodiment, the oligosaccharide is bonded with β-(1,2)-linkages, β-(1,3)-linkages, β-(1,4)-linkages, β-(1,6)-linkages, α-(1,2)-linkages, α-(1,3)-linkages, α-(1,4)-linkages, α-(1,6)-linkages, and any combination thereof.

In a particular embodiment, the present invention is the compound of formula 13-[(2-O-β-D-glucopyranosyl-3-O-β-D-glucopyranosyl-β-D-glucopyranosyl)oxy]ent-kaur-15-en-19-oic acid-[(2-O-β-D-glucopyranosyl-3-O-β-D-glucopyranosyl-β-D-glucopyranosyl)ester] (2a):

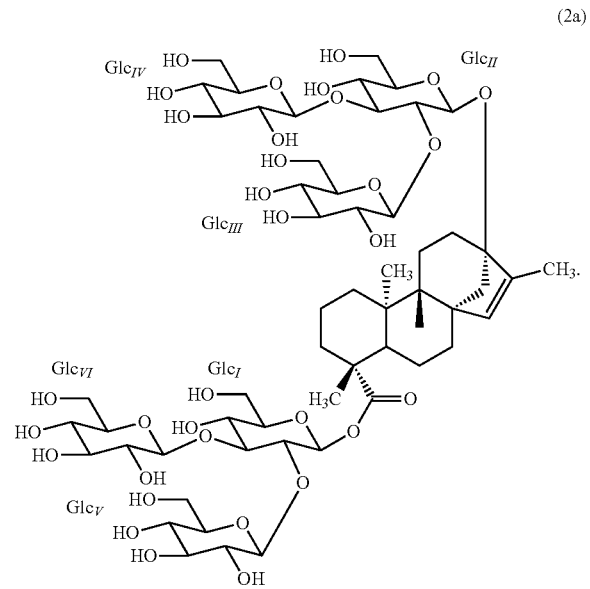

(2a)

In another particular embodiment, the present invention is the compound of formula (β-[(2-O-β-D-glucopyranosyl-3-O-β-D-glucopyranosyl-β-D-glucopyranosyl)oxy]ent-kaur-16-en-19-oic acid-[(2-O-β-D-xylopyranosyl-3-O-β-D-glucopyranosyl-β-D-glucopyranosyl)ester]) (2b).

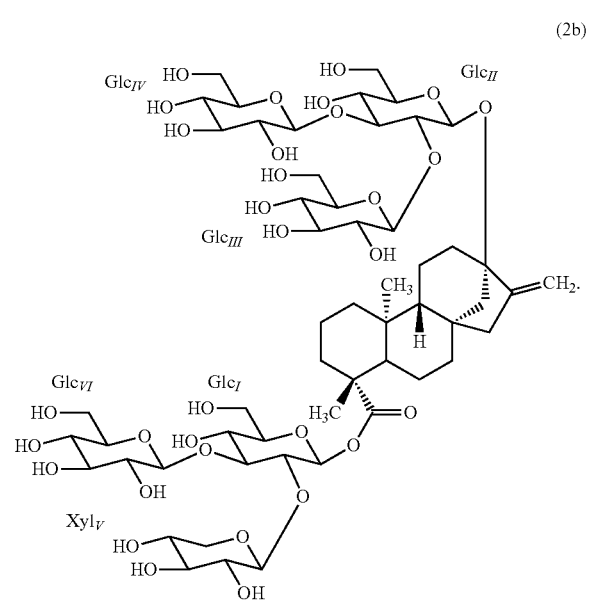

(2b)

In still another particular embodiment, the present invention is the compound of formula (13-[(2-O-6-deoxy-β-D-glucopyranosyl-3-O-β-D-glucopyranosyl-β-D-glucopyranosyl)oxy]ent-kaur-16-en-19-oic acid-[(2-O-β-D-glucopyranosyl-3-O-β-D-glucopyranosyl-β-D-glucopyranosyl)ester]) (2c):

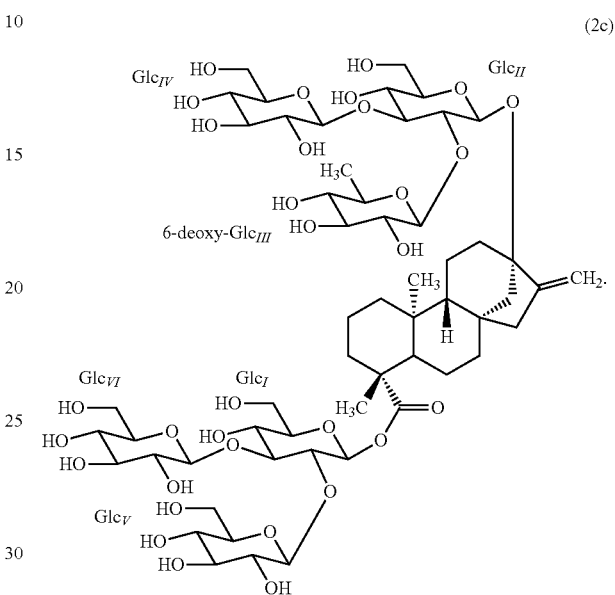

(2c)

In still another particular embodiment, the present invention is the compound of formula (13-[(2-O-β-D-glucopyranosyl-3-O-β-D-glucopyranosyl-β-D-glucopyranosyl)oxy]ent-kaur-16-hydroxy-19-oic acid-[(2-O-β-D-glucopyranosyl-3-O-β-D-glucopyranosyl-β-D-glucopyranosyl)ester]) (2d):

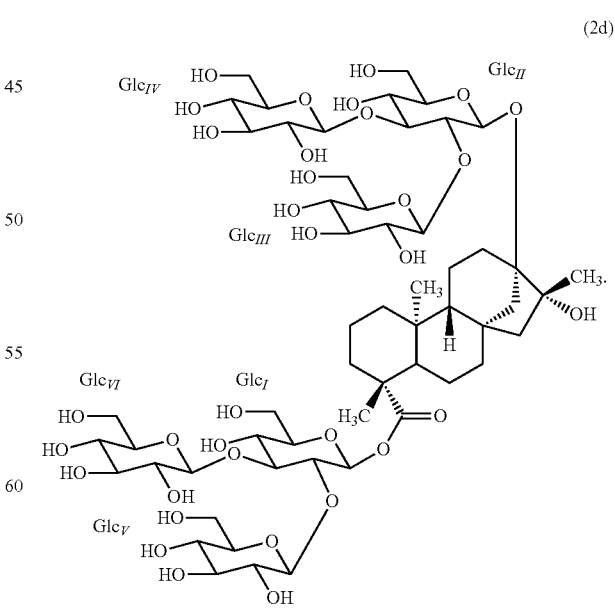

(2d)

In still another particular embodiment, the present invention is the compound of formula (13-methyl-16-oxo-17-norent-kauran-19-oic acid-[(2-O-β-D-glucopyranosyl-3-O-β-D-glucopyranosyl-β-D-glucopyranosyl)ester]) (2e):

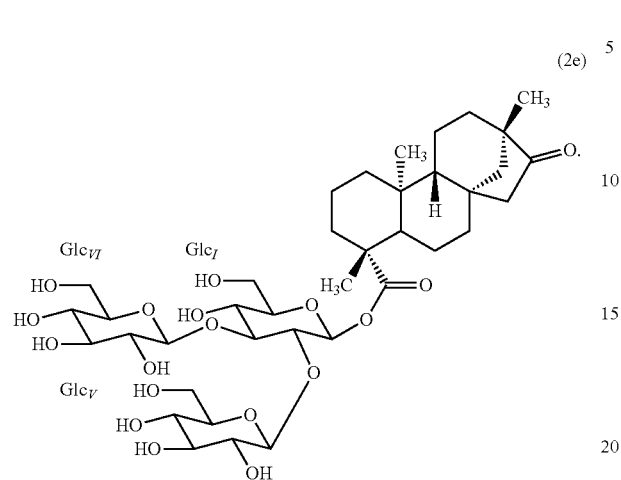

(2e)

In still another particular embodiment, the present invention is the compound of formula (13-[(2-O-β-D-glucopyranosyl-3-O-β-D-glucopyranosyl-β-D-glucopyranosyl)oxy] ent-kaur-16-en-19-oic acid-[(2-O-α-D-rhamnopyranosyl-3-O-β-D-glucopyranosyl-β-D-glucopyranosyl)ester]) (2f; also referred to as rebaudioside N):

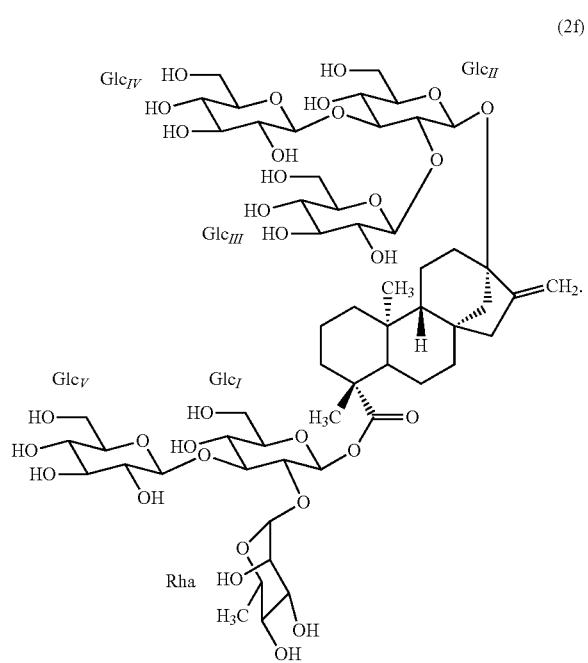

(2f)

In still another particular embodiment, the present invention is the compound of formula (13-[(2-O-β-D-glucopyranosyl-3-O-β-D-glucopyranosyl-β-D-glucopyranosyl)oxy] ent-kaur-16-en-19-oic acid-[(2-O-(3-O-β-D-glucopyranosyl-α-D-rhamnopyranosyl)-3-O-β-D-glucopyranosyl-β-D-glucopyranosyl)ester]) (2g; also referred to as rebaudioside O):

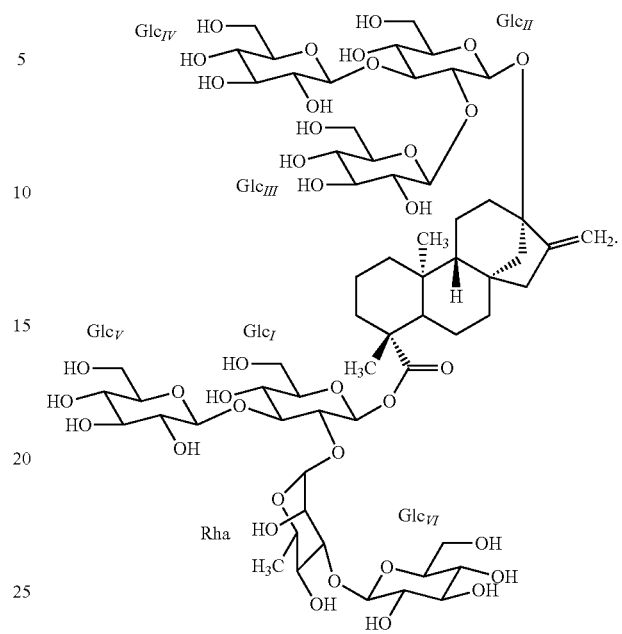

(2g)

In some embodiments, the compound of formula (1) or (2) is sweet.

In other embodiments, the compounds of formula (1) or (2) are flavor enhancers when added to a composition (e.g., a consumable) at a concentration lower than their threshold flavor recognition concentration, as described in Section II, herein.

In other embodiment, as described herein, the compounds of formula (1) or (2) are sweetness enhancers, when added to a composition (e.g., a consumable) at a concentration lower than their threshold sweetness recognition concentration, as described in Section II, herein.

II. Compositions

The present invention includes compositions comprising one or more steviol glycosides of the present invention. The composition may be, for example, a taste-enhancing composition, a sweetness-enhancing composition or a consumable, as described further herein.

In one embodiment, the composition comprises one or more steviol glycosides selected from the compounds of formula (1). In another embodiment, the composition comprises one or more steviol glycosides selected from the compounds of formula (2). In some embodiments, the composition comprises one or more steviol glycosides selected from the group consisting of (1a), (1b), (1c), (1d), (1e), (1f), (1g), (2), (2a), (2b), (2c), (2d), (2e), (2f), and (2g). In a particular embodiment, the composition comprises one or more steviol glycosides selected from the group consisting of (2a), (2b), (2c), (2d), (2e), (2f), (2g) and combinations thereof.

In one embodiment, the composition comprises a compound of the present invention provided as part of a mixture selected from the group consisting of a mixture of steviol glycosides, *stevia* extract, by-products of other steviol glycosides' isolation and purification processes, a commercially available *stevia* extract or any combination thereof. In another embodiment, the composition comprises a compound of the present invention provided as part of a mixture of a *stevia* extract which has been degraded in an acidic solution. Such mixtures may contain a compound of the present invention in an amount that ranges from about 1% to about 99% by weight on a dry basis, such as, for example, about 5% to about 99% by weight on a dry basis, from about 10% to about 99%, from about 20% to about 99%, from about 30% to about 99%, from about 40% to about 99%, from about 50% to about 99%, from about 60% to about 99%, from about 70% to about 99%, from about 80% to about 99% and from about 90% to about 99%. In still further embodiments, such mixtures contain a compound of the present invention in an amount greater than about 90% by weight on a dry basis, for example, greater than about 91%, greater than about 92%, greater than about 93%, greater than about 94%, greater than about 95%, greater than about 96%, greater than about 97%, greater than about 98% and greater than about 99%.

In one embodiment, the composition comprises a compound of the present invention, wherein the compound of the present invention is provided in the form of a *stevia* extract. The *stevia* extract contains one or more additional steviol glycosides—that are not compounds (2a)-(2g)—including, but not limited to, stevioside, rebaudioside A, rebaudioside C, dulcoside A, rubusoside, steviolbioside, rebaudioside B, rebaudioside D, rebaudioside F, and combinations thereof.

In still another embodiment, the present invention is a composition comprising a compound of the present invention, wherein the compound of formula (1) is provided as a pure compound, i.e. >99% content by weight on a dry basis.

The compound of the present invention can be present in the composition in an amount effective to provide a concentration from about 1 ppm to about 10,000 ppm when present in a consumable, such as, for example, from about 1 ppm to about 4,000 ppm, from about 1 ppm to about 3,000 ppm, from about 1 ppm to about 2,000 ppm, from about 1 ppm to about 1,000 ppm. In another embodiment, a compound of the present invention is present in the composition in an amount effective to provide a concentration from about 10 ppm to about 1,000 ppm when present in a consumable, such as, for example, from about 10 ppm to about 800 ppm, from about 50 ppm to about 800 ppm, from about 50 ppm to about 600 ppm or from about 200 ppm to about 250 ppm. In a particular embodiment, a compound of the present invention is present in the composition in an amount effective to provide a concentration from about 300 ppm to about 600 ppm.

In one embodiment, the present invention is a sweetener composition comprising a compound of the present invention. "Sweetener composition," as used herein, refers to a composition that is useful to sweeten a sweetenable composition that contains at least one sweet component in combination with at least one other substance.

In one embodiment, a compound of the present invention is the sole sweetener in the sweetener composition, i.e. a compound of the present invention is the only compound present in the sweetener composition that provides a detectable sweetness. In another embodiment, the sweetener composition includes a compound of the present invention is in combination with one or more sweetener compounds.

The amount of the compound of the present invention in the sweetener composition may vary. In one embodiment, a compound of the present invention is present in a sweetener composition in any amount to impart the desired sweetness when the sweetener composition is present in a consumable.

The sweetness of a non-sucrose sweetener can also be measured against a sucrose reference by determining the non-sucrose sweetener's sucrose equivalence. Typically, taste panelists are trained to detect sweetness of reference sucrose solutions containing between 1-15% sucrose (w/v). Other non-sucrose sweeteners are then tasted at a series of dilutions to determine the concentration of the non-sucrose sweetener that is as sweet as a given percent sucrose reference. For example, if a 1% solution of a sweetener is as sweet as a 10% sucrose solution, then the sweetener is said to be 10 times as potent as sucrose.

In one embodiment, a compound of the present invention is present in an amount effective to provide a sucrose equivalence of greater than about 10% (w/v) when present in a consumable, such as, for example, greater than about 11% (w/v), greater than about 12% (w/v), greater than about 13% (w/v) or greater than about 14% (w/v).

The amount of sucrose, and thus another measure of sweetness, in a reference solution may be described in degrees Brix (° Bx). One degree Brix is 1 gram of sucrose in 100 grams of solution and represents the strength of the solution as percentage by weight (% w/w) (strictly speaking, by mass). In one embodiment, a sweetener composition comprises a compound of formula (1) in an amount effective to provide sweetness equivalent from about 0.50 to 14 degrees Brix of sugar when present in a consumable, such as, for example, from about 5 to about 11 degrees Brix, from about 4 to about 7 degrees Brix, or about 5 degrees Brix. In yet another embodiment a steviol glycoside mixture comprising a compound of the present invention is present with at least one other sweetener in an amount effective to provide any one of the sweetness equivalents listed above.

In another embodiment, a compound of the present invention is present in the sweetener composition in an amount effective to provide a concentration from about 1 ppm to about 10,000 ppm when present in a consumable, such as, for example, from about 1 ppm to about 4,000 ppm, from about 1 ppm to about 3,000 ppm, from about 1 ppm to about 2,000 ppm or from about 1 ppm to about 1,000 ppm. In another embodiment, a compound of the present invention is present in the sweetener composition in an amount effective to provide a concentration from about 10 ppm to about 1,000 ppm when present in a consumable, such as, for example, from about 10 ppm to about 800 ppm, from about 50 ppm to about 800 ppm, from about 50 ppm to about 600 ppm or from about 200 ppm to about 250 ppm. In a particular embodiment, a compound of the present invention is present in the sweetener composition in an amount effective to provide a concentration from about 300 ppm to about 600 ppm.

In one aspect, the present invention is a flavor enhancing composition comprising a compound of formula (1).

As used herein, the term "flavor enhancer compositions" refers to a composition capable of enhancing or intensifying the perception of a particular flavor in a consumable. The terms "flavor enhancing compositions" or "flavor enhancer" are synonymous with the terms "flavor potentiator," "flavor amplifier," and "flavor intensifier." Generally, the flavor enhancing composition provided herein may enhance or potentiate the taste of flavor ingredients, i.e. any substance that provides sweetness, sourness, saltiness, savoriness, bitterness, metallic taste, astringency, sweet lingering aftertaste, sweetness onset, etc. Without being bound by any theory, the flavor enhancing composition likely does not contribute any noticeable taste to the consumable to which it is added because the compound of formula (1) is present in the consumable in a concentration at or below the flavor recognition threshold concentration of the compound of formula (1).

As used herein, the term "flavor recognition threshold concentration" refers to the lowest concentration at which the particular flavor or off-taste of a component (e.g., a compound) is perceptible in a consumable. The flavor recognition threshold concentration varies for different compounds, and may be varied with respect to the individual perceiving the flavor or the particular consumable. The flavor recognition threshold concentration can be specific for a particular compound.

In one embodiment, the flavor enhancing composition comprises a compound of formula (1), wherein the compound of formula (1) is present at a concentration effective to provide a concentration of the compound (1) that is at or below the threshold flavor recognition concentration of the compound of formula (1) when the flavor enhancing composition is added to a consumable.

In a particular embodiment, compound of formula (1) is present in the flavor-enhancing composition at a concentration effective to provide a concentration of the compound of formula (1) that is below the threshold flavor recognition concentration of the compound of formula (1) when the flavor-enhancing composition is added to a consumable.

In certain embodiment, the compound of formula (1) is present in the flavor-enhancing composition in a concentration effective to provide a concentration of the compound of formula (1) that is at least about 1%, at least about 5%, at least about 10%, at least about 15%, at least about 20%, at least about 25%, at least about 30%, at least about 35%, at least about 40%, at least about 45% or at least about 50% or more below the threshold flavor recognition concentration of the compound of formula (1) when the flavor-enhancing composition is added to a consumable.

In some embodiments, a compound of formula (1) is present in the composition in an amount that, when added to the consumable, will provide a concentration of the compound of formula (1) ranging from about 0.5 ppm to about 1000 ppm. For example, the compound of formula (1) is present in the composition in an amount that, when added to the consumable, will provide a concentration of the compound of formula (1) in an amount ranging from about 1 ppm to about 300 ppm, from about 0.1 ppm to about 75 ppm, or from about 500 ppm to about 3,000 ppm.

A person of skill in the art will be able to select the concentration of compound of formula (1) in the flavor enhancing composition so that it may impart an enhanced flavor to a consumable comprising at least one flavor ingredient. For example, a skilled artisan may select a concentration for compound of formula (1) in the flavor enhancing composition so that the flavor enhancing composition and/or the compound of formula (1) does not impart any perceptible flavor to a consumable when the flavor enhancing composition is added thereto.

In one embodiment, addition of the flavor enhancing composition increases the detected flavor of the at least one flavor ingredient in the consumable compared to the detected flavor of the same ingredient in the consumable in the absence of the flavor enhancer.

Suitable flavor ingredients include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Döhler™ Natural Flavoring Sweetness Enhancer K14323 (Döhler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

In another embodiment, the flavor enhancer composition comprising a compound of formula (1) enhances flavors (either individual flavors or the overall flavor) when added to the consumable. These flavors include, but are not limited to, fruit flavors, including tropical fruit flavors, and vanilla-caramel type flavors.

Alternatively, the compound of formula (1) may be added directly to the consumable, i.e., not provided in the form of a composition, to enhance flavor. In this embodiment, the compound of formula (1) is a sweetness enhancer and it is added to the consumable at a concentration at or below the threshold flavor recognition concentration of the compound of formula (1).

Sweetness Enhancing Compositions

In a particular embodiment, the present invention is a composition comprising the compound of the present invention.

As used herein, the term "sweetness enhancer" refers to a compound capable of enhancing or intensifying the perception of sweet taste in a consumable, such as a beverage. The term "sweetness enhancer" is synonymous with the terms "sweet taste potentiator," "sweetness potentiator," "sweetness amplifier," and "sweetness intensifier."

The term "sweetness recognition threshold," as generally used herein, is the lowest known concentration of a sweet compound that is perceivable by the human sense of taste. As such, a compound of the present invention enhances or potentiates the sweet taste of sweeteners without providing any noticeable sweet taste by itself when present at or below its sweetness recognition threshold concentration. However, a compound of the present invention may provide a detectable sweet taste at concentrations above its sweetness recognition threshold. For example, the sweetness recognition threshold of rebaudioside N (compound 2f) and rebaudioside O (compound 2g) is about 30 ppm.

The term "isosweet," as used herein, refers to compositions that have equivalent sweetness. Generally, the sweetness of a given composition is typically measured with reference to a solution of sucrose. See "A Systematic Study of Concentration-Response Relationships of Sweeteners," G. E. DuBois, D. E. Walters, S. S. Schiffman, Z. S. Warwick, B. J. Booth, S. D. Pecore, K. Gibes, B. T. Carr, and L. M. Brands, in Sweeteners: Discovery, Molecular Design and Chemoreception, D. E. Walters, F. T. Orthoefer, and G. E. DuBois, Eds., American Chemical Society, Washington, D.C. (1991), pp 261-276.

The term "sucrose equivalence," as used herein, refers to the sweetness of a composition containing at least one sweetener, where the sweetener is not a compound of formula (1), against a sucrose reference. Typically, taste panelists are trained to detect sweetness of reference sucrose solutions containing between 1-15% sucrose (w/v). Other non-sucrose sweeteners are then tasted at a series of dilutions to determine the concentration of the non-sucrose, i.e. compound of formula (1), sweetener that is as sweet (i.e. isosweet) to a given percent sucrose reference.

For example, if a 1% solution of a sweetener composition containing a carbohydrate sweetener and a compound of formula (1) is as sweet as a 10% sucrose solution, then the sweetener composition is said to be 10 times as potent as sucrose, and has 10% sucrose equivalence.

In one embodiment, the present invention is sweetness enhancer composition comprising a compound of formula (1).

In another embodiment, the present invention is a sweetness enhancing composition that comprises a compound of formula (2). More particularly, the present invention is a sweetness enhancing composition comprising a compound selected from the group consisting of compounds (2a), (2b), (2c), (2d), (2e), (2f), (2g) or combinations thereof.

In a particular embodiment, compound of formula (1) is present in the flavor-enhancing composition at a concentration effective to provide a concentration of the compound of formula (1) that is below the threshold sweetness recognition concentration of the compound of formula (1) when the sweetness enhancing composition is added to a consumable.

In certain embodiment, the compound of formula (1) is present in the sweetness enhancing composition in a concentration effective to provide a concentration of the compound of formula (1) that is at least about 1%, at least about 5%, at least about 10%, at least about 15%, at least about 20%, at least about 25%, at least about 30%, at least about 35%, at least about 40%, at least about 45% or at least about 50% or more below the threshold sweetness recognition concentration of the compound of formula (1) when the sweetness enhancing composition is added to a consumable.

In some embodiments, a compound of formula (1) is present in the composition in an amount that, when added to the consumable, will provide a concentration of the compound of formula (1) ranging from about 0.5 ppm to about 1000 ppm. For example, the compound of formula (1) is present in the composition in an amount that, when added to the consumable, will provide a concentration of the compound of formula (1) in an amount ranging from about 1 ppm to about 300 ppm, from about 0.1 ppm to about 75 ppm, or from about 500 ppm to about 3,000 ppm.

In some embodiments, the compound of formula (1) is present in an amount ranging from about 0.5 ppm to about 1000 ppm. For example, the compound of formula (1) may be present in an amount ranging from about 1 ppm to about 300 ppm, from about 0.1 ppm to about 75 ppm, or from about 500 ppm to about 3,000 ppm.

In one embodiment, the present invention provides a consumable comprising at least one sweetener and a compound of formula (1), wherein the at least one sweetener is present in a concentration above its sweetness recognition threshold, wherein the compound of formula (1) is present in a concentration at or below its sweetness recognition threshold, and wherein the compound of formula (1) enhances the sweetness of the consumable by an amount more than the detectable sweetness of a solution containing the same concentration of the compound of formula (1) in the absence of the at least one sweetener and/or the compound of formula (1) enhances the sweetness of the consumable by about 2.0% (w/v) sucrose equivalence or greater, such as, for example, about 2.5% (w/v) or greater. In another embodiment, the compound of formula (1) enhances the sweetness of the consumable by at least about 3.0% sucrose equivalence. In another embodiment, the compound of formula (1) enhances the sweetness of the consumable from about 2.0% (w/v) to about 3.0% (w/v) sucrose equivalence.

In a more particular embodiment, the present invention provides a consumable comprising at least one sweetener and a compound of formula (2), wherein the at least one sweetener is present in a concentration above its sweetness recognition threshold, wherein the compound of formula (2) is present in a concentration at or below its sweetness recognition threshold, and wherein the compound of formula (2) enhances the sweetness of the consumable by an amount more than the detectable sweetness of a solution containing the same concentration of the compound of formula (2) in the absence of the at least one sweetener and/or the compound of formula (2) enhances the sweetness of the consumable by about 2.0% (w/v) sucrose equivalence or greater, such as, for example, about 2.5% (w/v) or greater. In another embodiment, the compound of formula (2) enhances the sweetness of the consumable by at least about 3.0% sucrose equivalence. In another embodiment, the compound of formula (2) enhances the sweetness of the consumable from about 2.0% (w/v) to about 3.0% (w/v) sucrose equivalence.

It is contemplated that the composition can include one or more sweetness enhancers. In one embodiment, the composition can include one sweetness enhancer. In other embodiments, the composition can include two or more sweetness enhancers. In embodiments where two or more sweetness enhancers are utilized, each sweetness enhancer should be present below its respective sweetness recognition threshold concentration.

In some embodiments, the sweetness enhancer of the present invention is combined with one or more other sweetness enhancers selected from, but not limited to, the group consisting of 2-hydroxybenzoic acid, 3-hydroxybenzoic acid, 4-hydroxybenzoic acid, 2,4-dihydroxybenzoic acid, 3,4-dihydroxybenzoic acid, 2,5-dihydroxybenzoic acid, 2,6-dihydroxybenzoic acid, 2,3,4-trihydroxybenzoic acid, 2,4,6-trihydroxybenzoic acid, 3-aminobenzoic acid, 4-aminobenzoic acid, FEMA GRAS enhancer 4469, FEMA GRAS enhancer 4701, FEMA GRAS enhancer 4720, FEMA GRAS enhancer 4774, FEMA GRAS enhancer 4708, FEMA GRAS enhancer 4728, FEMA GRAS enhancer 4601 and combinations thereof.

Sweeteners can be selected from, but not limited to, the group consisting of sucrose, glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, fucose, rhamnose, arabinose, turanose, sialose, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside N, rebaudioside O, dulcoside A, dulcoside B, rubusoside, *stevia*, stevioside, mogroside IV, mogroside V, Luo han guo, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside and cyclocarioside I, sugar alcohols such as erythritol, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof.

Notably, the sweetener is not the same as the sweetness enhancer of the present invention.

In one embodiment, the sweetener is a caloric sweetener or mixture of caloric sweeteners. Accordingly, incorporation of the sweetness enhancer thereby reduces the quantity of the calorie-providing sweetener that must be used in a given consumable, thereby allowing the preparation of reduced-calorie consumables.

The caloric sweetener may be selected from, for example, sucrose, fructose, glucose, high fructose corn/starch syrup, a beet sugar, a cane sugar, and combinations thereof.

In one embodiment, the sweetener is a rare sugar.

In another embodiment, the sweetener is selected from the group consisting of sucrose, fructose, glucose, high fructose corn syrup, high fructose starch syrup, D-psicose, D-allose, D-turanose, D-tagatose, D-trehalose, D-leucrose, rare sugar syrup and/or a combination thereof.

In yet another embodiment, the sweetener is a non-caloric sweetener or mixture of non-caloric sweeteners. In one example, the non-caloric sweetener is a natural high-potency sweetener. As used herein, the phrase "natural high potency sweetener" refers to any composition which is not found naturally in nature and characteristically has a sweetness potency greater than sucrose, fructose, or glucose, yet has less calories. The natural high potency sweetener can be provided as a pure compound or, alternatively, as part of an extract.

In one embodiment, addition of the sweetness enhancer increases the detected sucrose equivalence of the at least one sweetener in a consumable compared to the sucrose equivalence of the same consumable in the absence of the sweetness enhancer.

The sweetness recognition threshold concentration can be specific for a particular compound. In some embodiments, the at least one sweetness enhancer is present in an amount ranging from about 0.5 ppm to about 1000 ppm. For example, the at least one sweetness enhancer may be present in an amount ranging from about 1 ppm to about 300 ppm, from about 0.1 ppm to about 75 ppm, or from about 500 ppm to about 3,000 ppm.

In one embodiment, the present invention provides a consumable comprising at least one sweetener and compound (2f). The at least one sweetener, which is not compound (2f), is present in a concentration above the sweetness recognition threshold. In contrast, compound (2f) is present in the consumable in a concentration at or below its sweetness recognition threshold. The sweetness recognition threshold of compound (2f) is about 30 ppm, which is sufficient to provide about a sucrose equivalence of about 1.0-1.5% (w/v).

Compound (2f), when present in the consumable in a concentration at or below the sweetness recognition threshold, enhances the sweetness of the consumable by an amount more than the detectable sweetness of a solution containing the same concentration of compound (2f) (in the absence of any additional sweeteners). In other words, the increase in isosweetness of a consumable containing compound (2f) in an amount at or below its sweetness recognition threshold concentration compared to the same consumable in the absence of compound (2f) is greater than the isosweetness of a solution of compound (2f) (in the absence of any additional sweeteners).

As an example, a solution containing 30 ppm of compound (2f) was found to be isosweet to a 1.0-1.5% (w/v) sucrose solution. A beverage containing 8% (w/v) sucrose and 30 ppm compound (2f) was isosweet to a 10.5-11.0% (w/v) sucrose solution. Accordingly, the increase in isosweetness provided by the 30 ppm compound (2f) (2.5-3.0% (w/v)) is greater than the sweetness of 30 ppm compound (2f) alone (1.0-1.5% (w/v)). Therefore, it can be said that the effect of compound (2f) is not merely additive to the sucrose in the beverage (if that were the case, one would expect an isosweetness of 9-9.5% (w/v)), but rather is acting to enhance the detected sweetness of the sucrose in beverage.

In another particular embodiment, compound (2f) enhances the sweetness of the consumable by about 2.0% (w/v) sucrose equivalence or greater. Compound (2f) enhances the sweetness of the consumable from about 2.0% to about 3.0% (w/v) sucrose equivalence, such as, for example, about 2.0%, about 2.1%, about 2.2%, about 2.3%, about 2.4%, about 2.5%, about 2.6%, about 2.7%, about 2.8%, about 2.9% or about 3.0% sucrose equivalence.

Compound (2f) can be provided as a purified material (e.g. >99% pure) or as part of a *Stevia* extract or mixture of steviol glycosides. In one embodiment, compound (2f) is from about 80% to about 99% pure, that is, compound (2f) comprises about 80% to about 99% by weight in a *Stevia* extract or steviol glycoside mixture. In a particular embodiment, compound (2f) is about 95% pure.

Moreover, the form of compound (2f) can be polymorphic, amorphous, any type of disordered crystalline material or a combination thereof.

In one embodiment, the present invention provides a consumable comprising at least one sweetener and compound (2g). The at least one sweetener, which is not compound (2g), is present in a concentration above the sweetness recognition threshold. In contrast, compound (2g) is present in the consumable in a concentration at or below its sweetness recognition threshold. The sweetness recognition threshold of compound (2g) is about 30 ppm, which is sufficient to provide about a sucrose equivalence of about 1.0-1.5% (w/v).

Compound (2g), when present in the consumable in a concentration at or below the sweetness recognition threshold, enhances the sweetness of the consumable by an amount more than the detectable sweetness of a solution containing the same concentration of compound (2g) (in the absence of any additional sweeteners). In other words, the increase in isosweetness of a consumable containing compound (2g) in an amount at or below its sweetness recognition threshold concentration compared to the same consumable in the absence of compound (2g) is greater than the isosweetness of a solution of compound (2g) (in the absence of any additional sweeteners).

As an example, a solution containing 30 ppm of compound (2g) was found to be isosweet to a 1.0-1.5% (w/v) sucrose solution. A beverage containing 8% (w/v) sucrose and 30 ppm compound (2g) was isosweet to a 10.0% (w/v) sucrose solution. Accordingly, the increase in isosweetness provided by the 30 ppm compound (2g) (2.0% (w/v)) is greater than the sweetness of 30 ppm compound (2g) alone (1.0-1.5% (w/v)). Therefore, it can be said that the effect of compound (2g) is not merely additive to the sucrose in the beverage (if that were the case, one would expect an isosweetness of 9-9.5% (w/v)), but rather is acting to enhance the detected sweetness of the sucrose in beverage.

In another particular embodiment, compound (2g) enhances the sweetness of the consumable by about 2.0% (w/v) sucrose equivalence or greater. Compound (2g) enhances the sweetness of the consumable from about 2.0% to about 3.0% (w/v) sucrose equivalence, such as, for example, about 2.0%, about 2.1%, about 2.2%, about 2.3%, about 2.4%, about 2.5%, about 2.6%, about 2.7%, about 2.8%, about 2.9% or about 3.0% sucrose equivalence.

Compound (2g) can be provided as a purified material (e.g. >99% pure) or as part of a *Stevia* extract or mixture of steviol glycosides. In one embodiment, compound (2g) is from about 80% to about 99% pure, that is, compound (2g) comprises about 80% to about 99% by weight in a *Stevia* extract or steviol glycoside mixture. In a particular embodiment, compound (2g) is about 95% pure.

Moreover, the form of compound (2g) can be polymorphic, amorphous, any disordered crystalline material or a combination thereof.

In one embodiment, a consumable comprises a compound of formula (1) having greater than about 95% purity and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup and/or a combination thereof, wherein the at least one sweetener is present in a concentration above the sweetness recognition threshold concentration, wherein the compound of formula (1) is present in a concentration at or below the sweetness recognition threshold, and wherein the compound of formula (1) enhances the sweetness of said consumable by an amount more than the detectable sweetness of a solution containing the same concentration of the compound of formula (1) (in the absence of any additional sweeteners). In a particular embodiment, the consumable is a beverage.

In another embodiment, a consumable comprises a compound of formula (2) having greater than about 95% purity and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup and/or a combination thereof, wherein the at least one sweetener is present in a concentration above the sweetness recognition threshold concentration, wherein the compound of formula (2) is present in a concentration at or below the sweetness recognition threshold, and wherein the compound of formula (2) enhances the sweetness of said consumable by an amount more than the detectable sweetness of a solution containing the same concentration of the compound of formula (2) (in the absence of any additional sweeteners). In a particular embodiment, the consumable is a beverage.

In yet another embodiment, a consumable comprises compound (2f) or (2g) having greater than about 95% purity and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup and/or a combination thereof, wherein the at least one sweetener is present in a concentration above the sweetness recognition threshold concentration, wherein compound (2f) or (2g) is present in a concentration at or below the sweetness recognition threshold, and wherein compound (2f) or (2g) enhances the sweetness of said consumable by an amount more than the detectable sweetness of a solution containing the same concentration of compound (2f) or (2g) (in the absence of any additional sweeteners). In a particular embodiment, the consumable is a beverage.

In a particular embodiment, a consumable comprises compound (2f) or (2g) having a purity greater than about 95% and sucrose, wherein sucrose is present in a concentration above the sweetness recognition threshold, wherein the compound (2f) or (2g) is present in a concentration at or below the sweetness recognition threshold, and wherein compound (2f) or (2g) enhances the sweetness of said consumable by an amount more than the detectable sweetness of a solution containing the same concentration of compound (2f) or (2g) (in the absence of any other sweetener). In a particular embodiment, the consumable is a beverage.

In another particular embodiment, a consumable comprises compound (2f) or (2g) having a purity greater than about 95% and fructose, wherein fructose is present in a concentration above the sweetness recognition threshold, wherein compound (2f) or (2g) is present in a concentration at or below the sweetness recognition threshold, and wherein compound (2f) or (2g) enhances the sweetness of said consumable by an amount more than the detectable sweetness of a solution containing the same concentration of compound (2f) or (2g) (in the absence of any other sweetener). In a particular embodiment, the consumable is a beverage.

In another particular embodiment, a consumable comprises compound (2f) or (2g) having a purity greater than about 95% and glucose, wherein glucose is present in a concentration above the sweetness recognition threshold, wherein compound (2f) or (2g) is present in a concentration at or below the sweetness recognition threshold, and wherein the compound (2f) or (2g) enhances the sweetness of said consumable by an amount more than the detectable sweetness of a solution containing the same concentration of compound (2f) or (2g) (in the absence of any other sweetener). In a particular embodiment, the consumable is a beverage.

In another particular embodiment, a consumable comprises compound (2f) or (2g) having a purity greater than about 95% and high fructose corn syrup, wherein high fructose corn syrup is present in a concentration above the sweetness recognition threshold, wherein compound (2f) or (2g) is present in a concentration at or below the sweetness recognition threshold, and wherein compound (2f) or (2g) enhances the sweetness of said consumable by an amount more than the detectable sweetness of a solution containing the same concentration of compound (2f) or (2g) (in the absence of any other sweetener). In a particular embodiment, the consumable is a beverage.

In another particular embodiment, a consumable comprises compound (2f) or (2g) having a purity greater than about 95% and D-psicose, wherein D-psicose is present in a concentration above the sweetness recognition threshold, wherein compound (2f) or (2g) is present in a concentration at or below the sweetness recognition threshold, and wherein compound (2f) or (2g) enhances the sweetness of said consumable by an amount more than the detectable sweetness of a solution containing the same concentration of compound (2f) or (2g) (in the absence of any other sweetener). In a particular embodiment, the consumable is a beverage.

In another particular embodiment, a consumable comprises compound (2f) or (2g) having a purity greater than about 95% and D-allose, wherein D-allose is present in a concentration above the sweetness recognition threshold, wherein compound (2f) or (2g) is present in a concentration at or below the sweetness recognition threshold, and wherein the compound (2f) or (2g) enhances the sweetness of said consumable by an amount more than the detectable sweetness of a solution containing the same concentration of compound (2f) or (2g) (in the absence of any other sweetener). In a particular embodiment, the consumable is a beverage.

In another particular embodiment, a consumable comprises compound (2f) or (2g) having a purity greater than about 95% and D-turanose, wherein D-turanose is present in a concentration above the sweetness recognition threshold, wherein compound (2f) or (2g) is present in a concentration at or below the sweetness recognition threshold, and wherein the compound (2f) or (2g) enhances the sweetness of said consumable by an amount more than the detectable sweetness of a solution containing the same concentration of compound (2f) or (2g) (in the absence of any other sweetener). In a particular embodiment, the consumable is a beverage.

In another particular embodiment, a consumable comprises compound (2f) or (2g) having a purity greater than about 95% and D-tagatose, wherein D-tagatose is present in a concentration above the sweetness recognition threshold, wherein compound (2f) or (2g) is present in a concentration at or below the sweetness recognition threshold, and wherein compound (2f) or (2g) enhances the sweetness of said consumable by an amount more than the detectable sweetness of a solution containing the same concentration of compound (2f) or (2g) (in the absence of any other sweetener). In a particular embodiment, the consumable is a beverage.

In another particular embodiment, a consumable comprises compound (2f) or (2g) having a purity greater than about 95% and D-trehalose, wherein D-trehalose is present in a concentration above the sweetness recognition threshold, wherein compound (2f) or (2g) is present in a concentration at or below the sweetness recognition threshold, and wherein the compound (2f) or (2g) enhances the sweetness of said consumable by an amount more than the detectable sweetness of a solution containing the same concentration of compound (2f) or (2g) (in the absence of any other sweetener). In a particular embodiment, the consumable is a beverage.

In another particular embodiment, a consumable comprises compound (2f) or (2g) having a purity greater than about 95% and D-leucrose, wherein D-leucrose is present in a concentration above the sweetness recognition threshold, wherein compound (2f) or (2g) is present in a concentration at or below the sweetness recognition threshold, and wherein compound (2f) or (2g) enhances the sweetness of said consumable by an amount more than the detectable sweetness of a solution containing the same concentration of compound (2f) or (2g) (in the absence of any other sweetener). In a particular embodiment, the consumable is a beverage.

In another particular embodiment, a consumable comprises compound (2f) or (2g) having a purity greater than about 95% and rare sugar syrup, wherein rare sugar syrup is present in a concentration above the sweetness recognition threshold, wherein compound (2f) or (2g) is present in a concentration at or below the sweetness recognition threshold, and wherein the compound (2f) or (2g) enhances the sweetness of said consumable by an amount more than the detectable sweetness of a solution containing the same concentration of compound (2f) or (2g) (in the absence of any other sweetener). In a particular embodiment, the consumable is a beverage.

In one embodiment, a consumable comprises a compound of formula (1) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof, wherein the at least one sweetener is present in a concentration above the sweetness recognition threshold concentration, wherein the compound of formula (1) is present in a concentration at or below the sweetness recognition threshold, and wherein the compound of formula (1) enhances the sweetness of the consumable by at least about 2.0% (w/v) sucrose equivalence. In a particular embodiment, the consumable is a beverage.

In another embodiment, a consumable comprises a compound of formula (2) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof, wherein the at least one sweetener is present in a concentration above the sweetness recognition threshold concentration, wherein the compound of formula (2) is present in a concentration at or below the sweetness recognition threshold, and wherein the compound of formula (2) enhances the sweetness of the consumable by at least about 2.0% (w/v) sucrose equivalence. In a particular embodiment, the consumable is a beverage.

In one embodiment, a consumable comprises compound (2f) or (2g) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof, wherein the at least one sweetener is present in a concentration above the sweetness recognition threshold concentration, wherein compound (2f) or (2g) is present in a concentration at or below the sweetness recognition threshold, and wherein compound (2f) or (2g) enhances the sweetness of the consumable by at least about 2.0% (w/v) sucrose equivalence. In a particular embodiment, the consumable is a beverage.

In a more particular embodiment, a consumable comprises compound (2f) or (2g) having a purity greater than about 95% and sucrose, wherein sucrose is present in a concentration above the sweetness recognition threshold concentration, wherein compound (2f) or (2g) is present in a concentration at or below the sweetness recognition threshold, and wherein compound (2f) or (2g) enhances the sweetness of the consumable by at least about 2.0% (w/v) sucrose equivalence. In a more particular embodiment, compound (2f) or (2g) the sweetness of the consumable from about 2.0% (w/v) to about 3.0% (w/v) sucrose equivalence. In a particular embodiment, the consumable is a beverage.

In another particular embodiment, a consumable comprises compound (2f) or (2g) having a purity greater than about 95% and fructose, wherein fructose is present in a concentration above the sweetness recognition threshold concentration, wherein compound (2f) or (2g) is present in a concentration at or below the sweetness recognition threshold, and wherein compound (2f) or (2g) enhances the sweetness of the consumable by at least about 2.0% (w/v) sucrose equivalence. In a more particular embodiment, compound (2f) or (2g) enhances the sweetness of the consumable from about 2.0% to about 3.0% (w/v) sucrose equivalence. In a particular embodiment, the consumable is a beverage.

In another particular embodiment, a consumable comprises compound (2f) or (2g) having a purity greater than about 95% and glucose, wherein glucose is present in a concentration above the sweetness recognition threshold concentration, wherein compound (2f) or (2g) is present in a concentration at or below the sweetness recognition threshold, and wherein compound (2f) or (2g) enhances the sweetness of the consumable by at least about 2.0% (w/v) sucrose equivalence. In a more particular embodiment, compound (2f) or (2g) enhances the sweetness of the consumable from about 2.0% to about 3.0% (w/v) sucrose equivalence. In a particular embodiment, the consumable is a beverage.

In another particular embodiment, a consumable comprises compound (2f) or (2g) having a purity greater than about 95% and high fructose corn syrup, wherein high fructose corn syrup is present in a concentration above the sweetness recognition threshold concentration, wherein compound (2f) or (2g) is present in a concentration at or below the sweetness recognition threshold, and wherein compound (2f) or (2g) enhances the sweetness of the consumable by at least about 2.0% (w/v) sucrose equivalence. In a more particular embodiment, compound (2f) or (2g) enhances the sweetness of the consumable from about 2.0% to about 3.0% (w/v) sucrose equivalence. In a particular embodiment, the consumable is a beverage.

In another particular embodiment, a consumable comprises compound (2f) or (2g) having a purity greater than about 95% and D-psicose, wherein D-psicose is present in a concentration above the sweetness recognition threshold concentration, wherein compound (2f) or (2g) is present in a concentration at or below the sweetness recognition threshold, and wherein compound (2f) or (2g) enhances the sweetness of the consumable by at least about 2.0% (w/v) sucrose equivalence. In a more particular embodiment, compound (2f) or (2g) enhances the sweetness of the consumable from about 2.0% to about 3.0% (w/v) sucrose equivalence. In a particular embodiment, the consumable is a beverage.

In another particular embodiment, a consumable comprises compound (2f) or (2g) having a purity greater than about 95% and D-allose, wherein D-allose is present in a concentration above the sweetness recognition threshold concentration, wherein compound (2f) or (2g) is present in a concentration at or below the sweetness recognition threshold, and wherein compound (2f) or (2g) enhances the sweetness of the consumable by at least about 2.0% (w/v) sucrose equivalence. In a more particular embodiment, compound (2f) or (2g) enhances the sweetness of the consumable from about 2.0% to about 3.0% (w/v) sucrose equivalence. In a particular embodiment, the consumable is a beverage.

In another particular embodiment, a consumable comprises compound (2f) or (2g) having a purity greater than about 95% and D-turanose, wherein D-turanose is present in a concentration above the sweetness recognition threshold concentration, wherein compound (2f) or (2g) is present in a concentration at or below the sweetness recognition threshold, and wherein compound (2f) or (2g) enhances the sweetness of the consumable by at least about 2.0% (w/v) sucrose equivalence. In a more particular embodiment, compound (2f) or (2g) enhances the sweetness of the consumable from about 2.0% to about 3.0% (w/v) sucrose equivalence. In a particular embodiment, the consumable is a beverage.

In another particular embodiment, a consumable comprises compound (2f) or (2g) having a purity greater than about 95% and D-tagatose, wherein D-tagatose is present in a concentration above the sweetness recognition threshold concentration, wherein compound (2f) or (2g) is present in a concentration at or below the sweetness recognition threshold, and wherein compound (2f) or (2g) enhances the sweetness of the consumable by at least about 2.0% (w/v) sucrose equivalence. In a more particular embodiment, compound (2f) or (2g) the sweetness of the consumable from about 2.0% to about 3.0% (w/v) sucrose equivalence. In a particular embodiment, the consumable is a beverage.

In another particular embodiment, a consumable comprises compound (2f) or (2g) having a purity greater than about 95% and D-trehalose, wherein D-trehalose is present in a concentration above the sweetness recognition threshold concentration, wherein compound (2f) or (2g) is present in a concentration at or below the sweetness recognition threshold, and wherein compound (2f) or (2g) enhances the sweetness of the consumable by at least about 2.0% (w/v) sucrose equivalence. In a more particular embodiment, compound (2f) or (2g) enhances the sweetness of the consumable from about 2.0% to about 3.0% (w/v) sucrose equivalence. In a particular embodiment, the consumable is a beverage.

In another particular embodiment, a consumable comprises compound (2f) or (2g) having a purity greater than about 95% and D-leucrose, wherein D-leucrose is present in a concentration above the sweetness recognition threshold concentration, wherein compound (2f) or (2g) is present in a concentration at or below the sweetness recognition threshold, and wherein compound (2f) or (2g) enhances the sweetness of the consumable by at least about 2.0% (w/v) sucrose equivalence. In a more particular embodiment, compound (2f) or (2g) enhances the sweetness of the consumable from about 2.0% to about 3.0% (w/v) sucrose equivalence. In a particular embodiment, the consumable is a beverage.

In another particular embodiment, a consumable comprises compound (2f) or (2g) having a purity greater than about 95% and rare sugar syrup, wherein rare sugar syrup is present in a concentration above the sweetness recognition threshold concentration, wherein compound (2f) or (2g) is present in a concentration at or below the sweetness recognition threshold, and wherein compound (2f) or (2g) enhances the sweetness of the consumable by at least about 2.0% (w/v) sucrose equivalence. In a more particular embodiment, compound (2f) or (2g) enhances the sweetness of the consumable from about 2.0% to about 3.0% (w/v) sucrose equivalence. In a particular embodiment, the consumable is a beverage.

The consumable can be any edible or oral composition suitable for use in the mouth or ingestion. Exemplary consumables include, for example, pharmaceutical compositions, edible gel mixes and compositions, dental compositions, foodstuffs (confections, condiments, chewing gum, cereal compositions, baked goods, dairy products, and table-top sweetener compositions), beverages and beverage products.

Additives

The compositions disclosed herein, e.g., consumables, can further contain one or more functional ingredients, detailed below. Functional ingredients include, but are not limited to, vitamins, minerals, antioxidants, preservatives, glucosamine, polyphenols and combinations thereof. Any suitable functional ingredient described herein can be used.

The consumable can further contain one or more additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, weighing agents, juice, dairy, cereal and other plant extracts, flavonoids, alcohols, polymers and combinations thereof. Any suitable additive described herein can be used.

a. Beverages

In a particular embodiment, the present invention is a beverage comprising a compound of the present invention.

As used herein, a "beverage" is a ready-to-drink beverage. Suitable ready-to-drink beverages include carbonated and non-carbonated beverages. Carbonated beverages include, but are not limited to, soft drinks, cola, lemon-lime flavored sparkling beverage, orange flavored sparkling beverage, grape flavored sparkling beverage, strawberry flavored sparkling beverage, pineapple flavored sparkling beverage, ginger-ale, soft drinks, root beer and malt beverages.

Non-carbonated beverages include, but are not limited to fruit juice, fruit-flavored juice, juice drinks, nectars, vegetable juice, vegetable-flavored juice, sports drinks, energy drinks, protein drinks, enhanced water with vitamins, near water drinks (e.g., water with natural or synthetic flavorants), coconut water, tea type (e.g. black tea, green tea, red tea, oolong tea), coffee, cocoa drink, beverage containing milk components (e.g. milk beverages, coffee containing milk components, café au lait, milk tea, fruit milk beverages), beverages containing cereal extracts, smoothies and combinations thereof.

Beverages contain a liquid matrix, i.e. the basic ingredient in which the ingredients—including the sweetener and compounds of the present invention—are dissolved. In one embodiment, the liquid matrix is water of beverage quality, such as, for example deionized water, distilled water, reverse osmosis water, carbon-treated water, purified water, demineralized water and combinations thereof, can be used. Additional suitable liquid matrices include, but are not limited to phosphoric acid, phosphate buffer, citric acid, citrate buffer and carbon-treated water.

In one embodiment, the beverage contains inclusions, i.e. pulp, seed, chunks, etc.

Carbohydrate sweeteners can be present in the beverage in a concentration from about 100 ppm to about 140,000 ppm. Rare sugars can be present in the beverage in a concentration from about 50 ppm to about 100,000 ppm. Synthetic sweeteners may be present in the beverage in a concentration from about 0.3 ppm to about 3,500 ppm. Natural high potency sweeteners may be preset in the beverage in a concentration from about 0.1 ppm to about 3,000 ppm.

The beverage can further include additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, weighing agents, juice, dairy, cereal and other plant extracts, flavonoids, alcohols, polymers and combinations thereof. Any suitable additive described herein can be used.

In one embodiment, the polyol can be present in the beverage in a concentration from about 100 ppm to about 250,000 ppm, such as, for example, from about 5,000 ppm to about 40,000 ppm.

In another embodiment, the amino acid can be present in the beverage in a concentration from about 10 ppm to about 50,000 ppm, such as, for example, from about 1,000 ppm to about 10,000 ppm, from about 2,500 ppm to about 5,000 ppm or from about 250 ppm to about 7,500 ppm.

In still another embodiment, the nucleotide can be present in the beverage in a concentration from about 5 ppm to about 1,000 ppm.

In yet another embodiment, the organic acid additive can be present in the beverage in a concentration from about 10 ppm to about 5,000 ppm.

In yet another embodiment, the inorganic acid additive can be present in the beverage in a concentration from about 25 ppm to about 25,000 ppm.

In still another embodiment, the bitter compound can be present in the beverage in a concentration from about 25 ppm to about 25,000 ppm.

In yet another embodiment, the flavorant can be present in the beverage a concentration from about 0.1 ppm to about 5,000 ppm.

In a still further embodiment, the polymer can be present in the beverage in a concentration from about 30 ppm to about 2,000 ppm.

In another embodiment, the protein hydrosylate can be present in the beverage in a concentration from about 200 ppm to about 50,000.

In yet another embodiment, the surfactant additive can be present in the beverage in a concentration from about 30 ppm to about 2,000 ppm.

In still another embodiment, the flavonoid additive can be present in the beverage a concentration from about 0.1 ppm to about 1,000 ppm.

In yet another embodiment, the alcohol additive can be present in the beverage in a concentration from about 625 ppm to about 10,000 ppm.

In a still further embodiment, the astringent additive can be present in the beverage in a concentration from about 10 ppm to about 5,000 ppm.

The beverage can further contain one or more functional ingredients, detailed below. Functional ingredients include, but are not limited to, vitamins, minerals, antioxidants, preservatives, glucosamine, polyphenols and combinations thereof. Any suitable functional ingredient described herein can be used.

It is contemplated that the pH of the beverage does not materially or adversely affect the sweetness enhancement. A non-limiting example of the pH range of the beverage may be from about 1.8 to about 10. A further example includes a pH range from about 2 to about 5. In a particular embodiment, the pH of beverage can be from about 2.5 to about 4.2. One of skill in the art will understand that the pH of the beverage can vary based on the type of beverage. Dairy beverages, for example, can have pHs greater than 4.2.

The titratable acidity of the beverage may, for example, range from about 0.01 to about 1.0% by weight of beverage.

In one embodiment, the sparkling beverage product has an acidity from about 0.01 to about 1.0% by weight of the beverage, such as, for example, from about 0.05% to about 0.25% by weight of beverage.

The carbonation of a sparkling beverage product has 0 to about 2% (w/w) of carbon dioxide or its equivalent, for example, from about 0.1 to about 1.0% (w/w).

The temperature of the beverage may, for example, range from about 4° C. to about 100° C., such as, for example, from about 4° C. to about 25° C.

The beverage can be a full-calorie beverage that has up to about 120 calories per 8 oz serving.

The beverage can be a mid-calorie beverage that has up to about 60 calories per 8 oz serving.

The beverage can be a low-calorie beverage that has up to about 40 calories per 8 oz serving.

The beverage can be a zero-calorie that has less than about 5 calories per 8 oz. serving.

In one embodiment, a beverage comprises a carbohydrate sweetener and about 30 ppm of a compound of formula (1), wherein the liquid matrix of the beverage is selected from the group consisting of water, phosphoric acid, phosphate buffer, citric acid, citrate buffer, carbon-treated water and combinations thereof. The pH of the beverage can be from about 2.5 to about 4.2. The beverage can further include additives, such as, for example, erythritol. The beverage can further include functional ingredients, such as, for example, vitamins.

In another embodiment, a beverage comprises a carbohydrate sweetener and about 30 ppm of a compound of formula (2), wherein the liquid matrix of the beverage is selected from the group consisting of water, phosphoric acid, phosphate buffer, citric acid, citrate buffer, carbon-treated water and combinations thereof. The pH of the beverage can be from about 2.5 to about 4.2. The beverage can further include additives, such as, for example, erythritol. The beverage can further include functional ingredients, such as, for example, vitamins.

In still another embodiment, a beverage comprises a carbohydrate sweetener and about 30 ppm of compound (2f), wherein the liquid matrix of the beverage is selected from the group consisting of water, phosphoric acid, phosphate buffer, citric acid, citrate buffer, carbon-treated water and combinations thereof. The pH of the beverage can be from about 2.5 to about 4.2. The beverage can further include additives, such as, for example, erythritol. The beverage can further include functional ingredients, such as, for example vitamins.

In still another embodiment, a beverage comprises a carbohydrate sweetener and about 30 ppm of compound (2g), wherein the liquid matrix of the beverage is selected from the group consisting of water, phosphoric acid, phosphate buffer, citric acid, citrate buffer, carbon-treated water and combinations thereof. The pH of the beverage can be from about 2.5 to about 4.2. The beverage can further include additives, such as, for example, erythritol. The beverage can further include functional ingredients, such as, for example vitamins.

In a more particular embodiment, a beverage comprises at least one sweetener and a compound of formula (1) having a purity greater than about 95%, wherein the at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof is present in a concentration above its sweetness recognition threshold, the compound of formula (1) is present in a concentration at or below its sweetness recognition threshold, and wherein the compound of formula (1) enhances the sweetness of the beverage by an amount more than the detectable sweetness of a solution containing the same concentration of the compound of formula (1) in the absence of the at least one sweetener.

In another more particular embodiment, a beverage comprises at least one sweetener and a compound of formula (2) having a purity greater than about 95%, wherein the at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof is present in a concentration above its sweetness recognition threshold, the compound of formula (2) is present in a concentration at or below its sweetness recognition threshold, and wherein the compound of formula (2) enhances the sweetness of the beverage by an amount more than the detectable sweetness of a solution containing the same concentration of the compound of formula (2) in the absence of the at least one sweetener.

In a more particular embodiment, a beverage comprises at least one sweetener and compound (2f) having a purity greater than about 95%, wherein the at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof is present in a concentration above its sweetness recognition threshold, compound (2f) is present in a concentration at or below its sweetness recognition threshold, and wherein compound (2f) enhances the sweetness of the beverage by an amount more than the detectable sweetness of a solution containing the same concentration of compound (2f) in the absence of the at least one sweetener.

In a more particular embodiment, a beverage comprises at least one sweetener and compound (2g) having a purity greater than about 95%, wherein the at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof is present in a concentration above its sweetness recognition threshold, the compound of formula (2g) is present in a concentration at or below its sweetness recognition threshold, and wherein compound (2g) enhances the sweetness of the beverage by an amount more than the detectable sweetness of a solution containing the same concentration of compound (2g) in the absence of the at least one sweetener.

In another embodiment, a beverage comprises a compound of formula (1) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof, wherein the at least one sweetener is present in a concentration above the sweetness recognition threshold concentration, wherein the compound of formula (1) is present in a concentration at or below the sweetness recognition threshold, and wherein the compound of formula (1) enhances the sweetness of the beverage by at least about 2.0% (w/v) sucrose equivalence, such as, for example, by at least about 2.5% (w/v) sucrose equivalence or from about 2.0% to about 3.0%.

In another embodiment, a beverage comprises a compound of formula (2) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof, wherein the at least one sweetener is present in a concentration above the sweetness recognition threshold concentration, wherein the compound of formula (2) is present in a concentration at or below the sweetness recognition threshold, and wherein the compound of formula (2) enhances the sweetness of the beverage by at least about 2.0% (w/v) sucrose equivalence, such as, for example, by at least about 2.5% (w/v) sucrose equivalence or from about 2.0% to about 3.0%.

In another embodiment, a beverage comprises compound (2f) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof, wherein the at least one sweetener is present in a concentration above the sweetness recognition threshold concentration, wherein compound (2f) is present in a concentration at or below the sweetness recognition threshold, and wherein compound (2f) enhances the sweetness of the beverage by at least about 2.0% (w/v) sucrose equivalence, such as, for example, by at least about 2.5% (w/v) sucrose equivalence or from about 2.0% to about 3.0%.

In another embodiment, a beverage comprises compound (2g) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof, wherein the at least one sweetener is present in a concentration above the sweetness recognition threshold concentration, wherein compound (2g) is present in a concentration at or below the sweetness recognition threshold, and wherein compound (2g) enhances the sweetness of the beverage by at least about 2.0% (w/v) sucrose equivalence, such as, by at least about 2.5% (w/v) sucrose equivalence or for example, from about 2.0% to about 3.0%.

In one embodiment, a reduced-calorie soda comprises, for example, caramel color, phosphoric acid, sugar (i.e. sucrose, HFCS or HFSS), compound (2f) and/or (2g), potassium benzoate, natural colors, citric acid, and caffeine.

In another embodiment, a reduced-calorie soda comprises, for example, caramel color, phosphoric acid, sugar, erythritol, compound (2f) and/or (2g), potassium benzoate, natural colors, citric acid, and caffeine.

In still another embodiment, a reduced-calorie soda comprises, for example, caramel color, phosphoric acid, sugar, erythritol, D-tagatose, compound (2f) and/or (2g), potassium benzoate, natural colors, citric acid, and caffeine.

In yet another embodiment, a reduced-calorie soda comprises, for example, caramel color, phosphoric acid, sugar, D-tagatose, compound (2f) and/or (2g), potassium benzoate, natural colors, citric acid, and caffeine.

In one embodiment, a reduced-calorie soda comprises, for example, caramel color, phosphoric acid, sugar, D-psicose, compound (2f) and/or (2g), potassium benzoate, natural colors, citric acid, and caffeine.

In another embodiment, a reduced-calorie lemon-lime carbonated soft drink comprises, for example, sugar, compound (2f) and/or (2g), natural flavors, citric acid, sodium citrate, sodium benzoate, malic acid and *Stevia* leaf extract.

In still another embodiment, a half-calorie lemon-lime carbonated soft drink comprises, for example, sugar, erythritol, compound (2f) and/or (2g), natural flavors, citric acid, malic acid, sodium citrate, sodium benzoate and *Stevia* leaf extract.

In one embodiment, a reduced-calorie orange-flavored carbonated soft drink comprises, for example, sugar, compound (2f) and/or (2g), natural flavors, citric acid, modified food starch, sodium hexametaphosphate, glycerol ester of rosin, yellow 6, sodium benzoate, *stevia* leaf extract, brominated vegetable oil and red 40.

In another embodiment, a reduced-calorie citrus-flavored carbonated soft drink comprises, for example, sugar, compound (2f) and/or (2g), natural flavors, citric acid, potassium citrate, concentrated grape fruit juice, potassium sorbate, potassium benzoate, EDTA, *acacia*, glycerol ester of rosin, brominated vegetable oil and carob bean gum.

In another embodiment, a reduced-calorie sports drink comprises, for example, compound (2f) and/or (2g), citric acid, salt, monopotassium phosphate, magnesium chloride, calcium chloride, natural flavors, sugar, vitamins B3, B6, B12, blue 1, ascorbic acid, and calcium disodium EDTA.

In still another embodiment, a reduced-calorie spicy cherry carbonated soft drink comprises, for example, compound (2f) and/or (2g), sugar, caramel color, phosphoric acid, potassium sorbate, potassium benzoate, artificial and natural flavors, caffeine, monosodium phosphate, lactic acid, and polyethylene glycol.

In yet another embodiment, an enhanced water beverage comprises, for example, compound (2f) and/or (2g), erythritol, sugar, magnesium and calcium lactate, potassium phosphate, citric acid, natural flavors, vitamin C (ascorbic acid), phosphoric acid, calcium phosphate, vitamins B3, E, B5, B6, B12, zinc gluconate and vitamin A palmitate Use of compound (2f) or (2g) in a concentration at or below its sweetness recognition threshold in a beverage containing a sweetener in a concentration above its sweetness recognition threshold means less caloric sweetener is required to provide the same sucrose equivalence. Accordingly, the amount of caloric sweetener in a beverage can be reduced by about 15% to about 20%, while providing the same sucrose equivalence.

Use of compound (2f) or (2g) in a concentration at or below its sweetness recognition threshold in a beverage containing a sweetener in a concentration above its sweetness recognition threshold can provide a reduced calorie beverage with a sucrose equivalence from about 7.5% to about 10.0% (w/v), where the amount of sucrose in the beverage is less than would normally be used to provide a 7.5%-10.0% (w/v) sucrose solution (in the absence of any additional sweeteners).

b. Concentrate Compositions

The present invention also includes concentrate compositions comprising the compounds of the present invention. Suitable concentrate compositions include, but are not limited to, syrups, powdered beverages, flavor packets and flavor enhancer drops.

Beverage syrups are prepared with an initial volume of liquid matrix (e.g. water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water. Flavor packets and flavor enhancer drops are often added to beverages (e.g. water) to provide enhanced water, that is, for example, sweeter, nutrient-enriched and/or fruit-flavored.

Accordingly, in one embodiment, a concentrate composition comprising at least one sweetener and a compound of formula (1) is provided. In embodiments where the compound of formula (1) is a sweetness enhancer, addition of the concentrate to a beverage enhances the sweetness of said beverage by an amount more than the detectable sweetness of a solution containing the same concentration of the compound of formula (1) in the concentrate composition. In another embodiment, the concentrate composition enhances the sweetness of the beverage by at least about 2.0% (w/v) sucrose equivalence.

In one embodiment, a concentrate composition comprises a compound of formula (1) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof. The at least one sweetener is present in a concentration above its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). The compound of formula (1) is present in a concentration at or below its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). The concentrate composition enhances the sweetness of the beverage by an amount more than the detectable sweetness of a solution containing the same concentration of the compound of formula (1) in the concentrate composition.

In one embodiment, a concentrate composition comprises a compound of formula (1) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof. The at least one sweetener is present in a concentration above its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). The compound of formula (1) is present in a concentration at or below its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). The concentrate composition enhances the sweetness of the beverage by at least about 2.0% (w/v) sucrose equivalence.

In one embodiment, a concentrate composition comprises a compound of formula (2) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof. The at least one sweetener is present in a concentration above its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). The compound of formula (2) is present in a concentration at or below its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). The concentrate composition enhances the sweetness of the beverage by an amount more than the detectable sweetness of a solution containing the same concentration of the compound of formula (2) in the concentrate composition.

In one embodiment, a concentrate composition comprises a compound of formula (2) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof. The at least one sweetener is present in a concentration above its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). The compound of formula (2) is present in a concentration at or below its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). The concentrate composition enhances the sweetness of the beverage by at least about 2.0% (w/v) sucrose equivalence.

In one embodiment, a concentrate composition comprises compound (2f) or (2g) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof. The at least one sweetener is present in a concentration above its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). Compound (2f) or (2g) is present in a concentration at or below its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). The concentrate composition enhances the sweetness of the beverage by an amount more than the detectable sweetness of a solution containing the same concentration of compound (2f) or (2g) in the concentrate composition.

In one embodiment, a concentrate composition comprises compound (2f) or (2g) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof. The at least one sweetener is present in a concentration above its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). Compound (2f) or (2g) is present in a concentration at or below its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). The concentrate composition enhances the sweetness of the beverage by at least about 2.0% (w/v) sucrose equivalence.

The concentrate composition can further contain a liquid matrix, i.e. water, citric acid or phosphate buffer.

The concentrate composition can further contain one or more functional ingredients, detailed below. Functional ingredients include, but are not limited to, vitamins, minerals, antioxidants, preservatives, glucosamine, polyphenols and combinations thereof. Any suitable functional ingredient described herein can be used.

The concentrate composition can further contain one or more additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, weighing agents, juice, dairy, cereal and other plant extracts, flavonoids, alcohols, polymers and combinations thereof. Any suitable additive described herein can be used.

c. Other Consumables

In one embodiment, the present invention is a consumable comprises a compound of the present invention.

In another embodiment, the consumable comprises a composition comprising a compound of the present invention.

The consumable can optionally include additives, additional sweeteners, functional ingredients and combinations thereof. Any of the additive, additional sweetener and functional ingredients described above can be present in the consumable.

i. Pharmaceutical Compositions

The present invention extends to pharmaceutical compositions comprising a compound o the present invention. In one embodiment, a pharmaceutical composition contains a pharmaceutically active substance and a compound of the present invention. In another embodiment, a pharmaceutical composition contains a pharmaceutically active substance and a composition comprising a compound of the present invention. A compound of the present invention or composition comprising the same can be present as an excipient material in the pharmaceutical composition, which can mask a bitter or otherwise undesirable taste of a pharmaceutically active substance or another excipient material. The pharmaceutical composition may be in the form of a tablet, a capsule, a liquid, an aerosol, a powder, an effervescent tablet or powder, a syrup, an emulsion, a suspension, a solution, or any other form for providing the pharmaceutical composition to a patient. In particular embodiments, the pharmaceutical composition may be in a form for oral administration, buccal administration, sublingual administration, or any other route of administration as known in the art.

As referred to herein, "pharmaceutically active substance" means any drug, drug formulation, medication, prophylactic agent, therapeutic agent, or other substance having biological activity. As referred to herein, "excipient material" refers to any inactive substance used as a vehicle for an active ingredient, such as any material to facilitate handling, stability, dispersibility, wettability, and/or release kinetics of a pharmaceutically active substance.

Suitable pharmaceutically active substances include, but are not limited to, medications for the gastrointestinal tract or digestive system, for the cardiovascular system, for the central nervous system, for pain or consciousness, for musculo-skeletal disorders, for the eye, for the ear, nose and oropharynx, for the respiratory system, for endocrine problems, for the reproductive system or urinary system, for contraception, for obstetrics and gynecology, for the skin, for infections and infestations, for immunology, for allergic disorders, for nutrition, for neoplastic disorders, for diagnostics, for euthanasia, or other biological functions or disorders. Examples of suitable pharmaceutically active substances for embodiments of the present invention include, but are not limited to, antacids, reflux suppressants, antiflatulents, antidopaminergics, proton pump inhibitors, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, peripheral activators, ACE inhibitors, angiotensin receptor blockers, alpha blockers, anticoagulants, heparin, antiplatelet drugs, fibrinolytics, anti-hemophilic factors, haemostatic drugs, hypolipidaemic agents, statins, hynoptics, anaesthetics, antipsychotics, antidepressants, anti-emetics, anticonvulsants, antiepileptics, anxiolytics, barbiturates, movement disorder drugs, stimulants, benzodiazepines, cyclopyrrolones, dopamine antagonists, antihistamines, cholinergics, anticholinergics, emetics, cannabinoids, analgesics, muscle relaxants, antibiotics, aminoglycosides, anti-virals, anti-fungals, anti-inflammatories, anti-gluacoma drugs, sympathomimetics, steroids, ceruminolytics, bronchodilators, NSAIDS, antitussive, mucolytics, decongestants, corticosteroids, androgens, anti-androgens, gonadotropins, growth hormones, insulin, antidiabetics, thyroid hormones, calcitonin, diphosponates, vasopressin analogues, alkalizing agents, quinolones, anticholinesterase, sildenafil, oral contraceptives, Hormone Replacement Therapies, bone regulators, follicle stimulating hormones, luteinizings hormones, gamolenic acid, progestogen, dopamine agonist, oestrogen, prostaglandin, gonadorelin, clomiphene, tamoxifen, diethylstilbestrol, antileprotics, antituberculous drugs, antimalarials, anthelmintics, antiprotozoal, antiserums, vaccines, interferons, tonics, vitamins, cytotoxic drugs, sex hormones, aromatase inhibitors, somatostatin inhibitors, or similar type substances, or combinations thereof. Such components generally are recognized as safe (GRAS) and/or are U.S. Food and Drug Administration (FDA)-approved.

The pharmaceutically active substance is present in the pharmaceutical composition in widely ranging amounts depending on the particular pharmaceutically active agent being used and its intended applications. An effective dose of any of the herein described pharmaceutically active substances can be readily determined by the use of conventional techniques and by observing results obtained under analogous circumstances. In determining the effective dose, a number of factors are considered including, but not limited to: the species of the patient; its size, age, and general health; the specific disease involved; the degree of involvement or the severity of the disease; the response of the individual patient; the particular pharmaceutically active agent administered; the mode of administration; the bioavailability characteristic of the preparation administered; the dose regimen selected; and the use of concomitant medication. The pharmaceutically active substance is included in the pharmaceutically acceptable carrier, diluent, or excipient in an amount sufficient to deliver to a patient a therapeutic amount of the pharmaceutically active substance in vivo in the absence of serious toxic effects when used in generally acceptable amounts. Thus, suitable amounts can be readily discerned by those skilled in the art.

According to particular embodiments of the present invention, the concentration of pharmaceutically active substance in the pharmaceutical composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimes should be adjusted over time according to the individual need and the professional judgment of the person administering or supervising the administration of the pharmaceutical compositions, and that the dosage ranges set forth herein are exemplary only and are not intended to limit the scope or practice of the claimed composition. The pharmaceutically active substance may be administered at once, or may be divided into a number of smaller doses to be administered at varying intervals of time.

The pharmaceutical composition also may comprise other pharmaceutically acceptable excipient materials in addition to the compound of the present invention or composition comprising the same. Examples of suitable excipient materials for embodiments of this invention include, but are not limited to, antiadherents, binders (e.g., microcrystalline cellulose, gum tragacanth, or gelatin), coatings, disintegrants, fillers, diluents, softeners, emulsifiers, flavoring agents, coloring agents, adjuvants, lubricants, functional agents (e.g., nutrients), viscosity modifiers, bulking agents, glidiants (e.g., colloidal silicon dioxide) surface active agents, osmotic agents, diluents, or any other non-active ingredient, or combinations thereof. For example, the pharmaceutical compositions of the present invention may include excipient materials selected from the group consisting of calcium carbonate, coloring agents, whiteners, preservatives, and flavors, triacetin, magnesium stearate, sterotes, natural or artificial flavors, essential oils, plant extracts, fruit essences, gelatins, or combinations thereof.

The excipient material of the pharmaceutical composition may optionally include other artificial or natural sweeteners, bulk sweeteners, or combinations thereof. Bulk sweeteners include both caloric and non-caloric compounds. In a particular embodiment, the additive functions as the bulk sweetener. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. In particular embodiments, the bulk sweetener is present in the pharmaceutical composition in widely ranging amounts depending on the degree of sweetness desired. Suitable amounts of both sweeteners would be readily discernable to those skilled in the art.

ii. Edible Gel Mixes and Edible Gel Compositions

The present invention extends to edible gel mixes or compositions comprising a compound of the present invention.

In one embodiment, an edible gel or edible gel mix comprises a compound of the present invention. In another embodiment, an edible gel or edible gel mix comprises a composition comprising a compound of the present invention.

Edible gels are gels that can be eaten. A gel is a colloidal system in which a network of particles spans the volume of a liquid medium. Although gels mainly are composed of liquids, and thus exhibit densities similar to liquids, gels have the structural coherence of solids due to the network of particles that spans the liquid medium. For this reason, gels generally appear to be solid, jelly-like materials. Gels can be used in a number of applications. For example, gels can be used in foods, paints, and adhesives.

Non-limiting examples of edible gel compositions for use in particular embodiments include gel desserts, puddings, jellies, pastes, trifles, aspics, marshmallows, gummy candies, or the like. Edible gel mixes generally are powdered or granular solids to which a fluid may be added to form an edible gel composition. Non-limiting examples of fluids for use in particular embodiments include water, dairy fluids, dairy analogue fluids, juices, alcohol, alcoholic beverages, and combinations thereof. Non-limiting examples of dairy fluids which may be used in particular embodiments include milk, cultured milk, cream, fluid whey, and mixtures thereof. Non-limiting examples of dairy analogue fluids which may be used in particular embodiments include, for example, soy milk and non-dairy coffee whitener. Because edible gel products found in the marketplace typically are sweetened with sucrose, it is desirable to sweeten edible gels with an alternative sweetener in order provide a low-calorie or non-calorie alternative.

As used herein, the term "gelling ingredient" denotes any material that can form a colloidal system within a liquid medium. Non-limiting examples of gelling ingredients for use in particular embodiments include gelatin, alginate, carageenan, gum, pectin, konjac, agar, food acid, rennet, starch, starch derivatives, and combinations thereof. It is well known to those having ordinary skill in the art that the amount of gelling ingredient used in an edible gel mix or an edible gel composition varies considerably depending on a number of factors, such as the particular gelling ingredient used, the particular fluid base used, and the desired properties of the gel.

It is well known to those having ordinary skill in the art that the edible gel mixes and edible gels may be prepared using other ingredients in addition to a compound of the present invention or the composition comprising the same and the gelling agent. Non-limiting examples of other ingredients for use in particular embodiments include a food acid, a salt of a food acid, a buffering system, a bulking agent, a sequestrant, a cross-linking agent, one or more flavors, one or more colors, and combinations thereof. Non-limiting examples of food acids for use in particular embodiments include citric acid, adipic acid, fumaric acid, lactic acid, malic acid, and combinations thereof. Non-limiting examples of salts of food acids for use in particular embodiments include sodium salts of food acids, potassium salts of food acids, and combinations thereof. Non-limiting examples of bulking agents for use in particular embodiments include raftilose, isomalt, sorbitol, polydextrose, maltodextrin, and combinations thereof. Non-limiting examples of sequestrants for use in particular embodiments include calcium disodium ethylene tetra-acetate, glucono delta-lactone, sodium gluconate, potassium gluconate, ethylenediaminetetraacetic acid (EDTA), and combinations thereof. Non-limiting examples of cross-linking agents for use in particular embodiments include calcium ions, magnesium ions, sodium ions, and combinations thereof.

iii. Dental Compositions

In one embodiment, a dental composition comprises a compound of the present invention. In another embodiment, a dental composition comprises a composition comprising a compound of the present invention. Dental compositions generally comprise an active dental substance and a base material. A compound of the present invention or a composition comprising the same can be used as the base material to sweeten the dental composition. The dental composition may be in the form of any oral composition used in the oral cavity such as mouth freshening agents, gargling agents, mouth rinsing agents, toothpaste, tooth polish, dentifrices, mouth sprays, teeth-whitening agent, dental floss, and the like, for example.

As referred to herein, "active dental substance" means any composition which can be used to improve the aesthetic appearance and/or health of teeth or gums or prevent dental caries. As referred to herein, "base material" refers to any inactive substance used as a vehicle for an active dental substance, such as any material to facilitate handling, stability, dispersibility, wettability, foaming, and/or release kinetics of an active dental substance.

Suitable active dental substances for embodiments of this invention include, but are not limited to, substances which remove dental plaque, remove food from teeth, aid in the elimination and/or masking of halitosis, prevent tooth decay, and prevent gum disease (i.e., Gingiva). Examples of suitable active dental substances for embodiments of the present invention include, but are not limited to, anticaries drugs, fluoride, sodium fluoride, sodium monofluorophosphate, stannos fluoride, hydrogen peroxide, carbamide peroxide (i.e., urea peroxide), antibacterial agents, plaque removing agents, stain removers, anticalculus agents, abrasives, baking soda, percarbonates, perborates of alkali and alkaline earth metals, or similar type substances, or combinations thereof. Such components generally are recognized as safe (GRAS) and/or are U.S. Food and Drug Administration (FDA)-approved.

According to particular embodiments of the invention, the active dental substance is present in the dental composition in an amount ranging from about 50 ppm to about 3000 ppm of the dental composition. Generally, the active dental substance is present in the dental composition in an amount effective to at least improve the aesthetic appearance and/or health of teeth or gums marginally or prevent dental caries. For example, a dental composition comprising a toothpaste may include an active dental substance comprising fluoride in an amount of about 850 to 1,150 ppm.

The dental composition also may comprise other base materials in addition to the compound of the present invention or composition comprising the same. Examples of suitable base materials for embodiments of this invention include, but are not limited to, water, sodium lauryl sulfate or other sulfates, humectants, enzymes, vitamins, herbs, calcium, flavorings (e.g., mint, bubblegum, cinnamon, lemon, or orange), surface-active agents, binders, preservatives, gelling agents, pH modifiers, peroxide activators, stabilizers, coloring agents, or similar type materials, and combinations thereof.

The base material of the dental composition may optionally include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. Generally, the amount of bulk sweetener present in the dental composition ranges widely depending on the particular embodiment of the dental composition and the desired degree of sweetness. Those of ordinary skill in the art will readily ascertain the appropriate amount of bulk sweetener. In particular embodiments, the bulk sweetener is present in the dental composition in an amount in the range of about 0.1 to about 5 weight percent of the dental composition.

According to particular embodiments of the invention, the base material is present in the dental composition in an amount ranging from about 20 to about 99 percent by weight of the dental composition. Generally, the base material is present in an amount effective to provide a vehicle for an active dental substance.

In a particular embodiment, a dental composition comprises a compound of the present invention and an active dental substance. In another particular embodiment, a dental composition comprises a composition comprising a compound of the present invention and an active dental substance. Generally, the amount of the sweetener varies widely depending on the nature of the particular dental composition and the desired degree of sweetness.

Foodstuffs include, but are not limited to, confections, condiments, chewing gum, cereal, baked goods, and dairy products.

iv. Confections

In one embodiment, a confection comprises a compound of the present invention. In another embodiment, a confection comprises a composition comprising a compound of the present invention.

As referred to herein, "confection" can mean a sweet, a lollie, a confectionery, or similar term. The confection generally contains a base composition component and a sweetener component. A compound of the present invention or a composition comprising the same can serve as the sweetener component. The confection may be in the form of any food that is typically perceived to be rich in sugar or is typically sweet. According to particular embodiments of the present invention, the confections may be bakery products such as pastries; desserts such as yogurt, jellies, drinkable jellies, puddings, Bavarian cream, blancmange, cakes, brownies, mousse and the like, sweetened food products eaten at tea time or following meals; frozen foods; cold confections, e. g. types of ice cream such as ice cream, ice milk, lacto-ice and the like (food products in which sweeteners and various other types of raw materials are added to milk products, and the resulting mixture is agitated and frozen), and ice confections such as sherbets, dessert ices and the like (food products in which various other types of raw materials are added to a sugary liquid, and the resulting mixture is agitated and frozen); general confections, e. g., baked confections or steamed confections such as crackers, biscuits, buns with bean-jam filling, halvah, alfajor, and the like; rice cakes and snacks; table top products; general sugar confections such as chewing gum (e.g. including compositions which comprise a substantially water-insoluble, chewable gum base, such as chicle or substitutes thereof, including jetulong, guttakay rubber or certain comestible natural synthetic resins or waxes), hard candy, soft candy, mints, nougat candy, jelly beans, fudge, toffee, taffy, Swiss milk tablet, licorice candy, chocolates, gelatin candies, marshmallow, marzipan, divinity, cotton candy, and the like; sauces including fruit flavored sauces, chocolate sauces and the like; edible gels; crèmes including butter crèmes, flour pastes, whipped cream and the like; jams including strawberry jam, marmalade and the like; and breads including sweet breads and the like or other starch products, and combinations thereof.

As referred to herein, "base composition" means any composition which can be a food item and provides a matrix for carrying the sweetener component.

Suitable base compositions for embodiments of this invention may include flour, yeast, water, salt, butter, eggs, milk, milk powder, liquor, gelatin, nuts, chocolate, citric acid, tartaric acid, fumaric acid, natural flavors, artificial flavors, colorings, polyols, sorbitol, isomalt, maltitol, lactitol, malic acid, magnesium stearate, lecithin, hydrogenated glucose syrup, glycerine, natural or synthetic gum, starch, and the like, and combinations thereof. Such components generally are recognized as safe (GRAS) and/or are U.S. Food and Drug Administration (FDA)-approved. According to particular embodiments of the invention, the base composition is present in the confection in an amount ranging from about 0.1 to about 99 weight percent of the confection. Generally, the base composition is present in the confection in an amount, in combination with a compound of formula (1) or a composition comprising a compound of formula (1) to provide a food product.

The base composition of the confection may optionally include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. Generally, the amount of bulk sweetener present in the confection ranges widely depending on the particular embodiment of the confection and the desired degree of sweetness. Those of ordinary skill in the art will readily ascertain the appropriate amount of bulk sweetener.

In a particular embodiment, a confection comprises a compound of the present invention or a composition comprising the same and a base composition. Generally, the amount of a compound of the present invention in the confection ranges widely depending on the particular embodiment of the confection and the desired degree of sweetness. Those of ordinary skill in the art will readily ascertain the appropriate amount. In a particular embodiment, a compound of the present invention is present in the confection in an amount in the range of about 30 ppm to about 6000 ppm of the confection. In another embodiment, a compound of the present invention is present in the confection in an amount in the range of about 1 ppm to about 10,000 ppm of the confection. In embodiments where the confection comprises hard candy, a compound of the present invention is present in an amount in the range of about 150 ppm to about 2250 ppm of the hard candy.

v. Condiment Compositions

In one embodiment, a condiment comprises a compound of the present invention. In another embodiment a condiment comprises a composition comprising a compound of the present invention. Condiments, as used herein, are compositions used to enhance or improve the flavor of a food or beverage. Non-limiting examples of condiments include ketchup (catsup); mustard; barbecue sauce; butter; chili sauce; chutney; cocktail sauce; curry; dips; fish sauce; horseradish; hot sauce; jellies, jams, marmalades, or preserves; mayonnaise; peanut butter; relish; remoulade; salad dressings (e.g., oil and vinegar, Caesar, French, ranch, bleu cheese, Russian, Thousand Island, Italian, and balsamic vinaigrette), salsa; sauerkraut; soy sauce; steak sauce; syrups; tartar sauce; and Worcestershire sauce.

Condiment bases generally comprise a mixture of different ingredients, non-limiting examples of which include vehicles (e.g., water and vinegar); spices or seasonings (e.g., salt, pepper, garlic, mustard seed, onion, paprika, turmeric, and combinations thereof); fruits, vegetables, or their products (e.g., tomatoes or tomato-based products (paste, puree), fruit juices, fruit juice peels, and combinations thereof); oils or oil emulsions, particularly vegetable oils; thickeners (e.g., xanthan gum, food starch, other hydrocolloids, and combinations thereof); and emulsifying agents (e.g., egg yolk solids, protein, gum arabic, carob bean gum, guar gum, gum karaya, gum tragacanth, carageenan, pectin, propylene glycol esters of alginic acid, sodium carboxymethyl-cellulose, polysorbates, and combinations thereof). Recipes for condiment bases and methods of making condiment bases are well known to those of ordinary skill in the art.

Generally, condiments also comprise caloric sweeteners, such as sucrose, high fructose corn syrup, molasses, honey, or brown sugar. In exemplary embodiments of the condiments provided herein, a compound of the present invention or a composition comprising the same is used instead of traditional caloric sweeteners. Accordingly, a condiment composition desirably comprises a compound of the present invention or a composition comprising a compound of the present invention and a condiment base.

The condiment composition optionally may include other natural and/or synthetic high-potency sweeteners, bulk sweeteners, pH modifying agents (e.g., lactic acid, citric acid, phosphoric acid, hydrochloric acid, acetic acid, and combinations thereof), fillers, functional agents (e.g., pharmaceutical agents, nutrients, or components of a food or plant), flavorings, colorings, or combinations thereof vi. Chewing Gum Compositions In one embodiment, a chewing gum composition comprises a compound of the present invention. In another embodiment, a chewing gum composition comprises a composition comprising a compound of the present invention. Chewing gum compositions generally comprise a water-soluble portion and a water-insoluble chewable gum base portion. The water soluble portion, which typically includes the composition of the present invention, dissipates with a portion of the flavoring agent over a period of time during chewing while the insoluble gum base portion is retained in the mouth. The insoluble gum base generally determines whether a gum is considered chewing gum, bubble gum, or a functional gum.

The insoluble gum base, which is generally present in the chewing gum composition in an amount in the range of about 15 to about 35 weight percent of the chewing gum composition, generally comprises combinations of elastomers, softeners (plasticizers), emulsifiers, resins, and fillers. Such components generally are considered food grade, recognized as safe (GRA), and/or are U.S. Food and Drug Administration (FDA)-approved.

Elastomers, the primary component of the gum base, provide the rubbery, cohesive nature to gums and can include one or more natural rubbers (e.g., smoked latex, liquid latex, or guayule); natural gums (e.g., jelutong, perillo, sorva, massaranduba balata, massaranduba chocolate, nispero, rosindinha, chicle, and gutta hang kang); or synthetic elastomers (e.g., butadiene-styrene copolymers, isobutylene-isoprene copolymers, polybutadiene, polyisobutylene, and vinyl polymeric elastomers). In a particular embodiment, the elastomer is present in the gum base in an amount in the range of about 3 to about 50 weight percent of the gum base.

Resins are used to vary the firmness of the gum base and aid in softening the elastomer component of the gum base. Non-limiting examples of suitable resins include a rosin ester, a terpene resin (e.g., a terpene resin from α-pinene, β-pinene and/or d-limonene), polyvinyl acetate, polyvinyl alcohol, ethylene vinyl acetate, and vinyl acetate-vinyl laurate copolymers. Non-limiting examples of rosin esters include a glycerol ester of a partially hydrogenated rosin, a glycerol ester of a polymerized rosin, a glycerol ester of a partially dimerized rosin, a glycerol ester of rosin, a pentaerythritol ester of a partially hydrogenated rosin, a methyl ester of rosin, or a methyl ester of a partially hydrogenated rosin. In a particular embodiment, the resin is present in the gum base in an amount in the range of about 5 to about 75 weight percent of the gum base.

Softeners, which also are known as plasticizers, are used to modify the ease of chewing and/or mouthfeel of the chewing gum composition. Generally, softeners comprise oils, fats, waxes, and emulsifiers. Non-limiting examples of oils and fats include tallow, hydrogenated tallow, large, hydrogenated or partially hydrogenated vegetable oils (e.g., soybean, canola, cottonseed, sunflower, palm, coconut, corn, safflower, or palm kernel oils), cocoa butter, glycerol monostearate, glycerol triacetate, glycerol abietate, leithin, monoglycerides, diglycerides, triglycerides acetylated monoglycerides, and free fatty acids. Non-limiting examples of waxes include polypropylene/polyethylene/Fisher-Tropsch waxes, paraffin, and microcrystalline and natural waxes (e.g., candelilla, beeswax and carnauba). Microcrystalline waxes, especially those with a high degree of crystallinity and a high melting point, also may be considered as bodying agents or textural modifiers. In a particular embodiment, the softeners are present in the gum base in an amount in the range of about 0.5 to about 25 weight percent of the gum base.

Emulsifiers are used to form a uniform dispersion of the insoluble and soluble phases of the chewing gum composition and also have plasticizing properties. Suitable emulsifiers include glycerol monostearate (GMS), lecithin (Phosphatidyl choline), polyglycerol polyricinoleic acid (PPGR), mono and diglycerides of fatty acids, glycerol distearate, tracetin, acetylated monoglyceride, glycerol triactetate, and magnesium stearate. In a particular embodiment, the emulsifiers are present in the gum base in an amount in the range of about 2 to about 30 weight percent of the gum base.

The chewing gum composition also may comprise adjuvants or fillers in either the gum base and/or the soluble portion of the chewing gum composition. Suitable adjuvants and fillers include lecithin, inulin, polydextrin, calcium carbonate, magnesium carbonate, magnesium silicate, ground limestome, aluminum hydroxide, aluminum silicate, talc, clay, alumina, titanium dioxide, and calcium phosphate. In particular embodiments, lecithin can be used as an inert filler to decrease the stickiness of the chewing gum composition. In other particular embodiments, lactic acid copolymers, proteins (e.g., gluten and/or zein) and/or guar can be used to create a gum that is more readily biodegradable. The adjuvants or fillers are generally present in the gum base in an amount up to about 20 weight percent of the gum base. Other optional ingredients include coloring agents, whiteners, preservatives, and flavors.

In particular embodiments of the chewing gum composition, the gum base comprises about 5 to about 95 weight percent of the chewing gum composition, more desirably about 15 to about 50 weight percent of the chewing gum composition, and even more desirably from about 20 to about 30 weight percent of the chewing gum composition.

The soluble portion of the chewing gum composition may optionally include other artificial or natural sweeteners, bulk sweeteners, softeners, emulsifiers, flavoring agents, coloring agents, adjuvants, fillers, functional agents (e.g., pharmaceutical agents or nutrients), or combinations thereof. Suitable examples of softeners and emulsifiers are described above.

Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. In particular embodiments, the bulk sweetener is present in the chewing gum composition in an amount in the range of about 1 to about 75 weight percent of the chewing gum composition.

Flavoring agents may be used in either the insoluble gum base or soluble portion of the chewing gum composition. Such flavoring agents may be natural or artificial flavors. In a particular embodiment, the flavoring agent comprises an essential oil, such as an oil derived from a plant or a fruit, peppermint oil, spearmint oil, other mint oils, clove oil, cinnamon oil, oil of wintergreen, bay, thyme, cedar leaf, nutmeg, allspice, sage, mace, and almonds. In another particular embodiment, the flavoring agent comprises a plant extract or a fruit essence such as apple, banana, watermelon, pear, peach, grape, strawberry, raspberry, cherry, plum, pineapple, apricot, and mixtures thereof. In still another particular embodiment, the flavoring agent comprises a citrus flavor, such as an extract, essence, or oil of lemon, lime, orange, tangerine, grapefruit, citron, or kumquat.

In a particular embodiment, a chewing gum composition comprises a compound of the present invention or a composition comprising the same and a gum base. In a particular embodiment, a compound of the present invention is present in the chewing gum composition in an amount in the range of about 1 ppm to about 10,000 ppm of the chewing gum composition.

vii. Cereal Compositions

In one embodiment, a cereal composition comprises a compound of the present invention. In another embodiment, a cereal composition comprises a composition comprising a compound of the present invention. Cereal compositions typically are eaten either as staple foods or as snacks. Non-limiting examples of cereal compositions for use in particular embodiments include ready-to-eat cereals as well as hot cereals. Ready-to-eat cereals are cereals which may be eaten without further processing (i.e. cooking) by the consumer. Examples of ready-to-eat cereals include breakfast cereals and snack bars. Breakfast cereals typically are processed to produce a shredded, flaky, puffy, or extruded form. Breakfast cereals generally are eaten cold and are often mixed with milk and/or fruit. Snack bars include, for example, energy bars, rice cakes, granola bars, and nutritional bars. Hot cereals generally are cooked, usually in either milk or water, before being eaten. Non-limiting examples of hot cereals include grits, porridge, polenta, rice, and rolled oats.

Cereal compositions generally comprise at least one cereal ingredient. As used herein, the term "cereal ingredient" denotes materials such as whole or part grains, whole or part seeds, and whole or part grass. Non-limiting examples of cereal ingredients for use in particular embodiments include maize, wheat, rice, barley, bran, bran endosperm, bulgur, soghums, millets, oats, rye, triticale, buchwheat, fonio, *quinoa*, bean, soybean, amaranth, teff, spelt, and kaniwa.

In a particular embodiment, the cereal composition comprises a compound of the present invention or a composition comprising the same and at least one cereal ingredient. A compound of the present invention or the composition comprising the same may be added to the cereal composition in a variety of ways, such as, for example, as a coating, as a frosting, as a glaze, or as a matrix blend (i.e. added as an ingredient to the cereal formulation prior to the preparation of the final cereal product).

Accordingly, in a particular embodiment, a compound of the present invention or a composition comprising the same is added to the cereal composition as a matrix blend. In one embodiment, a compound of the present invention or a composition comprising the same is blended with a hot cereal prior to cooking to provide a sweetened hot cereal product. In another embodiment, a compound of the present invention or a composition comprising the same is blended with the cereal matrix before the cereal is extruded.

In another particular embodiment, a compound of the present invention or a composition comprising the same is added to the cereal composition as a coating, such as, for example, by combining a compound of the present invention or a comprising the same with a food grade oil and applying the mixture onto the cereal. In a different embodiment, a compound of the present invention or a composition comprising the same and the food grade oil may be applied to the cereal separately, by applying either the oil or the sweetener first. Non-limiting examples of food grade oils for use in particular embodiments include vegetable oils such as corn oil, soybean oil, cottonseed oil, peanut oil, coconut oil, canola oil, olive oil, sesame seed oil, palm oil, palm kernel oil, and mixtures thereof. In yet another embodiment, food grade fats may be used in place of the oils, provided that the fat is melted prior to applying the fat onto the cereal.

In another embodiment, the a compound of the present invention or a composition comprising the same is added to the cereal composition as a glaze. Non-limiting examples of glazing agents for use in particular embodiments include corn syrup, honey syrups and honey syrup solids, maple syrups and maple syrup solids, sucrose, isomalt, polydextrose, polyols, hydrogenated starch hydrosylate, aqueous solutions thereof, and mixtures thereof. In another such embodiment, a compound of the present invention or a composition comprising the same is added as a glaze by combining with a glazing agent and a food grade oil or fat and applying the mixture to the cereal. In yet another embodiment, a gum system, such as, for example, gum *acacia*, carboxymethyl cellulose, or algin, may be added to the glaze to provide structural support. In addition, the glaze also may include a coloring agent, and also may include a flavor.

In another embodiment, a compound of the present invention or a composition comprising the same is added to the cereal composition as a frosting. In one such embodiment, a compound of the present invention or a composition comprising the same is combined with water and a frosting agent and then applied to the cereal. Non-limiting examples of frosting agents for use in particular embodiments include maltodextrin, sucrose, starch, polyols, and mixtures thereof. The frosting also may include a food grade oil, a food grade fat, a coloring agent, and/or a flavor.

Generally, the amount of a compound of the present invention in a cereal composition varies widely depending on the particular type of cereal composition and its desired sweetness. Those of ordinary skill in the art can readily discern the appropriate amount of sweetener to put in the cereal composition. In a particular embodiment, a compound of the present invention is present in the cereal composition in an amount in the range of about 0.02 to about 1.5 weight percent of the cereal composition and the at least one additive is present in the cereal composition in an amount in the range of about 1 to about 5 weight percent of the cereal composition.

viii. Baked Goods

In one embodiment, a baked good comprises a compound of the present invention. In another embodiment, a baked good comprises a composition comprising a compound of the present invention. Baked goods, as used herein, include ready to eat and all ready to bake products, flours, and mixes requiring preparation before serving. Non-limiting examples of baked goods include cakes, crackers, cookies, brownies, muffins, rolls, bagels, donuts, strudels, pastries, croissants, biscuits, bread, bread products, and buns.

Preferred baked goods in accordance with embodiments of this invention can be classified into three groups: bread-type doughs (e.g., white breads, variety breads, soft buns, hard rolls, bagels, pizza dough, and flour tortillas), sweet doughs (e.g., danishes, croissants, crackers, puff pastry, pie crust, biscuits, and cookies), and batters (e.g., cakes such as sponge, pound, devil's food, cheesecake, and layer cake, donuts or other yeast raised cakes, brownies, and muffins). Doughs generally are characterized as being flour-based, whereas batters are more water-based.

Baked goods in accordance with particular embodiments of this invention generally comprise a combination of sweetener, water, and fat. Baked goods made in accordance with many embodiments of this invention also contain flour in order to make a dough or a batter. The term "dough" as used herein is a mixture of flour and other ingredients stiff enough to knead or roll. The term "batter" as used herein consists of flour, liquids such as milk or water, and other ingredients, and is thin enough to pour or drop from a spoon. Desirably, in accordance with particular embodiments of the invention, the flour is present in the baked goods in an amount in the range of about 15 to about 60% on a dry weight basis, more desirably from about 23 to about 48% on a dry weight basis.

The type of flour may be selected based on the desired product. Generally, the flour comprises an edible non-toxic flour that is conventionally utilized in baked goods. According to particular embodiments, the flour may be a bleached bake flour, general purpose flour, or unbleached flour. In other particular embodiments, flours also may be used that have been treated in other manners. For example, in particular embodiments flour may be enriched with additional vitamins, minerals, or proteins. Non-limiting examples of flours suitable for use in particular embodiments of the invention include wheat, corn meal, whole grain, fractions of whole grains (wheat, bran, and oatmeal), and combinations thereof. Starches or farinaceous material also may be used as the flour in particular embodiments. Common food starches generally are derived from potato, corn, wheat, barley, oat, tapioca, arrow root, and sago. Modified starches and pregelatinized starches also may be used in particular embodiments of the invention.

The type of fat or oil used in particular embodiments of the invention may comprise any edible fat, oil, or combination thereof that is suitable for baking Non-limiting examples of fats suitable for use in particular embodiments of the invention include vegetable oils, tallow, lard, marine oils, and combinations thereof. According to particular embodiments, the fats may be fractionated, partially hydrogenated, and/or intensified. In another particular embodiment, the fat desirably comprises reduced, low calorie, or non-digestible fats, fat substitutes, or synthetic fats. In yet another particular embodiment, shortenings, fats, or mixtures of hard and soft fats also may be used. In particular embodiments, shortenings may be derived principally from triglycerides derived from vegetable sources (e.g., cotton seed oil, soybean oil, peanut oil, linseed oil, sesame oil, palm oil, palm kernel oil, rapeseed oil, safflower oil, coconut oil, corn oil, sunflower seed oil, and mixtures thereof). Synthetic or natural triglycerides of fatty acids having chain lengths from 8 to 24 carbon atoms also may be used in particular embodiments. Desirably, in accordance with particular embodiments of this invention, the fat is present in the baked good in an amount in the range of about 2 to about 35% by weight on a dry basis, more desirably from about 3 to about 29% by weight on a dry basis.

Baked goods in accordance with particular embodiments of this invention also comprise water in amounts sufficient to provide the desired consistency, enabling proper forming, machining and cutting of the baked good prior or subsequent to cooking. The total moisture content of the baked good includes any water added directly to the baked good as well as water present in separately added ingredients (e.g., flour, which generally includes about 12 to about 14% by weight moisture). Desirably, in accordance with particular embodiments of this invention, the water is present in the baked good in an amount up to about 25% by weight of the baked good.

Baked goods in accordance with particular embodiments of this invention also may comprise a number of additional conventional ingredients such as leavening agents, flavors, colors, milk, milk by-products, egg, egg by-products, cocoa, vanilla or other flavoring, as well as inclusions such as nuts, raisins, cherries, apples, apricots, peaches, other fruits, citrus peel, preservative, coconuts, flavored chips such a chocolate chips, butterscotch chips, and caramel chips, and combinations thereof. In particular embodiments, the baked goods may also comprise emulsifiers, such as lecithin and monoglycerides.

According to particular embodiments of this invention, leavening agents may comprise chemical leavening agents or yeast leavening agents. Non-limiting examples of chemical leavening agents suitable for use in particular embodiments of this invention include baking soda (e.g., sodium, potassium, or aluminum bicarbonate), baking acid (e.g., sodium aluminum phosphate, monocalcium phosphate, or dicalcium phosphate), and combinations thereof.

In accordance with another particular embodiment of this invention, cocoa may comprise natural or "Dutched" chocolate from which a substantial portion of the fat or cocoa butter has been expressed or removed by solvent extraction, pressing, or other means. In a particular embodiment, it may be necessary to reduce the amount of fat in a baked good comprising chocolate because of the additional fat present in cocoa butter. In particular embodiments, it may be necessary to add larger amounts of chocolate as compared to cocoa in order to provide an equivalent amount of flavoring and coloring.

Baked goods generally also comprise caloric sweeteners, such as sucrose, high fructose corn syrup, erythritol, molasses, honey, or brown sugar. In exemplary embodiments of the baked goods provided herein, the caloric sweetener is replaced partially or totally with a compound of the present invention or a composition comprising the same. Accordingly, in one embodiment a baked good comprises a compound of the present invention or a composition comprising the same in combination with a fat, water, and optionally flour. In a particular embodiment, the baked good optionally may include other natural and/or synthetic high-potency sweeteners and/or bulk sweeteners.

ix. Dairy Products

In one embodiment, a dairy product comprises a compound of the present invention. In another embodiment, a dairy product comprises a composition comprising a compound of the present invention. Dairy products and processes for making dairy products suitable for use in this invention are well known to those of ordinary skill in the art. Dairy products, as used herein, comprise milk or foodstuffs produced from milk. Non-limiting examples of dairy products suitable for use in embodiments of this invention include milk, milk cream, sour cream, crème fraiche, buttermilk, cultured buttermilk, milk powder, condensed milk, evaporated milk, butter, cheese, cottage cheese, cream cheese, yogurt, ice cream, frozen custard, frozen yogurt, gelato, vla, piima, filmjölk, kajmak, kephir, viili, kumiss, airag, ice milk, casein, ayran, lassi, khoa, or combinations thereof Milk is a fluid secreted by the mammary glands of female mammals for the nourishment of their young. The female ability to produce milk is one of the defining characteristics of mammals and provides the primary source of nutrition for newborns before they are able to digest more diverse foods. In particular embodiments of this invention, the dairy products are derived from the raw milk of cows, goats, sheep, horses, donkeys, camels, water buffalo, yaks, reindeer, moose, or humans.

In particular embodiments of this invention, the processing of the dairy product from raw milk generally comprises the steps of pasteurizing, creaming, and homogenizing. Although raw milk may be consumed without pasteurization, it usually is pasteurized to destroy harmful microorganisms such as bacteria, viruses, protozoa, molds, and yeasts. Pasteurizing generally comprises heating the milk to a high temperature for a short period of time to substantially reduce the number of microorganisms, thereby reducing the risk of disease.

Creaming traditionally follows pasteurization step, and involves the separation of milk into a higher-fat cream layer and a lower-fat milk layer. Milk will separate into milk and cream layers upon standing for twelve to twenty-four hours. The cream rises to the top of the milk layer and may be skimmed and used as a separate dairy product. Alternatively, centrifuges may be used to separate the cream from the milk. The remaining milk is classified according to the fat content of the milk, non-limiting examples of which include whole, 2%, 1%, and skim milk.

After removing the desired amount of fat from the milk by creaming, milk is often homogenized. Homogenization prevents cream from separating from the milk and generally involves pumping the milk at high pressures through narrow tubes in order to break up fat globules in the milk. Pasteurization, creaming, and homogenization of milk are common but are not required to produce consumable dairy products. Accordingly, suitable dairy products for use in embodiments of this invention may undergo no processing steps, a single processing step, or combinations of the processing steps described herein. Suitable dairy products for use in embodiments of this invention may also undergo processing steps in addition to or apart from the processing steps described herein.

Particular embodiments of this invention comprise dairy products produced from milk by additional processing steps. As described above, cream may be skimmed from the top of milk or separated from the milk using machine-centrifuges. In a particular embodiment, the dairy product comprises sour cream, a dairy product rich in fats that is obtained by fermenting cream using a bacterial culture. The bacteria produce lactic acid during fermentation, which sours and thickens the cream. In another particular embodiment, the dairy product comprises crème fraiche, a heavy cream slightly soured with bacterial culture in a similar manner to sour cream. Crème fraiche ordinarily is not as thick or as sour as sour cream. In yet another particular embodiment, the dairy product comprises cultured buttermilk. Cultured buttermilk is obtained by adding bacteria to milk. The resulting fermentation, in which the bacterial culture turns lactose into lactic acid, gives cultured buttermilk a sour taste. Although it is produced in a different manner, cultured buttermilk generally is similar to traditional buttermilk, which is a by-product of butter manufacture.

According to other particular embodiments of this invention, the dairy products comprise milk powder, condensed milk, evaporated milk, or combinations thereof. Milk powder, condensed milk, and evaporated milk generally are produced by removing water from milk. In a particular embodiment, the dairy product comprises a milk powder comprising dried milk solids with a low moisture content. In another particular embodiment, the dairy product comprises condensed milk. Condensed milk generally comprises milk with a reduced water content and added sweetener, yielding a thick, sweet product with a long shelf-life. In yet another particular embodiment, the dairy product comprises evaporated milk. Evaporated milk generally comprises fresh, homogenized milk from which about 60% of the water has been removed, that has been chilled, fortified with additives such as vitamins and stabilizers, packaged, and finally sterilized. According to another particular embodiment of this invention, the dairy product comprises a dry creamer and a compound of the present invention or a composition comprising a compound of the present invention.

In another particular embodiment, the dairy product provided herein comprises butter. Butter generally is made by churning fresh or fermented cream or milk. Butter generally comprises butterfat surrounding small droplets comprising mostly water and milk proteins. The churning process damages the membranes surrounding the microscopic globules of butterfat, allowing the milk fats to conjoin and to separate from the other parts of the cream. In yet another particular embodiment, the dairy product comprises buttermilk, which is the sour-tasting liquid remaining after producing butter from full-cream milk by the churning process.

In still another particular embodiment, the dairy product comprises cheese, a solid foodstuff produced by curdling milk using a combination of rennet or rennet substitutes and acidification. Rennet, a natural complex of enzymes produced in mammalian stomachs to digest milk, is used in cheese-making to curdle the milk, causing it to separate into solids known as curds and liquids known as whey. Generally, rennet is obtained from the stomachs of young ruminants, such as calves; however, alternative sources of rennet include some plants, microbial organisms, and genetically modified bacteria, fungus, or yeast. In addition, milk may be coagulated by adding acid, such as citric acid. Generally, a combination of rennet and/or acidification is used to curdle the milk. After separating the milk into curds and whey, some cheeses are made by simply draining, salting, and packaging the curds. For most cheeses, however, more processing is needed. Many different methods may be used to produce the hundreds of available varieties of cheese. Processing methods include heating the cheese, cutting it into small cubes to drain, salting, stretching, cheddaring, washing, molding, aging, and ripening. Some cheeses, such as the blue cheeses, have additional bacteria or molds introduced to them before or during aging, imparting flavor and aroma to the finished product. Cottage cheese is a cheese curd product with a mild flavor that is drained but not pressed so that some whey remains. The curd is usually washed to remove acidity. Cream cheese is a soft, mild-tasting, white cheese with a high fat content that is produced by adding cream to milk and then curdling to form a rich curd. Alternatively, cream cheese can be made from skim milk with cream added to the curd. It should be understood that cheese, as used herein, comprises all solid foodstuff produced by the curdling milk.

In another particular embodiment of this invention, the dairy product comprises yogurt. Yogurt generally is produced by the bacterial fermentation of milk. The fermentation of lactose produces lactic acid, which acts on proteins in milk to give the yogurt a gel-like texture and tartness. In particularly desirable embodiments, the yogurt may be sweetened with a sweetener and/or flavored. Non-limiting examples of flavorings include, but are not limited to, fruits (e.g., peach, strawberry, banana), vanilla, and chocolate. Yogurt, as used herein, also includes yogurt varieties with different consistencies and viscosities, such as dahi, dadih or dadiah, labneh or labaneh, bulgarian, kefir, and matsoni. In another particular embodiment, the dairy product comprises a yogurt-based beverage, also known as drinkable yogurt or a yogurt smoothie. In particularly desirable embodiments, the yogurt-based beverage may comprise sweeteners, flavorings, other ingredients, or combinations thereof.

Other dairy products beyond those described herein may be used in particular embodiments of this invention. Such dairy products are well known to those of ordinary skill in the art, non-limiting examples of which include milk, milk and juice, coffee, tea, vla, piima, filmjolk, kajmak, kephir, viili, kumiss, airag, ice milk, casein, ayran, lassi, and khoa.

According to particular embodiments of this invention, the dairy compositions also may comprise other additives. Non-limiting examples of suitable additives include sweeteners and flavorants such as chocolate, strawberry, and banana. Particular embodiments of the dairy compositions provided herein also may comprise additional nutritional supplements such as vitamins (e.g., vitamin D) and minerals (e.g., calcium) to improve the nutritional composition of the milk.

In a particularly desirable embodiment, the dairy composition comprises a compound of the present invention or a composition comprising the same in combination with a dairy product. In a particular embodiment, a compound of the present invention is present in the dairy composition in an amount in the range of about 200 to about 20,000 weight percent of the dairy composition.

A compound of the present invention or a composition comprising the same is also suitable for use in processed agricultural products, livestock products or seafood; processed meat products such as sausage and the like; retort food products, pickles, preserves boiled in soy sauce, delicacies, side dishes; soups; snacks such as potato chips, cookies, or the like; as shredded filler, leaf, stem, stalk, homogenized leaf cured and animal feed.

x. Tabletop Sweetener Compositions

Tabletop sweetener compositions containing a compound of the present invention is also contemplated herein. The tabletop composition can further include at least one bulking agent, additive, anti-caking agent, functional ingredient or combination thereof.

Suitable "bulking agents" include, but are not limited to, maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and the like, and mixtures thereof. Additionally, in accordance with still other embodiments of the invention, granulated sugar (sucrose) or other caloric sweeteners such as crystalline fructose, other carbohydrates, or sugar alcohol can be used as a bulking agent due to their provision of good content uniformity without the addition of significant calories.

As used herein, the phrase "anti-caking agent" and "flow agent" refer to any composition which assists in content uniformity and uniform dissolution. In accordance with particular embodiments, non-limiting examples of anti-caking agents include cream of tartar, calcium silicate, silicon dioxide, microcrystalline cellulose (Avicel, FMC BioPolymer, Philadelphia, Pa.), and tricalcium phosphate. In one embodiment, the anti-caking agents are present in the tabletop sweetener composition in an amount from about 0.001 to about 3% by weight of the tabletop sweetener composition.

The tabletop sweetener compositions can be packaged in any form known in the art. Non-limiting forms include, but are not limited to, powder form, granular form, packets, tablets, sachets, pellets, cubes, solids, and liquids.

In one embodiment, the tabletop sweetener composition is a single-serving (portion control) packet comprising a dry-blend. Dry-blend formulations generally may comprise powder or granules. Although the tabletop sweetener composition may be in a packet of any size, an illustrative non-limiting example of conventional portion control tabletop sweetener packets are approximately 2.5 by 1.5 inches and hold approximately 1 gram of a sweetener composition having a sweetness equivalent to 2 teaspoons of granulated sugar (~8 g). The amount of a compound of formula (1) in a dry-blend tabletop sweetener formulation can vary. In a particular embodiment, a dry-blend tabletop sweetener formulation may contain a compound of the present invention in an amount from about 1% (w/w) to about 10% (w/w) of the tabletop sweetener composition.

Solid tabletop sweetener embodiments include cubes and tablets. A non-limiting example of conventional cubes are equivalent in size to a standard cube of granulated sugar, which is approximately 2.2×2.2×2.2 cm$^3$ and weigh approximately 8 g. In one embodiment, a solid tabletop sweetener is in the form of a tablet or any other form known to those skilled in the art.

A tabletop sweetener composition also may be embodied in the form of a liquid, wherein a compound of the present invention is combined with a liquid carrier. Suitable non-limiting examples of carrier agents for liquid tabletop sweeteners include water, alcohol, polyol, glycerin base or citric acid base dissolved in water, and mixtures thereof. The sweetness equivalent of a tabletop sweetener composition for any of the forms described herein or known in the art may be varied to obtain a desired sweetness profile. For example, a tabletop sweetener composition may comprise a sweetness comparable to that of an equivalent amount of standard sugar. In another embodiment, the tabletop sweetener composition may comprise a sweetness of up to 100 times that of an equivalent amount of sugar. In another embodiment, the tabletop sweetener composition may comprise a sweetness of up to 90 times, 80 times, 70 times, 60 times, 50 times, 40 times, 30 times, 20 times, 10 times, 9 times, 8 times, 7 times, 6 times, 5 times, 4 times, 3 times, and 2 times that of an equivalent amount of sugar.

In some embodiments, the compositions, e.g. sweetener compositions and flavor enhanced compositions, contain one or more additional sweeteners. The additional sweetener can be any type of sweetener, for example, a natural or synthetic sweetener.

For example, the at least one additional sweetener may be a carbohydrate sweetener. Non-limiting examples of suitable carbohydrate sweeteners include sucrose, fructose, glucose, erythritol, maltitol, lactitol, sorbitol, mannitol, xylitol, tagatose, trehalose, galactose, rhamnose, cyclodextrin (e.g., α-cyclodextrin, β-cyclodextrin, and γ-cyclodextrin), ribulose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, glucosamine, mannosamine, fucose, fuculose, glucuronic acid, gluconic acid, glucono-lactone, abequose, galactosamine, xylo-oligosaccharides (xylotriose, xylobiose and the like), gentio-oligosaccharides (gentiobiose, gentiotriose, gentiotetraose and the like), galacto-oligosaccharides, sorbose, ketotriose (dehydroxyacetone), aldotriose (glyceraldehyde), nigero-oligosaccharides, fructooligosaccharides (kestose, nystose and the like), maltotetraose, maltotriol, tetrasaccharides, mannan-oligosaccharides, malto-oligosaccharides (maltotriose, maltotetraose, maltopentaose, maltohexaose, maltoheptaose and the like), dextrins, lactulose, melibiose, raffinose, rhamnose, ribose, isomerized liquid sugars such as high fructose corn/starch syrup (HFCS/HFSS) (e.g., HFCS55, HFCS42, or HFCS90), coupling sugars, soybean oligosaccharides, glucose syrup and combinations thereof. D- or L-configurations can be used when applicable.

In another embodiment, the additional sweetener is a carbohydrate sweetener selected from, but not limited to, the group of glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose.

In yet other embodiments, the at least one additional sweetener is a synthetic sweetener. As used herein, the phrase "synthetic sweetener" refers to any composition which is not found naturally occurring in nature and characteristically has a sweetness potency greater than sucrose, fructose, or glucose, yet has less calories. Non-limiting examples of synthetic high-potency sweeteners suitable for embodiments of this disclosure include sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof. The synthetic sweetener is present in the composition in an amount effective to provide a concentration from about 0.3 ppm to about 3,500 ppm when present in a consumable, such as, for example, a beverage.

In still other embodiments, the additional sweetener can be a natural high potency sweetener. Suitable natural high potency sweeteners include, but are not limited to, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside N, rebaudioside O, dulcoside A, dulcoside B, rubusoside, *stevia*, stevioside, mogroside IV, mogroside V, Luo han guo, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside and cyclocarioside I. The natural high potency sweetener can be provided as a pure compound or, alternatively, as part of an extract. For example, rebaudioside A can be provided as a sole compound or as part of a *Stevia* extract. The natural high potency sweetener is present in the composition in an amount effective to provide a concentration from about 0.1 ppm to about 3,000 ppm when present in a consumable, such as, for example, a beverage.

In still other embodiments, the additional sweetener can be chemically or enzymatically modified natural high potency sweetener. Modified natural high potency sweeteners include glycosylated natural high potency sweetener such as glucosyl-, galactosyl-, fructosyl-derivatives containing 1-50 glycosidic residues. Glycosylated natural high potency sweeteners may be prepared by enzymatic transglycosylation reaction catalyzed by various enzymes possessing transglycosylating activity.

The compositions can be customized to provide the desired calorie content. For example, compositions can be "full-calorie", such that they impart the desired sweetness when added to a consumable (such as, for example, a beverage) and have about 120 calories per 8 oz serving. Alternatively, compositions can be "mid-calorie", such that they impart the desired sweetness when added to a consumable (such as, for example, as beverage) and have less than about 60 calories per 8 oz serving. In other embodiments, compositions can be "low-calorie", such that they impart the desired sweetness when added to a consumable (such as, for example, as beverage) and have less than 40 calories per 8 oz serving. In still other embodiments, the compositions can be "zero-calorie", such that they impart the desired sweetness when added to a consumable (such as, for example, a beverage) and have less than 5 calories per 8 oz. serving.

d. Additives

The compositions of the present invention may optionally include additional additives, detailed herein below. In some embodiments, the compositions contain additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, emulsifiers, weighing agents, gums, colorants, flavonoids, alcohols, polymers, essential oils, anti-fungal agents and combinations thereof. In some embodiments, the additives act to improve the temporal and flavor profile of the sweetener(s) to provide a taste similar to sucrose.

Suitable amino acid additives include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid (α-, β-, and/or δ-isomers), glutamine, hydroxyproline, taurine, norvaline, sarcosine, and their salt forms such as sodium or potassium salts or acid salts. The amino acid additives also may be in the D- or L-configuration and in the mono-, di-, or tri-form of the same or different amino acids. Additionally, the amino acids may be α-, β-, γ- and/or δ-isomers if appropriate. Combinations of the foregoing amino acids and their corresponding salts (e.g., sodium, potassium, calcium, magnesium salts or other alkali or alkaline earth metal salts thereof, or acid salts) also are suitable additives in some embodiments. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine. Suitable polyamino acid additives include poly-L-aspartic acid, poly-L-lysine (e.g., poly-L-α-lysine or poly-L-ε-lysine), poly-L-ornithine (e.g., poly-L-α-ornithine or poly-L-ε-ornithine), poly-L-arginine, other polymeric forms of amino acids, and salt forms thereof (e.g., calcium, potassium, sodium, or magnesium salts such as L-glutamic acid mono sodium salt). The poly-amino acid additives also may be in the D- or L-configuration. Additionally, the poly-amino acids may be α-, β-, γ-, δ-, and ε-isomers if appropriate. Combinations of the foregoing poly-amino acids and their corresponding salts (e.g., sodium, potassium, calcium, magnesium salts or other alkali or alkaline earth metal salts thereof or acid salts) also are suitable additives in some embodiments. The poly-amino acids described herein also may comprise co-polymers of different amino acids. The poly-amino acids may be natural or synthetic. The poly-amino acids also may be modified, such that at least one atom has been added, removed, substituted, or combinations thereof (e.g., N-alkyl poly-amino acid or N-acyl poly-amino acid). As used herein, poly-amino acids encompass both modified and unmodified poly-amino acids. For example, modified poly-amino acids include, but are not limited to, poly-amino acids of various molecular weights (MW), such as poly-L-α-lysine with a MW of 1,500, MW of 6,000, MW of 25,200, MW of 63,000, MW of 83,000, or MW of 300,000.

In particular embodiments, the amino acid is present in an amount effective to provide a concentration from about 10 ppm to about 50,000 ppm when present in a consumable, such as, for example, a beverage. In another embodiment, the amino acid is present in an amount effective to provide a concentration from about 1,000 ppm to about 10,000 ppm when present in a consumable, such as, for example, from about 2,500 ppm to about 5,000 ppm or from about 250 ppm to about 7,500 ppm.

Suitable sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

Suitable nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil).

The nucleotide is present in an amount effective to provide a concentration from about 5 ppm to about 1,000 ppm when present in consumable, such as, for example, a beverage.

Suitable organic acid additives include any compound which comprises a —COOH moiety, such as, for example, C2-C30 carboxylic acids, substituted hydroxyl C2-C30 carboxylic acids, butyric acid (ethyl esters), substituted butyric acid (ethyl esters), benzoic acid, substituted benzoic acids (e.g., 2,4-dihydroxybenzoic acid, 3-hydroxybenzoic acid, 3,4,5-trihydroxybenzoic acid), substituted cinnamic acids, hydroxyacids, substituted hydroxybenzoic acids, anisic acid substituted cyclohexyl carboxylic acids, tannic acid, aconitic acid, lactic acid, tartaric acid, citric acid, isocitric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration.

Suitable organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), sorbic acid and adipic acid. The examples of the organic acid additives described optionally may be substituted with at least one group chosen from hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phosphor or phosphonato. In particular embodiments, the organic acid additive is present in an amount from about 10 ppm to about 5,000 ppm when present in a consumable, such as, for example, a beverage.

Suitable inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

The inorganic acid additive is present in an amount effective to provide a concentration from about 25 ppm to about 25,000 ppm when present in a consumable, such as, for example, a beverage.

Suitable bitter compound additives include, but are not limited to, caffeine, quinine, urea, bitter orange oil, naringin, quassia, and salts thereof.

The bitter compound is present in an amount effective to provide a concentration from about 25 ppm to about 25,000 ppm when present in a consumable, such as, for example, a beverage.

Suitable flavorant and flavoring ingredient additives for include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Döhler™ Natural Flavoring Sweetness Enhancer K14323 (Döhler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

The flavorant is present in an amount effective to provide a concentration from about 0.1 ppm to about 5,000 ppm when present in a consumable, such as, for example, a beverage.

Suitable polymer additives include, but are not limited to, chitosan, pectin, pectic, pectinic, polyuronic, polygalacturonic acid, starch, food hydrocolloid or crude extracts thereof (e.g., gum *acacia* senegal (Fibergum™), gum *acacia* seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers.

The polymer is present in an amount effective to provide a concentration from about 30 ppm to about 2,000 ppm when present in a consumable, such as, for example, a beverage.

Suitable protein or protein hydrolysate additives include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

The protein hydrosylate is present in an amount effective to provide a concentration from about 200 ppm to about 50,000 ppm when present in a consumable, such as, for example, a beverage.

Suitable flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like.

The flavonoid additive is present in an amount effective to provide a concentration from about 0.1 ppm to about 1,000 ppm when present in consumable, such as, for example, a beverage.

Suitable colorants include, but are not limited to, caramel color, natural colors such as Annatto, cochineal, betanin, turmeric, paprika, saffron, lycopene, elderberry juice, pandan, yellow No. 6, yellow No. 5, red No. 40, green No. 3 and blue No. 1.

Suitable alcohol additives include, but are not limited to, ethanol. In particular embodiments, the alcohol additive is present in the an amount effective to provide a concentration from about 625 ppm to about 10,000 ppm when present in a consumable, such as, for example, a beverage.

Suitable astringent compound additives include, but are not limited to, tannic acid, europium chloride ($EuCl_3$), gadolinium chloride ($GdCl_3$), terbium chloride ($TbCl_3$), alum, tannic acid, and polyphenols (e.g., tea polyphenols). The astringent additive is present in an amount effective to provide a concentration from about 10 ppm to about 5,000 ppm when present in a consumable, such as, for example, a beverage.

Suitable essential oils include, but are not limited to, mustard oil, bitter orange and sweet orange, menthe *arvensis*, peppermint, cedarwood, lemon, *eucalyptus globulus, litsea cubeba*, clove and spearmint.

Suitable anti-fungal agents include, but are not limited to, Natamycin, amphotericin, anidulafungin, caspofungin, fluconazole, itraconazole, micafungin, posaconazole, voriconazole, and flucytosine.

Other additives include typical beverages additives, i.e. glycerol ester of wood rosin, coconut oil, brominated vegetable oil, carob bean gum, sucrose acetate isobutyrate, modified food starch, zinc gluconate and vitamin A palmitate.

g. Functional Ingredients

The compositions provided herein can also contain one or more functional ingredients, which provide a real or perceived heath benefit to the composition. Functional ingredients include, but are not limited to, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

i. Saponin

In certain embodiments, the functional ingredient is at least one saponin. As used herein, the at least one saponin may comprise a single saponin or a plurality of saponins as a functional ingredient for the composition provided herein. Generally, according to particular embodiments of this invention, the at least one saponin is present in the composition in an amount sufficient to promote health and wellness.

Saponins are glycosidic natural plant products comprising an aglycone ring structure and one or more sugar moieties. The combination of the nonpolar aglycone and the water soluble sugar moiety gives saponins surfactant properties, which allow them to form a foam when shaken in an aqueous solution.

The saponins are grouped together based on several common properties. In particular, saponins are surfactants which display hemolytic activity and form complexes with cholesterol. Although saponins share these properties, they are structurally diverse. The types of aglycone ring structures forming the ring structure in saponins can vary greatly. Non-limiting examples of the types of aglycone ring structures in saponin for use in particular embodiments of the invention include steroids, triterpenoids, and steroidal alkaloids. Non-limiting examples of specific aglycone ring structures for use in particular embodiments of the invention include soyasapogenol A, soyasapogenol B and soyasopogenol E. The number and type of sugar moieties attached to the aglycone ring structure can also vary greatly. Non-limiting examples of sugar moieties for use in particular embodiments of the invention include glucose, galactose, glucuronic acid, xylose, rhamnose, and methylpentose moieties. Non-limiting examples of specific saponins for use in particular embodiments of the invention include group A acetyl saponin, group B acetyl saponin, and group E acetyl saponin.

Saponins can be found in a large variety of plants and plant products, and are especially prevalent in plant skins and barks where they form a waxy protective coating. Several common sources of saponins include soybeans, which have approximately 5% saponin content by dry weight, soapwort plants (*Saponaria*), the root of which was used historically as soap, as well as alfalfa, aloe, asparagus, grapes, chickpeas, *yucca*, and various other beans and weeds. Saponins may be obtained from these sources by using extraction techniques well known to those of ordinary skill in the art. A description of conventional extraction techniques can be found in U.S. Pat. Appl. No. 2005/0123662, the disclosure of which is expressly incorporated by reference.

ii. Antioxidant

In certain embodiments, the functional ingredient is at least one antioxidant. As used herein, the at least one antioxidant may comprise a single antioxidant or a plurality of antioxidants as a functional ingredient for the compositions provided herein. Generally, according to particular embodiments of this invention, the at least one antioxidant is present in the composition in an amount sufficient to promote health and wellness.

As used herein "antioxidant" refers to any substance which inhibits, suppresses, or reduces oxidative damage to cells and biomolecules. Without being bound by theory, it is believed that antioxidants inhibit, suppress, or reduce oxidative damage to cells or biomolecules by stabilizing free radicals before they can cause harmful reactions. As such, antioxidants may prevent or postpone the onset of some degenerative diseases.

Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-α-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), *aronia* extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains, or cereal grains.

Particular antioxidants belong to the class of phytonutrients called polyphenols (also known as "polyphenolics"), which are a group of chemical substances found in plants, characterized by the presence of more than one phenol group per molecule. A variety of health benefits may be derived from polyphenols, including prevention of cancer, heart disease, and chronic inflammatory disease and improved mental strength and physical strength, for example. Suitable polyphenols for embodiments of this invention include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials, and combinations thereof.

In particular embodiments, the antioxidant is a catechin such as, for example, epigallocatechin gallate (EGCG). Suitable sources of catechins for embodiments of this invention include, but are not limited to, green tea, white tea, black tea, oolong tea, chocolate, cocoa, red wine, grape seed, red grape skin, purple grape skin, red grape juice, purple grape juice, berries, pycnogenol, and red apple peel.

In some embodiments, the antioxidant is chosen from proanthocyanidins, procyanidins or combinations thereof. Suitable sources of proanthocyanidins and procyanidins for embodiments of this invention include, but are not limited to, red grapes, purple grapes, cocoa, chocolate, grape seeds, red wine, cacao beans, cranberry, apple peel, plum, blueberry, black currants, choke berry, green tea, sorghum, cinnamon, barley, red kidney bean, pinto bean, hops, almonds, hazelnuts, pecans, pistachio, pycnogenol, and colorful berries.

In particular embodiments, the antioxidant is an anthocyanin. Suitable sources of anthocyanins for embodiments of this invention include, but are not limited to, red berries, blueberries, bilberry, cranberry, raspberry, cherry, pomegranate, strawberry, elderberry, choke berry, red grape skin, purple grape skin, grape seed, red wine, black currant, red currant, cocoa, plum, apple peel, peach, red pear, red cabbage, red onion, red orange, and blackberries.

In some embodiments, the antioxidant is chosen from quercetin, rutin or combinations thereof. Suitable sources of quercetin and rutin for embodiments of this invention include, but are not limited to, red apples, onions, kale, bog whortleberry, lingonberrys, chokeberry, cranberry, blackberry, blueberry, strawberry, raspberry, black currant, green tea, black tea, plum, apricot, parsley, leek, broccoli, chili pepper, berry wine, and ginkgo.

In some embodiments, the antioxidant is reservatrol. Suitable sources of reservatrol for embodiments of this invention include, but are not limited to, red grapes, peanuts, cranberry, blueberry, bilberry, mulberry, Japanese Itadori tea, and red wine.

In particular embodiments, the antioxidant is an isoflavone. Suitable sources of isoflavones for embodiments of this invention include, but are not limited to, soy beans, soy products, legumes, alfalfa spouts, chickpeas, peanuts, and red clover.

In some embodiments, the antioxidant is curcumin. Suitable sources of curcumin for embodiments of this invention include, but are not limited to, turmeric and mustard.

In particular embodiments, the antioxidant is chosen from punicalagin, ellagitannin or combinations thereof. Suitable sources of punicalagin and ellagitannin for embodiments of this invention include, but are not limited to, pomegranate, raspberry, strawberry, walnut, and oak-aged red wine.

In some embodiments, the antioxidant is a citrus flavonoid, such as hesperidin or naringin. Suitable sources of citrus flavonoids, such as hesperidin or naringin, for embodiments of this invention include, but are not limited to, oranges, grapefruits, and citrus juices.

In particular embodiments, the antioxidant is chlorogenic acid. Suitable sources of chlorogenic acid for embodiments of this invention include, but are not limited to, green coffee, yerba mate, red wine, grape seed, red grape skin, purple grape skin, red grape juice, purple grape juice, apple juice, cranberry, pomegranate, blueberry, strawberry, sunflower, *Echinacea*, pycnogenol, and apple peel.

iii. Dietary Fiber

In certain embodiments, the functional ingredient is at least one dietary fiber source. As used herein, the at least one dietary fiber source may comprise a single dietary fiber source or a plurality of dietary fiber sources as a functional ingredient for the compositions provided herein. Generally, according to particular embodiments of this invention, the at least one dietary fiber source is present in the composition in an amount sufficient to promote health and wellness.

Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins, and combinations thereof.

Polysaccharides are complex carbohydrates composed of monosaccharides joined by glycosidic linkages. Non-starch polysaccharides are bonded with β-linkages, which humans are unable to digest due to a lack of an enzyme to break the β-linkages. Conversely, digestible starch polysaccharides generally comprise α-(1-4) linkages.

Lignin is a large, highly branched and cross-linked polymer based on oxygenated phenylpropane units. Cellulose is a linear polymer of glucose molecules joined by a β-(1-4) linkage, which mammalian amylases are unable to hydrolyze. Methylcellulose is a methyl ester of cellulose that is often used in foodstuffs as a thickener, and emulsifier. It is commercially available (e.g., Citrucel by GlaxoSmithKline, Celevac by Shire Pharmaceuticals). Hemicelluloses are highly branched polymers consisting mainly of glucurono- and 4-O-methylglucuroxylans. β-Glucans are mixed-linkage (1-3), (1-4) β-D-glucose polymers found primarily in cereals, such as oats and barley. Pectins, such as beta pectin, are a group of polysaccharides composed primarily of D-galacturonic acid, which is methoxylated to variable degrees.

Gums and mucilages represent a broad array of different branched structures. Guar gum, derived from the ground endosperm of the guar seed, is a galactomannan. Guar gum is commercially available (e.g., Benefiber by Novartis AG). Other gums, such as gum arabic and pectins, have still different structures. Still other gums include xanthan gum, gellan gum, tara gum, psylium seed husk gum, and locust been gum.

Waxes are esters of ethylene glycol and two fatty acids, generally occurring as a hydrophobic liquid that is insoluble in water.

Inulins comprise naturally occurring oligosaccharides belonging to a class of carbohydrates known as fructans. They generally are comprised of fructose units joined by β-(2-1) glycosidic linkages with a terminal glucose unit. Oligosaccharides are saccharide polymers containing typically three to six component sugars. They are generally found either O- or N-linked to compatible amino acid side chains in proteins or to lipid molecules. Fructooligosaccharides are oligosaccharides consisting of short chains of fructose molecules.

Food sources of dietary fiber include, but are not limited to, grains, legumes, fruits, and vegetables. Grains providing dietary fiber include, but are not limited to, oats, rye, barley, wheat. Legumes providing fiber include, but are not limited to, peas and beans such as soybeans. Fruits and vegetables providing a source of fiber include, but are not limited to, apples, oranges, pears, bananas, berries, tomatoes, green beans, broccoli, cauliflower, carrots, potatoes, celery. Plant foods such as bran, nuts, and seeds (such as flax seeds) are also sources of dietary fiber. Parts of plants providing dietary fiber include, but are not limited to, the stems, roots, leaves, seeds, pulp, and skin.

Although dietary fiber generally is derived from plant sources, indigestible animal products such as chitins are also classified as dietary fiber. Chitin is a polysaccharide composed of units of acetylglucosamine joined by β-(1-4) linkages, similar to the linkages of cellulose.

Sources of dietary fiber often are divided into categories of soluble and insoluble fiber based on their solubility in water. Both soluble and insoluble fibers are found in plant foods to varying degrees depending upon the characteristics of the plant. Although insoluble in water, insoluble fiber has passive hydrophilic properties that help increase bulk, soften stools, and shorten transit time of fecal solids through the intestinal tract.

Unlike insoluble fiber, soluble fiber readily dissolves in water. Soluble fiber undergoes active metabolic processing via fermentation in the colon, increasing the colonic microflora and thereby increasing the mass of fecal solids. Fermentation of fibers by colonic bacteria also yields end-products with significant health benefits. For example, fermentation of the food masses produces gases and short-chain fatty acids. Acids produced during fermentation include butyric, acetic, propionic, and valeric acids that have various beneficial properties such as stabilizing blood glucose levels by acting on pancreatic insulin release and providing liver control by glycogen breakdown. In addition, fiber fermentation may reduce atherosclerosis by lowering cholesterol synthesis by the liver and reducing blood levels of LDL and triglycerides. The acids produced during fermentation lower colonic pH, thereby protecting the colon lining from cancer polyp formation. The lower colonic pH also increases mineral absorption, improves the barrier properties of the colonic mucosal layer, and inhibits inflammatory and adhesion irritants. Fermentation of fibers also may benefit the immune system by stimulating production of T-helper cells, antibodies, leukocytes, splenocytes, cytokinins and lymphocytes.

iv. Fatty Acid

In certain embodiments, the functional ingredient is at least one fatty acid. As used herein, the at least one fatty acid may be single fatty acid or a plurality of fatty acids as a functional ingredient for the compositions provided herein. Generally, according to particular embodiments of this invention, the at least one fatty acid is present in the composition in an amount sufficient to promote health and wellness.

As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

Suitable omega-3 fatty acids for use in embodiments of the present invention can be derived from algae, fish, animals, plants, or combinations thereof, for example. Examples of suitable omega-3 fatty acids include, but are not limited to, linolenic acid, alpha-linolenic acid, eicosapentaenoic acid, docosahexaenoic acid, stearidonic acid, eicosatetraenoic acid and combinations thereof. In some embodiments, suitable omega-3 fatty acids can be provided in fish oils, (e.g., menhaden oil, tuna oil, salmon oil, bonito oil, and cod oil), microalgae omega-3 oils or combinations thereof. In particular embodiments, suitable omega-3 fatty acids may be derived from commercially available omega-3 fatty acid oils such as Microalgae DHA oil (from Martek, Columbia, Md.), OmegaPure (from Omega Protein, Houston, Tex.), Marinol C-38 (from Lipid Nutrition, Channahon, Ill.), Bonito oil and MEG-3 (from Ocean Nutrition, Dartmouth, NS), Evogel (from Symrise, Holzminden, Germany), Marine Oil, from tuna or salmon (from Arista Wilton, Conn.), OmegaSource 2000, Marine Oil, from menhaden and Marine Oil, from cod (from OmegaSource, RTP, NC).

Suitable omega-6 fatty acids include, but are not limited to, linoleic acid, gamma-linolenic acid, dihommo-gamma-linolenic acid, arachidonic acid, eicosadienoic acid, docosadienoic acid, adrenic acid, docosapentaenoic acid and combinations thereof.

Suitable esterified fatty acids for embodiments of the present invention may include, but are not limited to, monoacylglycerols containing omega-3 and/or omega-6 fatty acids, diacylglycerols containing omega-3 and/or omega-6 fatty acids, or triacylglycerols containing omega-3 and/or omega-6 fatty acids and combinations thereof.

v. Vitamin

In certain embodiments, the functional ingredient is at least one vitamin.

As used herein, the at least one vitamin may be single vitamin or a plurality of vitamins as a functional ingredient for the compositions provided herein. Generally, according to particular embodiments of this invention, the at least one vitamin is present in the composition in an amount sufficient to promote health and wellness.

Vitamins are organic compounds that the human body needs in small quantities for normal functioning. The body uses vitamins without breaking them down, unlike other nutrients such as carbohydrates and proteins. To date, thirteen vitamins have been recognized, and one or more can be used in the compositions herein. Suitable vitamins include vitamin A, vitamin D, vitamin E, vitamin K, vitamin B1, vitamin B2, vitamin B3, vitamin B5, vitamin B6, vitamin B7, vitamin B9, vitamin B12, and vitamin C. Many of vitamins also have alternative chemical names, non-limiting examples of which are provided below.

| Vitamin | Alternative names |
| --- | --- |
| Vitamin A | Retinol |
| | Retinaldehyde |
| | Retinoic acid |
| | Retinoids |
| | Retinal |
| | Retinoic ester |
| Vitamin D (vitamins D1-D5) | Calciferol |
| | Cholecalciferol |
| | Lumisterol |
| | Ergocalciferol |
| | Dihydrotachysterol |
| | 7-dehydrocholesterol |
| Vitamin E | Tocopherol |
| | Tocotrienol |
| Vitamin K | Phylloquinone |
| | Naphthoquinone |
| Vitamin B1 | Thiamin |
| Vitamin B2 | Riboflavin |
| | Vitamin G |
| Vitamin B3 | Niacin |
| | Nicotinic acid |
| | Vitamin PP |
| Vitamin B5 | Pantothenic acid |
| Vitamin B6 | Pyridoxine |
| | Pyridoxal |
| | Pyridoxamine |
| Vitamin B7 | Biotin |
| | Vitamin H |
| Vitamin B9 | Folic acid |
| | Folate |
| | Folacin |
| | Vitamin M |
| | Pteroyl-L-glutamic acid |
| Vitamin B12 | Cobalamin |
| | Cyanocobalamin |
| Vitamin C | Ascorbic acid |

Various other compounds have been classified as vitamins by some authorities. These compounds may be termed pseudo-vitamins and include, but are not limited to, compounds such as ubiquinone (coenzyme Q10), pangamic acid, dimethylglycine, taestrile, amygdaline, flavanoids, para-aminobenzoic acid, adenine, adenylic acid, and s-methyl-methionine. As used herein, the term vitamin includes pseudo-vitamins.

In some embodiments, the vitamin is a fat-soluble vitamin chosen from vitamin A, D, E, K and combinations thereof.

In other embodiments, the vitamin is a water-soluble vitamin chosen from vitamin B1, vitamin B2, vitamin B3, vitamin B6, vitamin B12, folic acid, biotin, pantothenic acid, vitamin C and combinations thereof vi. Glucosamine In certain embodiments, the functional ingredient is glucosamine.

Generally, according to particular embodiments of this invention, glucosamine is present in the compositions in an amount sufficient to promote health and wellness.

Glucosamine, also called chitosamine, is an amino sugar that is believed to be an important precursor in the biochemical synthesis of glycosylated proteins and lipids. D-glucosamine occurs naturally in the cartilage in the form of glucosamine-6-phosphate, which is synthesized from fructose-6-phosphate and glutamine. However, glucosamine also is available in other forms, non-limiting examples of which include glucosamine hydrochloride, glucosamine sulfate, N-acetyl-glucosamine, or any other salt forms or combinations thereof. Glucosamine may be obtained by acid hydrolysis of the shells of lobsters, crabs, shrimps, or prawns using methods well known to those of ordinary skill in the art. In a particular embodiment, glucosamine may be derived from fungal biomass containing chitin, as described in U.S. Patent Publication No. 2006/0172392.

The compositions can further comprise chondroitin sulfate.

vii. Mineral

In certain embodiments, the functional ingredient is at least one mineral.

As used herein, the at least one mineral may be single mineral or a plurality of minerals as a functional ingredient for the compositions provided herein. Generally, according to particular embodiments of this invention, the at least one mineral is present in the composition in an amount sufficient to promote health and wellness.

Minerals, in accordance with the teachings of this invention, comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages.

Minerals may be categorized as either bulk minerals, which are required in relatively large amounts, or trace minerals, which are required in relatively small amounts. Bulk minerals generally are required in amounts greater than or equal to about 100 mg per day and trace minerals are those that are required in amounts less than about 100 mg per day.

In particular embodiments of this invention, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In other particular embodiments of this invention, the mineral is a trace mineral, believed to be necessary for human nutrition, non-limiting examples of which include bismuth, boron, lithium, nickel, rubidium, silicon, strontium, tellurium, tin, titanium, tungsten, and vanadium.

The minerals embodied herein may be in any form known to those of ordinary skill in the art. For example, in a particular embodiment the minerals may be in their ionic form, having either a positive or negative charge. In another particular embodiment the minerals may be in their molecular form. For example, sulfur and phosphorous often are found naturally as sulfates, sulfides, and phosphates.

viii. Preservative

In certain embodiments, the functional ingredient is at least one preservative.

As used herein, the at least one preservative may be single preservative or a plurality of preservatives as a functional ingredient for the compositions provided herein. Generally, according to particular embodiments of this invention, the at least one preservative is present in the composition in an amount sufficient to promote health and wellness.

In particular embodiments of this invention, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone.

According to a particular embodiment, the preservative is a sulfite. Sulfites include, but are not limited to, sulfur dioxide, sodium bisulfite, and potassium hydrogen sulfite.

According to another particular embodiment, the preservative is a propionate. Propionates include, but are not limited to, propionic acid, calcium propionate, and sodium propionate.

According to yet another particular embodiment, the preservative is a benzoate. Benzoates include, but are not limited to, sodium benzoate and benzoic acid.

In another particular embodiment, the preservative is a sorbate. Sorbates include, but are not limited to, potassium sorbate, sodium sorbate, calcium sorbate, and sorbic acid.

In still another particular embodiment, the preservative is a nitrate and/or a nitrite. Nitrates and nitrites include, but are not limited to, sodium nitrate and sodium nitrite.

In yet another particular embodiment, the at least one preservative is a bacteriocin, such as, for example, nisin.

In another particular embodiment, the preservative is ethanol.

In still another particular embodiment, the preservative is ozone.

Non-limiting examples of antienzymatics suitable for use as preservatives in particular embodiments of the invention include ascorbic acid, citric acid, and metal chelating agents such as ethylenediaminetetraacetic acid (EDTA).

ix. Hydration Agent

In certain embodiments, the functional ingredient is at least one hydration agent.

As used herein, the at least one hydration agent may be single hydration agent or a plurality of hydration agents as a functional ingredient for the compositions provided herein. Generally, according to particular embodiments of this invention, the at least one hydration agent is present in the composition in an amount sufficient to promote health and wellness.

Hydration products help the body to replace fluids that are lost through excretion. For example, fluid is lost as sweat in order to regulate body temperature, as urine in order to excrete waste substances, and as water vapor in order to exchange gases in the lungs. Fluid loss can also occur due to a wide range of external causes, non-limiting examples of which include physical activity, exposure to dry air, diarrhea, vomiting, hyperthermia, shock, blood loss, and hypotension. Diseases causing fluid loss include diabetes, cholera, gastroenteritis, shigellosis, and yellow fever. Forms of malnutrition that cause fluid loss include the excessive consumption of alcohol, electrolyte imbalance, fasting, and rapid weight loss.

In a particular embodiment, the hydration product is a composition that helps the body replace fluids that are lost during exercise. Accordingly, in a particular embodiment, the hydration product is an electrolyte, non-limiting examples of which include sodium, potassium, calcium, magnesium, chloride, phosphate, bicarbonate, and combinations thereof. Suitable electrolytes for use in particular embodiments of this invention are also described in U.S. Pat. No. 5,681,569, the disclosure of which is expressly incorporated herein by reference. In particular embodiments, the electrolytes are obtained from their corresponding water-soluble salts. Non-limiting examples of salts for use in particular embodiments include chlorides, carbonates, sulfates, acetates, bicarbonates, citrates, phosphates, hydrogen phosphates, tartrates, sorbates, citrates, benzoates, or combinations thereof. In other embodiments, the electrolytes are provided by juice, fruit extracts, vegetable extracts, tea, or teas extracts.

In particular embodiments of this invention, the hydration product is a carbohydrate to supplement energy stores burned by muscles. Suitable carbohydrates for use in particular embodiments of this invention are described in U.S. Pat. Nos. 4,312,856, 4,853,237, 5,681,569, and 6,989,171, the disclosures of which are expressly incorporated herein by reference. Non-limiting examples of suitable carbohydrates include monosaccharides, disaccharides, oligosaccharides, complex polysaccharides or combinations thereof. Non-limiting examples of suitable types of monosaccharides for use in particular embodiments include trioses, tetroses, pentoses, hexoses, heptoses, octoses, and nonoses. Non-limiting examples of specific types of suitable monosaccharides include glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose. Non-limiting examples of suitable disaccharides include sucrose, lactose, and maltose. Non-limiting examples of suitable oligosaccharides include saccharose, maltotriose, and maltodextrin. In other particular embodiments, the carbohydrates are provided by a corn syrup, a beet sugar, a cane sugar, a juice, or a tea.

In another particular embodiment, the hydration is a flavanol that provides cellular rehydration. Flavanols are a class of natural substances present in plants, and generally comprise a 2-phenylbenzopyrone molecular skeleton attached to one or more chemical moieties. Non-limiting examples of suitable flavanols for use in particular embodiments of this invention include catechin, epicatechin, gallocatechin, epigallocatechin, epicatechin gallate, epigallocatechin 3-gallate, theaflavin, theaflavin 3-gallate, theaflavin 3'-gallate, theaflavin 3,3' gallate, thearubigin or combinations thereof. Several common sources of flavanols include tea plants, fruits, vegetables, and flowers. In preferred embodiments, the flavanol is extracted from green tea.

In a particular embodiment, the hydration product is a glycerol solution to enhance exercise endurance. The ingestion of a glycerol containing solution has been shown to provide beneficial physiological effects, such as expanded blood volume, lower heart rate, and lower rectal temperature.

x. Probiotics/Prebiotics

In certain embodiments, the functional ingredient is chosen from at least one probiotic, prebiotic and combination thereof.

As used herein, the at least one probiotic or prebiotic may be single probiotic or prebiotic or a plurality of probiotics or prebiotics as a functional ingredient for the compositions provided herein. Generally, according to particular embodiments of this invention, the at least one probiotic, prebiotic or combination thereof is present in the composition in an amount sufficient to promote health and wellness.

Probiotics, in accordance with the teachings of this invention, comprise microorganisms that benefit health when consumed in an effective amount. Desirably, probiotics beneficially affect the human body's naturally-occurring gastrointestinal microflora and impart health benefits apart from nutrition. Probiotics may include, without limitation, bacteria, yeasts, and fungi.

Prebiotics, in accordance with the teachings of this invention, are compositions that promote the growth of beneficial bacteria in the intestines. Prebiotic substances can be consumed by a relevant probiotic, or otherwise assist in keeping the relevant probiotic alive or stimulate its growth. When consumed in an effective amount, prebiotics also beneficially affect the human body's naturally-occurring gastrointestinal microflora and thereby impart health benefits apart from just nutrition. Prebiotic foods enter the colon and serve as substrate for the endogenous bacteria, thereby indirectly providing the host with energy, metabolic substrates, and essential micronutrients. The body's digestion and absorption of prebiotic foods is dependent upon bacterial metabolic activity, which salvages energy for the host from nutrients that escaped digestion and absorption in the small intestine.

According to particular embodiments, the probiotic is a beneficial microorganisms that beneficially affects the human body's naturally-occurring gastrointestinal microflora and imparts health benefits apart from nutrition. Examples of probiotics include, but are not limited to, bacteria of the genus *Lactobacilli, Bifidobacteria, Streptococci*, or combinations thereof, that confer beneficial effects to humans.

In particular embodiments of the invention, the at least one probiotic is chosen from the genus *Lactobacilli*. *Lactobacilli* (i.e., bacteria of the genus *Lactobacillus*, hereinafter "L.") have been used for several hundred years as a food preservative and for promoting human health. Non-limiting examples of species of *Lactobacilli* found in the human intestinal tract include *L. acidophilus, L. casei, L. fermentum, L. saliva roes, L. brevis, L. leichmannii, L. plantarum, L. cellobiosus, L. reuteri, L. rhamnosus, L. GG, L. bulgaricus*, and *L. thermophilus*.

According to other particular embodiments of this invention, the probiotic is chosen from the genus *Bifidobacteria*. *Bifidobacteria* also are known to exert a beneficial influence on human health by producing short chain fatty acids (e.g., acetic, propionic, and butyric acids), lactic, and formic acids as a result of carbohydrate metabolism. Non-limiting species of *Bifidobacteria* found in the human gastrointestinal tract include *B. angulatum, B. animalis, B. asteroides, B. bifidum, B. boum, B. breve, B. catenulatum, B. choerinum, B. coryneforme, B. cuniculi, B. dentium, B. gallicum, B. gallinarum, B indicum, B. longum, B. magnum, B. merycicum, B. minimum, B. pseudocatenulatum, B. pseudolongum, B. psychraerophilum, B. pullorum, B. ruminantium, B. saeculare, B. scardovii, B. simiae, B. subtile, B. thermacidophilum, B. thermophilum, B. urinalis*, and B. sp.

According to other particular embodiments of this invention, the probiotic is chosen from the genus *Streptococcus*. *Streptococcus thermophilus* is a gram-positive facultative anaerobe. It is classified as a lactic acid bacteria and commonly is found in milk and milk products, and is used in the production of yogurt. Other non-limiting probiotic species of this bacteria include *Streptococcus salivarus* and *Streptococcus cremoris*.

Probiotics that may be used in accordance with this invention are well-known to those of skill in the art. Non-limiting examples of foodstuffs comprising probiotics include yogurt, sauerkraut, kefir, kimchi, fermented vegetables, and other foodstuffs containing a microbial element that beneficially affects the host animal by improving the intestinal microbalance.

Prebiotics, in accordance with the embodiments of this invention, include, without limitation, mucopolysaccharides, oligosaccharides, polysaccharides, amino acids, vitamins, nutrient precursors, proteins and combinations thereof.

According to a particular embodiment of this invention, the prebiotic is chosen from dietary fibers, including, without limitation, polysaccharides and oligosaccharides. These compounds have the ability to increase the number of probiotics, which leads to the benefits conferred by the probiotics. Non-limiting examples of oligosaccharides that are categorized as prebiotics in accordance with particular embodiments of this invention include fructooligosaccharides, inulins, isomalto-oligosaccharides, lactitol, lactosucrose, lactulose, pyrodextrins, soy oligosaccharides, trans-galacto-oligosaccharides, and xylo-oligosaccharides.

According to other particular embodiments of the invention, the prebiotic is an amino acid. Although a number of known prebiotics break down to provide carbohydrates for probiotics, some probiotics also require amino acids for nourishment.

Prebiotics are found naturally in a variety of foods including, without limitation, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans).

xi. Weight Management Agent

In certain embodiments, the functional ingredient is at least one weight management agent.

As used herein, the at least one weight management agent may be single weight management agent or a plurality of weight management agents as a functional ingredient for the compositions provided herein. Generally, according to particular embodiments of this invention, the at least one weight management agent is present in the composition in an amount sufficient to promote health and wellness.

As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant" describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

Suitable weight management agents include macronutrient selected from the group consisting of proteins, carbohydrates, dietary fats, and combinations thereof. Consumption of proteins, carbohydrates, and dietary fats stimulates the release of peptides with appetite-suppressing effects. For example, consumption of proteins and dietary fats stimulates the release of the gut hormone cholecytokinin (CCK), while consumption of carbohydrates and dietary fats stimulates release of Glucagon-like peptide 1 (GLP-1).

Suitable macronutrient weight management agents also include carbohydrates. Carbohydrates generally comprise sugars, starches, cellulose and gums that the body converts into glucose for energy. Carbohydrates often are classified into two categories, digestible carbohydrates (e.g., monosaccharides, disaccharides, and starch) and non-digestible carbohydrates (e.g., dietary fiber). Studies have shown that non-digestible carbohydrates and complex polymeric carbohydrates having reduced absorption and digestibility in the small intestine stimulate physiologic responses that inhibit food intake. Accordingly, the carbohydrates embodied herein desirably comprise non-digestible carbohydrates or carbohydrates with reduced digestibility. Non-limiting examples of such carbohydrates include polydextrose; inulin; monosaccharide-derived polyols such as erythritol, mannitol, xylitol, and sorbitol; disaccharide-derived alcohols such as isomalt, lactitol, and maltitol; and hydrogenated starch hydrolysates. Carbohydrates are described in more detail herein below.

In another particular embodiment weight management agent is a dietary fat. Dietary fats are lipids comprising combinations of saturated and unsaturated fatty acids. Poly-unsaturated fatty acids have been shown to have a greater satiating power than mono-unsaturated fatty acids. Accordingly, the dietary fats embodied herein desirably comprise poly-unsaturated fatty acids, non-limiting examples of which include triacylglycerols.

In a particular embodiment, the weight management agents is an herbal extract. Extracts from numerous types of plants have been identified as possessing appetite suppressant properties. Non-limiting examples of plants whose extracts have appetite suppressant properties include plants of the genus *Hoodia, Trichocaulon, Caralluma, Stapelia, Orbea, Asclepias*, and *Camelia*. Other embodiments include extracts derived from Gymnema *Sylvestre*, Kola Nut, Citrus Auran tium, Yerba Mate, Griffonia *Simplicifolia*, Guarana, myrrh, guggul Lipid, and black current seed oil.

The herbal extracts may be prepared from any type of plant material or plant biomass. Non-limiting examples of plant material and biomass include the stems, roots, leaves, dried powder obtained from the plant material, and sap or dried sap. The herbal extracts generally are prepared by extracting sap from the plant and then spray-drying the sap. Alternatively, solvent extraction procedures may be employed. Following the initial extraction, it may be desirable to further fractionate the initial extract (e.g., by column chromatography) in order to obtain an herbal extract with enhanced activity. Such techniques are well known to those of ordinary skill in the art.

In a particular embodiment, the herbal extract is derived from a plant of the genus *Hoodia*, species of which include *H. alstonii, H. currorii, H. dregei, H. flava, H. gordonii, H. jutatae, H. mossamedensis, H. officinalis, H. parviflorai, H. pedicellata, H. pilifera, H. ruschii*, and *H. triebneri*. *Hoodia* plants are stem succulents native to southern Africa. A sterol glycoside of *Hoodia*, known as P57, is believed to be responsible for the appetite-suppressant effect of the *Hoodia* species.

In another particular embodiment, the herbal extract is derived from a plant of the genus *Caralluma*, species of which include *C. indica, C. fimbriata, C. attenuate, C. tuberculate, C. edulis, C. adscendens, C. stalagmifera, C. umbellate, C. penicillata, C. russeliana, C. retrospicens, C. Arabica*, and *C. lasiantha*. *Carralluma* plants belong to the same Subfamily as *Hoodia*, Asclepiadaceae. *Caralluma* are small, erect and fleshy plants native to India having medicinal properties, such as appetite suppression, that generally are attributed to glycosides belonging to the pregnane group of glycosides, non-limiting examples of which include caratuberside A, caratuberside B, bouceroside I, bouceroside II, bouceroside III, bouceroside IV, bouceroside V, bouceroside VI, bouceroside VII, bouceroside VIII, bouceroside IX, and bouceroside X.

In another particular embodiment, the at least one herbal extract is derived from a plant of the genus *Trichocaulon*. *Trichocaulon* plants are succulents that generally are native to southern Africa, similar to *Hoodia*, and include the species *T. piliferum* and *T. officinale*.

In another particular embodiment, the herbal extract is derived from a plant of the genus *Stapelia* or *Orbea*, species of which include *S. gigantean* and *O. variegate*, respectively. Both *Stapelia* and *Orbea* plants belong to the same Subfamily as *Hoodia*, Asclepiadaceae. Not wishing to be bound by any theory, it is believed that the compounds exhibiting appetite suppressant activity are saponins, such as pregnane glycosides, which include stavarosides A, B, C, D, E, F, G, H, I, J, and K.

In another particular embodiment, the herbal extract is derived from a plant of the genus *Asclepias*. *Asclepias* plants also belong to the Asclepiadaceae family of plants. Non-limiting examples of *Asclepias* plants include *A. incarnate, A. curassayica, A. syriaca*, and *A. tuberose*. Not wishing to be bound by any theory, it is believed that the extracts comprise steroidal compounds, such as pregnane glycosides and pregnane aglycone, having appetite suppressant effects.

In a particular embodiment, the weight management agent is an exogenous hormone having a weight management effect. Non-limiting examples of such hormones include CCK, peptide YY, ghrelin, bombesin and gastrin-releasing peptide (GRP), enterostatin, apolipoprotein A-IV, GLP-1, amylin, somastatin, and leptin.

In another embodiment, the weight management agent is a pharmaceutical drug. Non-limiting examples include phentenime, diethylpropion, phendimetrazine, sibutramine, rimonabant, oxyntomodulin, floxetine hydrochloride, ephedrine, phenethylamine, or other stimulants.

xii. Osteoporosis Management Agent

In certain embodiments, the functional ingredient is at least one osteoporosis management agent.

As used herein, the at least one osteoporosis management agent may be single osteoporosis management agent or a plurality of osteoporosis management agent as a functional ingredient for the compositions provided herein. Generally, according to particular embodiments of this invention, the at least one osteoporosis management agent is present in the composition in an amount sufficient to promote health and wellness.

Osteoporosis is a skeletal disorder of compromised bone strength, resulting in an increased risk of bone fracture. Generally, osteoporosis is characterized by reduction of the bone mineral density (BMD), disruption of bone microarchitecture, and changes to the amount and variety of non-collagenous proteins in the bone.

In certain embodiments, the osteoporosis management agent is at least one calcium source. According to a particular embodiment, the calcium source is any compound containing calcium, including salt complexes, solubilized species, and other forms of calcium. Non-limiting examples of calcium sources include amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium citrate malate, calcium gluconate, calcium tartrate, calcium lactate, solubilized species thereof, and combinations thereof.

According to a particular embodiment, the osteoporosis management agent is a magnesium source. The magnesium source is any compound containing magnesium, including salt complexes, solubilized species, and other forms of magnesium. Non-limiting examples of magnesium sources include magnesium chloride, magnesium citrate, magnesium gluceptate, magnesium gluconate, magnesium lactate, magnesium hydroxide, magnesium picolate, magnesium sulfate, solubilized species thereof, and mixtures thereof. In another particular embodiment, the magnesium source comprises an amino acid chelated or creatine chelated magnesium.

In other embodiments, the osteoporosis agent is chosen from vitamins D, C, K, their precursors and/or beta-carotene and combinations thereof.

Numerous plants and plant extracts also have been identified as being effective in the prevention and treatment of osteoporosis. Not wishing to be bound by any theory, it is believed that the plants and plant extracts stimulates bone morphogenic proteins and/or inhibits bone resorption, thereby stimulating bone regeneration and strength. Non-limiting examples of suitable plants and plant extracts as osteoporosis management agents include species of the genus *Taraxacum* and *Amelanchier*, as disclosed in U.S. Patent Publication No. 2005/0106215, and species of the genus *Lindera, Artemisia, Acorus, Carthamus, Carum, Cnidium, Curcuma, Cyperus, Juniperus, Prunus, Iris, Cichorium, Dodonaea, Epimedium, Erigonoum, Soya, Mentha, Ocimum, thymus, Tanacetum, Plantago, Spearmint, Bixa, Vitis, Rosemarinus, Rhus,* and *Anethum*, as disclosed in U.S. Patent Publication No. 2005/0079232.

xiii. Phytoestrogen

In certain embodiments, the functional ingredient is at least one phytoestrogen.

As used herein, the at least one phytoestrogen may be single phytoestrogen or a plurality of phytoestrogens as a functional ingredient for the compositions provided herein. Generally, according to particular embodiments of this invention, the at least one phytoestrogen is present in the composition in an amount sufficient to promote health and wellness.

Phytoestrogens are compounds found in plants which can typically be delivered into human bodies by ingestion of the plants or the plant parts having the phytoestrogens. As used herein, "phytoestrogen" refers to any substance which, when introduced into a body causes an estrogen-like effect of any degree. For example, a phytoestrogen may bind to estrogen receptors within the body and have a small estrogen-like effect.

Examples of suitable phytoestrogens for embodiments of this invention include, but are not limited to, isoflavones, stilbenes, lignans, resorcyclic acid lactones, coumestans, coumestrol, equol, and combinations thereof. Sources of suitable phytoestrogens include, but are not limited to, whole grains, cereals, fibers, fruits, vegetables, black cohosh, agave root, black currant, black haw, chasteberries, cramp bark, dong quai root, devil's club root, false unicorn root, *ginseng* root, groundsel herb, licorice, liferoot herb, motherwort herb, peony root, raspberry leaves, rose family plants, sage leaves, sarsaparilla root, saw *palmetto* berried, wild yam root, yarrow blossoms, legumes, soybeans, soy products (e.g., miso, soy flour, soymilk, soy nuts, soy protein isolate, tempen, or tofu) chick peas, nuts, lentils, seeds, clover, red clover, dandelion leaves, dandelion roots, fenugreek seeds, green tea, hops, red wine, flaxseed, garlic, onions, linseed, borage, butterfly weed, caraway, chaste tree, vitex, dates, dill, fennel seed, gotu kola, milk thistle, pennyroyal, pomegranates, southernwood, soya flour, tansy, and root of the kudzu vine (*pueraria* root) and the like, and combinations thereof.

Isoflavones belong to the group of phytonutrients called polyphenols. In general, polyphenols (also known as "polyphenolics"), are a group of chemical substances found in plants, characterized by the presence of more than one phenol group per molecule.

Suitable phytoestrogen isoflavones in accordance with embodiments of this invention include genistein, daidzein, glycitein, biochanin A, formononetin, their respective naturally occurring glycosides and glycoside conjugates, matairesinol, secoisolariciresinol, enterolactone, enterodiol, textured vegetable protein, and combinations thereof.

Suitable sources of isoflavones for embodiments of this invention include, but are not limited to, soy beans, soy products, legumes, alfalfa spouts, chickpeas, peanuts, and red clover.

xiv. Long-Chain Primary Aliphatic Saturated Alcohol

In certain embodiments, the functional ingredient is at least one long chain primary aliphatic saturated alcohol.

As used herein, the at least one long chain primary aliphatic saturated alcohol may be single long chain primary aliphatic saturated alcohol or a plurality of long chain primary aliphatic saturated alcohols as a functional ingredient for the compositions provided herein. Generally, according to particular embodiments of this invention, the at least one long chain primary aliphatic saturated alcohol is present in the composition in an amount sufficient to promote health and wellness.

Long-chain primary aliphatic saturated alcohols are a diverse group of organic compounds. The term alcohol refers to the fact these compounds feature a hydroxyl group (—OH) bound to a carbon atom. The term primary refers to the fact that in these compounds the carbon atom which is bound to the hydroxyl group is bound to only one other carbon atom. The term saturated refers to the fact that these compounds feature no carbon to carbon pi bonds. The term aliphatic refers to the fact that the carbon atoms in these compounds are joined together in straight or branched chains rather than in rings. The term long-chain refers to the fact that the number of carbon atoms in these compounds is at least 8 carbons).

Non-limiting examples of particular long-chain primary aliphatic saturated alcohols for use in particular embodiments of the invention include the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In a particularly desirable embodiment of the invention, the long-chain primary aliphatic saturated alcohols are policosanol. Policosanol is the term for a mixture of long-chain primary aliphatic saturated alcohols composed primarily of 28 carbon 1-octanosol and 30 carbon 1-triacontanol, as well as other alcohols in lower concentrations such as 22 carbon 1-docosanol, 24 carbon 1-tetracosanol, 26 carbon 1-hexacosanol, 27 carbon 1-heptacosanol, 29 carbon 1-nonacosanol, 32 carbon 1-dotriacontanol, and 34 carbon 1-tetracontanol.

Long-chain primary aliphatic saturated alcohols are derived from natural fats and oils. They may be obtained from these sources by using extraction techniques well known to those of ordinary skill in the art. Policosanols can be isolated from a variety of plants and materials including sugar cane (*Saccharum officinarium*), yams (e.g. *Dioscorea opposite*), bran from rice (e.g. *Oryza sativa*), and beeswax. Policosanols may be obtained from these sources by using extraction techniques well known to those of ordinary skill in the art. A description of such extraction techniques can be found in U.S. Pat. Appl. No. 2005/0220868, the disclosure of which is expressly incorporated by reference.

xv. Phytosterols

In certain embodiments, the functional ingredient is at least one phytosterol, phytostanol or combination thereof.

Generally, according to particular embodiments of this invention, the at least one phytosterol, phytostanol or combination thereof is present in the composition in an amount sufficient to promote health and wellness.

As used herein, the phrases "stanol", "plant stanol" and "phytostanol" are synonymous.

Plant sterols and stanols are present naturally in small quantities in many fruits, vegetables, nuts, seeds, cereals, legumes, vegetable oils, bark of the trees and other plant sources. Although people normally consume plant sterols and stanols every day, the amounts consumed are insufficient to have significant cholesterol-lowering effects or other health benefits. Accordingly, it would be desirable to supplement food and beverages with plant sterols and stanols.

Sterols are a subgroup of steroids with a hydroxyl group at C-3. Generally, phytosterols have a double bond within the steroid nucleus, like cholesterol; however, phytosterols also may comprise a substituted sidechain (R) at C-24, such as an ethyl or methyl group, or an additional double bond. The structures of phytosterols are well known to those of skill in the art.

At least 44 naturally-occurring phytosterols have been discovered, and generally are derived from plants, such as corn, soy, wheat, and wood oils; however, they also may be produced synthetically to form compositions identical to those in nature or having properties similar to those of naturally-occurring phytosterols. According to particular embodiments of this invention, non-limiting examples of phytosterols well known to those or ordinary skill in the art include 4-desmethylsterols (e.g., β-sitosterol, campesterol, stigmasterol, brassicasterol, 22-dehydrobrassicasterol, and Δ5-avenasterol), 4-monomethyl sterols, and 4,4-dimethyl sterols (triterpene alcohols) (e.g., cycloartenol, 24-methylenecycloartanol, and cyclobranol).

As used herein, the phrases "stanol", "plant stanol" and "phytostanol" are synonymous. Phytostanols are saturated sterol alcohols present in only trace amounts in nature and also may be synthetically produced, such as by hydrogenation of phytosterols. According to particular embodiments of this invention, non-limiting examples of phytostanols include β-sitostanol, campestanol, cycloartanol, and saturated forms of other triterpene alcohols.

Both phytosterols and phytostanols, as used herein, include the various isomers such as the α and β isomers (e.g., α-sitosterol and β-sitostanol, which comprise one of the most effective phytosterols and phytostanols, respectively, for lowering serum cholesterol in mammals).

The phytosterols and phytostanols of the present invention also may be in their ester form. Suitable methods for deriving the esters of phytosterols and phytostanols are well known to those of ordinary skill in the art, and are disclosed in U.S. Pat. Nos. 6,589,588, 6,635,774, 6,800,317, and U.S. Patent Publication Number 2003/0045473, the disclosures of which are incorporated herein by reference in their entirety. Non-limiting examples of suitable phytosterol and phytostanol esters include sitosterol acetate, sitosterol oleate, stigmasterol oleate, and their corresponding phytostanol esters. The phytosterols and phytostanols of the present invention also may include their derivatives.

Generally, the amount of functional ingredient in the composition varies widely depending on the particular composition and the desired functional ingredient. Those of ordinary skill in the art will readily acertain the appropriate amount of functional ingredient for each composition.

In one embodiment, a method for preparing a composition comprises combining a compound of formula (1) and at least one sweetener and/or additive and/or functional ingredient.

III. Methods of Use

The compounds and compositions of the present invention can be used to impart sweetness or to enhance the flavor or sweetness of compositions, such as consumables.

In one embodiment, the present invention is a method for impart sweetness to a consumable comprising providing a sweetenable consumable and adding a compound of the present invention to the sweetenable consumable, to provide a sweetened consumable.

In one embodiment, the sweetenable consumable is a liquid or beverage matrix.

In one embodiment, the compound is added at a concentration that is above, equal to or below its sweetness or flavor recognition threshold concentration.

In one embodiment, the present invention is a method for enhancing the sweetness of a consumable comprising (i) providing a consumable comprising at least one sweet ingredient and (i) adding a compound of the present invention to the consumable to provide a consumable with enhanced sweetness.

In another embodiment, the present invention is a method for enhancing the sweetness of a beverage comprising (i) providing a beverage comprising at least one sweet ingredient and (ii) adding a compound of the present invention to the consumable to provide a beverage with enhanced sweetness. According to this embodiment, the compound is added at a concentration at or below its sweetness recognition threshold concentration.

The compound may be added as such, or in the form of a composition comprising the compound.

In another embodiment, the present invention is method for enhancing the flavor of a consumable comprising (i) providing a consumable comprising at least one flavor ingredient and (ii) adding a flavor enhancer that is a compound of formula (1) to provide a flavor enhanced consumable, wherein the compound of formula (1) is present in the flavor enhanced consumable in an amount below the flavor recognition threshold concentration of the compound. In a particular embodiment, the consumable is a beverage.

In still another embodiment, a method for enhancing the flavor of a beverage comprising (i) providing a beverage comprising at least one flavor ingredient and (ii) adding a compound of formula (1) to the beverage to provide a flavor enhanced beverage, wherein the compound of formula (1) is present in the flavor enhanced beverage in a concentration below the flavor recognition threshold concentration of the compound.

The present invention also includes methods of preparing consumables and flavor enhanced compositions by adding the compounds of formula (1) or compositions comprising the compounds of formula (1) to consumables.

In another embodiment, a method for preparing a sweetened consumable comprises (i) providing a compound comprising at least one sweet ingredient and (ii) adding a compound of formula (1) to provide a sweetened consumable, wherein the compound of formula (1) has a sweetness recognition threshold concentration and the compound of formula (1) is present in an amount at or below the sweetness recognition threshold concentration. In this embodiment, the compound of formula (1) is a sweetness enhancer. In a particular embodiment, the consumable is a beverage.

In another embodiment, a method for preparing a sweetened consumable comprises providing a consumable comprising at least one sweetener and adding a compound of formula (2), wherein the compound of formula (2) has a sweetness recognition threshold concentration and the compound of formula (2) is present in an amount at or below the sweetness recognition threshold concentration. In this embodiment, the compound of formula (2) is a sweetness enhancer. In a particular embodiment, the consumable is a beverage.

In another embodiment, a method for preparing a sweetened consumable comprises providing a consumable comprising at least one sweetener and adding a compound of formula (2f) or (2g), wherein compound (2f) or (2g) is present in an amount at or below the sweetness recognition threshold concentration. In a particular embodiment, the consumable is a beverage.

In one embodiment, the present invention provides a method for enhancing the sweetness of a consumable comprising at least one sweetener in a concentration above its sweetness recognition threshold by adding a compound of formula (1) in a concentration at or below its sweetness recognition threshold. As stated previously, a compound of formula (1) enhances the sweetness of the consumable by an amount more than the detectable sweetness of a solution containing the same concentration of the compound of formula (1) and/or enhances the sweetness of the consumable by at least about 2.0% (w/v) sucrose equivalence, such as, for example from about 2.0% (w/v) to about 3.0% (w/v). In a particular embodiment, the consumable is a beverage.

In one embodiment, the present invention provides a method for enhancing the sweetness of a consumable comprising at least one sweetener in a concentration above its sweetness recognition threshold by adding a compound of formula (2) in a concentration at or below its sweetness recognition threshold. As stated previously, a compound of formula (2) enhances the sweetness of the consumable by an amount more than the detectable sweetness of a solution containing the same concentration of the compound of formula (2) and/or enhances the sweetness of the consumable by at least about 2.0% (w/v) sucrose equivalence, such as, for example from about 2.0% (w/v) to about 3.0% (w/v). In a particular embodiment, the consumable is a beverage.

In a more particular embodiment, a method for enhancing the sweetness of a consumable comprising at least one sweetener in a concentration above its sweetness recognition threshold by adding compound (2f) or (2g) in a concentration at or below its sweetness recognition threshold. As stated previously, compound (2f) or (2g) enhances the sweetness of the consumable by an amount more than the detectable sweetness of a solution containing the same concentration of compound (2f) or (2g) and/or enhances the sweetness of the consumable by at least about 2.0% (w/v) sucrose equivalence, such as, for example by at least about 2.5% (w/v) sucrose equivalence or from about 2.0% (w/v) to about 3.0% (w/v). In a particular embodiment, the consumable is a beverage.

In a particular embodiment, a method for enhancing the sweetness of a beverage comprising at least one sweetener in a concentration above its sweetness recognition threshold comprises adding a compound of formula (1) to said beverage in an amount at or below its sweetness recognition threshold, wherein the compound of formula (1) enhances the sweetness of the beverage by an amount more than the detectable sweetness of a solution containing the same concentration of the compound of formula (1) and/or enhances the sweetness of the beverage by at least 2.0% sucrose equivalence, such as, for example by at least 2.5% sucrose equivalence or from about 2.0% to about 3.0%.

In a particular embodiment, a method for enhancing the sweetness of a beverage comprising at least one sweetener in a concentration above its sweetness recognition threshold comprises adding a compound of formula (2) to said beverage in an amount at or below its sweetness recognition threshold, wherein the compound of formula (2) enhances the sweetness of the beverage by an amount more than the detectable sweetness of a solution containing the same concentration of the compound of formula (2) and/or enhances the sweetness of the beverage by at least 2.0% sucrose equivalence, such as, for example by at least 2.5% sucrose equivalence or from about 2.0% to about 3.0%.

In a more particular embodiment, a method for enhancing the sweetness of a beverage comprising at least one sweetener in a concentration above its sweetness recognition threshold comprises adding compound (2f) or (2g) to said beverage in an amount at or below its sweetness recognition threshold, wherein compound (2f) or (2g) enhances the sweetness of the beverage by an amount more than the detectable sweetness of a solution containing the same concentration of compound (2f) or (2g) and/or enhances the sweetness of the beverage by at least 2.0% (w/v) sucrose equivalence, such as, for example by at least about 2.5% (w/v) sucrose equivalence or from about 2.0% (w/v) to about 3.0% (w/v).

In another embodiment, the sweetener is selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof.

In still another embodiment, a compound of the present invention is added in an amount to provide a final concentration of about 30 ppm in the beverage.

In another embodiment, the present invention provides a method for enhancing the sweetness of a beverage comprising at least one sweetener in a concentration above its sweetness recognition threshold by adding a concentrate composition of the present invention, i.e. a concentrate composition comprising a compound of formula (1) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof.

In another embodiment, the present invention provides a method for enhancing the sweetness of a beverage comprising at least one sweetener in a concentration above its sweetness recognition threshold by adding a concentrate composition of the present invention, i.e. a concentrate composition comprising a compound of formula (2) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof In another embodiment, the present invention provides a method for enhancing the sweetness of a beverage comprising at least one sweetener in a concentration above its sweetness recognition threshold by adding a concentrate composition of the present invention, i.e. a concentrate composition comprising compound (2f) or (2g) having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof.

In another embodiment, sweeteners are selected from, but not limited to, the group consisting of sucrose, glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, fucose, rhamnose, arabinose, turanose, sialose, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside N, rebaudioside O, dulcoside A, dulcoside B, rubusoside, stevia, stevioside, mogroside IV, mogroside V, Luo han guo, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside and cyclocarioside I, sugar alcohols such as erythritol, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof.

In one embodiment, the sweetener is a caloric sweetener or mixture of caloric sweeteners. In another embodiment, the caloric sweetener is selected from, sucrose, fructose, glucose, high fructose corn/starch syrup, a beet sugar, a cane sugar, and combinations thereof.

In another embodiment, the sweetener is a rare sugar selected from D-psicose, D-allose, L-ribose, D-tagatose, L-glucose, L-fucose, L-arbinose, turanose and combinations thereof.

In yet another embodiment, the sweetener is a non-caloric sweetener or mixture of non-caloric sweeteners. In one example, the non-caloric sweetener is a natural high-potency sweetener. As used herein, the phrase "natural high potency sweetener" refers to any composition which is not found naturally in nature and characteristically has a sweetness potency greater than sucrose, fructose, or glucose, yet has less calories. The natural high potency sweetener can be provided as a pure compound or, alternatively, as part of an extract.

In yet another example, the non-caloric sweetener is a synthetic high-potency sweetener.

IV. Method of Preparation

Compounds of the present invention are derived from a degradation process carried out on rebaudioside X, where rebaudioside X is:

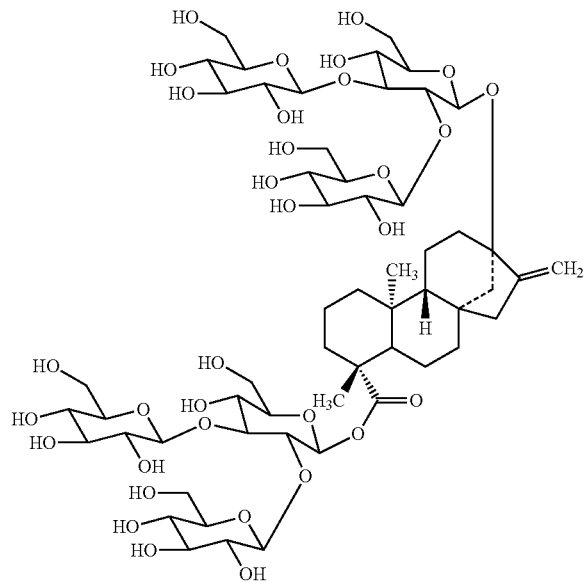

Rebaudioside X can be obtained via purification from compositions comprising steviol glycosides, including, but not limited to a mixture of steviol glycosides, stevia extract, by-products of other steviol glycosides' isolation and purification processes, a commercially available stevia extract or any combination thereof. An exemplary method for purifying and identifying rebaudioside X is provided in Example 15. Rebaudioside X is also commercially available from ChromaDex (under the name "Rebaudioside M").

In one embodiment, a method of preparing compounds of formula (1) comprises (i) contacting a solution comprising rebaudioside X with an inorganic acid, (ii) heating the solution for sufficient time to provide a compound of formula (1) and (iii) recovering the compound of formula (1) from the solution.

In another embodiment, a method of preparing compounds of formula (2) comprises (i) contacting a solution comprising rebaudioside X with an inorganic acid, (ii) heating the solution for sufficient time to provide a compound of formula (2) and (iii) recovering the compound of formula (2) from the solution.

In particular embodiments, the method provided herein can be used to isolate compounds (2a), (2b), (2c), (2d), (2e), (2f) and (2g).

In some embodiments, the inorganic acid comprises phosphoric acid, phosphorous acid, polyphosphoric acid, hydrochloric acid, sulfuric acid, nitric acid, carbonic acid, sodium dihydrogen phosphate or combinations thereof.

In a particular embodiment, the inorganic acid is phosphoric acid.

In one embodiment, the pH is adjusted using a buffer. In another embodiment, the pH is adjusted using ammonium hydroxide. In a particular embodiment, the pH is between about 1 and about 6. In a particular embodiment, the pH is between about 1 and about 3. In another embodiment, the pH is about 2.

In one embodiment, the solution is heated between about 25° C. and about 100° C. In another embodiment, the solution is heated between about 50° C. and about 90° C. In one embodiment, the solution is heated between about 75° C. and about 85° C. In yet another embodiment, the solution is heated to about 80° C.

In another embodiment, the time sufficient to obtain a compound of the present invention is in the range of about 0.5 to about 48 hours. In another embodiment, the time sufficient to obtain a compound of the present invention is in the range of about 2 to about 40 hours. In yet another embodiment, the time sufficient to obtain a compound of the present invention is in the range of about 15 to about 30 hours. In one embodiment, the time sufficient to obtain a compound of the present invention is about 24 hours.

In another embodiment, the degradation mixture is analyzed by LCMS.

In one embodiment, the inorganic acid is replaced with an inorganic base. In another embodiment, the inorganic base is selected from, but not limited to, the group of sodium hydroxide, potassium hydroxide, sodium carbonate, potassium carbonate, magnesium carbonate, calcium carbonate and combinations thereof.

In one embodiment, the step of recovering a compound of the present invention comprises isolating the rebaudioside X derivative product from a supernatant, a precipitate, or a combination thereof. The compound the present invention may be recovered using any suitable solid-liquid separation techniques. For example, the derivative product of the supernatant and precipitate may be isolated from each other by decanting the supernatant from the precipitate. Other separation techniques may utilize centrifugal force, non-limiting examples of which include vertical and horizontal perforated basket centrifuge, solid bowl centrifuge, decanter centrifuge, peeler type centrifuge, pusher type centrifuge, Heinkel type centrifuge, disc stack centrifuge and cyclone separation. In addition, separation of the compound of the present invention in the supernatant and precipitate may be enhanced by any of pressure, vacuum, and gravity filtration methods, that include, without limitation, the use of belt, drum, nutsche type, leaf, plate, Rosenmund type, sparkler type, and bag filters and filter press.

In other particular embodiments, the method further comprises purifying the compound of the present invention (detailed further below for HPLC). For example, compound(s) may be purified from the supernatant or precipitate by normal phase and/or reversed-phase column chromatography. Suitable columns for purifying may be determined by one of ordinary skill in the art without undue experimentation. In particular embodiments, the resulting fractions of may be reprocessed (e.g., using column chromatography or other methods of purification) to further purify the products. In still other embodiments, the resulting fractions may be concentrated using any suitable concentration method known to those of ordinary skill in the art (e.g., high performance liquid chromatography).

IV. Method of Purification

As used herein, the term "preparative HPLC" refers to an HPLC system which is capable of producing high (500 or more) microgram, milligram, or gram sized product fractions. The term "preparative" includes both preparative and semi-preparative columns, but is not intended to include analytical columns, which provide fractions in the nanogram to low microgram range.

As used herein, an "HPLC compatible detector" is a detector suitable for use in an HPLC system which is capable of providing a detectable signal upon elution of a compound peak. For example, a detector capable of generating a signal when a compound elutes from the compound is an HPLC compatible detector. Where component absorbance varies widely, it may be necessary to utilize more than one detector. A detector capable of detecting a desired component is not an "incompatible" detector due to its inability to detect a non-desired peak.

Displacement chromatography (an example of which is HPLC) is based on the principle that in a sample the balance between stationary phase (SP) and mobile phase (MP) is shifted the direction of SP. Single components of a sample displace each other like a train and the displacing agent with the greater affinity to SP pushes this train by fractions out of the column. Gas chromatography, liquid chromatography and HPLC chromatography are some of the most well known examples of displacement chromatography.

An HPLC device typically includes at least the following components: a column, packed with a suitable stationary phase, a mobile phase, a pump for forcing the mobile phase through the column under pressure, and a detector for detecting the presence of compounds eluting off of the column. The devices can optionally include a means for providing for gradient elution, although such is not necessary using the methods described herein. Routine methods and apparatus for carrying out HPLC separations are well known in the art.

Suitable stationary phases are those in which the compound of interest elutes. Preferred columns can be, and are not limited to, normal phase columns (neutral, acidic or basic), reverse phase columns (of any length alkyl chain), a synthetic cross-linked polymer columns (e.g., styrene and divinylbenzene), size exclusion columns, ion exchange columns, bioaffinity columns, and any combination thereof. The particle size of the stationary phase is within the range from a few µm to several 100 µm.

Suitable detection devices include, but are not limited to, mass spectrometers, UV detectors, IR detectors and light scattering detectors. The methods described herein use any combination of these detectors. The most preferable embodiment uses mass spectrometers and UV detectors.

a. HPLC Purification

In one embodiment, a preparative or semi-preparative HPLC protocol is used to purify or partially purify a mixture of steviol glycosides or *stevia* extract. In another embodiment, a preparative or semi-preparative HPLC protocol is used to purify or partially purify a compound of the present invention prepared as set forth above.

In one embodiment, a representative analytical HPLC protocol is correlated to a preparative or semi-preparative HPLC protocol used to purify a compound.

In another embodiment, appropriate conditions for purifying a compound of the present invention can be worked out by route scouting a representative sample for a given analytical HPLC column, solvent system and flow rate. In yet another embodiment, a correlated preparative or semi-preparative HPLC method can be applied to purify a compound of the present invention with modifications to the purification parameters or without having to change the purification parameters.

In one embodiment, a method for purifying the compound of formula (1) comprises:
(a) passing a solution comprising steviol glycosides through a preparative HPLC using an eluent; and
(b) eluting fractions comprising the compound of formula (1).

In some embodiments, the eluent (mobile phase) is selected from the group consisting of water, acetonitrile, methanol, 2-propanol, ethylacetate, dimethylformamide, dimethylsulfide, pyridine, triethylamine, formic acid, trifluoroacetic acid, acetic acid, an aqueous solution containing ammonium acetate, heptafluorobutyric acid, and any combination thereof. In another embodiment, the purification is carried out over a gradient.

In one embodiment, impurities are eluted off of the HPLC column before eluting a fraction containing steviol glycosides. In another embodiment, impurities are eluted off of the HPLC column before eluting a fraction containing a compound of formula (1).

The method can further include removal of solvent from the eluted solution. Removal of solvent can be performed by any known means to one of skill in the art including evaporation, distillation, vacuum drying and spray drying.

In one embodiment, the mixture being purified is a steviol glycosides source selected from the group consisting of *stevia* extract, by-products of other steviol glycosides' isolation and purification processes, a commercially available *stevia* extract and combinations thereof. In one embodiment, the mixture being purified is a fraction collected from a previous HPLC purification.

In one embodiment, steviol glycosides isolated from a preparative or semi-preparative HPLC protocol, are subjected to further HPLC protocols 2, 3, 4 or more times. In one embodiment, a compound of formula (1) isolated from a preparative or semi-preparative HPLC protocol, is subjected to further HPLC protocols 2, 3, 4 or more times.

In one embodiment, the method provides compounds of formula (1) in a purity greater than about 80% by weight on a dry basis, such as, for example, greater than about 85%, 90%, 95% and 97%. In a particular embodiment, the method provides compounds of formula (1) in a purity greater than about 99% by weight on a dry basis.

EXAMPLES

Instrumentation
Sciex API150 EX Single Quadrupole and Sciex API2000 Triple Quadrupole Mass Spectrometers Mass spectrometry was carried out either on a Sciex API150 EX single quadrupole or a Sciex API2000 triple quadrupole mass spectrometer with a TurbolonSpray ionization source operating in negative ion mode. Sedere Sedex 75 ELS detector was used operating at 50° C. and 3.5 bar. Analysis of the samples was performed using the following method: Column: Phenomenex Synergi Hydro RP, 4.6×250 mm, 4 µm (p/n 00G-4375-E0); Column Temp: 55° C.; Mobile Phase A: $H_2O$ (0.0284% $NH_4OAc$, 0.0116% HOAc); Mobile Phase B: Acetonitrile; Flow Rate: 1.0 mL/min; Injection volume: 100 µL. Detection was by UV (210 nm), ELSD, and MSD (−ESI m/z 200-1450 or 120-2000).

| Gradient: | | |
|---|---|---|
| Time (min) | % A | % B |
| 0.0 | 75 | 25 |
| 8.5 | 75 | 25 |
| 10.0 | 71 | 29 |
| 16.5 | 70 | 30 |
| 18.5 | 66 | 34 |
| 24.5 | 66 | 34 |
| 26.5 | 48 | 52 |
| 29.0 | 48 | 52 |
| 31.0 | 30 | 70 |
| 37.0 | 30 | 70 |
| 37.1 | 75 | 25 |
| 45.0 | 75 | 25 |

Waters Premier QTof Mass Spectrometer

MS and MS/MS data were generated with a Waters Premier QTof mass spectrometer equipped with an electrospray ionization source. A sample was diluted with $H_2O$:acetonitrile (1:1) containing 0.1% formic acid and introduced via infusion using the onboard syringe pump. The dilution was adjusted to yield good s/n which occurred at an approximate concentration of 0.01 mg/mL.

Bruker Avance 500 MHz NMR

A sample was prepared in pyridine-$d_5$ or a mixture of pyridine-$d_5$ and deuterium oxide (10:1). The NMR data were acquired on a Bruker Avance 500 MHz instrument with a 5 mm inverse detection probe, The spectrum was referenced to the residual solvent signal ($\delta_H$ 8.71, $\delta_C$ 149.9 for pyridine-$d_5$).

Agilent 1100 HPLC or Waters 600 HPLC

Semi-preparative HPLC was carried out using a Waters 600E pump connected to a Waters 996 diode-array detector and controlled by Waters Empower software. Preparative scale HPLC was carried out using an Agilent 1100 Preparative HPLC System controlled by ChemStation software.

Method 1:
Column: Phenomenex Prodigy ODS(3) with a Phenomenex guard column, 250×21.2 mm, 5 µm (p/n 00G-4097-P0); UV Detection: 210 nm; Mobile Phase A: $H_2O$; Mobile Phase B: Acetonitrile; Flow Rate: 20 mL/min; Injection volume: 1500 µL at 40 mg/ml prepared in water-acetonitrile (75:25). The initial solution was somewhat cloudy and was heated in water bath at 40° C. until clear. The Mobile Phase gradient is provided in Table 1.

TABLE 1

| Mobile Phase gradient of method 1. | | |
|---|---|---|
| Time (min) | % A | % B |
| 0.0 | 75 | 25 |
| 20.0 | 69 | 31 |
| 20.5 | 50 | 50 |
| 25.0 | 50 | 50 |

Method 2:
Column: Phenomenex Gemini $C_{18}$, with guard column, 250×10 mm, 5 µm (p/n 00G-4435-N0); Column Temp: 25° C.; UV Detection: 210 nm; Mobile Phase A: $H_2O$; Mobile Phase B: Acetonitrile; Flow Rate: 5.0 mL/min; Injection volume: 150 µL prepared in $H_2O$. The Mobile Phase gradient is provided in Table 2.

TABLE 2

| Mobile Phase gradient of method 2. | | |
|---|---|---|
| Time (min) | % A | % B |
| 0.0 | 75 | 25 |
| 20.0 | 69 | 31 |
| 20.5 | 50 | 50 |
| 25.0 | 40 | 60 |
| 25.1 | 75 | 25 |
| 30.0 | 75 | 25 |

Method 3:
Column: Phenomenex Gemini $C_{18}$, with guard column, 250×10 mm, 5 µm (p/n 00G-4435-N); Column Temp: 25° C.; UV Detection: 210 nm; Mobile Phase A: $H_2O$; Mobile Phase B: Acetonitrile; Flow Rate: 5.0 mL/min; Injection volume: 300 µL at 10 mg/mL prepared in water-acetonitrile (75:25). The Mobile Phase gradient is provided in Table 3.

TABLE 3

| Mobile Phase gradient of method 3. | | |
|---|---|---|
| Time (min) | % A | % B |
| 0.0 | 75 | 25 |
| 20.0 | 69 | 31 |
| 20.5 | 50 | 50 |
| 25.0 | 40 | 60 |
| 25.1 | 75 | 25 |
| 30.0 | 75 | 25 |

Method 4:
Column: Phenomenex Gemini NX $C_{18}$, 250×10 mm, 5 µm (p/n 00G-4097-P0) with a Phenomenex guard column; UV Detection: 210 nm; Mobile Phase A: $H_2O$; Mobile Phase B: Acetonitrile; Flow Rate: 20 mL/min. Injection volume: 1500 uL at 40 mg/mL prepared in water-acetonitrile (75:25). The Mobile Phase gradient is provided in Table 4.

TABLE 4

| Mobile Phase gradient of method 4. | | |
|---|---|---|
| Time (min) | % A | % B |
| 0.0 | 75 | 25 |
| 8.5 | 75 | 25 |

TABLE 4-continued

Mobile Phase gradient of method 4.

| Time (min) | % A | % B |
|---|---|---|
| 10.0 | 71 | 29 |
| 16.5 | 70 | 30 |
| 18.5 | 66 | 34 |
| 24.5 | 66 | 34 |
| 26.5 | 48 | 52 |
| 29.0 | 48 | 52 |
| 31.0 | 30 | 70 |
| 37.0 | 30 | 70 |
| 37.1 | 75 | 25 |
| 45.0 | 75 | 25 |

Method 5:

Column: ZIC-HILIC, 250×10 mm, 5 µm (p/n HX 129616) with a Phenomenex guard column; UV Detection: 210 nm; Mobile Phase A: H$_2$O; Mobile Phase B: acetonitrile; Flow Rate: 5 mL/min. The Mobile Phase gradients are provided in Tables 5 and 6.

TABLE 5

Mobile Phase gradient of method 5A.

| Time (min) | % A | % B |
|---|---|---|
| 0.0 | 5 | 95 |
| 20.0 | 17 | 83 |
| 30.0 | 30 | 70 |
| 31.0 | 95 | 5 |
| 36.0 | 95 | 5 |
| 37.0 | 5 | 95 |
| 42.0 | 5 | 95 |

TABLE 6

Mobile Phase gradient of method 5B.

| Time (min) | % A | % B |
|---|---|---|
| 0.0 | 5 | 95 |
| 15.0 | 35 | 65 |
| 20.0 | 95 | 5 |
| 21.0 | 95 | 5 |
| 22.0 | 5 | 95 |
| 27.0 | 5 | 95 |

Example 1

Degradation of Rebaudioside X 0.1 M phosphoric acid solution was adjusted to pH 2.0 with concentrated ammonium hydroxide. Ten mg of rebaudioside X (Lot VSPC-2973-6B, obtained from Pure Circle Malaysia) was added to 10 mL of the phosphoric acid solution. The solution was placed on a heat block at 80° C. for 24 hours.

Example 2

Isolation and Purification of (2a)

The material from Example 1 was analyzed by LC-MS using the LC-MS method above. Rebaudioside X was observed at 11.57 min in the UV (210 nm) chromatogram. The mass spectrum for the degradation mixture peak provided the expected [M−H]$^-$ ion at m/z 1289.7. The (2a) peak was observed to elute at 13.19 min in the UV chromatogram and showed an [M−H]$^-$ ion at m/z 1289.7. This indicated that (2a) is component of the rebaudioside X degradation mixture. A preliminary round of HPLC purification was performed using HPLC Method 1 and the material eluting at 14.4 min as a shoulder after the rebaudioside X degradation mixture peak was collected and dried by rotary evaporation under reduced pressure as the crude impurity fraction). Final fractionation was then performed using HPLC Method 2 by injecting the crude impurity fraction over several injections. The residual rebaudioside X degradation mixture peak was observed to elute just before 12 min and the (2a) peak was observed to elute at 13.3 min and was collected from multiple injections, pooled, and dried by rotary evaporation under reduced pressure to provide the sample of (2a) for characterization.

Example 3

Structural Elucidation of (2a)

Mass Spectrometry

The results of an LC-MS analysis of the isolated peak confirmed that it corresponded to (2a) (FIG. 1). A single peak was observed in the TIC, UV and ELS chromatograms. The mass spectrum of the isolate of (2a) showed an [M−H]$^-$ ion at m/z 1290.2 suggesting a nominal mass of 1290 Daltons.

The ESI+ TOF mass spectrum acquired by infusing a sample of (2a) showed [M+H]$^+$ and [M+Na]$^+$ ions at m/z 1291.5439 and 1313.5254, respectively. The mass of the [M+H]$^+$ ion was in good agreement with the molecular formula $C_{56}H_{90}O_{33}$ (calcd for $C_{56}H_{91}O_{33}$: 1291.5443, error: −0.3 ppm) for (2a). The ESI− mass spectrum provided [M−H]$^-$ and [M+HCOOH—H]$^-$ ions at m/z 1289.5304 and 1335.5366, respectively. As above, the mass of the [M−H]$^-$ ion was in good agreement with the molecular formula $C_{56}H_{90}O_{33}$ (calcd for $C_{56}H_{89}O_{33}$: 1289.5286, error: 1.4 ppm) for (2a). The +ESI and −ESI data indicated that (2a) has a nominal mass of 1290 Daltons with the molecular formula $C_{56}H_{90}O_{33}$. This confirms that (2a) is an isomer of rebaudioside X.

The +ESI TOF MS/MS spectrum of (2a), fragmenting on the [M+H]$^+$ ion at m/z 1291 and provided fragment ions corresponding to the sequential loss of glucose residues at m/z 1129.4908, 967.4387, 805.3853, and 643.3348. A fragment ion was also observed at m/z 973.3253 corresponding to six glucose residues. This ion underwent sequential loss glucose to yield fragment ions at m/z 811.2714, 649.2180, 487.1656, and 325.1151. This was identical to the fragmentation pattern observed for rebaudioside X.

The −ESI TOF MS/MS spectrum of (2a), fragmenting on the [M−H]$^-$ ion at m/z 1289 indicated that the most abundant and readily formed ion is present at m/z 803.3706 and corresponds to the loss of three glucose residues. Since this fragmentation likely results at C-19 it suggested that the glycoside at C-19 is composed of three glucose residues as found in rebaudioside X.

NMR Spectrometry

Figure 2:
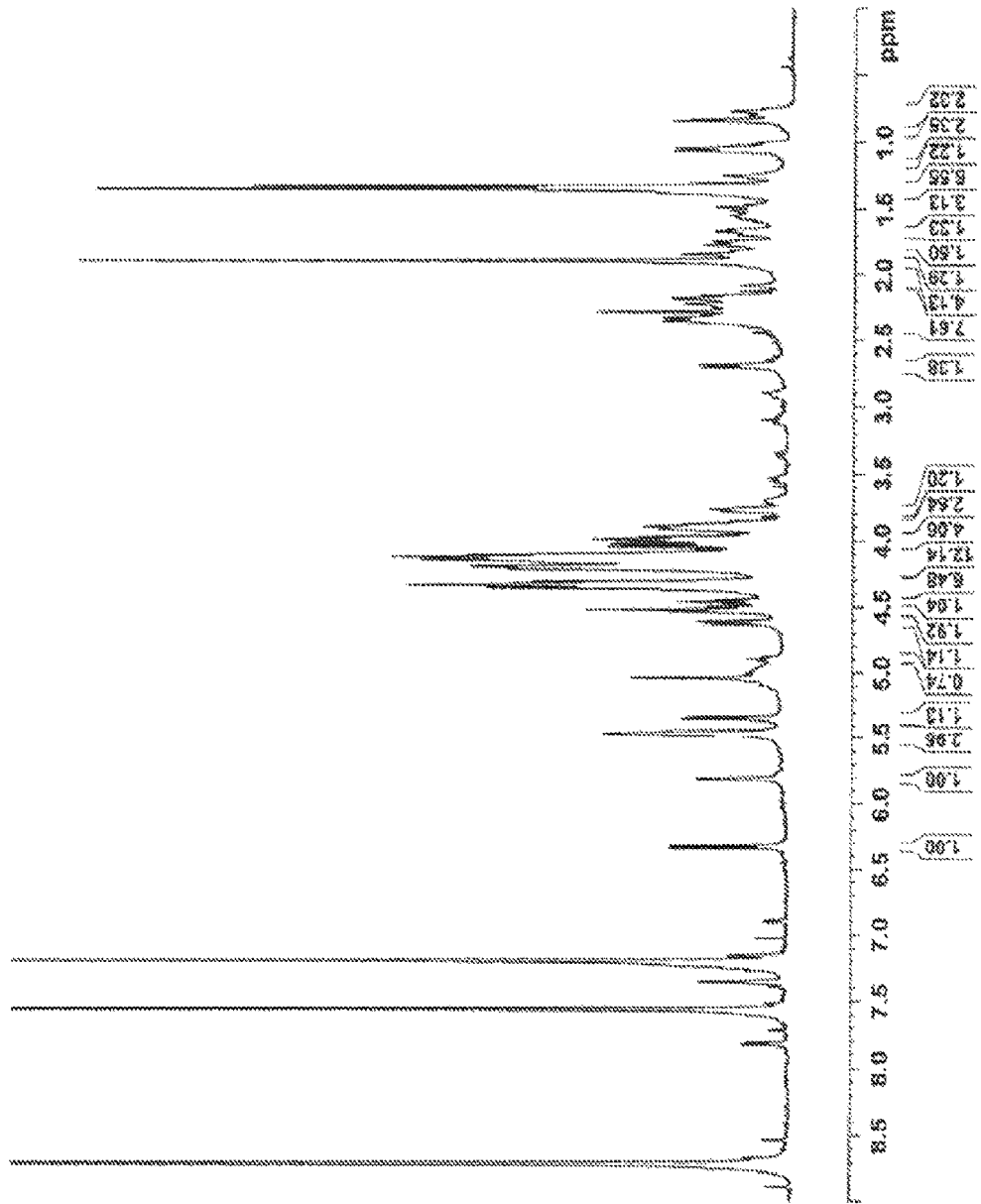
FIG. 2: $^1$H NMR (500 MHz, pyridine-$d_5$) of (2a).

A series of NMR experiments including $^1$H NMR (FIG. 2), $^1$H—$^1$H COSY, HSQC, HMBC were performed to allow the assignment of (2a).

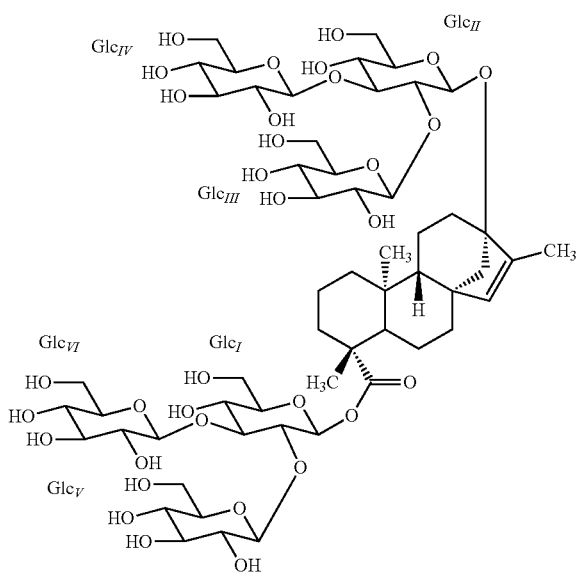

An HMBC correlation from the methyl protons at $\delta_H$ 1.35 ppm to the carbonyl at $\delta_C$ 176.7 allowed assignment of one of the tertiary methyl groups (C-18) as well as C-19 and provided a starting point for assignment of the rest of the aglycone. Additional HMBC correlations from the methyl protons (H-18) to carbons at $\delta_C$ 38.0, 44.0, and 56.9 allowed assignment of C3 to C5 in comparison with the data for rebaudioside X. The $^1$H chemical shifts for C-3 ($\delta_H$ 1.03 and 2.33) and C-5 ($\delta_H$ 1.05) were assigned using the HSQC data. A COSY correlation between one of the H-3 protons ($\delta_H$ 1.03) and a proton at $\delta_H$ 1.36 allowed assignment of one of the H-2 protons which in turn showed a correlation with a proton at $\delta_H$ 0.77 which was assigned to C-1. The remaining $^1$H and $^{13}$C chemical shifts for C-1 and C-2 were then assigned on the basis of additional COSY and HSQC correlations and are summarized in Table 7.

TABLE 7

$^1$H and $^{13}$C NMR (500 and 125 MHz, pyridine-$d_5$) assignments of the (2a) aglycone.[a,b,c]

| Position | $^{13}$C NMR | $^1$H NMR |
|---|---|---|
| 1 | 40.2 | 0.77 t (12.8) |
|   |   | 1.76 d (12.8) |
| 2 | 19.3 | 1.36 m |
|   |   | 2.25 m |
| 3 | 38.0 | 1.03 m |
|   |   | 2.33 m |
| 4 | 44.0 | — |
| 5 | 56.9 | 1.05 d (12.7) |
| 6 | 21.8 | 2.21 m |
|   |   | 2.31 m |
| 7 | 40.0 | 1.49 m |
|   |   | 1.89 m |
| 8 | — | — |
| 9 | 47.0 | 0.82 d (8.4) |
| 10 | 39.6 | — |
| 11 | 20.9 | 1.56 m |
|   |   | 1.67 m |
| 12 | 29.9 | 1.84 t (12.2) |
|   |   | 2.36 m |
| 13 | 89.6 | — |
| 14 | 47.1 | 2.17 d (9.8) |
|   |   | 2.69 d (9.8) |
| 15 | 134.3 | 5.03 s |
| 16 | 144.4 | — |

TABLE 7-continued $^1$H and $^{13}$C NMR (500 and 125 MHz, pyridine-$d_5$) assignments of the (2a) aglycone.[a,b,c]

| Position | $^{13}$C NMR | $^1$H NMR |
|---|---|---|
| 17 | 12.7 | 1.89 s |
| 18 | 28.0 | 1.35 s |
| 19 | 176.7 | — |
| 20 | 16.4 | 1.33 s |

[a] assignments made on the basis of COSY, HSQC, HMBC, TOCSY and HSQC-TOCSY correlations;
[b] Chemical shift values are in δ (ppm);
[c] Coupling constants are in Hz.

A second tertiary methyl singlet, observed at $\delta_H$ 1.33 showed HMBC correlations to C-1 and C-5 and was assigned as C-20. The methyl protons showed additional HMBC correlations to a quaternary carbon ($\delta_C$ 39.6) and a methine ($\delta_H$ 0.83, $\delta_C$ 47.0) which were assigned as C-10 and C-9, respectively. COSY correlations between H-5 ($\delta_H$ 1.05) and protons at $\delta_H$ 2.21 and 2.31 then allowed assignment of the H-6 protons which in turn showed correlations to protons at $\delta_H$ 1.49 and 1.89 which were assigned to C-7. The $^{13}$C chemical shifts for C-6 ($\delta_C$ 21.8) and C-7 ($\delta_C$ 40.0) were then determined from the HSQC data.

COSY correlations between H-9 ($\delta_H$ 0.83) and protons at $\delta_H$ 1.56 and 1.67 allowed assignment of the H-11 protons which in turn showed COSY correlations to protons at $\delta_H$ 1.84 and 2.36 which were assigned as the H-12 protons. The HSQC data was then used to assign C-11 ($\delta_C$ 20.9) and C-12 ($\delta_C$ 29.9).

A third tertiary methyl group was observed in the $^1$H NMR spectrum of (2a) at $\delta_H$ 1.89 which was not observed for rebaudioside X and suggested a change in the aglycone for this impurity. This methyl group showed HMBC correlations to carbons at $\delta_C$ 89.6, 134.3, and 144.4. HMBC correlations were also observed between the methylene protons at C-12 ($\delta_H$ 1.84 and 2.36) and carbons at $\delta_C$ 89.6 and 144.4 allowing them to be assigned as C-13 and C-16, respectively. The olefinic proton observed as a singlet at $\delta_H$ 5.03 showed an HSQC correlation to the carbon at $\delta_C$ 134.3 which was assigned as C-15 and a methyl carbon at $\delta_C$ 12.7 which was assigned as C-17. An HMBC correlation was also observed between H-9 and the carbon at $\delta_C$ 144.4 confirming the assignment of C-15. An additional HMBC correlation between H-9 and an isolated methylene group ($\delta_H$ 2.17 and 2.69, $\delta_C$ 47.1) allowed the assignment of C-14. HMBC correlations between the H-14 protons and C-13, C-15, and C-16 confirmed the assignment of the methylene group at C-14.

Analysis of the NMR data indicated that (2a) has a rearrangement in the aglycone resulting in a shift in the unsaturation from C-16 to C-15. A summary of the $^1$H and $^{13}$C chemical shifts for the aglycone are found in Table 7.

An analysis of the HSQC data for (2a) confirmed the presence of 6 anomeric positions. Three of the anomeric protons were well resolved at $\delta_H$ 6.33 ($\delta_C$ 94.5), 5.81 ($\delta_C$ 103.8), and 5.33 ($\delta_C$ 103.9) in the $^1$H NMR spectrum. The remaining three anomeric protons were observed at $\delta_H$ 5.47 ($\delta_C$ 95.7), 5.45 ($\delta_C$ 104.5), and 5.44 ($\delta_C$ 103.9) and were overlapped in the $^1$H spectrum. The anomeric proton observed at $\delta_H$ 6.33 showed an HMBC correlation to C-19 which indicated that it corresponds to the anomeric proton of Glc$_I$. Similarly, the anomeric proton observed at $\delta_H$ 5.47 showed an HMBC correlation to C-13 allowing it to be assigned as the anomeric proton of Glc$_{II}$.

The Glc$_I$ anomeric proton ($\delta_H$ 6.33) showed a COSY correlation to a proton at $\delta_H$ 4.51 which was assigned as Glc$_I$ H-2 and in turn showed a COSY correlation to a proton at $\delta_H$ 4.99 (Glc$_I$ H-3) which showed a correlation with a proton at $\delta_H$ 4.19 (Glc$_I$ H-4). Assignment of the $^{13}$C chemical shifts for Glc$_I$ C-2 ($\delta_C$ 76.6), C-3 ($\delta_C$ 88.3), and C-4 ($\delta_C$ 69.6) was made using the HSQC data. An HMBC correlation between H-1 and a carbon at $\delta_C$ 78.1 allowed assignment of C-5 in comparison with the data for rebaudioside X with H-5 ($\delta_H$ 4.10) then assigned from the HSQC data. The assignment at Glc$_I$ C-6 was made using the $^1$H and HSQC data in comparison with the data for rebaudioside X.

Assignment of Glc$_{II}$ was carried out in a similar fashion. The Glc$_{II}$ anomeric proton ($\delta_H$ 5.47) showed a COSY correlation to a proton at $\delta_H$ 4.13 which was assigned as Glc$_{II}$ H-2 and in turn showed a COSY correlation to a proton at $\delta_H$ 4.89 (Glc$_{II}$ H-3) which showed an additional correlation with a proton at $\delta_H$ 4.04 (Glc$_{II}$ H-4) which showed a correlation to a proton at $\delta_H$ 3.90 (Glc$_{II}$ H-5).

Assignment of the $^{13}$C chemical shifts for Glc$_{II}$ C-2 ($\delta_C$ 81.1), C-3 ($\delta_C$ 87.6), C-4 ($\delta_C$ 70.0) and C-5 ($\delta_C$ 77.4) was then completed using the HSQC data. The assignment at Glc$_{II}$ C-6 was made using the $^1$H, COSY and HSQC data in comparison with the data for rebaudioside X.

Two of the remaining unassigned glucose moieties were assigned as substituents at C-2 and C-3 of Glc$_I$ on the basis of HMBC correlations. The anomeric proton observed at $\delta_H$ 5.81 showed an HMBC correlation to Glc$_I$ C-2 and was assigned as the anomeric proton of Glc$_V$. The anomeric proton observed at $\delta_H$ 5.33 showed an HMBC correlation to Glc$_I$ C-3 and was assigned as the anomeric proton of Glc$_{VI}$. The reciprocal HMBC correlations between Glc$_I$ H-2 and anomeric carbon of Glc$_V$ and between Glc$_I$ H-3 and anomeric carbon of Glc$_{VI}$ were also observed. The assignments for C-2 through C-6 of Glc$_V$ and Glc$_{VI}$ were made using the $^1$H, COSY and HSQC data in comparison with the assignment of rebaudioside X.

A summary of the $^1$H and $^{13}$C chemical shifts for the glycoside at C-19 are found in Table 8.

TABLE 8

$^1$H and $^{13}$C NMR (500 and 125 MHz, pyridine-d$_5$) assignments of the (2a) C-19 glycoside.[a,b,c]

| Position | $^{13}$C NMR | $^1$H NMR |
|---|---|---|
| Glc$_I$-1 | 94.5 | 6.33 d (8.4) |
| Glc$_I$-2 | 76.6 | 4.51 t (8.8) |
| Glc$_I$-3 | 88.3 | 4.99 m |
| Glc$_I$-4 | 69.6 | 4.19 m |
| Glc$_I$-5 | 78.1 | 4.10 m |
| Glc$_I$-6 | 61.5 | 4.21 m |
|  |  | 4.33 m |
| Glc$_V$-1 | 103.8 | 5.81 d (6.9) |
| Glc$_V$-2 | 75.2 | 4.20 m |
| Glc$_V$-3 | 78.2 | 4.20 m |
| Glc$_V$-4 | 73.1 | 4.10 m |
| Glc$_V$-5 | 77.8 | 3.89 m |
| Glc$_V$-6 | 63.6 | 4.31 m |
|  |  | 4.62 d (11.1) |
| Glc$_{VI}$-1 | 103.9 | 5.33 d (7.7) |
| Glc$_{VI}$-2 | 75.1 | 3.97 m |
| Glc$_{VI}$-3 | 77.7 | 4.35 t (8.3) |
| Glc$_{VI}$-4 | 70.9 | 4.11 m |
| Glc$_{VI}$-5 | 77.7 | 3.85 m |
| Glc$_{VI}$-6 | 61.8 | 4.12 m |
|  |  | 4.33 m |

[a]assignments made on the basis of COSY, HSQC, HMBC, TOCSY and HSQC-TOCSY correlations;
[b]Chemical shift values are in δ (ppm);
[c]Coupling constants are in Hz.

The two remaining unassigned sugar moieties were assigned as substituents at C-2 and C-3 of Glc$_{II}$ on the basis of HMBC correlations. The anomeric proton observed at $\delta_H$ 5.45 showed an HMBC correlation to Glc$_{II}$ C-2 and was assigned as the anomeric proton of Glc$_{III}$. The anomeric proton observed at $\delta_H$ 5.44 showed an HMBC correlation to Glc$_{II}$ C-3 and was assigned as the anomeric proton of Glc$_{IV}$. The reciprocal HMBC correlation between Glc$_{II}$ H-2 and anomeric carbon of Glc$_{III}$ was observed as was the HMBC correlation between Glc$_{II}$ H-3 and the anomeric carbon of Glc$_{IV}$. The assignments for C-2 through C-6 of Glc$_{III}$ and Glc$_{IV}$ were made using the $^1$H, COSY and HSQC data in comparison with the assignment of rebaudioside X.

Analysis of the data indicated that the C-13 glycoside found in (2a) is identical to that found in rebaudioside X. A summary of the $^1$H and 13C chemical shifts for the glycoside at C-13 are found in Table 9.

TABLE 9

$^1$H and $^{13}$C NMR (500 and 125 MHz, pyridine-d$_5$) assignments of the (2a) C-13 glycoside.[a,b,c]

| Position | $^{13}$C NMR | $^1$H NMR |
|---|---|---|
| Glc$_{II}$-1 | 95.7 | 5.47 d (8.0) |
| Glc$_{II}$-2 | 81.1 | 4.13 m |
| Glc$_{II}$-3 | 87.6 | 4.89 t (8.9) |
| Glc$_{II}$-4 | 70.0 | 4.04 t (8.9) |
| Glc$_{II}$-5 | 77.4 | 3.90 m |
| Glc$_{II}$-6 | 62.4 | 4.17 m |
|  |  | 4.31 m |
| Glc$_{III}$-1 | 104.5 | 5.45 d (7.0) |
| Glc$_{III}$-2 | 75.6 | 4.15 m |
| Glc$_{III}$-3 | 78.1 | 4.14 m |
| Glc$_{III}$-4 | 72.8 | 4.02 m |
| Glc$_{III}$-5 | 77.3 | 3.77 m |
| Glc$_{III}$-6 | 63.5 | 4.31 m |
|  |  | 4.53 d (10.9) |
| Glc$_{IV}$-1 | 103.9 | 5.44 d (7.5) |
| Glc$_{IV}$-2 | 75.3 | 3.98 m |
| Glc$_{IV}$-3 | 77.6 | 4.46 (9.0) |
| Glc$_{IV}$-4 | 71.0 | 4.14 m |
| Glc$_{IV}$-5 | 77.8 | 3.99 m |
| Glc$_{IV}$-6 | 61.8 | 4.12 m |
|  |  | 4.33 m |

[a]assignments made on the basis of COSY, HSQC, HMBC, TOCSY and HSQC-TOCSY correlations;
[b]Chemical shift values are in δ (ppm);
[c]Coupling constants are in Hz.

Example 4

Isolation and Purification of (2b)

Figure 3:
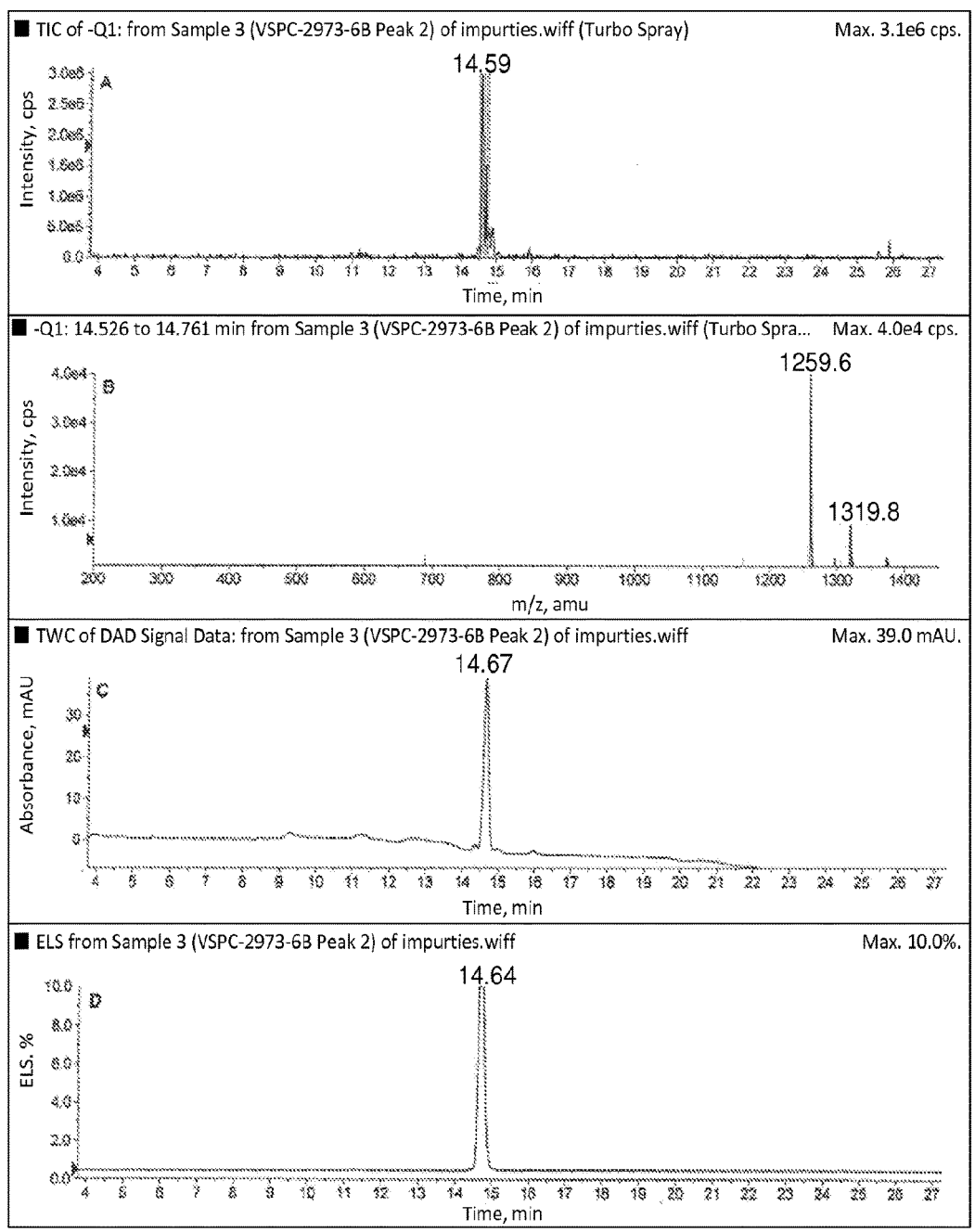
FIG. 3: LC-MS analysis of isolated sample of (2b) showing, from top to bottom, TIC, mass spectrum of the (2b) peak at 14.6 min, UV (210 nm) chromatogram and ELS chromatogram.

The material in Example 1 was analyzed by LC-MS using the LCMS method and the results are given in FIG. 3. Rebaudioside X was observed at 11.57 min in the UV (210 nm) chromatogram. The mass spectrum for the rebaudioside X peak provided the expected [M–H]$^-$ ion at m/z 1289.7. The (2b) peak was observed to elute at 14.67 min in the UV chromatogram and showed an [M–H]$^-$ ion at m/z 1259.7. Relative to rebaudioside X, this indicated a net loss of 30 Daltons. HPLC purification was performed using HPLC Method 1 and the peak eluting at 17.18 min was collected over several injections and dried by rotary evaporation under reduced pressure.

Example 5

Structural Elucidation of (2b)

Mass Spectrometry

The results of an LC-MS analysis of the isolated peak confirmed that it corresponded to (2b) (FIG. 3). A single peak was observed in the TIC, UV and ELS chromatograms.

The mass spectrum of the isolate of (2b) showed an [M−H]⁻ ion at m/z 1259.6 suggesting a nominal mass of 1260 Daltons.

The ESI+ TOF mass spectrum acquired by infusing a sample of (2b) showed [M+H]⁺ and [M+Na]⁺ ions at m/z 1261.5353 and 1283.5179, respectively. The mass of the [M+H]⁺ ion was in good agreement with the molecular formula C₅₅H₈₈O₃₂ (calcd for C₅₅H₈₉O₃₂: 1261.5337, error: 1.3 ppm) for (2b). The ESI− mass spectrum provided [M−H]⁻ and [M+HCOOH—H]⁻ ions at m/z 1259.5203 and 1305.5271, respectively. As above, the mass of the [M−H]⁻ ion was in good agreement with the molecular formula C₅₅H₈₈O₃₂ (calcd for C₅₅H₈₇O₃₂: 1259.5180, error: 1.8 ppm) for (2b). The +ESI and −ESI data indicated that (2b) has a nominal mass of 1260 Daltons with the molecular formula, C₅₅H₈₈O₃₂. The molecular formula of (2b) differs from that of rebaudioside X by the net loss of CH₂O suggesting the substitution of a pentose in place of one of the glucose residues.

The +ESI TOF MS/MS spectrum of (2b), fragmenting on the [M+H]⁺ ion at m/z 1261 provided fragment ions corresponding to loss of either a pentose moiety (m/z 1129.4924) or glucose moiety (m/z 1099.4807). A fragment ion was also observed at m/z 943.3131 corresponding to five glucose and one pentose residues. This ion underwent sequential loss of either a pentose or glucose to yield fragment ions at m/z 811.2704, 781.2599, 649.2180, 619.2078, 487.1655, 457.1554, 325.1136, and 295.1038.

The −ESI TOF MS/MS spectrum of (2b), fragmenting on the [M−H]⁻ ion at m/z 1259 indicated that the most abundant and readily formed ion is present at m/z 803.3705 and corresponds to the loss of two glucose residues and a pentose moiety. Since this fragmentation likely results at C-19 it suggested that the glycoside at C-19 is likely due to the substitution of a pentose in place of one of the glucose residues.

NMR Spectrometry

Figure 4:
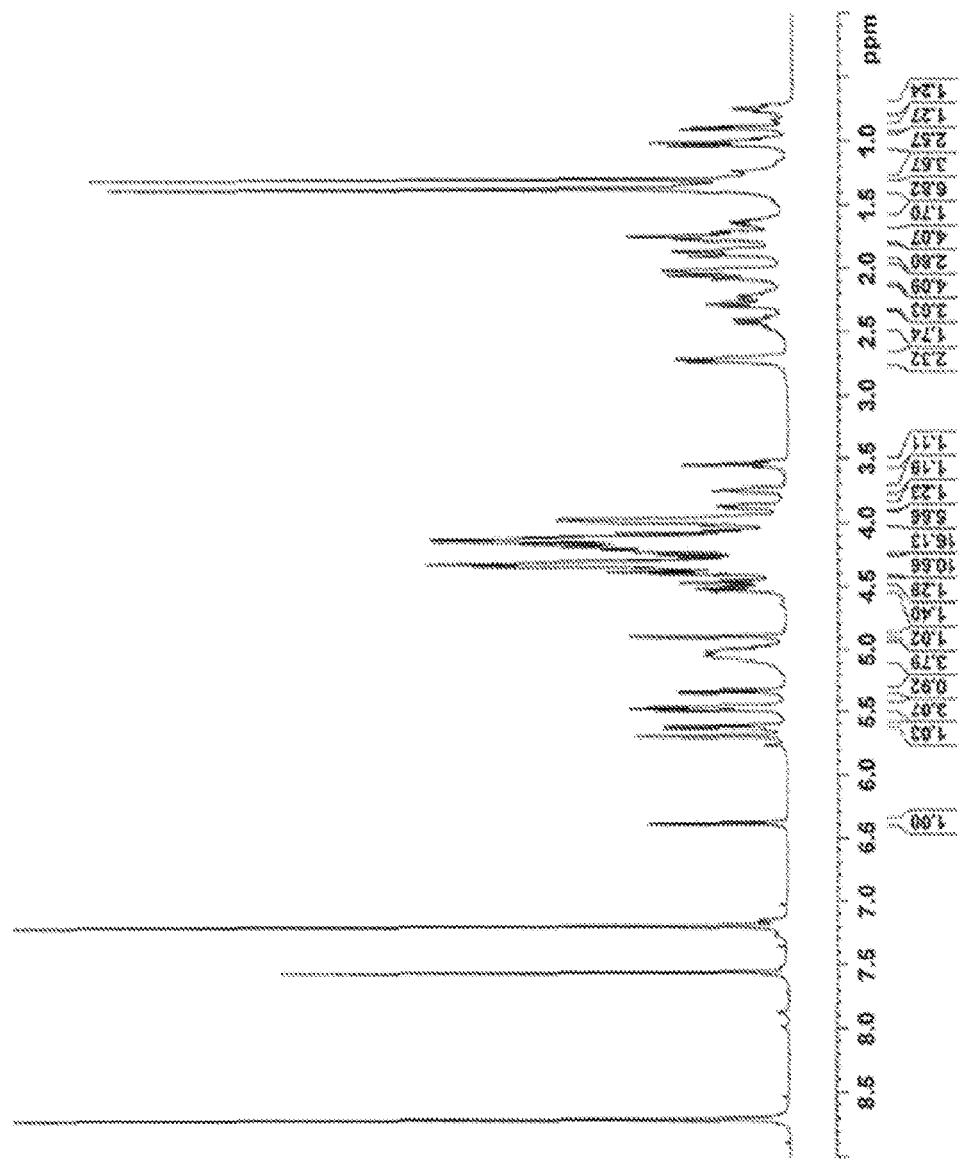
FIG. 4: $^1$H NMR (500 MHz, pyridine-$d_5$) of (2b).

A series of NMR experiments including ¹H NMR (FIG. 4), ¹H—¹H COSY, HSQC HMBC were performed to allow the assignment of (2b).

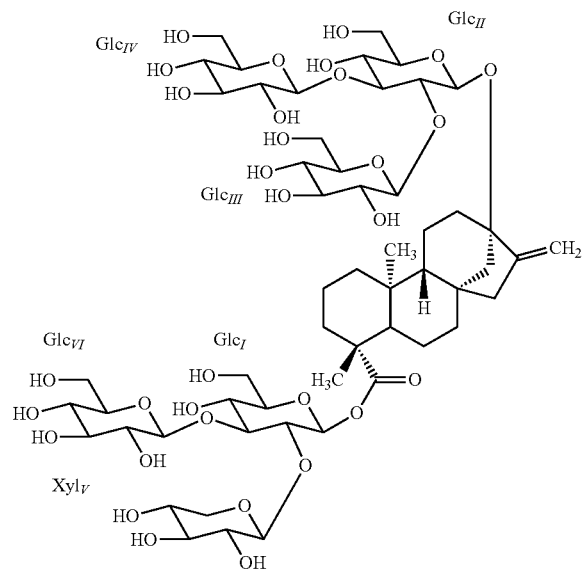

An HMBC correlation from the methyl protons at $\delta_H$ 1.29 ppm to the carbonyl at $\delta_C$ 176.7 allowed assignment of one of the tertiary methyl groups (C-18) as well as C-19 and provided a starting point for assignment of the rest of the aglycone. Additional HMBC correlations from the methyl protons (H-18) to carbons at $\delta_C$ 38.0, 43.9, and 57.0 allowed assignment of C3 to C5 in comparison with the data for rebaudioside X. The ¹H chemical shifts for C-3 ($\delta_H$ 1.01 and 2.29) and C-5 ($\delta_H$ 1.02) were assigned using the HSQC data. A COSY correlation between one of the H-3 protons ($\delta_H$ 1.01) and a proton at $\delta_H$ 1.35 allowed assignment of one of the H-2 protons which in turn showed a correlation with a proton at $\delta_H$ 0.75 which was assigned to C-1, The remaining ¹H and ¹³C chemical shifts for C-1 and C-2 were then assigned on the basis of additional COSY and HSQC correlations and are summarized in Table 10.

TABLE 10

¹H and ¹³C NMR (500 and 125 MHz, pyridine-d₅) assignments of the (2b) aglycone.[a,b,c]

| Position | ¹³C NMR | ¹H NMR |
|---|---|---|
| 1 | 40.0 | 0.75 t (13.2) |
|  |  | 1.76 m |
| 2 | 19.4 | 1.35 m |
|  |  | 2.23 m |
| 3 | 38.0 | 1.01 m |
|  |  | 2.29 m |
| 4 | 43.9 | — |
| 5 | 57.0 | 1.02 d (13.0) |
| 6 | 23.1 | 2.07 m |
|  |  | 2.42 q (13.5) |
| 7 | 42.2 | 1.37 m |
|  |  | 1.73 m |
| 8 | 39.2 | — |
| 9 | 54.0 | 0.90 d (8.1) |
| 10 | 41.3 | — |
| 11 | 19.9 | 1.65 m |
|  |  | 1.75 m |
| 12 | 38.2 | 1.86 m |
|  |  | 2.70 m |
| 13 | 87.5 | — |
| 14 | 42.9 | 2.01 m |
|  |  | 2.72 m |
| 15 | 46.3 | 1.88 d (17.0) |
|  |  | 2.04 m |
| 16 |  | — |
| 17 | 104.6 | 4.89 s |
|  |  | 5.69 s |
| 18 | 27.9 | 1.29 s |
| 19 | 176.7 | — |
| 20 | 16.4 | 1.36 s |

[a]assignments made on the basis of COSY, HSQC, HMBC, TOCSY and HSQC-TOCSY correlations;
[b]Chemical shift values are in δ (ppm);
[c]Coupling constants are in Hz.

The other tertiary methyl singlet, observed at $\delta_H$ 1.36 showed HMBC correlations to C-1 and C-5 and was assigned as C-20. The methyl protons showed additional HMBC correlations to a quaternary carbon ($\delta_C$ 41.3) and a methine ($\delta_H$ 0.90, $\delta_C$ 54.0) which were assigned as C-10 and C-9, respectively. COSY correlations between H-5 ($\delta_H$ 1.02) and protons at $\delta_H$ 2.07 and 2.42 then allowed assignment of the H-6 protons which in turn showed correlations to protons at $\delta_H$ 1.37 and 1.73 which were assigned to C-7. The ¹³C chemical shifts for C-6 ($\delta_C$ 23.1) and C-7 ($\delta_C$ 42.2) were then determined from the HSQC data.

COSY correlations between H-9 ($\delta_H$ 0.90) and protons at $\delta_H$ 1.65 and 1.75 allowed assignment of the H-11 protons which in turn showed COSY correlations to protons at $\delta_H$ 1.86 and 2.70 which were assigned as the H-12 protons. The HSQC data was then used to assign C-11 ($\delta_C$ 19.9) and C-12 ($\delta_C$ 38.2). The olefinic protons observed at $\delta_H$ 4.89 and 5.69 were assigned to C-17 in comparison with rebaudioside X and showed HMBC correlations to a carbon at $\delta_C$ 87.5 which was assigned as C-13. The $^{13}$C chemical shift for C-17 ($\delta_C$ 104.6) was then determined from the HSQC data. The isolated methylene groups at C-14 ($\delta_H$ 2.01 and 2.72, $\delta_C$ 42.9) and C-15 ($\delta_H$ 1.88 and 2.04, $\delta_C$ 46.3) were assigned in comparison with the data for rebaudioside X. An HMBC correlation was observed between one of the H-11 protons ($\delta_H$ 1.65) and C-15.

A summary of the $^1$H and $^{13}$C chemical shifts for the aglycone are found in Table 10.

An analysis of the HSQC data for (2b) confirmed the presence of 6 anomeric positions. Three of the anomeric protons were well resolved at $\delta_H$ 6.38 ($\delta_C$ 94.4), 5.62 ($\delta_C$ 104.7), and 5.33 ($\delta_C$ 103.9) in the $^1$H NMR spectrum. The remaining three anomeric protons were observed at $\delta_H$ 5.48 ($\delta_C$ 104.5), 5.46 ($\delta_C$ 103.8), and 5.45 ($\delta_C$ 96.0) and were overlapped in the $^1$H spectrum. The anomeric proton observed at $\delta_H$ 6.38 showed an HMBC correlation to C-19 which indicated that it corresponds to the anomeric proton of Glc$_I$. Similarly, the anomeric proton observed at $\delta_H$ 5.45 showed an HMBC correlation to C-13 allowing it to be assigned as the anomeric proton of Glc$_{II}$.

The Glc$_I$ anomeric proton ($\delta_H$ 6.38) showed a COSY correlation to a proton at $\delta_H$ 4.38 which was assigned as Glc$_I$ H-2 and in turn showed a COSY correlation to a proton at $\delta_H$ 5.04 (Glc$_I$ H-3) which showed a correlation with a proton at $\delta_H$ 4.24 (Glc$_I$ H-4) which showed a correlation with a proton at $\delta_H$ 4.14 (Glc$_I$ H-5).

Assignment of the $^{13}$C chemical shifts for Glc$_I$ C-2 ($\delta_C$ 77.1), C-3 ($\delta_C$ 88.2), C-4 ($\delta_C$ 69.8), and C-5 ($\delta_C$ 78.3) was made using the HSQC data. The assignment at Glc$_I$ C-6 was made using the $^1$H and HSQC data in comparison with the data for rebaudioside X. Assignment of Glc$_{II}$ was carried out in a similar fashion. The Glc$_{II}$ anomeric proton ($\delta_H$ 5.45) showed a COSY correlation to a proton at $\delta_H$ 4.13 which was assigned as Glc$_{II}$ H-2 and in turn showed a COSY correlation to a proton at $\delta_H$ 4.96 (Glc$_{II}$ H-3) which showed an additional correlation with a proton at $\delta_H$ 4.06 (Glc$_{II}$ H-4). Assignment of the $^{13}$C chemical shifts for Glc$_{II}$ C-2 ($\delta_C$ 61.0), C-3 ($\delta_C$ 67.6), and C-4 ($\delta_C$ 70.1) was then completed using the HSQC data. The assignments at Glc$_{II}$ C-5 and C-6 were made using the $^1$H, COSY and HSQC data in comparison with the data for rebaudioside X.

Two of the remaining unassigned glucose moieties were assigned as substituents at C-2 and C-3 of Glc$_I$ on the basis of HMBC correlations. The anomeric proton observed at $\delta_H$ 5.62 showed an HMBC correlation to Glc$_I$ C-2 and was assigned as the anomeric proton of sugar V. The anomeric proton observed at $\delta_H$ 5.33 showed an HMBC correlation to Glc$_I$ C-3 and was assigned as the anomeric proton of Glc$_{VI}$. The reciprocal HMBC correlation between Glc$_I$ H-2 and anomeric carbon of sugar V was also observed.

The chemical shift for the anomeric proton of sugar V ($\delta_H$ 5.62) differed significantly from that observed for rebaudioside X and suggested that this residue is modified in rebaudioside X. The anomeric proton showed a COSY correlation with a proton at $\delta_H$ 4.17 which was assigned as H-2. Sugar III C-2 ($\delta_C$ 75.2) was then assigned using the HSQC data. A series of 1-D TOCSY experiments selecting the anomeric proton showed correlations with H-2 and protons at $\delta_H$ 3.54, 4.12, and 4.32. The HSQC data indicated that the proton at $\delta_H$ 3.54 is part of a methylene group ($\delta_H$ 3.54 and 4.32, $\delta_C$ 66.6). The TOCSY correlation between the anomeric proton and the methylene protons confirmed that sugar V is a pentose residue. Although the methylene proton at $\delta_H$ 3.54 appeared as triplet (J=11.0 Hz) indicative of two large couplings, this proton showed COSY correlations only with the multiplet at $\delta_H$ 4.32 suggesting that both the other H-5 proton and H-4 must be overlapped at $\delta_H$ 4.32. An examination of the HSQC data allowed assignment of C-4 ($\delta_C$ 71.3). The remaining correlation observed in the TOCSY spectra ($\delta_H$ 4.12) was assigned as H-3 with C-3 ($\delta_C$ 76.3) assigned in turn from the HSQC data. The coupling constants for H-1 through H-4 were on the order of 6.0-9.0 Hz allowing sugar V to be assigned as a xylose residue in place of the glucose found in this position for rebaudioside X.

The anomeric proton of Glc$_{VI}$ ($\delta_H$ 5.33) showed a COSY correlation with a proton at $\delta_H$ 3.97 which was assigned as Glc$_{VI}$ H-2 and showed a COSY correlation with a proton at $\delta_H$ 4.36 which was assigned as Glc$_{VI}$ H-3. Glc$_{VI}$ C-2 ($\delta_C$ 75.2) and C-3 ($\delta_C$ 77.5) were then assigned using the HSQC data. Additional COSY correlations then allowed assignment of Glc$_{VI}$ H-4 ($\delta_H$ 4.11), Glc$_{VI}$ H-5 ($\delta_H$ 3.67), and the Glc$_{VI}$ H-6 protons ($\delta_H$ 4.10 and 4.31) with the corresponding $^{13}$C chemical shifts ($\delta_C$ 70.9, 77.6, and 61.6) determined using the HSQC data. A summary of the $^1$H and $^{13}$C chemical shifts for the glycoside at C-19 are found in Table 11.

TABLE 11

$^1$H and $^{13}$C NMR (500 and 125 MHz, pyridine-d$_5$) assignments of the (2b) C-19 glycoside.[a,b,c]

| Position | $^{13}$C NMR | $^1$H NMR |
|---|---|---|
| Glc$_I$-1 | 94.4 | 638 d (8.4) |
| Glc$_I$-2 | 77.1 | 4.38 m |
| Glc$_I$-3 | 88.2 | 5.04 m |
| Glc$_I$-4 | 69.8 | 4.24 m |
| Glc$_I$-5 | 78.3 | 4.14 m |
| Glc$_I$-6 | 61.7 | 4.20 m |
|   |   | 4.33 m |
| Xyl$_v$-1 | 104.7 | 5.62 d (7.8) |
| Xyl$_v$-2 | 75.2 | 4.17 m |
| Xyl$_v$-3 | 78.3 | 4.12 m |
| Xyl$_v$-4 | 71.3 | 4.32 m |
| Xyl$_v$-5 | 66.6 | 3.54 t (11.0) |
|   |   | 4.32 m |
| Glc$_{vI}$-1 | 103.9 | 5.33 d (8.1) |
| Glc$_{vI}$-2 | 75.2 | 3.97 m |
| Glc$_{vI}$-3 | 77.5 | 4.38 m |
| Glc$_{vI}$-4 | 70.9 | 4.11 m |
| Glc$_{vI}$-5 | 77.8 | 3.87 m |
| Glc$_{vI}$-6 | 61.8 | 4.10 m |
|   |   | 4.31 m |

[a]assignments made on the basis of COSY, HSQC, HMBC, TOCSY and HSQC-TOCSY correlations;
[b]Chemical shift values are in δ (ppm);
[c]Coupling constants are in Hz.

The two remaining unassigned sugar moieties were assigned as substituents at C-2 and C-3 of Glc$_{II}$ on the basis of HMBC correlations. The anomeric proton observed at $\delta_H$ 5.48 showed an HMBC correlation to Glc$_{II}$ C-2 and was assigned as the anomeric proton of Glc$_{III}$. The anomeric proton observed at $\delta_H$ 5.46 showed an HMBC correlation to Glc$_{II}$ C-3 and was assigned as the anomeric proton of Glc$_{IV}$. The reciprocal HMBC correlations between Glc$_{II}$ H-2 and anomeric carbon of Glc$_{III}$ was also observed. The assignments for C-2 through C-6 of Glc$_{III}$ and Glc$_{IV}$ were made using the $^1$H, COSY and HSQC data in comparison with the assignment of rebaudioside X.

A summary of the $^1$H and $^{13}$C chemical shifts for the glycoside at C-13 are found in Table 12.

TABLE 12

$^1$H and $^{13}$C NMR (500 and 125 MHz, pyridine-$d_5$) assignments of the (2b) C-13 glycoside.[a,b,c]

| Position | $^{13}$C NMR | $^1$H NMR |
|---|---|---|
| Glc$_{II}$-1 | 96.0 | 5.45 d (7.8) |
| Glc$_{II}$-2 | 81.0 | 4.13 m |
| Glc$_{II}$-3 | 87.6 | 4.98 t (9.1) |
| Glc$_{II}$-4 | 70.1 | 4.08 t (9.1) |
| Glc$_{II}$-5 | 77.4 | 3.95 m |
| Glc$_{II}$-6 | 62.4 | 4.21 m |
|  |  | 4.35 m |
| Glc$_{III}$-1 | 104.5 | 5.48 d (7.9) |
| Glc$_{III}$-2 | 75.3 | 4.16 m |
| Glc$_{III}$-3 | 78.2 | 4.13 m |
| Glc$_{III}$-4 | 72.9 | 3.99 m |
| Glc$_{III}$-5 | 77.3 | 3.75 ddd (3.1, 6.5, 9.7) |
| Glc$_{III}$-6 | 63.6 | 4.28 m |
|  |  | 4.51 dd (1.1, 11.6) |
| Glc$_{IV}$-1 | 103.8 | 5.46 d (7.5) |
| Glc$_{IV}$-2 | 75.2 | 3.98 m |
| Glc$_{IV}$-3 | 77.6 | 4.47 t (8.6) |
| Glc$_{IV}$-4 | 70.9 | 4.14 m |
| Glc$_{IV}$-5 | 77.7 | 3.99 m |
| Glc$_{IV}$-6 | 61.7 | 4.20 m |
|  |  | 4.33 m |

[a] assignments made on the basis of COSY, HSQC, HMBC, TOCSY and HSQC-TOCSY correlations;
[b] Chemical shift values are in δ (ppm);
[c] Coupling constants are in Hz.

Example 6

Isolation and Purification of (2c)

The material from Example 1 was analyzed by LC-MS using the LCMS method described above. Rebaudioside X was observed at 11.57 min in the UV (210 nm) chromatogram. The mass spectrum for the rebaudioside X peak provided the expected [M−H]$^−$ ion at m/z 1289.7. The (2c) peak was observed to elute at 15.99 min in the UV chromatogram and showed an [M−H]$^−$ ion at m/z 1274.0. Relative to rebaudioside X, this indicated a net loss of 16 Daltons. HPLC purification was performed using HPLC Method 1 and the peak eluting at 18.29 min was collected over several injections and dried by rotary evaporation under reduced pressure.

Example 7

Structural Elucidation of (2c)

Mass Spectrometry

Figure 5:
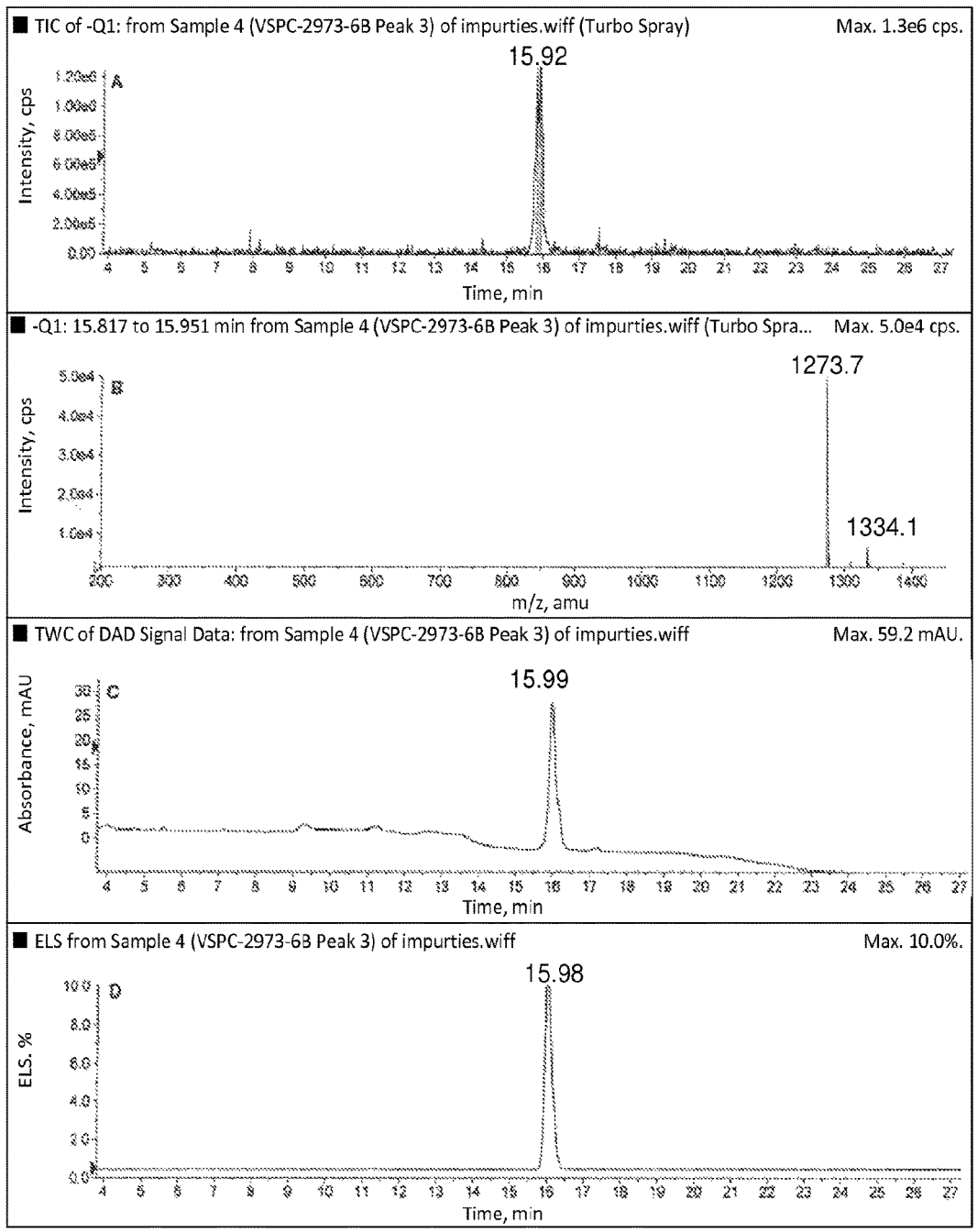
FIG. 5: LC-MS analysis of isolated sample of (2c) showing, from top to bottom, TIC, mass spectrum of the (2c) peak at 15.9 min, UV (210 nm) chromatogram and ELS chromatogram.

The results of an LC-MS analysis of the isolated peak confirmed that it corresponded to (2c) (FIG. 5). A single peak was observed in the TIC, UV and ELS chromatograms. The mass spectrum of the isolate of (2c) showed an [M−H]$^−$ ion at m/z 1273.7 suggesting a nominal mass of 1274 Daltons.

The ESI+ TOF mass spectrum acquired by infusing a sample of (2c) showed [M+H]$^+$ and [M+Na]$^+$ ions at m/z 1275.5485 and 1297.5297, respectively. The mass of the [M+H]$^+$ ion was in good agreement with the molecular formula $C_{56}H_{90}O_{32}$ (calcd for $C_{56}H_{91}O_{32}$: 1275.5493, error: −0.6 ppm) for rebaudioside X. The ESI− mass spectrum provided [M−H]$^−$ and [M+HCOOH−H]$^−$ ions at m/z 1273.5349 and 1319.5414, respectively. As above, the mass of the [M−H]$^−$ ion was in good agreement with the molecular formula $C_{56}H_{90}O_{33}$ (calcd for $C_{56}H_{89}O_{32}$: 1273.5337, error: 0.9 ppm) for (2c). The +ESI and −ESI data indicated that (2c) has a nominal mass of 1274 Daltons with the molecular formula, $C_{56}H_{90}O_{33}$. The molecular formula of (2c) differs from that of rebaudioside X by the net loss of one oxygen atom.

The +ESI TOF MS/MS spectrum of (2c), fragmenting on the [M+H]$^+$ ion at m/z 1275 and provided fragment ions corresponding to loss of either a deoxyhexose moiety (m/z 1129.4969) or glucose moiety (m/z 1113.4985). A fragment ion was also observed at m/z 957.3300 corresponding to five glucose and one deoxyhexose residues. This ion underwent sequential loss of either a deoxyhexose or glucose to yield fragment ions at m/z 811.2729, 795.2766, 649.2191, 633.2243, 487.1664, 471.1717, 325.1144, and 309.1202.

The −ESI TOf MS/MS spectrum of (2c), fragmenting on the [M−H]$^−$ ion at m/z 1273 indicated that the most abundant and readily formed ion is present at m/z 787.3767 and corresponds to the loss of three glucose residues. This suggested that the glycoside at C-19 is likely composed of three glucose residues and by inference indicated that the deoxyglucose is present as part of the glycoside at C-13.

NMR Spectrometry

Figure 6:
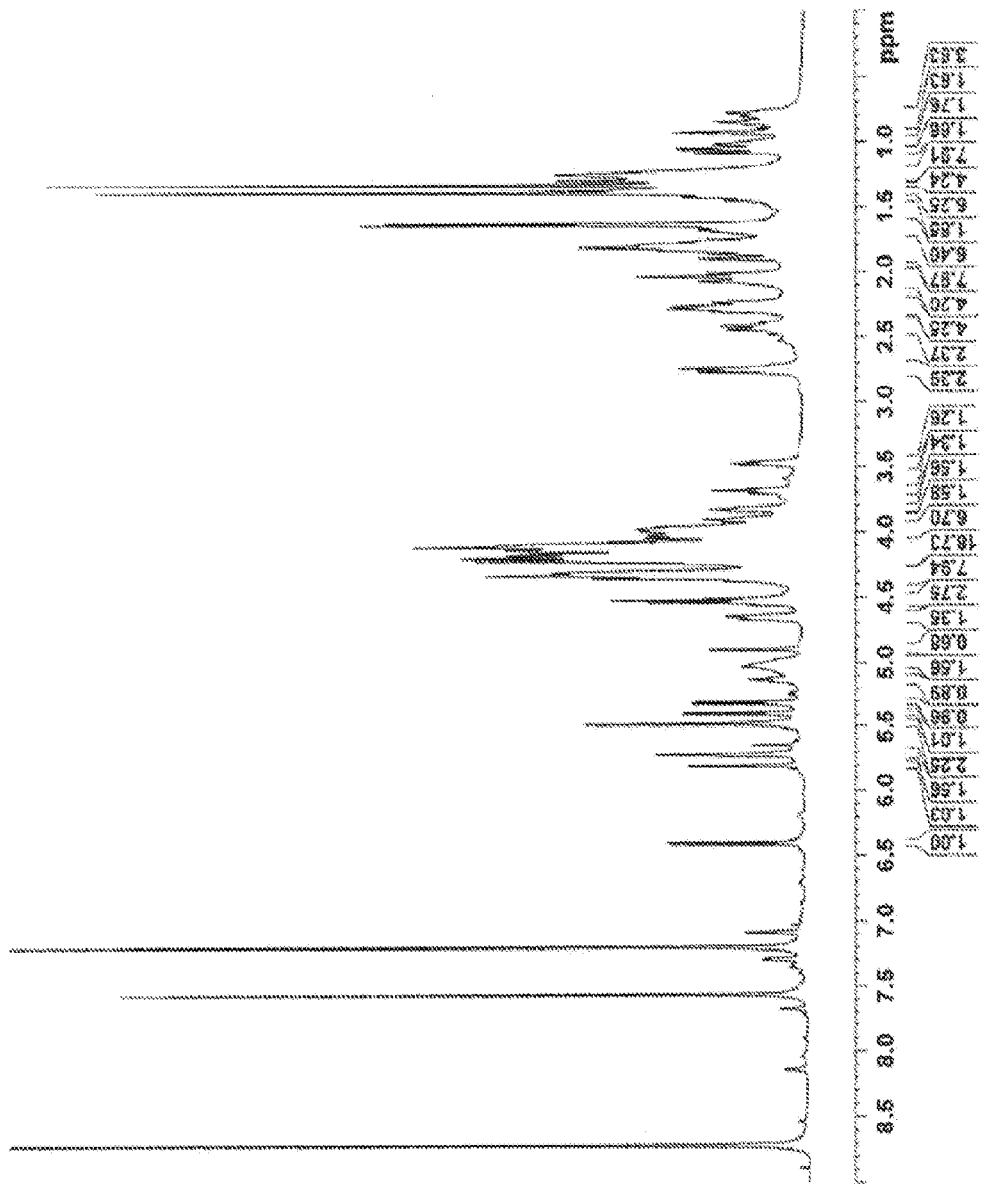
FIG. 6: $^1$H NMR (500 MHz, pyridine-$d_5$) of (2c).

A series of NMR experiments including $^1$H NMR (FIG. 6), $^1$H—$^1$H COSY, HSQC, and HMBC were performed to allow the assignment of (2c).

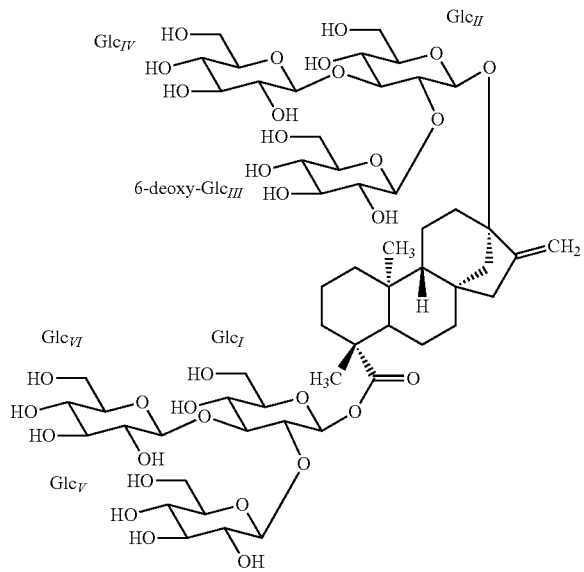

An HMBC correlation from the methyl protons at $\delta_H$ 1.32 ppm to the carbonyl at $\delta_C$ 177.0 allowed assignment of one of the tertiary methyl groups (C-18) as well as C-19 and provided a starting point for assignment of the rest of the aglycone. Additional HMBC correlations from the methyl protons (H-18) to carbons at $\delta_C$ 38.1, 44.0, and 57.0 allowed assignment of C3 to C5 in comparison with the data for rebaudioside X. The $^1$H chemical shifts for C-3 ($\delta_H$ 1.02 and 2.29) and C-5 ($\delta_H$ 1.06) were assigned using the HSQC data. A COSY correlation between one of the H-3 protons ($\delta_H$ 1.02) and a proton at $\delta_H$ 1.37 allowed assignment of one of the H-2 protons which in turn showed a correlation with a proton at $\delta_H$ 0.77 which was assigned to C-1. The remaining $^1$H and $^{13}$C chemical shifts for C-1 and C-2 were then assigned on the basis of additional COSY and HSQC correlations and are summarized in Table 13.

TABLE 13

$^1$H and $^{13}$C NMR (500 and 125 MHz, pyridine-d$_5$) assignments of the (2c) aglycone.[a,b,c]

| Position | $^{13}$C NMR | $^1$H NMR |
|---|---|---|
| 1 | 39.9 | 0.77 t (12.3) |
|   |      | 1.79 m |
| 2 | 19.3 | 1.37 m |
|   |      | 2.28 m |
| 3 | 38.1 | 1.02 m |
|   |      | 2.79 m |
| 4 | 44.0 | — |
| 5 | 57.0 | 1.06 d (12.9) |
| 6 | 23.2 | 2.24 m |
|   |      | 2.41 m |
| 7 | 42.3 | 1.42 m |
|   |      | 1.81 m |
| 8 | 39.7 | — |
| 9 | 54.0 | 0.92 d (7.7) |
| 10 | 41.4 | — |
| 11 | 19.8 | 1.67 m |
|    |      | 1.76 m |
| 12 | 38.1 | 1.81 m |
|    |      | 2.74 m |
| 13 | 87.4 | — |
| 14 | 42.9 | 2.01 m |
|    |      | 2.75 m |
| 15 | 46.1 | 1.88 m |
|    |      | 2.05 m |
| 16 | 153.7 | — |
| 17 | 104.5 | 4.89 s |
|    |       | 5.72 s |
| 18 | 27.9 | 1.32 s |
| 19 | 177.0 | — |
| 20 | 16.6 | 1.38 s |

[a] assignments made on the basis of COSY, HSQC, HMBC, TOCSY and HSQC-TOCSY correlations;
[b] Chemical shift values are in δ (ppm);
[c] Coupling constants are in Hz.

The other tertiary methyl singlet, observed at $\delta_H$ 1.38 showed HMBC correlations to C-1 and C-5 and was assigned as C-20. The methyl protons showed additional HMBC correlations to a quaternary carbon ($\delta_C$ 41.4) and a methine ($\delta_H$ 0.92, $\delta_C$ 54.0) which were assigned as C-10 and C-9, respectively. COSY correlations between H-5 ($\delta_H$ 1.06) and protons at $\delta_H$ 2.24 and 2.41 then allowed assignment of the H-6 protons which in turn showed correlations to protons at $\delta_H$ 1.42 and 1.81 which were assigned to C-7. The $^{13}$C chemical shifts for C-6 ($\delta_C$ 23.2) and C-7 ($\delta_C$ 42.3) were then determined from the HSQC data.

COSY correlations between H-9 ($\delta_H$ 0.92) and protons at $\delta_H$ 1.67 and 1.76 allowed assignment of the H-11 protons which in turn showed COSY correlations to protons at $\delta_H$ 1.81 and 2.74 which were assigned as the H-12 protons. The HSQC data was then used to assign C-11 ($\delta_C$ 19.8) and C-12 ($\delta_C$ 38.1). An HMBC correlation between the H-12 protons and a carbon at $\delta_C$ 87.4 allowed assignment of C-13. The olefinic protons observed at $\delta_H$ 4.89 and 5.72 showed HMBC correlations to C-13 and were assigned to C-17 ($\delta_C$ 104.5 via HSQC). The isolated methylene groups at C-14 ($\delta_H$ 2.01 and 2.75, $\delta_C$ 42.9) and C-15 OH 1.88 and 2.05, $\delta_C$ 46.1) were assigned in comparison with the data for rebaudioside X. A HMBC correlation between one of the H-15 protons ($\delta_H$ 1.88) and a carbon at $\delta_C$ 153.7 allowed assignment of C-16.

A summary of the $^1$H and $^{13}$C chemical shifts for the aglycone are found in Table 13.

An analysis of the HSQC data for (2c) confirmed the presence of 6 anomeric positions. Four of the anomeric protons were well resolved at $\delta_H$ 6.41 ($\delta_C$ 94.5), 5.81 ($\delta_C$ 103.9), 5.39 ($\delta_C$ 104.3), and 5.30 ($\delta_C$ 103.9) in the $^1$H NMR spectrum. The remaining two anomeric protons were observed at $\delta_H$ 5.49 ($\delta_C$ 95.9) and 5.48 ($\delta_C$ 103.5) and were overlapped in the $^1$H spectrum. The anomeric proton observed at $\delta_H$ 6.41 showed a HMBC correlation to C-19 which indicated that it corresponds to the anomeric proton of Glc$_I$. Similarly, the anomeric proton observed at $\delta_H$ 5.49 showed a HMBC correlation to C-13 allowing it to be assigned as the anomeric proton of Glc$_{II}$.

The Glc$_I$ anomeric proton ($\delta_H$ 6.41) showed a COSY correlation to a proton at $\delta_H$ 4.52 which was assigned as Glc$_I$ H-2 and in turn showed a COSY correlation to a proton at $\delta_H$ 5.14 (Glc$_I$ H-3) which showed a correlation with a proton at $\delta_H$ 4.20 (Glc$_I$ H-4). Assignment of the $^{13}$C chemical shifts for Glc$_I$ C-2 ($\delta_C$ 76.5), C-3 ($\delta_C$ 88.2), and C-4 ($\delta_C$ 69.7) was made using the HSQC data. The assignments at Glc$_I$ C-5 and C-6 were made using the $^1$H and HSQC data in comparison with the data for rebaudioside X.

Assignment of Glc$_{II}$ was carried out in a similar manner. The Glc$_{II}$ anomeric proton ($\delta_H$ 5.49) showed a COSY correlation to a proton at $\delta_H$ 4.08 which was assigned as Glc$_{II}$ H-2 and in turn showed a COSY correlation to a proton at $\delta_H$ 5.01 (Glc$_{II}$ H-3) which showed an additional correlation with a proton at $\delta_H$ 4.09 (Glc$_{II}$ H-4). Assignment of the $^{13}$C chemical shifts for Glc$_{II}$ C-2 ($\delta_C$ 81.1), C-3 ($\delta_C$ 87.7), and C-4 ($\delta_C$ 70.3) was then completed using the HSQC data. The assignments at Glc$_{II}$ C-5 and C-6 were made using the $^1$H, COSY and HSQC data in comparison with the data for rebaudioside X.

Two of the remaining unassigned glucose moieties were assigned as substituents at C-2 and C-3 of Glc$_I$ on the basis of HMBC correlations. The anomeric proton observed at $\delta_H$ 5.81 showed an HMBC correlation to Glc$_I$ C-2 and was assigned as the anomeric proton of Glc$_V$. The anomeric proton observed at $\delta_H$ 5.30 showed an HMBC correlation to Glc$_I$ C-3 and was assigned as the anomeric proton of Glc$_{VI}$. The reciprocal HMBC correlation between Glc$_I$ H-2 and anomeric carbon of Glc$_V$ was also observed. The assignments for C-2 through C-6 of Glc$_V$ and Glc$_{VI}$ were made using the $^1$H, COSY and HSQC data in comparison with the assignment of rebaudioside X.

A summary of the $^1$H and $^{13}$C chemical shifts for the glycoside at C-19 are found in Table 14.

TABLE 14

$^1$H and $^{13}$C NMR (500 and 125 MHz, pyridine-d$_5$) assignments of the (2c) C-19 glycoside.[a,b,c]

| Position | $^{13}$C NMR | $^1$H NMR |
|---|---|---|
| Glc$_I$-1 | 94.5 | 6.41 d (8.2) |
| Glc$_I$-2 | 76.5 | 4.52 t (8.7) |
| Glc$_I$-3 | 88.2 | 5.14 t (8.7) |
| Glc$_I$-4 | 69.7 | 4.20 m |
| Glc$_I$-5 | 78.0 | 4.14 m |
| Glc$_I$-6 | 61.7 | 4.20 m |
|           |      | 4.30 m |
| Glc$_V$-1 | 103.9 | 5.81 d (7.5) |
| Glc$_V$-2 | 75.0 | 4.25 m |
| Glc$_V$-3 | 78.0 | 4.18 m |
| Glc$_V$-4 | 73.3 | 4.10 m |
| Glc$_V$-5 | 77.4 | 3.90 ddd (3.3, 6.8, 9.3) |
| Glc$_V$-6 | 63.6 | 4.32 m |
|           |      | 4.66 d (11.3) |
| Glc$_{VI}$-1 | 103.9 | 5.30 d (8.0) |
| Glc$_{VI}$-2 | 75.1 | 3.95 m |
| Glc$_{VI}$-3 | 77.6 | 4.33 m |
| Glc$_{VI}$-4 | 70.6 | 4.09 m |
| Glc$_{VI}$-5 | 77.7 | 3.82 m |

TABLE 14-continued $^1$H and $^{13}$C NMR (500 and 125 MHz, pyridine-d$_5$)
assignments of the (2c) C-19 glycoside.$^{a,b,c}$

| Position | $^{13}$C NMR | $^1$H NMR |
|---|---|---|
| Glc$_{VI}$-6 | 61.7 | 4.10 m |
|  |  | 4.32 m |

$^a$assignments made on the basis of COSY, HSQC, HMBC, TOCSY and HSQC-TOCSY correlations;
$^b$Chemical shift values are in δ (ppm);
$^c$Coupling constants are in Hz.

The two remaining unassigned sugar moieties were assigned as substituents at C-2 and C-3 of Glc$_{II}$ on the basis of HMBC correlations. The anomeric proton observed at $δ_H$ 5.39 showed an HMBC correlation to Glc$_{II}$ C-2 and was assigned as the anomeric proton of Sugar III which was subsequently determined to be 6-deoxyglucose (see below). The anomeric proton observed at $δ_H$ 5.48 showed an HMBC correlation to Glc$_{II}$ C-3 and was assigned as the anomeric proton of Glc$_{IV}$. The reciprocal HMBC correlations between Glc$_{II}$ H-2 and anomeric carbon of Glc$_{III}$ was also observed.

The anomeric proton of sugar III ($δ_H$ 5.39) showed a COSY correlation with a proton at $δ_H$ 4.14 which was assigned as H-2. Sugar III C-2 ($δ_C$ 75.5) was then assigned using the HSQC data. A series of 1-D TOCSY experiments selecting the anomeric proton showed correlations with H-2 and protons at $δ_H$ 1.63, 3.47, 3.69, and 4.04. The TOCSY correlation between the anomeric proton and the methyl doublet at $δ_H$ 1.63 indicated that sugar III is a 6-deoxyhexose. The methyl protons (H-6, $δ_H$ 1.63) showed a COSY correlation with the proton at $δ_H$ 3.47 which in turn showed a COSY correlation with the proton at $δ_H$ 3.69 which showed a COSY correlation with the proton at $δ_H$ 4.04 allowing assignment of H-5 through H-3, respectively. The $^{13}$C chemical shifts for C-3 ($δ_C$ 78.1), C-4 ($δ_C$ 76.7), C-5 ($δ_C$ 72.4), and C-6 ($δ_C$ 18.3) were subsequently determined from the HSQC spectrum. All of the coupling constants for H-1 through H-5 were on the order of 8.0-9.0 Hz allowing sugar III to be assigned as a 6-deoxyglucose (quinivose).

The anomeric proton of Glc$_{IV}$ ($δ_H$ 5.48) showed a COSY correlation with a proton at $δ_H$ 4.00 which was assigned as Glc$_{IV}$ H-2 and showed a COSY correlation with a proton at $δ_H$ 4.55 which was assigned as Glc$_{IV}$ H-3. Glc$_{IV}$ C-2 ($δ_C$ 75.2) and C-3 ($δ_C$ 77.4) were then assigned using the HSQC data. Additional COSY correlations then allowed assignment of Glc$_{IV}$ H-4 ($δ_H$ 4.18) and Glc$_{IV}$ H-5 ($δ_H$ 4.01) with the corresponding $^{13}$C chemical shifts ($δ_C$ 71.0 and 77.6) determined using the HSQC data. The remaining oxymethylene group ($δ_H$ 4.20 and 4.30, $δ_C$ 61.7) was assigned in comparison with rebaudioside X.

A summary of the $^1$H and $^{13}$C chemical shifts for the glycoside at C-13 are found in Table 15.

TABLE 15

$^1$H and $^{13}$C NMR (500 and 125 MHz, pyridine-d$_5$)
assignments of the (2c) C-13 glycoside.$^{a,b,c}$

| Position | $^{13}$C NMR | $^1$H NMR |
|---|---|---|
| Glc$_{II}$-1 | 95.9 | 5.49 d (7.9) |
| Glc$_{II}$-2 | 81.1 | 4.08 m |
| Glc$_{II}$-3 | 87.7 | 5.01 m |
| Glc$_{II}$-4 | 70.3 | 4.09 m |
| Glc$_{II}$-5 | 77.4 | 3.96 m |
| Glc$_{II}$-6 | 62.2 | 4.20 m |
|  |  | 4.32 m |
| 6-deoxy-Glc$_{III}$-1 | 104.3 | 5.39 d (8.0) |
| 6-deoxy-Glc$_{III}$-2 | 75.5 | 4.14 m |
| 6-deoxy-Glc$_{III}$-3 | 78.1 | 4.04 m |
| 6-deoxy-Glc$_{III}$-4 | 76.7 | 3.69 t (8.9) |
| 6-deoxy-Glc$_{III}$-5 | 72.4 | 3.47 dq (6.0, 8.9) |
| 6-deoxy-Glc$_{III}$-6 | 18.3 | 1.63 d (6.1) |
| Glc$_{IV}$-1 | 103.5 | 5.48 d (7.9) |
| Glc$_{IV}$-2 | 75.2 | 4.00 m |
| Glc$_{IV}$-3 | 77.4 | 4.55 t (9.2) |
| Glc$_{IV}$-4 | 71.0 | 4.18 m |
| Glc$_{IV}$-5 | 77.6 | 4.01 m |
| Glc$_{IV}$-6 | 61.7 | 4.20 m |
|  |  | 4.30 m |

$^a$assignments made on the basis of COSY, HSQC, HMBC, TOCSY and HSQC-TOCSY correlations;
$^b$Chemical shift values are in δ (ppm);
$^c$Coupling constants are in Hz.

Example 8

Isolation and Purification of (2d)

The material from Example 1 was analyzed by LC-MS using the method described above. Rebaudioside X was observed at 11.5 min in the UV (210 nm) chromatogram. The mass spectrum for the rebaudioside X peak provided the expected [M−H]$^−$ ion at m/z 1290.3. The (2d) peak was observed to elute at 7.1 min in the UV chromatogram and showed an [M−H]$^−$ ion at m/z 1308.0. Relative to rebaudioside X, this indicated a net addition of 18 Daltons. HPLC purification was performed using HPLC Method 3 and the peak eluting at 7.86 min was collected over several injections and dried by rotary evaporation under reduced pressure.

Example 9

Structural Elucidation of (2d)

Mass Spectrometry

Figure 7:
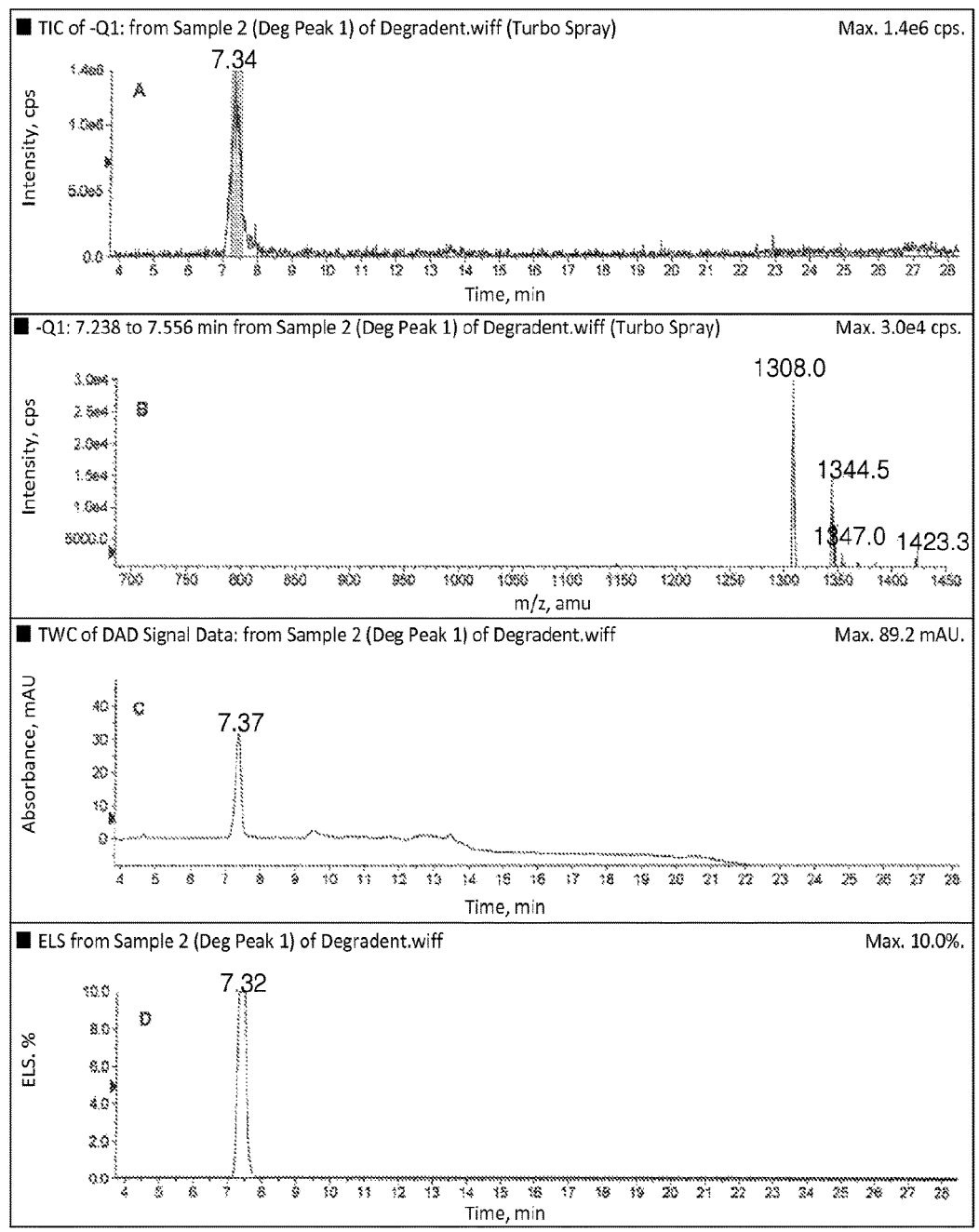
FIG. 7: LC-MS analysis of isolated sample of (2d) showing, from top to bottom, TIC, mass spectrum of the (2d) peak at 7.3 min, UV (210 nm) chromatogram and ELS chromatogram.

The results of an LC-MS analysis of the isolated peak confirmed that it corresponded to (2d) (FIG. 7). A single peak was observed in the TIC, UV and ELS chromatograms. The mass spectrum of the isolate of (2d) showed an [M−H]$^−$ ion at m/z 1308.0 suggesting a nominal mass of 1308 Daltons.

The ESI+ TOF mass spectrum acquired by infusing a sample of (2d) showed [M+H]$^+$ and [M+Na]$^+$ ions at m/z 1309.5588 and 1331.5414, respectively. The mass of the [M+H]$^+$ ion was in good agreement with the molecular formula $C_{56}H_{92}O_{34}$ (calcd for $C_{56}H_{93}O_{34}$: 1309.5548, error: 3.0 ppm) for (2d). The ESI− mass spectrum provided [M−H]$^−$ and [M+HCOOH—H]$^−$ ions at m/z 1307.5353 and 1353.5399, respectively. As above, the mass of the [M−H]$^−$ ion was in good agreement with the molecular formula $C_{56}H_{92}O_{34}$ (calcd for $C_{56}H_{91}O_{34}$: 1307.5392, error: −2.8 ppm) for (2d). The +ESI and −ESI data indicated that (2d) has a nominal mass of 1308 Daltons with the molecular formula, $C_{56}H_{92}O_{34}$. The molecular formula of (2d) differs from that of rebaudioside X by the net addition of $H_2O$.

The +ESI TOF MS/MS of (2d), fragmenting on the [M+H]$^+$ ion at m/z 1309 showed an ion at m/z 1291.5469 corresponding to the loss of $H_2O$. A series of fragment ions were observed at m/z 1147.5048, 985.4510, 823.3992, and 661.3459 due to the sequential loss of 4 glucose moieties. A second series of fragment ions were observed at m/z 1129.4951, 967.4416, 805.3882, 643.3328, 481.2800, and 319.2282 due to the sequential loss of 6 glucose moieties from the ion at m/z 1291.5469. A fragment ion was also observed at m/z 973.3272 corresponding to 6 glucose moieties and this ion underwent sequential loss of 5 glucose residues to yield fragment ions at m/z 811.2730, 649.2197, 487.1658, 325.1145, and 163.0630. The fragmentation pattern observed for (2d) was very similar to that observed for rebaudioside X and indicated the presence of 6 glucose residues.

The −ESI TOf MS/MS spectrum of (2d), fragmenting on the [M−H]⁻ ion at m/z 1307 indicated that the most abundant and readily formed ion is present at m/z 821.3790 and corresponds to the loss of three glucose residues. This suggested that the glycoside at C-19 is likely composed of three glucose residues and by inference indicated that the glycoside at C-13 also likely is composed of three glucose residues.

NMR Spectrometry

Figure 8:
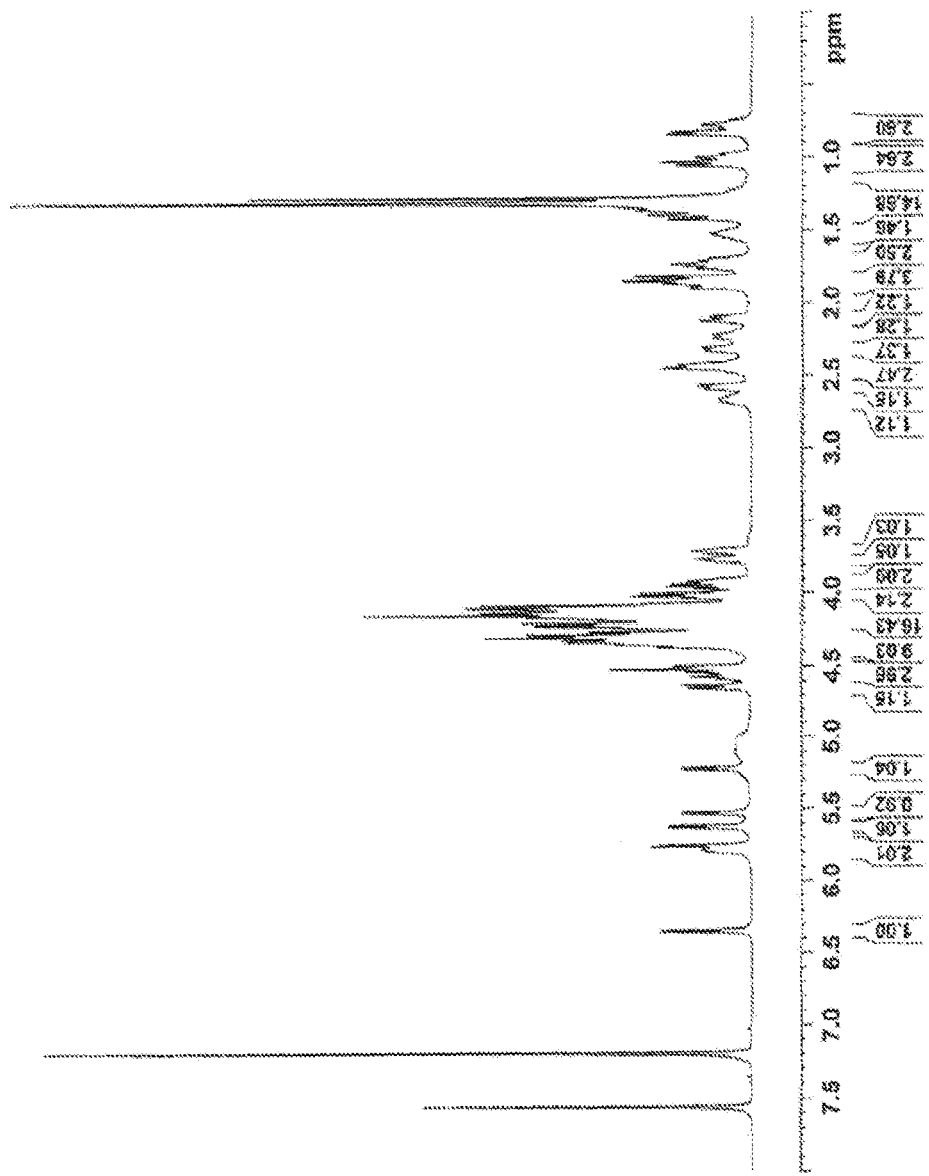
FIG. 8: $^1$H NMR (500 MHz, pyridine-$d_5$) of (2d).

A series of NMR experiments including $^1$H NMR (FIG. 8), $^1$H—$^1$H COSY, HSQC, HMBC were performed to allow the assignment of (2d). A preliminary inspection of the NMR data indicated that the olefinic protons observed for rebaudioside X were absent. Together with the MS data this suggested that addition of $H_2O$ at the C-16 unsaturation may have occurred during degradation.

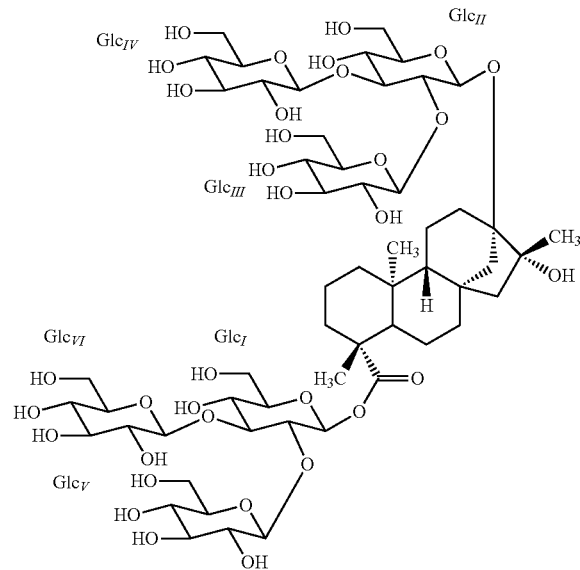

An HMBC correlation from the methyl protons at $\delta_H$ 1.28 ppm to the carbonyl at $\delta_C$ 176.9 allowed assignment of one of the tertiary methyl groups (C-18) as well as C-19 and provided a starting point for assignment of the rest of the aglycone. Additional HMBC correlations from the methyl protons (H-18) to carbons at $\delta_C$ 38.4, 43.8, and 57.1 allowed assignment of C3 to C5 in comparison with the data for rebaudioside X. The $^1$H chemical shifts for C-3 ($\delta_H$ 1.00 and 2.32) and C-5 ($\delta_H$ 1.04) were assigned using the HSQC data. A COSY correlation between one of the H-3 protons ($\delta_H$ 1.00) and a proton at $\delta_H$ 1.34 allowed assignment of one of the H-2 protons which in turn showed a correlation with a proton at $\delta_H$ 0.78 which was assigned to C-1. The remaining $^1$H and $^{13}$C chemical shifts for C-1 and C-2 were then assigned on the basis of additional COSY and HSQC correlations and are summarized in Table 16.

TABLE 16

$^1$H and $^{13}$C NMR (500 and 125 MHz, pyridine-d₅) assignments of the (2d) aglycone.[a,b,c]

| Position | $^{13}$C NMR | $^1$H NMR |
|---|---|---|
| 1 | 40.3 | 0.78 t (13.2) |
|   |      | 1.75 d (13.0) |
| 2 | 19.3 | 1.34 m |
|   |      | 2.23 m |
| 3 | 38.4 | 1.00 td (3.9, 12.8) |
|   |      | 2.32 d (12.3) |
| 4 | 43.8 | — |
| 5 | 57.1 | 1.04 d (12.7) |
| 6 | 23.1 | 2.11 d (13.5) |
|   |      | 2.43 m |
| 7 | 42.8 | 1.37 m |
|   |      | 1.88 m |
| 8 |      | — |
| 9 | 54.8 | 0.84 d (8.1) |
| 10 |     | — |
| 11 | 19.8 | 1.52 m |
|    |      | 1.71 m |
| 12 | 31.6 | 1.85 m |
|    |      | 2.67 m |
| 13 | 87.6 | — |
| 14 | 40.3 | 2.44 m |
|    |      | 2.58 d (9.9) |
| 15 | 54.3 | 1.41 d (14.3) |
|    |      | 1.83 m |
| 16 | 77.1 | — |
| 17 | 22.2 | 1.31 s |
| 18 | 27.7 | 1.28 s |
| 19 | 176.9 | — |
| 20 | 16.0 | 1.31 s |

[a]assignments made on the basis of COSY, HSQC, HMBC, TOCSY and HSQC-TOCSY correlations;
[b]Chemical shift values are in δ (ppm);
[c]Coupling constants are in Hz.

Two additional tertiary methyl singlets were observed as a single overlapped singlet at $\delta_H$ 1.31 in the $^1$H NMR spectrum but showed HSQC correlations to separate carbons at $\delta_C$ 16.0 and 22.2. One of these overlapped singlets ($\delta_H$ 1.31, $\delta_C$ 16.0) was tentatively assigned as C-20 in comparison with the data for rebaudioside X and showed HMBC correlations to C-1 and C-5. The methyl protons showed an additional HMBC correlation to a methine ($\delta_H$ 0.84, $\delta_C$ 54.8) which was assigned as C-9. An HMBC correlation between H-9 and a carbon at $\delta_C$ 16.0 then confirmed the assignment of the C-20 methyl group. COSY correlations between H-5 ($\delta_H$ 1.04) and protons at $\delta_H$ 2.11 and 2.43 then allowed assignment of the H-6 protons which in turn showed correlations to protons at $\delta_H$ 1.37 and 1.88 which were assigned to C-7. The $^{13}$C chemical shifts for C-6 ($\delta_C$ 23.1) and C-7 ($\delta_C$ 42.8) were then determined from the HSQC data.

COSY correlations between H-9 ($\delta_H$ 0.84) and protons at $\delta_H$ 1.52 and 1.71 allowed assignment of the H-11 protons which in turn showed COSY correlations to protons at $\delta_H$ 1.85 and 2.67 which were assigned as the H-12 protons. The HSQC data was then used to assign C-11 ($\delta_C$ 19.8) and C-12 ($\delta_C$ 31.6). An HMBC correlation between the H-11 protons and a carbon at $\delta_C$ 87.6 allowed assignment of C-13. As noted above signals for the olefinic H-17 protons were not observed. The remaining methyl singlet ($\delta_H$ 1.31, $\delta_C$ 22.2) showed an HMBC correlation to C-13 and was assigned to C-17. Additional HMBC correlations between the H-17 protons and carbons at $\delta_C$ 54.3 and 77.1 then allowed assignment of C-15 and C-16, respectively. The $^{13}$C chemical shift for C-16 indicated substitution with a hydroxyl group at this position. The H-15 protons ($\delta_H$ 1.41 and 1.83) were assigned from the HSQC data and showed HMBC correlations to C-9, C-16 and a carbon at $\delta_C$ 40.3 which was assigned as C-14. The $^1$H chemical shifts for the H-14 protons ($\delta_H$ 2.44 and 2.58) were assigned from the HSQC data. Additional HMBC correlations between H-9 and C-12, C-14, and C-15 confirmed their assignments.

Analysis of the NMR data for the aglycone, together with MS data, indicated that addition of H$_2$O had occurred at C-16 with concomitant loss of the double bond. A summary of the $^1$H and $^{13}$C chemical shifts for the aglycone are found in Table 16.

An analysis of the HSQC data for (2d) confirmed the presence of 6 anomeric positions. Four of the anomeric protons were well resolved at $\delta_H$ 6.35 ($\delta_C$ 94.5), 5.63 ($\delta_C$ 103.8), 5.53 ($\delta_C$ 103.8), and 5.22 ($\delta_C$ 104.0) in the $^1$H NMR spectrum. The remaining two anomeric protons were observed at $\delta_H$ 5.79 ($\delta_C$ 96.0) and 5.76 ($\delta_C$ 104.0) and were partially overlapped in the $^1$H NMR spectrum. The anomeric proton observed at $\delta_H$ 6.35 showed an HMBC correlation to C-19 which indicated that it corresponds to the anomeric proton of Glc$_I$. The anomeric proton observed at $\delta_H$ 5.79 was assigned as the anomeric proton of Glc$_{II}$.

The Glc$_I$ anomeric proton ($\delta_H$ 6.35) showed a COSY correlation to a proton at $\delta_H$ 4.53 which was assigned as Glc$_I$ H-2 and in turn showed a COSY correlation to a proton at $\delta_H$ 4.98 (Glc$_I$ H-3) which showed a correlation with a proton at $\delta_H$ 4.21 (Glc$_I$ H-4). Assignment of the $^{13}$C chemical shifts for Glc$_I$ C-2 ($\delta_C$ 76.4), C-3 ($\delta_C$ 88.5), and C-4 ($\delta_C$ 69.7) was made using the HSQC data. The assignments at Glc$_I$ C-5 and C-6 were made using the $^1$H and HSQC data in comparison with the data for rebaudioside X.

Assignment of Glc$_{II}$ was carried out in a similar manner. The Glc$_{II}$ anomeric proton ($\delta_H$ 5.79) showed a COSY correlation to a proton at $\delta_H$ 4.14 which was assigned as Glc$_{II}$ H-2 and in turn showed a COSY correlation to a proton at $\delta_H$ 5.09 (Glc$_{II}$ H-3) which showed an additional correlation with a proton at $\delta_H$ 4.00 (Glc$_{II}$ H-4). Assignment of the 13C chemical shifts for Glc$_{II}$ C-2 ($\delta_C$ 80.4), C-3 ($\delta_C$ 87.9), and C-4 ($\delta_C$ 69.9) was then completed using the HSQC data. The assignments at Glc$_{II}$ C-5 and C-6 were made using the $^1$H, COSY and HSQC data.

Two of the remaining unassigned glucose moieties were assigned as substituents at C-2 and C-3 of Glc$_I$ on the basis of HMBC correlations. The anomeric proton observed at $\delta_H$ 5.76 showed an HMBC correlation to Glc$_I$ C-2 and was assigned as the anomeric proton of Glc$_V$. The anomeric proton observed at $\delta_H$ 5.22 showed an HMBC correlation to Glc$_I$ C-3 and was assigned as the anomeric proton of Glc$_{VI}$. The reciprocal HMBC correlation between Glc$_I$ H-2 and anomeric carbon of Glc$_V$ was also observed. The assignments for C-2 through C-6 of Glc$_V$ and Glc$_{VI}$ were made using the $^1$H, COSY and HSQC data in comparison with the assignment of rebaudioside X.

A summary of the $^1$H and $^{13}$C chemical shifts for the glycoside at C-19 are found in Table 17.

TABLE 17

$^1$H and $^{13}$C NMR (500 and 125 MHz, pyridine-d$_5$) assignments of the (2d) C-19 glycoside.[a,b,c]

| Position | $^{13}$C NMR | $^1$H NMR |
|---|---|---|
| Glc$_I$-1 | 94.5 | 6.35 d (8.3) |
| Glc$_I$-2 | 76.4 | 4.53 t (8.7) |

TABLE 17-continued $^1$H and $^{13}$C NMR (500 and 125 MHz, pyridine-d$_5$) assignments of the (2d) C-19 glycoside.[a,b,c]

| Position | $^{13}$C NMR | $^1$H NMR |
|---|---|---|
| Glc$_I$-3 | 88.5 | 4.98 m |
| Glc$_I$-4 | 69.7 | 4.21 m |
| Glc$_I$-5 | 78.3 | 4.14 m |
| Glc$_I$-6 | 61.5 | 4.22 m |
|  |  | 4.30 m |
| Glc$_V$-1 | 104.0 | 5.76 d (7.8) |
| Glc$_V$-2 | 74.8 | 4.28 m |
| Glc$_V$-3 | 78.1 | 4.20 m |
| Glc$_V$-4 | 73.5 | 4.13 m |
| Glc$_V$-5 | 77.6 | 3.92 |
| Glc$_V$-6 | 63.8 | 4.29 m |
|  |  | 4.64 dd (2.6, 11.6) |
| Glc$_{VI}$-1 | 104.0 | 5.22 d (7.8) |
| Glc$_{VI}$-2 | 75.1 | 3.95 m |
| Glc$_{VI}$-3 | 77.7 | 4.28 m |
| Glc$_{VI}$-4 | 70.8 | 4.08 m |
| Glc$_{VI}$-5 | 77.8 | 3.76 m |
| Glc$_{VI}$-6 | 62.0 | 4.13 m |
|  |  | 4.34 m |

[a] assignments made on the basis of COSY, HSQC, HMBC, TOCSY and HSQC-TOCSY correlations;
[b] Chemical shift values are in $\delta$ (ppm);
[c] Coupling constants are in Hz.

The two remaining unassigned sugar moieties were assigned as substituents at C-2 and C-3 of Glc$_{II}$ on the basis of HMBC correlations. The anomeric proton observed at $\delta_H$ 5.63 showed an HMBC correlation to Glc$_{II}$ C-2 and was assigned as the anomeric proton of Glc$_{III}$. The anomeric proton observed at $\delta_H$ 5.53 showed an HMBC correlation to Glc$_{II}$ C-3 and was assigned as the anomeric proton of Glc$_{IV}$. The reciprocal HMBC correlation between Glc$_{II}$ H-2 and the anomeric carbon of Glc$_{III}$ was also observed. The assignments for C-2 through C-6 of Glc$_{III}$ and Glc$_{IV}$ were made using the $^1$H, COSY and HSQC data in comparison with the assignment of rebaudioside X.

A summary of the $^1$H and $^{13}$C chemical shifts for the glycoside at C-13 are found in Table 18. The NMR data for the glycoside regions showed that they were unchanged relative to rebaudioside X.

TABLE 18

$^1$H and $^{13}$C NMR (500 and 125 MHz, pyridine-d$_5$) assignments of the (2d) C-13 glycoside.[a,b,c]

| Position | $^{13}$C NMR | $^1$H NMR |
|---|---|---|
| Glc$_{II}$-1 | 96.0 | 5.79 d (6.7) |
| Glc$_{II}$-2 | 80.4 | 4.14 m |
| Glc$_{II}$-3 | 87.9 | 5.09 m |
| Glc$_{II}$-4 | 69.9 | 4.00 m |
| Glc$_{II}$-5 | 77.2 | 4.17 m |
| Glc$_{II}$-6 | 62.0 | 4.13 m |
|  |  | 4.34 m |
| Glc$_{III}$-1 | 103.8 | 5.63 d (7.3) |
| Glc$_{III}$-2 | 75.6 | 4.13 m |
| Glc$_{III}$-3 | 78.0 | 4.09 m |
| Glc$_{III}$-4 | 72.2 | 4.08 m |
| Glc$_{III}$-5 | 77.5 | 3.70 m |
| Glc$_{III}$-6 | 63.2 | 4.32 m |
|  |  | 4.49 m |
| Glc$_{IV}$-1 | 103.8 | 5.53 d (7.9) |
| Glc$_{IV}$-2 | 75.3 | 4.02 m |
| Glc$_{IV}$-3 | 77.6 | 4.55 t (9.0) |
| Glc$_{IV}$-4 | 71.0 | 4.22 m |
| Glc$_{IV}$-5 | 78.0 | 4.09 m |

TABLE 18-continued $^1$H and $^{13}$C NMR (500 and 125 MHz, pyridine-d$_5$) assignments of the (2d) C-13 glycoside.[a,b,c]

| Position | $^{13}$C NMR | $^1$H NMR |
|---|---|---|
| Glc$_{IV}$-6 | 62.0 | 4.13 m |
|  |  | 4.34 m |

[a]assignments made on the basis of COSY, HSQC, HMBC, TOCSY and HSQC-TOCSY correlations;
[b]Chemical shift values are in δ (ppm);
[c]Coupling constants are in Hz.

Example 9

Isolation and Purification of (2e)

The material from Example 1 was analyzed by LC-MS using the LC-MS method described above. The rebaudioside X peak was observed at 11.1 min in the UV (210 nm) chromatogram. The mass spectrum for the rebaudioside X peak provided the expected [M−H]$^−$ ion at m/z 1290.5. The (2e) peak was observed to elute at 24.1 min in the UV chromatogram and showed an [M−H]$^−$ ion at m/z 803.9. Relative to rebaudioside X this indicated a net loss of 486 Daltons. HPLC purification was performed using HPLC Method 3 and the peak eluting at 23.98 min was collected over several injections and dried by rotary evaporation under reduced pressure.

Example 10

Structural Elucidation of (2e)

Mass Spectrometry

Figure 9:
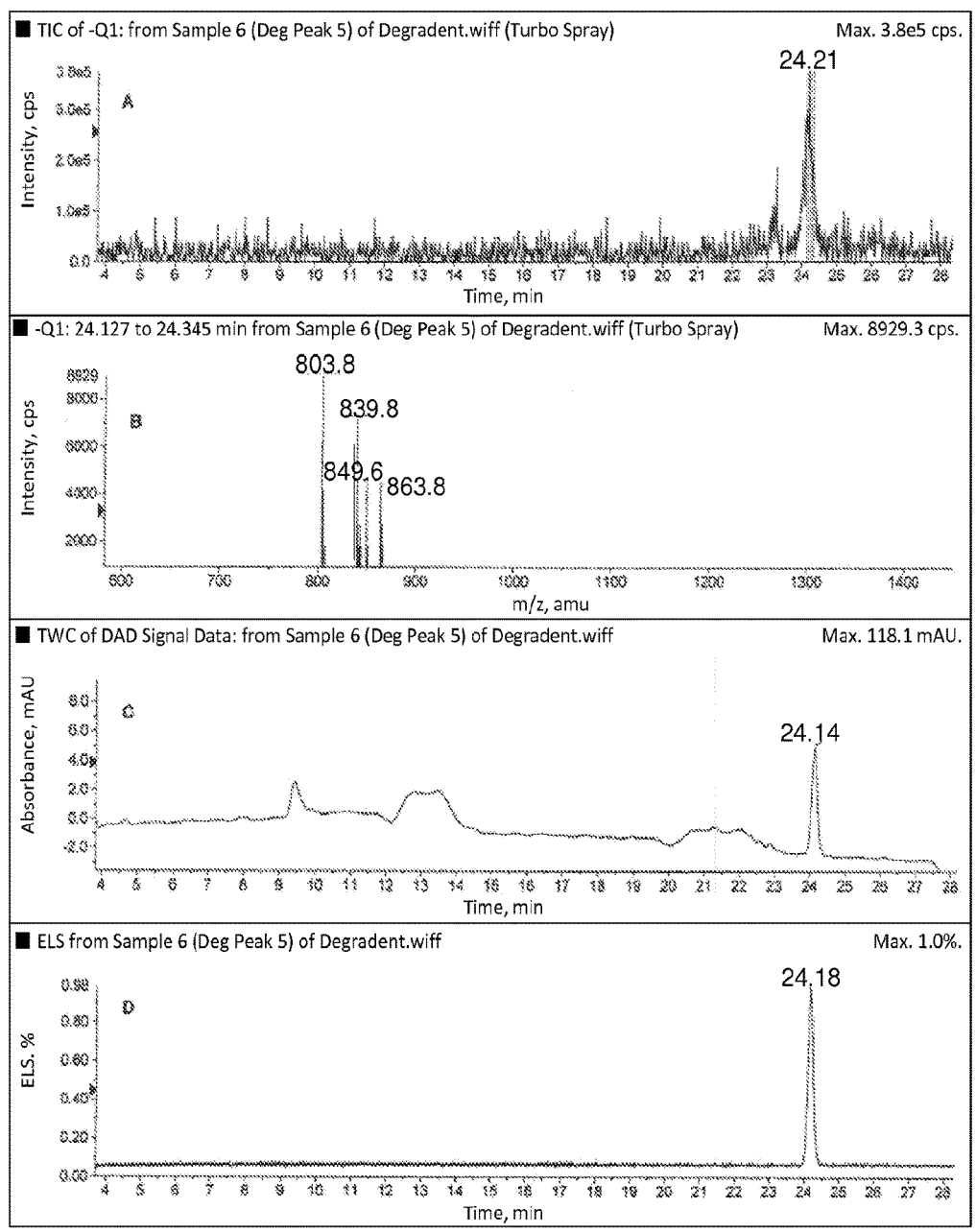
FIG. 9: LC-MS analysis of isolated sample of (2e) showing, from top to bottom, TIC, mass spectrum of the (2e) peak at 24.2 min, UV (210 nm) chromatogram and ELS chromatogram.

The results of an LC-MS analysis of confirmed that it corresponded to (2e) (FIG. 9). A single peak was observed in the TIC, UV and ELS chromatograms. The mass spectrum of the isolate of (2e) showed an [M−H]$^−$ ion at m/z 803.8 suggesting a nominal mass of 804 Daltons.

The ESI+ TOF mass spectrum acquired by infusing a sample of (2e) showed [M+H]$^+$ and [M+Na]$^+$ ions at m/z 805.3890 and 827.3707, respectively. The mass of the [M+H]$^+$ ion was in good agreement with the molecular formula $C_{38}H_{60}O_{18}$ (calcd for $C_{38}H_{61}O_{18}$: 805.3858, error: 4.0 ppm) for (2e). The ESI− mass spectrum provided [M−H]$^−$ and [M+HCOOH−H]$^−$ ions at m/z 803.3691 and 849.3774, respectively. As above, the mass of the [M−H]$^−$ ion was in good agreement with the molecular formula $C_{38}H_{60}O_{18}$ (calcd for $C_{38}H_{59}O_{18}$: 803.3701, error: −1.4 ppm) for (2e). The +ESI and −ESI data indicated that (2e) has a nominal mass of 804 Daltons with the molecular formula, $C_{38}H_{60}O_{18}$. The molecular formula of (2e) differs from that of rebaudioside X by the net loss of $C_{18}H_{30}O_{15}$ which corresponds to three units of glucose.

The MS/MS spectrum of (2e), selecting the [M+H]$^+$ ion at m/z 805 for fragmentation indicated the sequential loss of 3 glucose moieties at m/z 643.3341, 481.2809, and 319.2302. A fragment ion was also observed at m/z 487.1670 corresponding to 3 glucose moieties and this ion underwent loss of glucose to yield a fragment ion at m/z 325.1151.

The −ESI TOF MS/MS spectrum of (2e), fragmenting on the [M−H]$^−$ ion at m/z 803 showed an ion at m/z 317.2130 corresponding to the loss of three glucose residues. Fragment ions were also observed at m/z 641.3160 and 479.2651 corresponding to the loss of one or two glucose residues, respectively.

NMR Spectrometry

Figure 10:
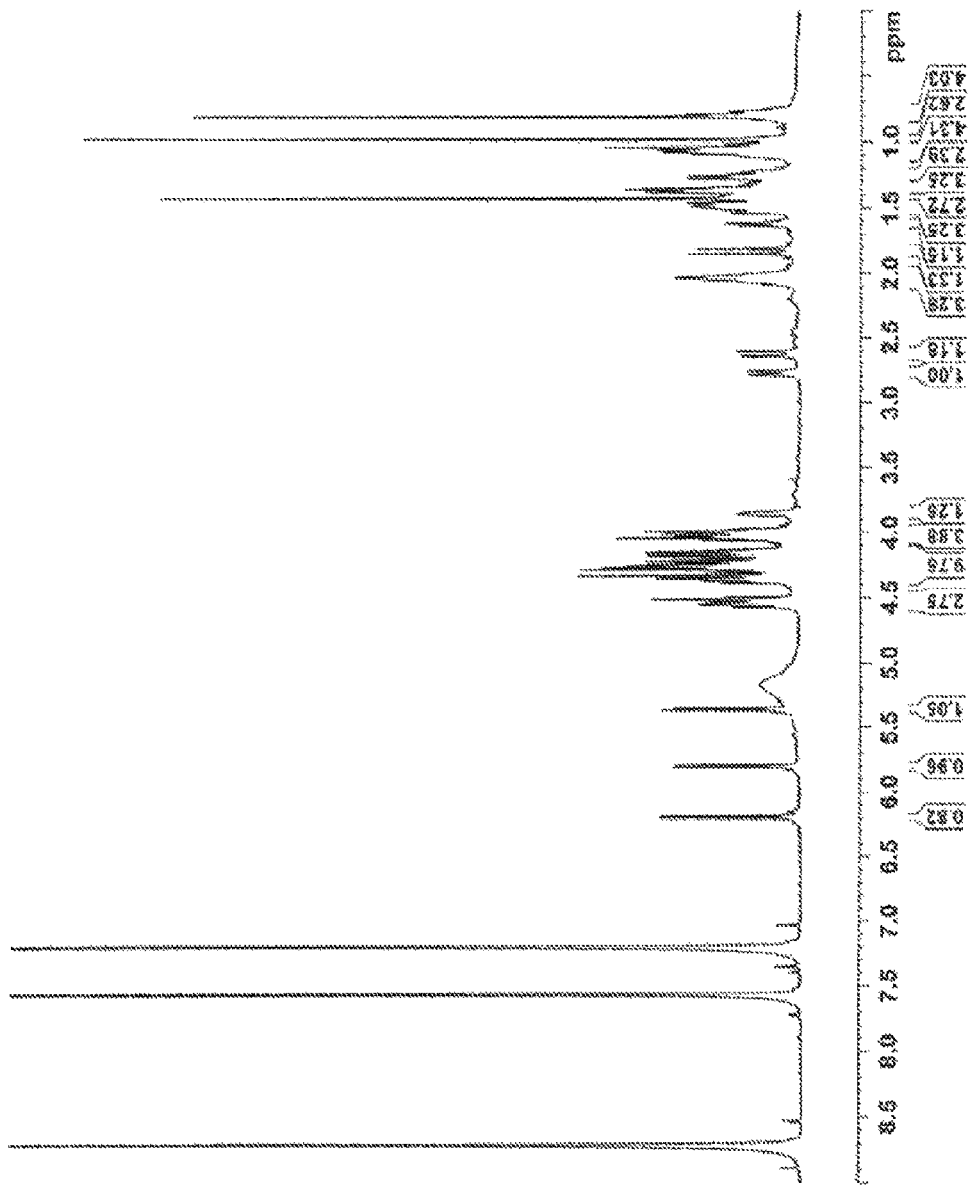
FIG. 10: $^1$H NMR (500 MHz, pyridine-$d_5$) of (2e).

A series of NMR experiments including $^1$H NMR (FIG. 10), $^1$H—$^1$H COSY, HSQC, HMBC were performed to allow the assignment of (2e). A preliminary inspection of the NMR data indicated that the olefinic protons observed for rebaudioside X were absent. Together with the MS data this suggested that a rearrangement of the aglycone had occurred with concomitant loss of three sugar residues.

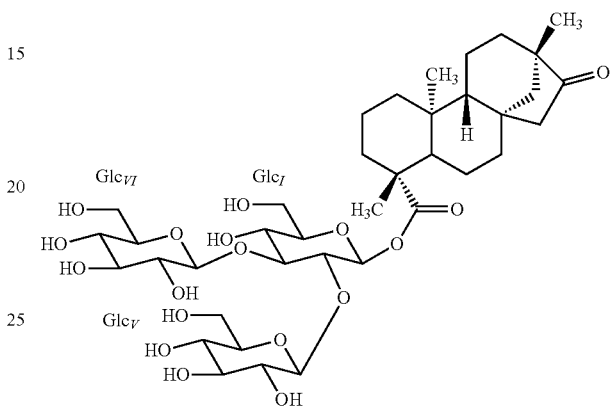

A HMBC correlation from the methyl protons at δ$_H$ 1.42 ppm to the carbonyl at δ$_C$ 175.8 allowed assignment of one of the tertiary methyl groups (C-18) as well as C-19 and provided a starting point for assignment of the rest of the aglycone.

Additional HMBC correlations from the methyl protons (H-18) to carbons at δ$_C$ 37.3, 44.1, and 57.1 allowed assignment of C3 to C5 in comparison with the data for rebaudioside X. The $^1$H chemical shifts for C-3 (δ$_H$ 1.07 and 2.77) and C-5 (δ$_H$ 1.06) were assigned using the HSQC data. A COSY correlation between one of the H-3 protons (δ$_H$ 1.07) and protons at δ$_H$ 2.02 allowed assignment of the H-2 protons which in turn showed a correlation with a proton at δ$_H$ 0.77 which was assigned to C-1. The remaining $^1$H and $^{13}$C chemical shifts for C-1 and C-2 were then assigned on the basis of additional COSY and HSQC correlations and are summarized in Table 19.

TABLE 19

$^1$H and $^{13}$C NMR (500 and 125 MHz, pyridine-d$_5$) assignments of the (2e) aglycone.[a,b,c]

| Position | $^{13}$C NMR | $^1$H NMR |
|---|---|---|
| 1 | 39.4 | 0.77 td (3.8, 13.2) |
|  |  | 1.47 m |
| 2 | 21.6 | 2.02 m |
| 3 | 37.3 | 1.07 m |
|  |  | 2.77 d (13.1) |
| 4 | 44.1 | — |
| 5 | 57.1 | 1.06 m |
| 6 | 19.4 | 1.38 m |
|  |  | 2.04 m |
| 7 | 41.3 | 1.34 m |
|  |  | 1.61 m |
| 8 |  | — |
| 9 | 54.4 | 1.04 m |
| 10 |  | — |
| 11 | 20.1 | 1.04 m |
|  |  | 1.46 m |

TABLE 19-continued $^1$H and $^{13}$C NMR (500 and 125 MHz, pyridine-d$_5$) assignments of the (2e) aglycone.$^{a,b,c}$

| Position | $^{13}$C NMR | $^1$H NMR |
|---|---|---|
| 12 | 37.1 | 1.24 m |
|  |  | 1.51 m |
| 13 | 54.2 | — |
| 14 | 48.4 | 1.83 d (18.5) |
|  |  | 2.62 dd (3.1, 18.5) |
| 15 | 53.8 | 1.27 m |
|  |  | 1.36 m |
| 16 | 220.7 | — |
| 17 | 19.9 | 0.98 s |
| 18 | 28.8 | 1.42 s |
| 19 | 175.8 | — |
| 20 | 13.8 | 0.81 s |

$^a$assignments made on the basis of COSY, HSQC, HMBC, TOCSY and HSQC-TOCSY correlations;
$^b$Chemical shift values are in δ (ppm);
$^c$Coupling constants are in Hz.

Two additional tertiary methyl singlets were observed at $\delta_H$ 0.81 and 0.98 in the $^1$H NMR spectrum and showed HSQC correlations to carbons at $\delta_C$ 13.8 and 19.9, respectively. One of these overlapped singlets ($\delta_H$ 0.81, $\delta_C$ 13.8) showed HMBC correlations to C-1 and C-5 and was assigned as C-20 in comparison with the data for rebaudioside X. The methyl protons showed an additional HMBC correlation to a methine ($\delta_H$ 1.04, $\delta_C$ 54.4) which was assigned as C-9. COSY correlations between H-5 ($\delta_H$ 1.06) and protons at $\delta_H$ 1.38 and 2.04 then allowed assignment of the H-6 protons which in turn showed correlations to protons at $\delta_H$ 1.34 and 1.61 which were assigned to C-7. The $^{13}$C chemical shifts for C-6 ($\delta_C$ 19.4) and C-7 ($\delta_C$ 41.3) were then determined from the HSQC data.

COSY correlations between H-9 ($\delta_H$ 1.04) and protons at $\delta_H$ 1.04 and 1.46 allowed assignment of the H-11 protons which in turn showed COSY correlations to protons at $\delta_H$ 1.24 and 1.51 which were assigned as the H-12 protons. The HSQC data was then used to assign C-11 ($\delta_C$ 20.1) and C-12 ($\delta_C$ 37.1). As noted above signals for the olefinic H-17 protons were not observed suggesting a change in this region of the aglycone. The remaining methyl singlet ($\delta_H$ 0.98, $\delta_C$ 19.9) showed a HMBC correlation to C-12 indicating that it must be attached at C-13. The methyl protons showed additional HMBC correlations to carbons at $\delta_C$ 48.4, 54.2, and 220.7. The HSQC data indicated that the carbon at $\delta_C$ 48.4 is a methylene group ($\delta_H$ 1.83 and 2.62) which was assigned as C-14. The ketone ($\delta_C$ 220.7) was assigned to C-16 indicating that the aglycone had undergone rearrangement to isosteviol. The quaternary carbon at $\delta_C$ 54.2 was assigned as C-13. The HSQC data indicated the presence of one additional methylene group ($\delta_H$ 1.27 and 1.36, $\delta_C$ 53.8) which was assigned to C-15.

Analysis of the NMR data for the aglycone, together with MS data, indicated that a rearrangement of the aglycone to isosteviol with concomitant loss of the glycoside at C-13. A summary of the $^1$H and $^{13}$C chemical shifts for the aglycone are found in Table 19.

An analysis of the HSQC data for (2e) indicated the presence of three anomeric positions rather than the six found in rebaudioside X. All three of the anomeric protons were well resolved at $\delta_H$ 6.19 ($\delta_C$ 93.0), 5.79 ($\delta_C$ 103.4), and 5.35 ($\delta_C$ 104.5) in the $^1$H NMR spectrum. The anomeric proton observed at $\delta_H$ 6.19 showed a HMBC correlation to C-19 which indicated that it corresponds to the anomeric proton of Glc$_I$. This was in agreement with the NMR data described above for the aglycone which indicated that the glycoside at C-13 was absent while the glycoside at C-19 was retained in the degradant.

The Glc$_I$ anomeric proton ($\delta_H$ 6.19) showed a COSY correlation to a proton at $\delta_H$ 4.51 which was assigned as Glc$_I$ H-2 and in turn showed a COSY correlation to a proton at $\delta_H$ 4.27 (Glc$_I$ H-3) which showed a correlation with a proton at $\delta_H$ 4.17 (Glc$_I$ H-4). Assignment of the $^{13}$C chemical shifts for Glc$_I$ C-2 ($\delta_C$ 76.8), C-3 ($\delta_C$ 88.4), and C-4 ($\delta_C$ 69.1) was made using the HSQC data. The assignments at Glc$_I$ C-5 and C-6 were made using the $^1$H and HSQC data in comparison with the data for rebaudioside X.

The two remaining unassigned glucose moieties were assigned as substituents at C-2 and C-3 of Glc$_I$ in comparison with the data for rebaudioside X. The anomeric proton observed at $\delta_H$ 5.79 was assigned as the anomeric proton of Glc$_V$ in comparison with the data for rebaudioside X. Similarly, the anomeric proton observed at $\delta_H$ 5.35 was assigned as the anomeric proton of Glc$_{VI}$ in comparison with rebaudioside X. The assignments for C-2 through C-6 of Glc$_V$ and Glc$_{VI}$ were made using the $^1$H, COSY and HSQC data in comparison with the assignment of rebaudioside X.

A summary of the $^1$H and $^{13}$C chemical shifts for the glycoside at C-19 are found in Table 20.

TABLE 20

$^1$H and $^{13}$C NMR (500 and 125 MHz, pyridine-d$_5$) assignments of (2e) C-19 glycoside.$^{a,b,c}$

| Position | $^{13}$C NMR | $^1$H NMR |
|---|---|---|
| Glc$_I$-1 | 93.0 | 6.19 d (8.1) |
| Glc$_I$-2 | 76.8 | 4.51 t (8.9) |
| Glc$_I$-3 | 88.4 | 4.27 t m |
| Glc$_I$-4 | 69.1 | 4.17 m |
| Glc$_I$-5 | 78.1 | 3.98 m |
| Glc$_I$-6 | 62.0 | 4.24 m |
|  |  | 4.52 m |
| Glc$_v$-1 | 103.4 | 5.79 d (7.9) |
| Glc$_v$-2 | 75.7 | 3.99 m |
| Glc$_v$-3 | 78.3 | 4.32 m |
| Glc$_v$-4 | 72.4 | 4.13 m |
| Glc$_v$-5 | 78.4 | 4.02 m |
| Glc$_v$-6 | 63.2 | 4.36 m |
|  |  | 4.56 m |
| Glc$_{vI}$-1 | 104.5 | 5.35 d (7.9) |
| Glc$_{vI}$-2 | 75.2 | 4.04 t (8.2) |
| Glc$_{vI}$-3 | 78.3 | 4.21 m |
| Glc$_{vI}$-4 | 71.2 | 4.14 m |
| Glc$_{vI}$-5 | 78.7 | 3.85 m |
| Glc$_{vI}$-6 | 61.6 | 4.24 m |
|  |  | 4.33 m |

$^a$assignments made on the basis of COSY, HSQC, HMBC, TOCSY and HSQC-TOCSY correlations;
$^b$Chemical shift values are in δ (ppm);
$^c$Coupling constants are in Hz.

Example 11

Isolation and Purification of Rebaudioside N (2f)

The material from Example 1 was analyzed by the LC-MS method described above. Under this method, (2f) eluted at 11.2 min. The ESI− mass spectrum showed the expected [M−H]-ion at m/z 1273. A first round of purification using the HPLC method 4 was carried out. Under this method, (2f) eluted between 7.8 and 11 min. A second round of HPLC purification using method 5A was performed. Under this method, (2f) eluted at 29.1 min. A third HPLC purification was then performed using HPLC method 5A and the peak eluting at 29.1 min was collected over several injections and dried by rotary evaporation under reduced pressure.

Example 12

Structural Elucidation of Rebaudioside N (2f)

Mass Spectrometry

Figure 11:
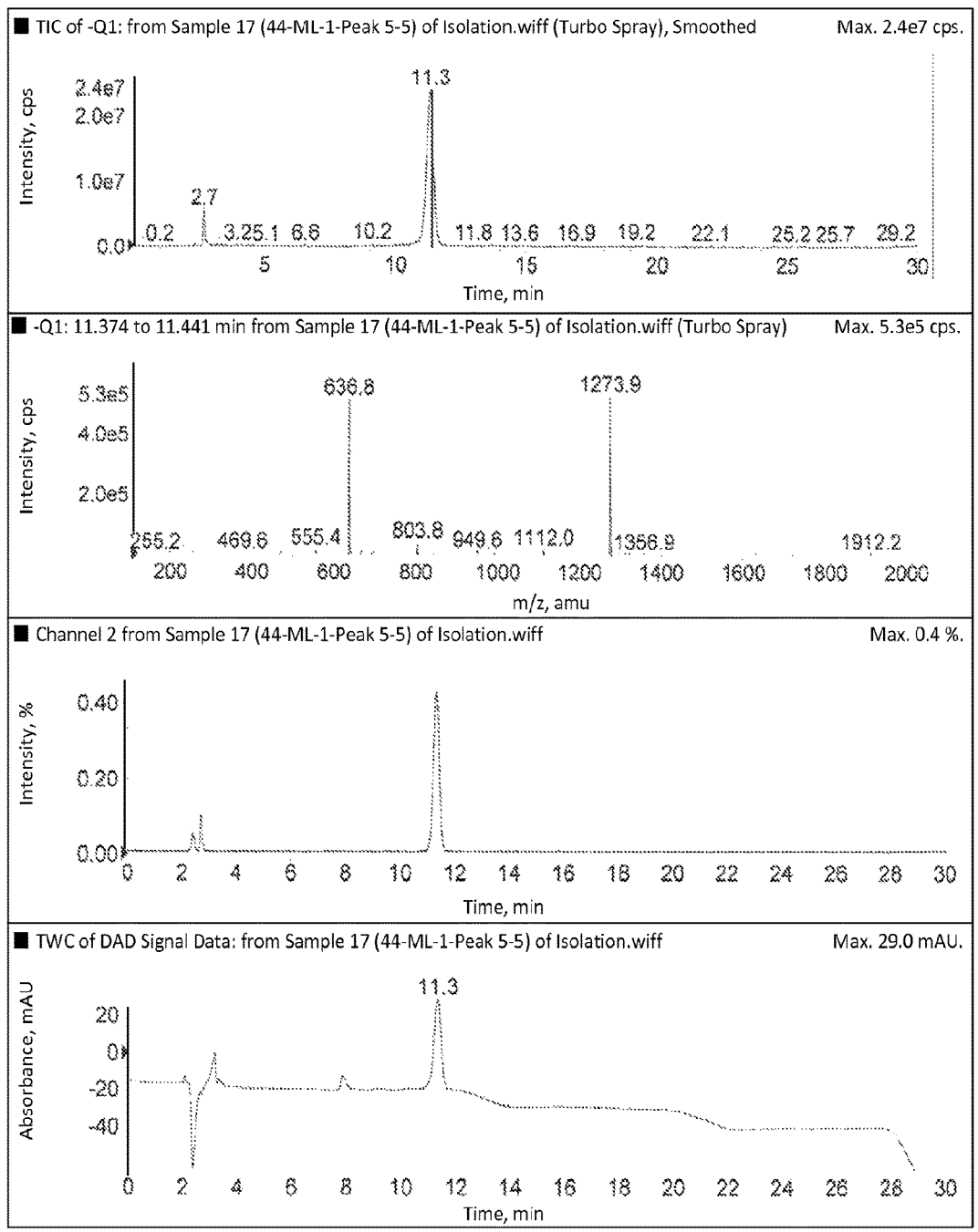
FIG. 11: LC-MS analysis of isolated sample of (2f) showing, from top to bottom, TIC, mass spectrum of the (2f) peak at 11.3 min, ELS chromatogram and UV (PDA) chromatogram.

The results of an LC-MS analysis of the isolated peak confirmed that it corresponded to (2f) (FIG. 11). A single peak was observed in the TIC, UV and ELS chromatograms. The ESI-TOF mass spectrum of the isolate of (2f) showed [M−H]⁻ ions at m/z 1273.5345. The mass of the [M−H]⁻ ion was in good agreement with the molecular formula $C_{56}H_{90}O_{32}$ (calcd for $C_{56}H_{89}O_{32}$: 1273.5337, error: 0.8 mDa) expected for (2f). The MS data confirmed that (2f) has a nominal mass of 1274 Daltons with the molecular formula, $C_{56}H_{90}O_{32}$. The MS/MS spectrum of (2f), selecting the [M−H]⁻ ion at m/z 1273 for fragmentation, indicated the sequential loss of 6 sugar moieties at m/z 1111.4790, 949.4274, 803.3708, 641.3181, 479.2654, and 317.2145. The base peak at m/z 803.3708 strongly suggested the linkage of 3 sugars to C-19 of a steviol glycoside. The difference of 162 mass units suggests the presence of glucose moieties, characteristic of steviol glycosides.

NMR Spectrometry

Figure 12:
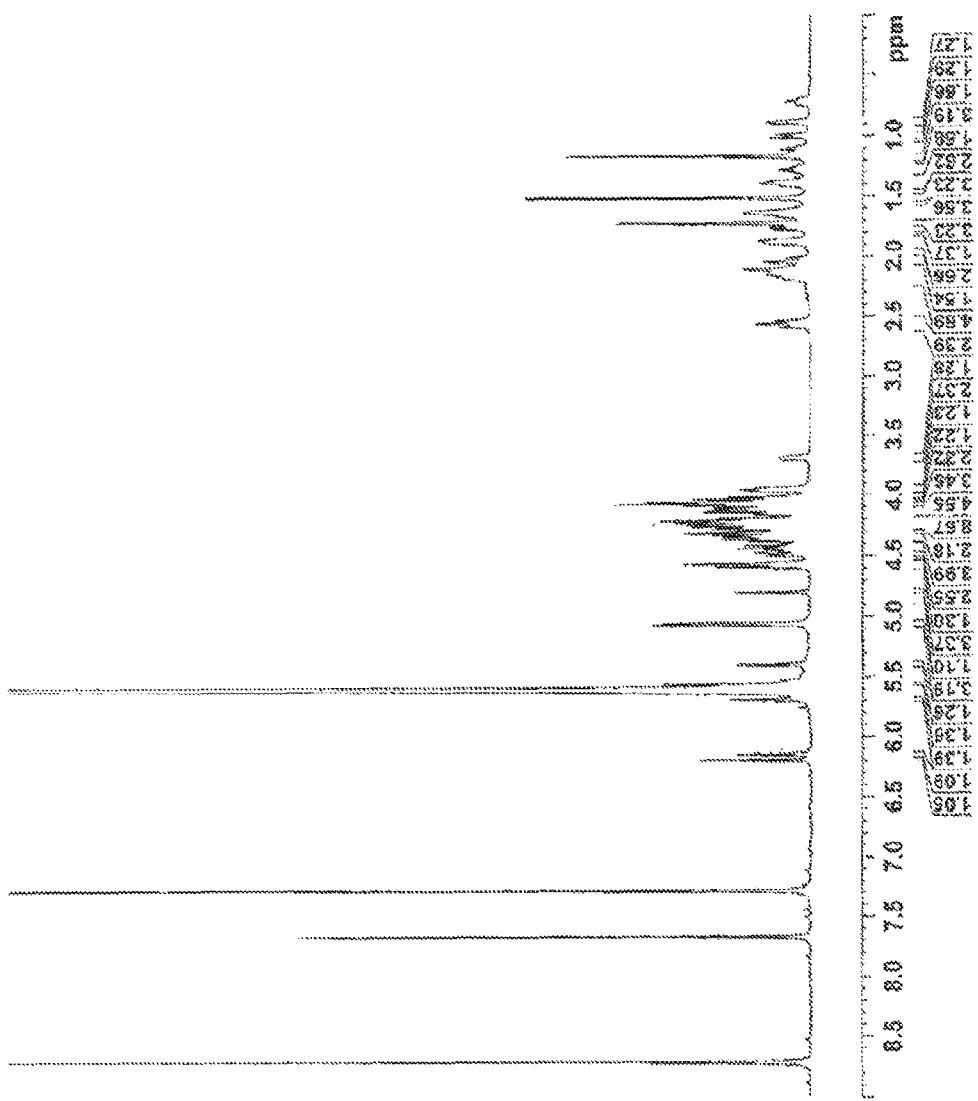
FIG. 12: 500 MHz $^1$H NMR Spectrum of (2f) in pyridine-$d_5$/$D_2O$ (10:1).

A series of NMR experiments including ¹H NMR (FIG. 12), ¹H—¹H COSY, HSQC, HMBC, and HSQC-TOCSY were performed to allow assignment of (2f).

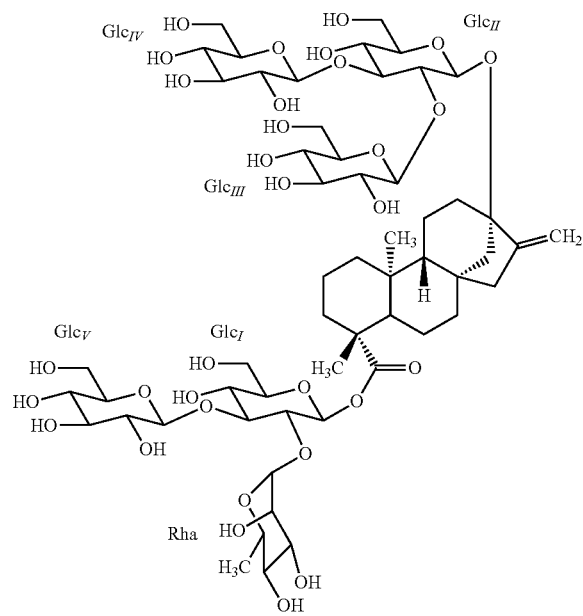

A HMBC correlation from the methyl protons at $\delta_H$ 1.52 ppm to the carbonyl at $\delta_C$ 176.0 allowed assignment of the methyl singlet C-18 as well as the carbonyl C-19 and provided a starting point for assignment of the rest of the aglycone. Additional HMBC correlations from the methyl protons (H-18) to carbons at $\delta_C$ 37.5, 44.2, and 58.2 allowed assignment of C-3, C4, and C-5, respectively. These assignments were supported by comparison of chemical shifts and similar correlations previously reported for rebaudioside X, as well as the observation that the carbon at $\delta_C$ 44.2 did not show a correlation in the HSQC spectrum. The ¹H and ¹³C chemical shifts for C-3 ($\delta_H$ 1.11 and 2.58) and C-5 ($\delta_H$ 1.00) were assigned using the HSQC data. COSY correlations between the H-3 proton at $\delta_H$ 2.58 and the protons at $\delta_H$ 1.41 and $\delta_H$ 2.11 allowed assignment of the H-2 protons. These protons showed subsequent COSY correlations with a proton at $\delta_H$ 0.72 which was assigned to C-1. The ¹H and ¹³C chemical shifts for C-1 and C-2 were then assigned using the HSQC data (Table 21).

TABLE 21

¹H and ¹³C NMR (500 and 125 MHz, pyridine-d₅/D₂O (10:1)) assignments of the (2f) aglycone.[a,b,c]

| Position | ¹³C NMR | ¹H NMR |
|---|---|---|
| 1 | 40.6 | 0.72 dd (11, 13) |
|   |      | 1.67 m |
| 2 | 19.8 | 1.41 m |
|   |      | 2.11 m |
| 3 | 37.5 | 1.11 bt (13) |
|   |      | 2.58 d (14) |
| 4 | 44.2 | — |
| 5 | 58.2 | 1.00 d (12) |
| 6 | 22.1 | 1.89 m |
|   |      | 2.15 m |
| 7 | 41.7 | 1.28 dd (10, 13) |
|   |      | 1.38 d (10) |
| 8 | ~41 | — |
| 9 | 53.8 | 0.89 bs |
| 10 | 39.3 | — |
| 11 | 20.5 | 1.64 m |
| 12 | 37.6 | 1.87 m |
|    |      | 2.19 d (11) |
| 13 | 87.9 | — |
| 14 | 44.6 | 1.77 d (11) |
|    |      | 2.55 d (11) |
| 15 | 47.8 | 2.03 d (17) |
|    |      | 2.13 m |
| 16 | ~153 | — |
| 17 | 105.0 | 5.06 m |
|    |       | 5.69 bs |
| 18 | 29.3 | 1.52 s |
| 19 | 176.0 | — |
| 20 | 17.0 | 1.17 s |

[a] assignments made on the basis of COSY, HSQC, HMBC, TOCSY and HSQC-TOCSY correlations;
[b] Chemical shift values are in δ (ppm);
[c] Coupling constants are in Hz.

A second methyl singlet, observed at $\delta_H$ 1.17, showed HMBC correlations to C-1 and C-5 and was assigned as C-20. The methyl protons showed additional MBC correlations to a quaternary carbon ($\delta_C$ 39.3) and a methine ($\delta_H$ 0.89, $\delta_C$ 53.8) which were assigned as C-10 and C-9, respectively. COSY correlations between H-5 ($\delta_H$ 1.00) and protons at $\delta_H$ 2.15 and 1.89 then allowed assignment of the H-6 protons which in turn showed correlations to protons at $\delta_H$ 1.28 and 1.38 which were assigned to C-7. The ¹³C chemical shifts for C-6 ($\delta_C$ 22.1) and C-7 ($\delta_C$ 41.7) were then assigned from the HSQC data (Table 21).

COSY correlations between H-9 ($\delta_H$ 0.89) and protons at $\delta_H$ 1.64 allowed assignment of the H-11 protons which in turn showed COSY correlations to protons at $\delta_H$ 1.87 and 2.19 which were assigned as the H-12 protons. The HSQC data was then used to assign C-1 ($\delta_C$ 20.5) and C-12 ($\delta_C$ 37.6). The HSQC correlations observed for the protons at $\delta_H$ 5.06 and 5.69 indicated that they are linked to the carbon at $\delta_C$ 105.0, which confirmed the presence of a terminal olefin as in rebaudioside X and, consequently, assigned to C-17. The olefinic proton at $\delta_H$ 5.69 has a negligible coupling constant, and its COSY correlations to the protons at $\delta_H$ 2.03 and 2.13 indicated the presence of an allylic coupling. Therefore, these protons at $\delta_H$ 2.03 and 2.13 can be assigned to C-15 ($\delta_C$ 47.8) by HSQC data. The protons at $\delta_H$ 1.77 and 2.55 were the only ones remaining in the aglycone of (2f) and can be assigned to C-14 ($\delta_C$ 44.6) based on comparison with analog protons in rebaudioside X. C-13 resonates at $\delta_C$ 87.9 based on the observation of a HMBC correlation with the olefinic proton at $\delta_H$ 5.69. No correlations were observed to C-8 and C-16 and their chemical shifts could not be determined; however, it is estimated that they should resonate at approximately 41 and 153 ppm, respectively, as in rebaudioside X.

A summary of the $^1$H and $^{13}$C chemical shifts for the aglycone are found in Table 21.

A third methyl group was observed as a doublet at $\delta_H$ 1.73. It only showed HMBC correlations to carbons at $\delta_C$ 70.2 and 73.5 whose respective protons ($\delta_H$ 4.45 and 4.32) were assigned by HSQC data. The carbon at $\delta_C$ 70.2 is correlated to an anomeric proton at $\delta_H$ 6.20 ($\delta_C$ 101.5) by HMBC, suggesting that the protons at $\delta_H$ 4.45 and 1.73 are respectively linked to C-5 and C-6 of a sugar moiety. This leaves the proton at $\delta_H$ 4.32 ($\delta_C$ 73.5) to be assigned as C-4. The proton at $\delta_H$ 6.20 showed a COSY correlation to a proton at $\delta_H$ 4.80 which, subsequently, correlated to a proton at $\delta_H$ 4.49. Additional HMBC correlations of the proton at $\delta_H$ 6.20 to the carbons at $\delta_C$ 72.0 and 76.3, and analysis of HSQC and HSQC-TOCSY data allowed the assignment of C-2 ($\delta_C$ 71.9, $\delta_H$ 4.80) and C-3 ($\delta_C$ 72.0, $\delta_H$ 4.49). The carbon at $\delta_C$ 76.3 does not belong to this sugar, as corroborated by analysis of HSQC-TOCSY data, but it established the connectivity with a contiguous unit. The identity of this sugar is proposed as D-α-rhamnose based on our data, that included the negligible coupling constants of H-1 and H-2, and the fact that this sugar is part of other steviol glycosides as described in the literature (*J. Appl Glycoscience* 2010, 57, 199-209).

An analysis of the HSQC data for (2f) confirmed the presence of other five anomeric protons. Two of them were well resolved in the $^1$H NMR spectrum at $\delta_H$ 6.15 ($\delta_C$ 93.5), and 5.39 ($\delta_C$ 104.4). A third anomeric proton was overlapped by the water signal at $\delta_H$ 5.60 ($\delta_C$ 104.1), while the remaining two resonated at $\delta_H$ 5.06 ($\delta_C$ 97.6 and 104.2).

The anomeric proton observed at $\delta_H$ 6.15 showed a HMBC correlation to C-19 which indicated that it belongs to Glc$_I$. This proton also showed a COSY correlation to a proton at $\delta_H$ 4.31 which was assigned as Glc$_I$ H-2 by HSQC data. Due to overlap in the data the COSY spectrum did not allow further assignments in this sugar. Therefore, a series of 1-D TOCSY experiments were performed using selective irradiation of the Glc$_I$ anomeric proton with several different mixing times. In addition to confirming the assignments for Glc$_I$ H-2, the TOCSY data showed protons at $\delta_H$ 4.11, 4.21, 3.96, 4.27/4.43 assigned as Glc$_I$ H-3, H-4, H-5, and H-6, respectively. Assignment of the $^{13}$C chemical shifts for Glc$_I$ C-2 ($\delta_C$ 76.3), C-3 ($\delta_C$ 88.2), C-4 ($\delta_C$ 68.9), C-5 ($\delta_C$ 77.8), and C-6 ($\delta_C$ 61.8) was straightforward using the HSQC and HSQC-TOCSY data.

Two anomeric protons were observed at $\delta_H$ 5.06, one of them showing an HMBC correlation to C-13 and the other to a carbon at $\delta_C$ 88.2 (Glc$_I$ C-3). Therefore, the first of the $\delta_H$ 5.06 protons was assigned to Glc$_{II}$ H-1 and the latter to Glc$_V$ H-1. COSY correlations of the $\delta_H$ 5.06 protons to both $\delta_H$ 4.02 and 4.38 were observed. Their HSQC correlations to carbons at $\delta_C$ 74.8 and 80.3 allowed their respective assignments to Glc$_V$ C-2 and Glc$_{II}$ C-2. Analysis of HSQC-TOCSY data of the proton at $\delta_H$ 4.38 indicated that it correlates to the carbon at $\delta_C$ 77.2 which is linked to the proton at $\delta_H$ 3.69 through HSQC. A series of 1-D TOCSY experiments selecting this proton at $\delta_H$ 3.69 together with the HSQC and HSQC-TOCSY data allowed assignment of Glc$_{II}$ C-5 ($\delta_H$ 3.69/$\delta_C$ 77.2), C-4 ($\delta_H$ 4.05/$\delta_C$ 69.7), and C-3 ($\delta_H$ 4.35/$\delta_C$ 87.2). Due to overlap, the $^{13}$C chemical shift Glc$_{II}$ C-6 was tentatively assigned as $\delta_C$ 61.9 which are correlated to protons at $\delta_H$ 4.14 and 4.29 by HSQC.

The assignment of Glc$_V$ was achieved by observation of the HSQC-TOCSY correlations of the protons at $\delta_H$ 5.06 which showed correlations to both the carbons of Glc$_{II}$ and Glc$_V$. Since Glc$_{II}$ was already assigned, the $^{13}$C chemical shifts of Glc$_V$ at $\delta_C$ 62.2, 71.3, 78.1, 78.4, and 104.2 should correspond to Glc$_V$. HSQC correlations and comparison with chemical shifts of Glc$_V$ in rebaudioside X H-5 ($\delta_H$ 4.07), H-3 ($\delta_H$ 4.22), and H-1 ($\delta_H$ 5.06), respectively.

The HMBC correlation of the anomeric proton at $\delta_H$ 5.39 ($\delta_C$ 104.4) with Glc$_{II}$ C-3 ($\delta_C$ 87.2) allowed its assignment to Glc$_{IV}$ H-1. This anomeric proton showed a COSY correlation with $\delta_H$ 4.03. A series of 1-D TOCSY experiments selecting this anomeric proton together with the HSQC and HSQC-TOCSY data allowed assignment of Glc$_{IV}$ C-2 ($\delta_H$ 4.03/$\delta_C$ 75.0), C-3 ($\delta_H$ 4.23/$\delta_C$ 78.0), C-4 ($\delta_H$ 4.07/$\delta_C$ 71.4), and C-5 ($\delta_H$ 4.08/$\delta_C$ 78.4). Due to overlap, the $^{13}$C chemical shift of C-6 was tentatively assigned as $\delta_C$ 62.2 which are correlated to protons at $\delta_H$ 4.21 and 4.58 through HSQC.

The HMBC correlation of the anomeric proton at $\delta_H$ 5.60 with Glc$_{II}$ C-2 ($\delta_C$ 80.3) allowed its assignment to Glc$_{III}$ H-1. This anomeric proton showed a COSY correlation with a proton at $\delta_H$ 4.11 which was assigned as Glc$_{III}$ H-2. A series of 1-D TOCSY experiments selecting the anomeric proton at $\delta_H$ 5.60 together with the HSQC and HSQC-TOCSY data allowed assignment of Glc$_{III}$ C-3 ($\delta_H$ 4.26/$\delta_C$ 78.0), C-4 ($\delta_H$ 4.14/$\delta_C$ 71.9), C-5 ($\delta_H$ 3.95/$\delta_C$ 78.1), and C-6 ($\delta_H$ 4.35, 4.56/$\delta_C$ 62.9).

A summary of the $^1$H and $^{13}$C chemical shifts for the glycoside at C-19 are found in Table 22.

TABLE 22

$^1$H and $^{13}$C NMR (500 and 125 MHz, pyridine-d$_5$/D$_2$O (10:1)) assignments of the (2f) C-19 glycoside.[a,b,c]

| Position | $^{13}$C NMR | $^1$H NMR |
|---|---|---|
| Glc$_I$-1 | 93.5 | 6.15 d (8.0) |
| Glc$_I$-2 | 76.3 | 4.31 m |
| Glc$_I$-3 | 88.2 | 4.11 m |
| Glc$_I$-4 | 68.9 | 4.21 m |
| Glc$_I$-5 | 77.8 | 3.96 m |
| Glc$_I$-6 | 61.8 | 4.27 m |
|  |  | 4.43 m |
| Glc$_V$-1 | 104.2 | 5.06 d (7.2) |
| Glc$_V$-2 | 74.8 | 4.02 m |
| Glc$_V$-3 | 78.1 | 4.22 m |
| Glc$_V$-4 | 71.3 | 4.07 m |
| Glc$_V$-5 | 78.4 | 4.07 m |
| Glc$_V$-6 | 62.2 | 4.29 m |
|  |  | 4.58 d (11) |
| Rha-1 | 101.5 | 6.20 bs |
| Rha-2 | 71.9 | 4.80 bs |
| Rha-3 | 72.0 | 4.49 m |
| Rha-4 | 73.5 | 4.32 m |
| Rha-5 | 70.2 | 4.45 m |
| Rha-6 | 18.9 | 1.73 d (6.0) |

[a] assignments made on the basis of COSY, HSQC, HMBC, TOCSY and HSQC-TOCSY correlations;
[b] Chemical shift values are in δ (ppm);
[c] Coupling constants are in Hz.

A summary of the $^1$H and $^{13}$C chemical shifts for the glycoside at C-13 are found in Table 23. It is identical to the structure proposed for Rebaudioside N (*J. Appl Glycoscience* 2010, 57, 199-209).

TABLE 23

$^1$H and $^{13}$C NMR (500 and 125 MHz, pyridine-$d_5$/$D_2$O (10:1)) assignments of the (2f) C-13 glycoside.[a,b,c]

| Position | $^{13}$C NMR | $^1$H NMR |
|---|---|---|
| Glc$_{II}$-1 | 97.6 | 5.06 d (7.2) |
| Glc$_{II}$-2 | 80.3 | 4.38 m |
| Glc$_{II}$-3 | 87.2 | 4.35 m |
| Glc$_{II}$-4 | 69.7 | 4.05 m |
| Glc$_{II}$-5 | 77.2 | 3.69 m |
| Glc$_{II}$-6 | 61.9 | 4.14 m |
|  |  | 4.29 m |
| Glc$_{III}$-1 | 104.8 | 5.60 m |
| Glc$_{III}$-2 | 76.3 | 4.11 m |
| Glc$_{III}$-3 | 78.0 | 4.26 m |
| Glc$_{III}$-4 | 71.9 | 4.14 m |
| Glc$_{III}$-5 | 78.1 | 3.95 m |
| Glc$_{III}$-6 | 62.9 | 4.35 m |
|  |  | 4.56 m |
| Glc$_{IV}$-1 | 104.4 | 5.39 d (8.0) |
| Glc$_{IV}$-2 | 75.0 | 4.03 m |
| Glc$_{IV}$-3 | 78.0 | 4.23 m |
| Glc$_{IV}$-4 | 71.4 | 4.07 m |
| Glc$_{IV}$-5 | 78.4 | 4.08 m |
| Glc$_{IV}$-6 | 62.2 | 4.21 m |
|  |  | 4.58 d (11) |

[a] assignments made on the basis of COSY, HSQC, HMBC, TOCSY and HSQC-TOCSY correlations;
[b] Chemical shift values are in δ (ppm);
[c] Coupling constants are in Hz.

Example 13

Isolation and Purification of Rebaudioside O (2g)

The material in Example 1 was analyzed by the LC-MS method described above. Under this method, (2g) eluted at 9.5 min. The ESI– mass spectrum showed the expected [M–H]$^-$ ion at m/z 1435. A first round of purification using the HPLC method 4 was performed. Under this method, (2g) eluted between 7.0 and 7.6 min. A second round of HPLC purification using method 5B was performed. Under this method, (2g) eluted at 15.4 min. A third round of HPLC purification was performed using method 5B and the peak eluting at 15.4 min was collected over several injections and dried by rotary evaporation under reduced pressure.

Example 14

Structural Elucidation of Rebaudioside O (2g)

Mass Spectrometry

Figure 13:
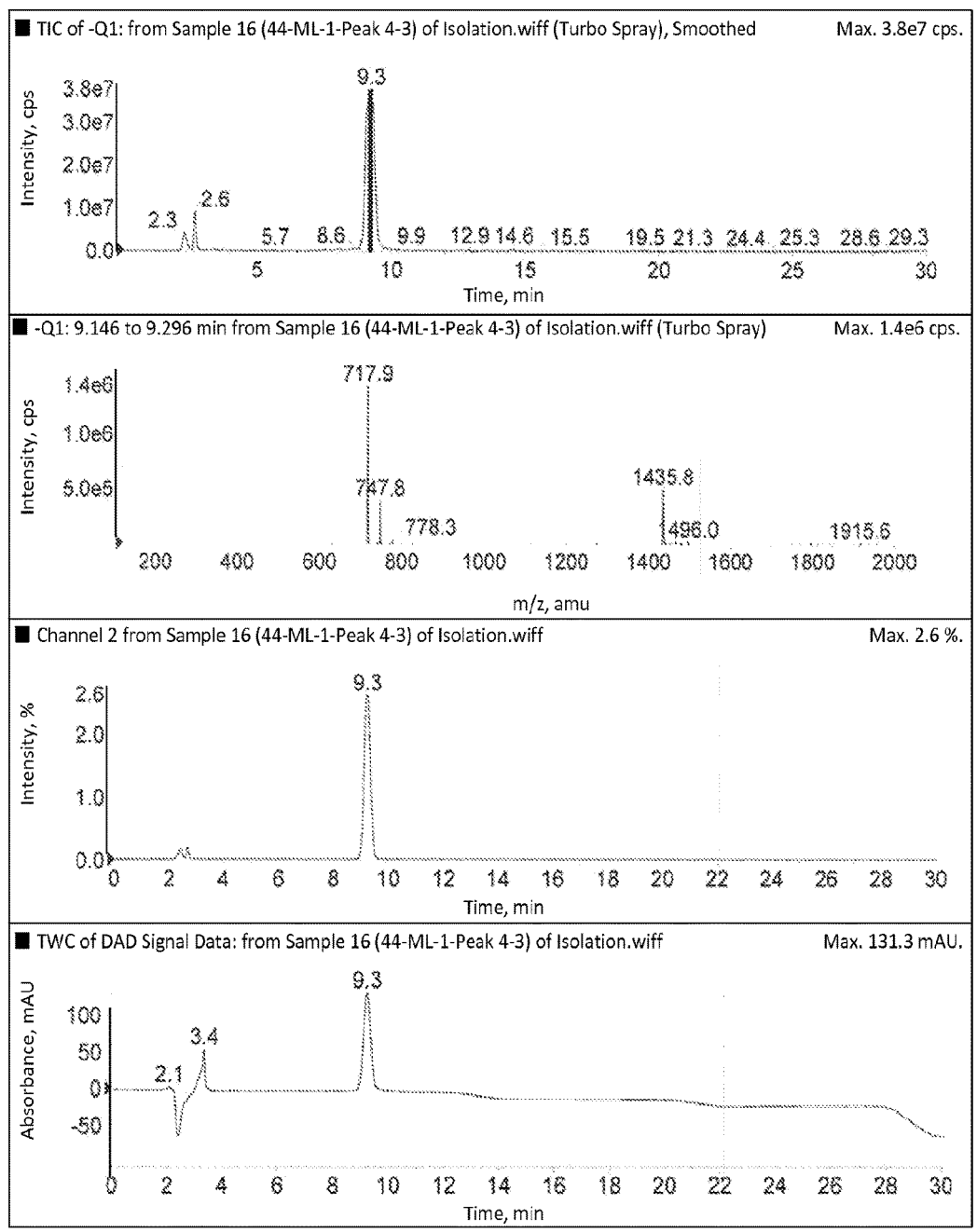
FIG. 13: LC-MS analysis of isolated sample of (2g) showing, from top to bottom, TIC, mass spectrum of the (2g) peak at 9.3 min, ELS chromatogram and UV (PDA) chromatogram.

The results of an LC-MS analysis of the isolated peak confirmed that it corresponded to (2g) (FIG. 13). A single peak was observed in the TIC, UV and ELS chromatograms. The ESI-TOF mass spectrum of (2g) showed [M–H]$^-$ ions at m/z 1435.5853 and [M+HCOOH—H]$^-$ ions at m/z 1481.5912. The mass of the [M–H]$^-$ ion was in good agreement with the molecular formula $C_{62}H_{100}O_{37}$ (calcd for $C_{62}H_{99}O_{37}$: 1435.5865, error: 1.2 mDa) expected for (2g). The MS data confirmed that (2g) has a nominal mass of 1436 Daltons with the molecular formula, $C_{62}H_{100}O_{37}$.

The MS/MS spectrum of (2g), selecting the [M–H]$^-$ ion at m/z 1435 for fragmentation, indicated the sequential loss of 7 sugar moieties at m/z 1273.5350, 1111.4779, 949.4272, 803.3721, 641.3179, 479.2661, and 317.2141. The base peak at m/z 803.3721 strongly suggested the linkage of 4 sugars to the C-19 of a steviol glycoside. The difference of 162 mass units suggests the presence of glucose moieties, characteristic of steviol glycosides.

NMR Spectrometry

Figure 14:
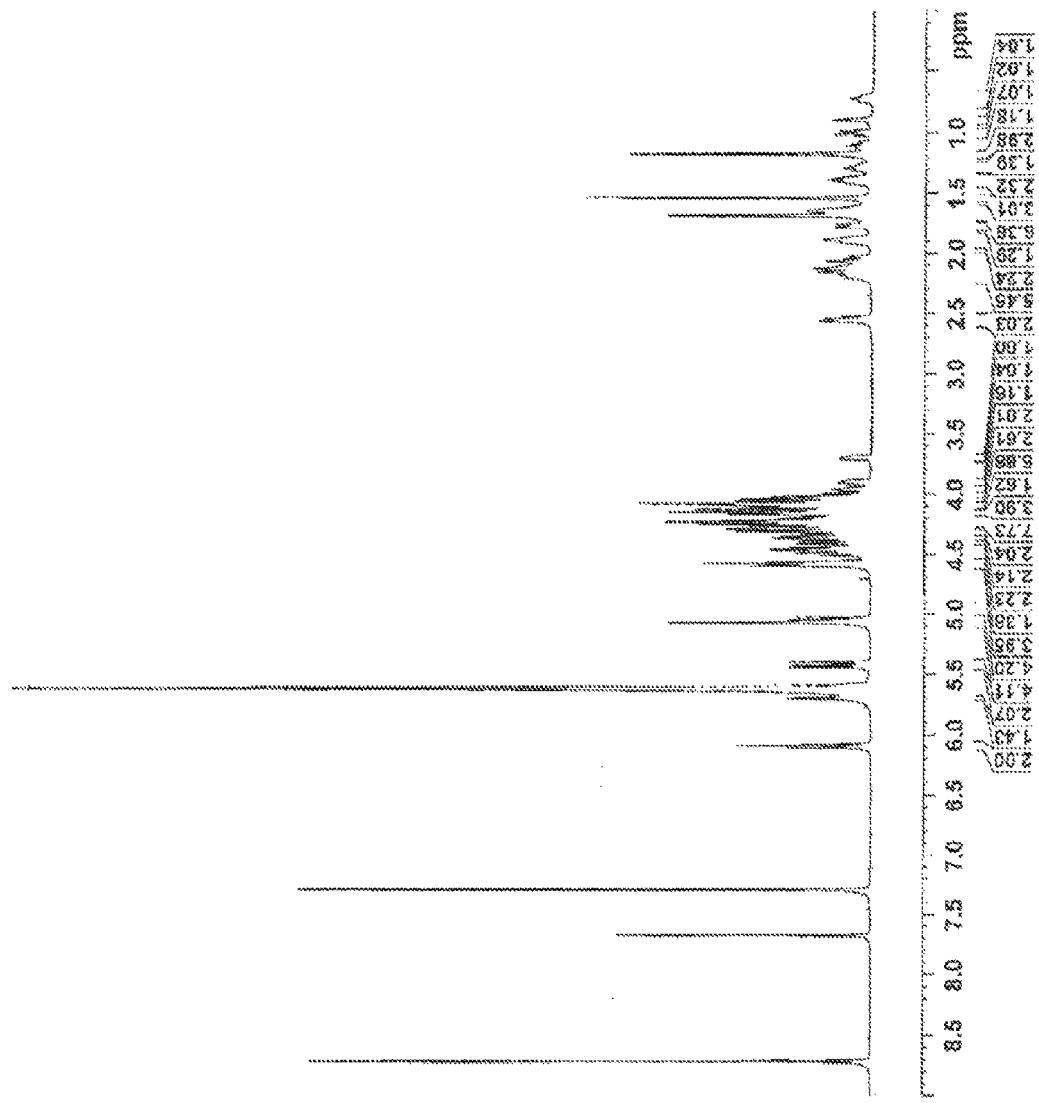
FIG. 14: 500 MHz $^1$H NMR Spectrum of (2g) in pyridine-$d_5$/$D_2O$ (10:1).

A series of NMR experiments including $^1$H NMR (FIG. 14), $^1$H—$^1$H COSY, HSQC, HMBC, and HSQC-TOCSY were performed to allow assignment of (2g).

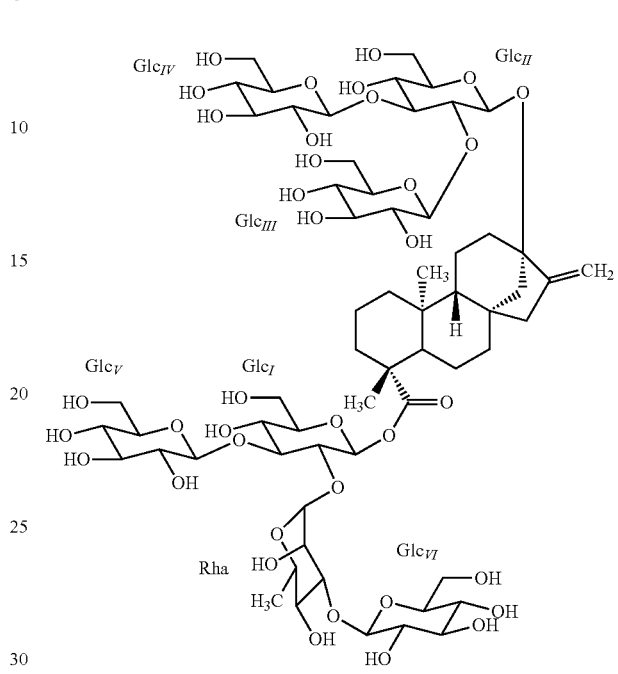

An HMBC correlation from the methyl protons at $\delta_H$ 1.54 ppm to the carbonyl at $\delta_C$ 176.4 allowed assignment of the methyl singlet C-18 as well as the carbonyl C-19 and provided a starting point for assignment of the rest of the aglycone. Additional HMBC correlations from the methyl protons (H-18) to carbons at $\delta_C$ 37.4, 44.7, and 58.2 allowed assignment of C-3, C-4, and C-5. These assignments were supported by comparison of chemical shifts and similar correlations previously reported for rebaudioside X and (2f) as well as the observation that the carbon at $\delta_C$ 44.7 did not show a correlation in the HSQC spectrum. The $^1$H and $^{13}$C chemical shifts for C-3 ($\delta_H$ 1.10 and 2.55) and C-5 ($\delta_H$ 1.00) were assigned using the HSQC data. COSY correlations between the H-3 proton at $\delta_H$ 2.55 and the protons at $\delta_H$ 1.41 and $\delta_H$ 2.09 allowed assignment of the H-2 protons. These protons showed subsequent COSY correlations with a proton at $\delta_H$ 0.72 which was assigned to C-1. The $^1$H and $^{13}$C chemical shifts for C-1 and C-2 were then assigned using the HSQC data (Table 24).

TABLE 24

$^1$H and $^{13}$C NMR (500 and 125 MHz, pyridine-$d_5$) assignments of the (2g) aglycone.[a,b,c]

| Position | $^{13}$C NMR | $^1$H NMR |
|---|---|---|
| 1 | 40.6 | 0.72 bt (12) |
|  |  | 1.67 m |
| 2 | 19.7 | 1.41 m |
|  |  | 2.09 m |
| 3 | 37.4 | 1.10 bt (13) |
|  |  | 2.55 d (11) |
| 4 | 44.7 | . . . |
| 5 | 58.2 | 1.00 d (12) |
| 6 | 21.9 | 1.90 m |
|  |  | 2.14 m |

TABLE 24-continued $^1$H and $^{13}$C NMR (500 and 125 MHz, pyridine-$d_5$) assignments of the (2g) aglycone.[a,b,c]

| Position | $^{13}$C NMR | $^1$H NMR |
|---|---|---|
| 7 | 41.7 | 1.28 bt (12) |
|   |      | 1.38 d (11) |
| 8 | ~41 | ... |
| 9 | 53.8 | 0.89 bs |
| 10 | 39.9 | ... |
| 11 | 20.4 | 1.63 m |
| 12 | 37.4 | 1.87 m |
|    |      | 2.19 m |
| 13 | 87.3 | ... |
| 14 | 44.6 | 1.76 d (11) |
|    |      | 2.55 d (11) |
| 15 | 47.7 | 2.04 d (17) |
|    |      | 2.12 m |
| 16 | ~153 | ... |
| 17 | 105.0 | 5.07 m |
|    |       | 5.69 bs |
| 18 | 29.3 | 1.54 s |
| 19 | 176.4 | ... |
| 20 | 16.9 | 1.17 s |

[a]assignments made on the basis of COSY, HSQC, HMBC, TOCSY and HSQC-TOCSY correlations;
[b]Chemical shift values are in δ (ppm);
[c]Coupling constants are in Hz.

A second methyl singlet, observed at $\delta_H$ 1.17, showed HMBC correlations to C-1 and C-5 and was assigned as C-20. The methyl protons showed additional HMBC correlations to a quaternary carbon ($\delta_C$ 39.9) and a methine ($\delta_H$ 0.89, $\delta_C$ 53.8) which were assigned as C-10 and C-9, respectively, by HSQC. COSY correlations between H-5 ($\delta_H$ 1.00) and protons at $\delta_H$ 2.14 and 1.90 then allowed assignment of the H-6 protons which in turn showed correlations to a protons at $\delta_H$ 1.28 and 1.38 which were assigned to C-7. The $^{13}$C chemical shifts for C-6 ($\delta_C$ 21.9) and C-7 ($\delta_C$ 41.7) were then assigned from the HSQC data (Table 24).

COSY correlations between H-9 ($\delta_H$ 0.89) and protons at $\delta_H$ 1.63 allowed assignment of the H-11 protons which in turn showed COSY correlations to protons at $\delta_H$ 1.87 and 2.19 which were assigned as the H-12 protons. The HSQC data was then used to assign C-11 ($\delta_C$ 20.4) and C-12 ($\delta_C$ 37.4). The HSQC correlations observed for the protons at $\delta_H$ 5.07 and 5.69 indicated that they are linked to the carbon at $\delta_C$ 105.0, which confirmed the presence of a terminal olefin as in rebaudioside X and (2f), and consequently, assigned to C-17. The olefinic proton at $\delta_H$ 5.69 has a negligible coupling constant, and its COSY correlations to the protons at $\delta_H$ 2.04 and 2.12 indicated the presence of an allylic coupling. Therefore, these protons at $\delta_H$ 2.04 and 2.12 can be assigned to C-15 ($\delta_C$ 47.7) by HSQC data. The protons at $\delta_H$ 1.76 and 2.55 were the only ones remaining in the aglycone of (2g) and can be assigned to C-14 ($\delta_C$ 44.6) based on comparison with analog protons in rebaudioside X and (2f). C-13 resonates at $\delta_C$ 87.3 based on the observation of a HMBC correlation with the olefinic proton at $\delta_H$ 5.69. No correlations were observed to C-8 and C-16 and their chemical shifts could not be determined; however, it is estimated that they should resonate at about 41 and 153 ppm, respectively, as in rebaudioside X.

A summary of the $^1$H and $^{13}$C chemical shifts for the aglycone are found in Table 24.

A third methyl group was observed as a doublet at $\delta_H$ 1.68. It only showed HMBC correlations to carbons at $\delta_C$ 69.7 and 72.3 whose respective protons ($\delta_H$ 4.46 and 4.45) were assigned by HSQC data. The carbon at $\delta_C$ 69.7 is correlated to an anomeric proton at $\delta_H$ 6.08 ($\delta_C$ 101.4) by HMBC, suggesting that the protons at $\delta_H$ 4.46 and 1.68 are respectively linked to C-5 and C-6 of a sugar moiety. This leaves the proton at $\delta_H$ 4.45 ($\delta_C$ 72.3) to be assigned as C-4. The proton at $\delta_H$ 6.08 showed a COSY correlation to a proton at $\delta_H$ 5.07 which, subsequently, correlated to a proton at $\delta_H$ 4.57. Additional HMBC correlations of the proton at $\delta_H$ 6.08 to the carbons at $\delta_C$ 76.7 and 82.8, and analysis of HSQC and HSQC-TOCSY data allowed the assignment of C-2 ($\delta_C$ 70.9, $\delta_H$ 5.07) and C-3 ($\delta_C$ 82.8, $\delta_H$ 4.57). The carbon at $\delta_C$ 76.7 does not belong to this sugar, as corroborated by analysis of HSQC-TOCSY data, but it established the connectivity with a contiguous unit. This sugar is similar to the one encountered in (2f) and based on our data can be identified as D-α-rhamnose. It has the negligible coupling constants of H-1 and H-2, as in (2f), and the fact that this sugar is part of other steviol glycosides as described in the literature (J. Appl. Glycoscience 2010, 57, 199-209). The chemical shifts of Rha H-2 and C-3 appeared downfield compared to those in (2f) due to the presence of an additional sugar connected to Rha C-3 that was absent in (2f). This connection was supported by the HMBC correlation observed from the anomeric proton at $\delta_H$ 5.43 to Rha C-3.

An analysis of the HSQC data for (2g) confirmed the presence of a total of seven anomeric protons. Two of them were already mentioned, the protons at $\delta_H$ 6.08 ($\delta_C$ 101.4) and 5.43 ($\delta_C$ 105.7). A third anomeric proton was overlapped by the water signal at $\delta_H$ 5.60 ($\delta_C$ 104.0), while the remaining four resonated at $\delta_H$ 6.10 ($\delta_C$ 93.4), 5.40 ($\delta_C$ 104.4), 5.06 ($\delta_C$ 97.6), and 5.04 ($\delta_C$ 104.3).

The anomeric proton observed at $\delta_H$ 6.10 showed an HMBC correlation to C-19 which indicated that it belongs to Glc$_I$. This proton also showed a COSY correlation to a proton at $\delta_H$ 4.23 which was assigned as Glc$_I$ H-2 ($\delta_C$ 76.7) by HSQC data. Due to overlap in the data the COSY spectrum did not allow further assignments in this sugar. Therefore, a series of 1-D TOCSY experiments were performed using selective irradiation of the Glc$_I$ anomeric proton with several different mixing times. The irradiation partially affected Rha H-1 ($\delta_H$ 6.08), but a careful analysis of HSQC, HSQC-TOCSY and the 1-D TOCSY experiments allowed us to assign Glc$_I$ C-3 ($\delta_H$ 4.03/$\delta_C$ 88.1), Glc$_I$ C-4 ($\delta_H$ 4.17/$\delta_C$ 69.0), Glc$_I$ C-5 ($\delta_H$ 3.89/$\delta_C$ 77.7), and C-6 ($\delta_H$ 4.26, 4.42/$\delta_C$ 61.7).

The HMBC correlation of Rha H-1 ($\delta_H$ 6.08) to Glc$_I$ C-2 ($\delta_C$ 76.7) indicates the same connectivity as observed in (2f). This fact also allowed the assignment of the anomeric proton at $\delta_H$ 5.43, which is connected to Rha C-3, as Glc$_{VI}$ H-1. This anomeric proton showed a COSY correlation to a proton at $\delta_H$ 4.15 which was assigned as Glc$_{VI}$ H-2 ($\delta_C$ 75.5) by HSQC. A series of 1-D TOCSY experiments were performed using selective irradiation of the Glc$_V$ anomeric proton with several different mixing times. In addition to confirming the assignments for Glc$_I$ H-2, the TOCSY data showed protons at $\delta_H$ 4.30, 4.08, 4.14, and 4.22/4.49 assigned as Glc$_I$ H-3, H-4, H-5, and H-6, respectively. Assignment of the $^{13}$C chemical shifts for Glc$_I$ C-2 ($\delta_C$ 75.5), C-3 ($\delta_C$ 77.8), C-4 ($\delta_C$ 71.4), C-5 ($\delta_C$ 77.9), and C-6 ($\delta_C$ 62.1) was straightforward using the HSQC and HSQC-TOCSY data.

The anomeric proton at $\delta_H$ 5.04 showed a HMBC correlation to Glc$_I$ C-3 which allowed its assignment as Glc$_V$ H-1, establishing the same connectivity as in (2f). Irradiation of this anomeric proton affected also the protons at $\delta_H$ 5.06 and 5.07 in the 1-D TOCSY experiments. These experiments did not provide conclusive information to assign the protons in Glc$_V$. Therefore, the assignment was achieved mostly by analysis of HSQC and HSQC-TOCSY correlations of the anomeric proton and comparison with the chemical shifts observed of Glc$_V$ from (2f). This analysis allowed the tentative assignment of the Glc$_V$ C-2 ($\delta_H$ 4.01/$\delta_C$ 74.8), C-3 ($\delta_H$ 4.29/$\delta_C$ 77.8), C-4 ($\delta_H$ 4.04/$\delta_C$ 75.1), C-5 ($\delta_H$ 4.08/$\delta_C$ 78.2), and C-6 ($\delta_H$ 4.24, 4.58/$\delta_C$ 62.1) which are very similar to those observed in (2f).

The anomeric proton at $\delta_H$ 5.06 overlapped with H-15 and Rha H-2, but it was possible to assign it to Glc$_{II}$ H-1 due to the HMBC correlation observed with the carbon at $\delta_C$ 87.3. This correlation and the chemical shifts observed are very similar to those of Glc$_{II}$ H-1 from (2f). The COSY correlation between the anomeric proton and the proton at $\delta_H$ 4.38 is clearly observed and allowed to assign it to Glc$_{II}$ H-2 ($\delta_C$ 80.1) by HSQC. Analysis of HSQC-TOCSY data of the proton at $\delta_H$ 4.38 indicated that it correlates to the carbon at $\delta_C$ 77.2 which is linked to the proton at $\delta_H$ 3.70 through HSQC, similar to (2f). A series of 1-D TOCSY experiments selecting this proton at $\delta_H$ 3.70 together with the HSQC and HSQC-TOCSY data allowed assignment of Glc$_{II}$ C-6 $\delta_H$ 4.14, 4.29/$\delta_C$ 61.9), C-5 ($\delta_H$ 3.70/$\delta_C$ 77.2), C-4 ($\delta_H$ 4.05/$\delta_C$ 69.6), and C-3 4.35/$\delta_C$ 87.3).

The HMBC correlation of the anomeric proton at $\delta_H$ 5.40 ($\delta_C$ 104.4) with Glc$_{II}$ C-3 ($\delta_C$ 87.3) allowed its assignment to Glc$_{IV}$ H-1. This anomeric proton showed a COSY correlation with $\delta_H$ 4.02 which allowed its assignment as Glc$_{IV}$ H-2 ($\delta_C$ 74.8) by HSQC. A series of 1-D TOCSY experiments selecting the anomeric proton together with the HSQC and HSQC-TOCSY data allowed assignment of C-3 ($\delta_H$ 4.24/$\delta_C$ 78.2), C-4 ($\delta_H$ 4.08/$\delta_C$ 71.4), C-5 ($\delta_H$ 4.08/$\delta_C$ 78.2), and C-6 ($\delta_H$ 4.22, 4.58/$\delta_C$ 62.2).

The HMBC correlation of the anomeric proton at $\delta_H$ 5.60 with Glc$_{II}$ C-2 ($\delta_C$ 80.1) allowed its assignment to Glc$_{III}$ H-1. This anomeric proton showed a COSY correlation with a proton at $\delta_H$ 4.11, which allowed its assignment as Glc$_{III}$ H-2 ($\delta_C$ 76.2) by HSQC. The HSQC-TOCSY data were virtually identical for the anomeric and the $\delta_H$ 3.95 protons with those of (2f). Therefore, the HSQC-TOCSY, together with the HSQC and COSY data, as well as comparison of chemical shifts with those of Glc$_{III}$ in (2f), allowed the assignment of Glc$_{III}$ C-3 ($\delta_H$ 4.28/$\delta_C$ 77.8), C-4 (@$_H$ 4.14/$\delta_C$ 71.6), C-5 ($\delta_H$ 3.95/$\delta_C$ 78.2), and C-6 ($\delta_H$ 4.34, 4.56/$\delta_C$ 62.9).

A summary of the $^1$H and $^{13}$C chemical shifts for the glycoside at C-19 are found in Table 25.

TABLE 25

$^1$H and $^{13}$C NMR (500 and 125 MHz, pyridine-d$_5$) assignments of the (2g) C-19 glycoside.$^{a,b,c}$

| Position | $^{13}$C NMR | $^1$H NMR |
|---|---|---|
| Glc$_I$-1 | 93.4 | 6.10 d (7.8) |
| Glc$_I$-2 | 76.7 | 4.23 m |
| Glc$_I$-3 | 88.1 | 4.03 m |
| Glc$_I$-4 | 69.0 | 4.17 m |
| Glc$_I$-5 | 77.7 | 3.89 m |
| Glc$_I$-6 | 61.7 | 4.26 m |
|  |  | 4.42 m |
| Glc$_V$-1 | 104.3 | 5.04 d (7.4) |
| Glc$_V$-2 | 74.8 | 4.01 m |
| Glc$_V$-3 | 77.8 | 4.29 m |
| Glc$_V$-4 | 75.1 | 4.04 m |
| Glc$_V$-5 | 78.2 | 4.08 m |
| Glc$_V$-6 | 62.1 | 4.24 m |
|  |  | 4.58 m |
| Rha-1 | 101.4 | 6.08 bs |
| Rha-2 | 70.9 | 5.07 m |
| Rha-3 | 82.8 | 4.57 m |
| Rha-4 | 72.3 | 4.45 m |
| Rha-5 | 69.7 | 4.46 m |
| Rha-6 | 18.7 | 1.68 d (5.1) |
| Glc$_{VI}$-1 | 105.7 | 5.43 d (7.8) |

TABLE 25-continued $^1$H and $^{13}$C NMR (500 and 125 MHz, pyridine-d$_5$) assignments of the (2g) C-19 glycoside.$^{a,b,c}$

| Position | $^{13}$C NMR | $^1$H NMR |
|---|---|---|
| Glc$_{VI}$-2 | 75.5 | 4.15 m |
| Glc$_{VI}$-3 | 77.8 | 4.30 m |
| Glc$_{VI}$-4 | 71.4 | 4.08 m |
| Glc$_{VI}$-5 | 77.9 | 4.14 m |
| Glc$_{VI}$-6 | 62.1 | 4.22 m |
|  |  | 4.49 m |

$^a$assignments made on the basis of COSY, HSQC, HMBC, TOCSY and HSQC-TOCSY correlations;
$^b$Chemical shift values are in $\delta$ (ppm);
$^c$Coupling constants are in Hz.

A summary of the $^1$H and $^{13}$C chemical shifts for the glycoside at C-13 are found in Table 26. (2g) is identical to the structure proposed for Rebaudioside O (*J Appl. Glycoscience* 2010, 57, 199-209).

TABLE 26

$^1$H and $^{13}$C NMR (500 and 125 MHz, pyridine-d$_5$) assignments of the (2g) C-13 glycoside.$^{a,b,c}$

| Position | $^{13}$C NMR | $^1$H NMR |
|---|---|---|
| Glc$_{II}$-1 | 97.6 | 5.06 m |
| Glc$_{II}$-2 | 80.1 | 4.38 m |
| Glc$_{II}$-3 | 87.3 | 4.35 m |
| Glc$_{II}$-4 | 69.6 | 4.05 m |
| Glc$_{II}$-5 | 77.2 | 3.70 m |
| Glc$_{II}$-6 | 61.9 | 4.14 m |
|  |  | 4.29 m |
| Glc$_{III}$-1 | 104.0 | 5.60 m |
| Glc$_{III}$-2 | 76.2 | 4.11 m |
| Glc$_{III}$-3 | 77.8 | 4.28 m |
| Glc$_{III}$-4 | 71.6 | 4.14 m |
| Glc$_{III}$-5 | 78.2 | 3.95 m |
| Glc$_{III}$-6 | 62.9 | 4.34 m |
|  |  | 4.56 m |
| Glc$_{IV}$-1 | 104.4 | 5.40 d (7.9) |
| Glc$_{IV}$-2 | 74.8 | 4.02 m |
| Glc$_{IV}$-3 | 78.2 | 4.24 m |
| Glc$_{IV}$-4 | 71.4 | 4.08 m |
| Glc$_{IV}$-5 | 78.2 | 4.08 m |
| Glc$_{IV}$-6 | 62.2 | 4.22 m |
|  |  | 4.58 m |

$^a$assignments made on the basis of COSY, HSQC, HMBC, TOCSY and HSQC-TOCSY correlations;
$^b$Chemical shift values are in $\delta$ (ppm);
$^c$Coupling constants are in Hz.

Example 15

Purification of Rebaudioside X (Reb X) from *Stevia rebaudiana* Bertoni Plant Leaves Two kg of *Stevia rebaudiana* Bertoni plant leaves were dried at 45° C. to an 8.0% moisture content and ground to 10-20 mm particles. The content of different glycosides in the leaves was as follows: Stevioside—2.55%, Reb A—7.78%, Reb B—0.01%, Reb C—1.04%, Reb D—0.21%, Reb F—0.14%, Reb X—0.10% Dulcoside A—0.05%, and Steviolbioside—0.05%. The dried material was loaded into a continuous extractor and the extraction was carried out with 40.0 L of water at a pH of 6.5 at 40° C. for 160 min. The filtrate was collected and subjected to chemical treatment. Calcium oxide in the amount of 400 g was added to the filtrate to adjust the pH within the range of 8.5-9.0, and the mixture was maintained for 15 min with slow agitation. Then, the pH was adjusted to around 3.0 by adding 600 g of $FeCl_3$ and the mixture was maintained for 15 min with slow agitation. A small amount of calcium oxide was further added to adjust the pH to 8.5-9.0 and the mixture was maintained for 30 min with slow agitation. The precipitate was removed by filtration on a plate-and-frame filter press using cotton cloth as the filtration material. The slightly yellow filtrate was passed through the column, packed with cation-exchange resin Amberlite FCP22 ($H^+$) and then, through the column with anion-exchange resin Amberlite FPA53 ($OH^-$). The flow rate in both columns was maintained at SV=0.8 $hour^{-1}$. After completion both columns were washed with RO water to recover the steviol glycosides left in the columns and the filtrates were combined. The portion of combined solution containing 120 g total steviol glycosides was passed through seven columns, wherein each column was packed with specific macroporous polymeric adsorbent YWD-03 (Cangzhou Yuanwei, China). The first column with the size of ⅓ of the others acted as a "catcher column". The SV was around 1.0 $hour^{-1}$. After all extract was passed through the columns, the resin sequentially was washed with 1 volume of water, 2 volumes of 0.5% NaOH, 1 volume of water, 2 volumes of 0.5% HCl, and finally with water until the pH was 7.0. The "catcher column" was washed separately. Desorption of the adsorbed steviol glycosides was carried out with 52% ethanol at SV=1.0 $hour^{-1}$. Desorption of the first "catcher column" was carried out separately and the filtrate was not mixed with the main solution obtained from other columns. Desorption of the last column also was carried out separately. The quality of extract from different columns with specific macroporous adsorbent is shown in Table 27.

TABLE 27

| Columns | total steviol glycosides % (TSG) |
|---|---|
| 1 (catcher) | 55.3 |
| 2 | 92.7 |
| 3 | 94.3 |
| 4 | 96.1 |
| 5 | 96.3 |
| 6 | 95.8 |
| 7 | 80.2 |

Eluents from second to sixth columns were combined and treated separately. The combined solution of steviol glycosides was mixed with 0.3% of activated carbon from the total volume of solution. The suspension was maintained at 25° C. for 30 min with continuous agitation. Separation of carbon was carried out on a press-filtration system. For additional decolorization the filtrate was passed through the columns packed with cation-exchange resin Amberlite FCP22 ($H^+$) followed with anion-exchange resin Amberlite FPA53 A30B ($OH^-$). The flow rate in both columns was around SV=0.5 $hour^{-1}$. The ethanol was distilled using a vacuum evaporator. The solids content in the final solution was around 15%. The concentrate was passed through the columns packed with cation-exchange resin Amberlite FCP22 ($H^+$) and anion-exchange resin Amberlite FPA53 ($OH^-$) with SV=0.5 $hour^{-1}$. After all the solution was passed through the columns, both resins were washed with RO water to recover the steviol glycosides left in the columns. The resulting refined extract was transferred to the nanofiltration device, concentrated to around 52% of solids content and spray dried to provide a highly purified mixture of steviol glycosides. The yield was 99.7 g. The mixture contained Stevioside—20.5%, Reb A—65.6%, Reb B—0.1%, Reb C—8.4%, Reb D-0.5%, Reb F—1.1%, Reb X—0.1%, Dulcoside A—0.4%, and Steviolbioside—0.4%.

The combined eluate from the last column, contained about 5.3 g of total steviol glycosides including 2.3 g Reb D and around 1.9 g Reb X (35.8% Reb X/TSG ratio). It was deionized and decolorized as discussed above and then concentrated to a 33.5% content of total solids.

The concentrate was mixed with two volumes of anhydrous methanol and maintained at 20-22° C. for 24 hours with intensive agitation.

The resulting precipitate was separated by filtration and washed with about two volumes of absolute methanol. The yield of Reb X was 1.5 g with around 80% purity.

For the further purification the precipitate was suspended in three volumes of 60% methanol and treated at 55° C. for 30 min, then cooled down to 20-22° C. and agitated for another 2 hours.

The resulting precipitate was separated by filtration and washed with about two volumes of absolute methanol and subjected to similar treatment with a mixture of methanol and water.

The yield of Reb X was 1.2 g with 97.3% purity. The structure of rebaudioside X was determined to be:

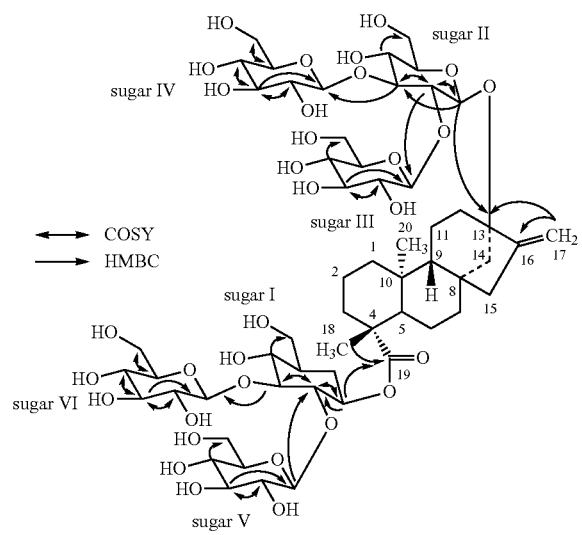

TABLE 28

$^1H$ and $^{13}C$ NMR spectral data for Rebaudioside X in $C_5D_5N^{a-c}$.

| Position | $^{13}C$ NMR | $^1H$ NMR |
|---|---|---|
| 1 | 40.3 | 0.75 t (13.2) |
| | | 1.76 m |

TABLE 28-continued $^1$H and $^{13}$C NMR spectral data for Rebaudioside X in $C_5D_5N^{a-c}$.

| Position | $^{13}$C NMR | $^1$H NMR |
|---|---|---|
| 2 | 19.6 | 1.35 m |
|  |  | 2.24 m |
| 3 | 38.4 | 1.01 m |
|  |  | 2.30 d (13.3) |
| 4 | 44.3 | — |
| 5 | 57.4 | 1.06 d (12.8) |
| 6 | 23.5 | 2.23 m |
|  |  | 2.41 q (13.2) |
| 7 | 42.6 | 1.41 m |
|  |  | 1.80 m |
| 8 | 41.2 | — |
| 9 | 54.3 | 0.91 d (7.7) |
| 10 | 39.7 | — |
| 11 | 20.2 | 1.65 m |
|  |  | 1.75 m |
| 12 | 38.5 | 1.86 m |
|  |  | 2.73 m |
| 13 | 87.6 | — |
| 14 | 43.3 | 2.02 m |
|  |  | 2.74 m |
| 15 | 46.5 | 1.88 d (16.4) |
|  |  | 2.03 m |
| 16 | 153.3 | — |
| 17 | 104.9 | 4.90 s |
|  |  | 5.69 s |
| 18 | 28.2 | 1.32 s |
| 19 | 176.9 | — |
| 20 | 16.8 | 1.38 s |
| 1' | 94.9 | 6.39 d (8.2) |
| 2' | 76.9 | 4.51 t (8.5) |
| 3' | 88.6 | 5.09 t (8.5) |
| 4' | 70.1 | 4.18 m |
| 5' | 78.4 | 4.13 m |
| 6' | 61.8 | 4.20 m |
|  |  | 4.31 m |
| 1" | 96.2 | 5.46 d (7.1) |
| 2" | 81.4 | 4.13 m |
| 3" | 87.9 | 4.98 t (8.5) |
| 4" | 70.4 | 4.07 t (9.6) |
| 5" | 77.7 | 3.94 m |
| 6" | 62.6 | 4.19 m |
|  |  | 4.32 m |
| 1''' | 104.8 | 5.48 d (7.7) |
| 2''' | 75.8 | 4.15 m |
| 3''' | 78.6 | 4.13 m |
| 4''' | 73.2 | 3.98 m |
| 5''' | 77.6 | 3.74 ddd (2.8, 6.4, 9.9) |
| 6''' | 64.0 | 4.27 m |
|  |  | 4.51 m |
| 1'''' | 103.9 | 5.45 d (7.5) |
| 2'''' | 75.6 | 3.98 m |
| 3'''' | 77.8 | 4.50 t (7.8) |
| 4'''' | 71.3 | 4.14 m |
| 5'''' | 78.0 | 3.99 m |
| 6'''' | 62.1 | 4.20 m |
|  |  | 4.32 m |
| 1''''' | 104.2 | 5.81 d (7.2) |
| 2''''' | 75.5 | 4.20 m |
| 3''''' | 78.4 | 4.20 m |
| 4''''' | 73.6 | 4.10 m |
| 5''''' | 77.8 | 3.90 ddd (2.8, 6.4, 9.9) |
| 6''''' | 64.0 | 4.32 m |
|  |  | 4.64 d (10.3) |
| 1'''''' | 104.1 | 5.31 d (8.0) |
| 2'''''' | 75.5 | 3.95 m |
| 3'''''' | 78.0 | 4.37 t (9.1) |
| 4'''''' | 71.1 | 4.10 m |
| 5'''''' | 78.1 | 3.85 ddd (1.7, 6.1, 9.9) |
| 6'''''' | 62.1 | 4.10 m |
|  |  | 4.32 m |

$^a$assignments made on the basis of COSY, HMQC and HMBC correlations;
$^b$Chemical shift values are in δ (ppm);
$^c$Coupling constants are in Hz.

Based on the results from NMR spectral data, it was concluded that there are six glucosyl units. A close comparison of the $^1$H and $^{13}$C NMR spectrum of Reb X with rebaudioside D suggested that Reb X was also a steviol glycoside which had three glucose residues that attached at the C-13 hydroxyl as a 2,3-branched glucotriosyl substituent and another 2,3-branched glucotriosyl moiety in the form of an ester at C-19.

The key COSY and HMBC correlations suggested the placement of the sixth glucosyl moiety at the C-3 position of Sugar I. The large coupling constants observed for the six anomeric protons of the glucose moieties at δ 5.31 (d, J=8.0 Hz), 5.45 (d, J=7.5 Hz), 5.46 (d, J=7.1 Hz), 5.48 (d, J=7.7 Hz), 5.81 (d, J=7.2 Hz), and 6.39 (d, J=8.2 Hz), suggested their β-orientation as reported for steviol glycosides. Based on the results of NMR and mass spectral studies and in comparison with the spectral values of rebaudioside A and rebaudioside D, Reb X was assigned as 13-[(2-O-β-D-glucopyranosyl-3-O-β-D-glucopyranosyl-β-D-glucopyranosyl)oxy]ent-kaur-16-en-19-oic acid-[(2-O-β-D-glucopyranosyl-3-O-β-D-glucopyranosyl-β-D-glucopyranosyl) ester].

Example 16

Evaluation of Rebaudioside N (2f) and Rebaudioside O (2g) as Sucrose Enhancers in Beverages Solutions were made by dissolving all ingredients in treated water. For citric acid buffer, citric acid and potassium citrate were added in a sufficient amount to bring the pH to 3.2. Finished products were filled in 300 ml glass bottles and stored in the refrigerator and tasted the following day. Products were prepared with the ingredients provided in Tables 29 and 30.

TABLE 29

Controls with Sucrose in Citric Acid/Sodium Citrate Buffer Solutions

| Ingredients | 1% Sucrose | 1.5% Sucrose | 2% Sucrose | 8% Sucrose | 9% Sucrose | 10% Sucrose |
|---|---|---|---|---|---|---|
| Water | 98.86 | 98.36 | 97.86 | 91.86 | 90.86 | 89.86 |
| Citric Acid | 0.117 | 0.117 | 0.117 | 0.117 | 0.117 | 0.117 |
| Sodium Citrate | 0.027 | 0.027 | 0.027 | 0.027 | 0.027 | 0.027 |
| Sucrose | 1 | 1.5 | 2 | 8 | 9 | 10 |
| TOTAL | 100 g | 100 g | 100 g | 100 g | 100 g | 100 g |

TABLE 30

Rebaudioside N (2f) and Rebaudioside O (2g) in Citric Acid/Sodium Citrate Buffer Solution

| Ingredients (grams) | 30 ppm 2f | 30 ppm 2g |
|---|---|---|
| Water | 99.85 | 99.85 |
| Citric Acid | 0.117 | 0.117 |
| Sodium Citrate | 0.027 | 0.027 |
| 2f/2g | 0.003 | 0.003 |
| TOTAL | 100 g | 100 g |

Taste Evaluation

Beverages in citric acid/sodium citrate buffer were kept at 4° C. in the refrigerator and tasted the following day. Four panelists evaluated the beverages. Bottles were removed from the refrigerator and about 20 ml of beverage poured in 2 oz. plastic cups. Panelists were instructed not to swallow the samples and additional cups were provided to spit the sample in. Mineral water was given for palate rinsing before tasting and between tasting different samples.

To evaluate 30 ppm of rebaudioside N and rebaudioside O for overall sweetness, panelists were provided solutions of 1%, 1.5%, and 2% sucrose in citric acid/sodium citrate buffer as controls. All panelists determined the overall sweetness of 30 ppm of rebaudioside N and rebaudioside O solutions in citric acid/sodium citrate buffer to fall between 1% and 1.5% sucrose controls. Accordingly, 30 ppm was determined to be the sweetness recognition threshold concentration for both compounds.

Sweetness enhancement of rebaudioside N and rebaudioside O was evaluated by adding 30 ppm to a solution of 8% sucrose in citric acid/sodium citrate buffer (pH 3.2). The new solutions were then evaluated for their overall sweetness against three controls of 8%, 9%, and 10% sucrose in citric acid/sodium citrate buffer solutions (pH 3.2).

All panelists determined that the beverage containing 30 ppm rebaudioside N and 8% sucrose in citric acid/sodium citrate buffer was sweeter than the 10% sucrose control, specifically from about 10.5% to about 11% sucrose. Accordingly, addition of rebaudioside N in the amount at or below its sweetness recognition threshold (30 ppm) to a beverage containing 8% sucrose resulted in a sweetness enhancement of about 2.5-3.0%

The overall sweetness of the beverage containing 30 ppm rebaudioside O and 8% sucrose in citric acid/sodium citrate was similar to the 10% sucrose control. Accordingly, addition of rebaudioside O in the amount at or below its sweetness recognition threshold (30 ppm) to a beverage containing 8% sucrose resulted in a sweetness enhancement of about 2.0%

We claim:

1. A consumable comprising sucrose and a compound of formula (1), wherein
   the sucrose is present in a concentration above its sweetness recognition threshold;
   the compound of formula (1) is present in a concentration at or below its sweetness recognition threshold;
   the compound of formula (1) enhances the sweetness of the consumable by at least about 2.0% sucrose equivalence; and the compound of formula (1) is selected from the following:

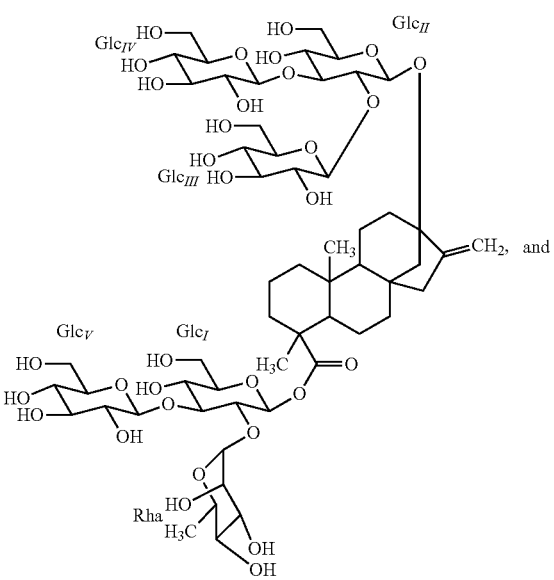

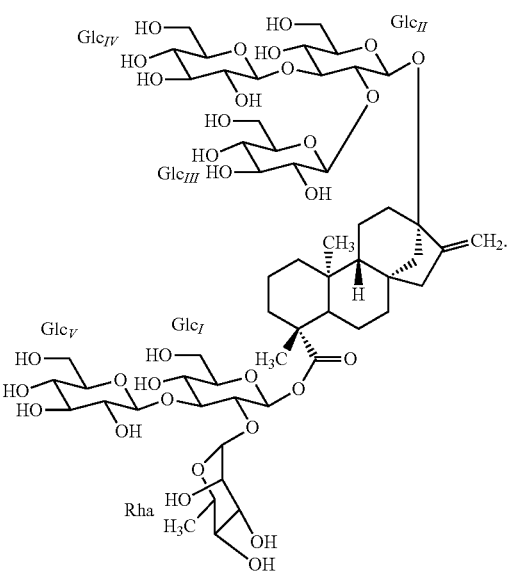

2. The consumable of claim 1, wherein the consumable is selected from the group consisting of pharmaceutical compositions, edible gel mixes and compositions, dental compositions, foodstuffs, confections, condiments, chewing gum, cereal compositions, baked goods, dairy products, tabletop sweetener compositions, beverages and beverage products.

3. The consumable of claim 2, wherein the consumable is a beverage.

4. The consumable of claim 3, wherein the beverage is selected from a a sparkling beverage, a juice, a sports drink, an energy drink, an enhanced water drink, a near water drink, a coconut water, a tea, a coffee, a cocoa drink, a beverage containing milk components, a beverage containing cereal extracts and a smoothie.

5. The consumable of claim 3, wherein the beverage is selected from a mid-calorie beverage, a low-calorie beverage and a zero-calorie beverage.

6. The consumable of claim 1, wherein the concentration of the compound of formula (1) is about 30 ppm.

7. The consumable of claim 4, wherein the juice is selected from the group consisting of a fruit juice, a fruit-flavored juice, a vegetable juice, and a vegetable-flavored juice.

8. The consumable of claim 4, wherein the sparkling beverage is selected from the group consisting of cola, lemon-lime flavored sparkling beverage, orange flavored sparkling beverage, grape flavored sparkling beverage, strawberry flavored sparkling beverage, pineapple flavored sparkling beverage, ginger-ale, root beer, and enhanced sparkling beverage.

* * * * *